United States Patent
Iwahashi et al.

(10) Patent No.: US 7,351,705 B2
(45) Date of Patent: *Apr. 1, 2008

(54) CARBOXYLIC ACID COMPOUNDS AND A PHARMACEUTICAL AGENT COMPRISING THE COMPOUND AS THE ACTIVE INGREDIENT

(75) Inventors: Maki Iwahashi, Mishima-gun (JP); Kaoru Kobayashi, Mishima-gun (JP); Fumio Nambu, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 192 days.

This patent is subject to a terminal disclaimer.

(21) Appl. No.: 10/507,885

(22) PCT Filed: Mar. 6, 2003

(86) PCT No.: PCT/JP03/02635

§ 371 (c)(1),
(2), (4) Date: May 17, 2005

(87) PCT Pub. No.: WO03/078409

PCT Pub. Date: Sep. 25, 2003

(65) Prior Publication Data

US 2005/0222216 A1    Oct. 6, 2005

(30) Foreign Application Priority Data

Mar. 19, 2002    (JP) .............................. 2002-76456

(51) Int. Cl.
*C07D 413/12* (2006.01)
*C07D 265/36* (2006.01)
*A61K 31/538* (2006.01)

(52) U.S. Cl. .................... 514/230.5; 544/105

(58) Field of Classification Search ................. 544/105; 514/230.5
See application file for complete search history.

(56) References Cited

U.S. PATENT DOCUMENTS 4,994,479 A    2/1991 Mase et al.

FOREIGN PATENT DOCUMENTS

WO    WO 86/05779 A1    10/1986
WO    WO 98/25919 A1    6/1998
WO    WO 01/66520 A1    9/2001

OTHER PUBLICATIONS

Lily et al. American Journal of Respiratory Cell and Molecular Biology vol. 22, 2005, pp. 224-226.*

* cited by examiner

*Primary Examiner*—Kahsay T. Habte
(74) *Attorney, Agent, or Firm*—Sughrue Mion, PLLC

(57) ABSTRACT

A carboxylic acid compound represented by formula (I):

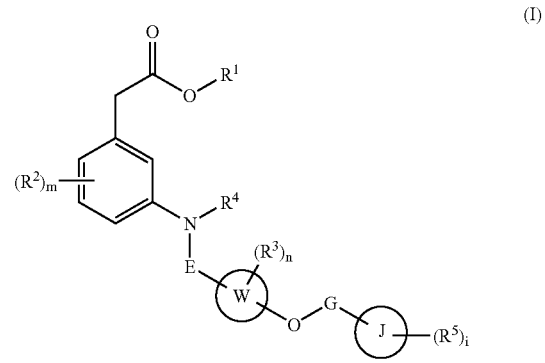

(meanings of the symbols in the formula are as mentioned in the specification) and a pharmaceutical agent comprising the compound.

Since the compound represented by formula (I) binds to a DP receptor and shows antagonistic activity for the DP receptor, it is useful for prevention and/or treatment of diseases such as allergic disease (such as allergic rhinitis, allergic conjunctivitis, atopic dermatitis, bronchial asthma and food allergy), systemic mastocytosis, disorders accompanied by systemic mast cell activation, anaphylaxis shock, bronchoconstriction, urticaria, eczema, diseases accompanied by itch (such as atopic dermatitis and urticaria), diseases (such as cataract, retinal detachment, inflammation, infection and sleeping disorders) which is generated secondarily as a result of behavior accompanied by itch (such as scratching and beating), inflammation, chronic obstructive pulmonary diseases, ischemic reperfusion injury, cerebrovascular accident, chronic rheumatoid arthritis, pleurisy, ulcerative colitis and the like.

5 Claims, No Drawings

CARBOXYLIC ACID COMPOUNDS AND A PHARMACEUTICAL AGENT COMPRISING THE COMPOUND AS THE ACTIVE INGREDIENT

TECHNICAL FIELD

The present invention relates to a carboxylic acid compound. More particularly, the present invention relates to:
(1) a carboxylic acid compound represented by formula (I)

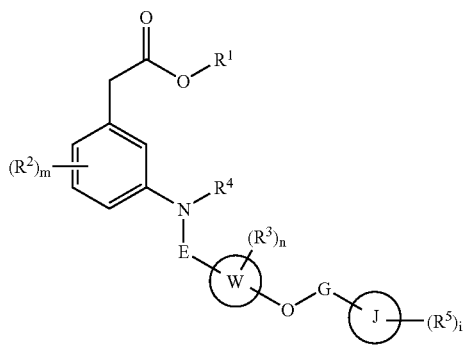

(in the formula, all symbols have the same meanings as those which will be mentioned later) and a non-toxic salt thereof,
(2) a process for producing the same and
(3) a pharmaceutical agent containing the same as an active ingredient.

BACKGROUND OF THE INVENTION

Prostaglandin $D_2$ (abbreviated as $PGD_2$) has been known as one of metabolites produced via an arachidonic acid cascade and is considered to be one of chemical mediators participating in allergic diseases such as allergic rhinitis, bronchial asthma and allergic conjunctivitis. It has been known that $PGD_2$ is mainly produced in and released from mast cells and that the $PGD_2$ released shows contraction of bronchus, promotion of vascular permeability, dilation or contraction of blood vessels, promotion of mucus secretion and inhibition of platelet aggregation. It has been also reported that $PGD_2$ induces bronchoconstriction and nasal obstruction in vivo as well and increased amounts of production of $PGD_2$ in pathological lesion of patients suffering from systemic mastocytosis, allergic rhinitis, bronchial asthma, atopic dermatitis, urticaria, etc. (*N. Engl. J. Med.* 1989; 303: 1400-4, *Am. Rev. Respir. Dis.* 1983; 128: 597-602, *J. Allergy Clin. Immunol.* 1991; 88: 33-42, *Arch. Otolaryngol. Head Neck Surg.* 1987; 113: 179-83, *J. Allergy Clin. Immunol.* 1988; 82: 869-77, *J. Immunol.* 1991; 146: 671-6, *J. Allergy Clin. Immunol.* 1989; 83: 905-12, *N. Eng. J. Med.* 1986; 315: 800-4, *Am. Rev. Respir. Dis.* 1990; 142, 126-32, *J. Allergy Clin. Immunol.* 1991; 87: 540-8, *J. Allergy Clin. Immunol* 1986; 78: 458-61). $PGD_2$ has been also reported to participate in nerve activity, particularly in sleeping, hormone secretion and pain. Furthermore, it has been also reported that it participates in platelet aggregation, glycogen metabolism and adjustment of intraocular pressure.

$PGD_2$ exerts its biological activity via binding to a DP receptor, which is one of $PGD_2$ receptors. Since DP receptor antagonists bind to its receptor and show antagonistic activity, DP receptor antagonists have been believed to be useful for prevention and/or treatment of diseases such as allergic diseases (e.g., allergic rhinitis, allergic conjunctivitis, atopic dermatitis, bronchial asthma and food allergy), systemic mastocytosis, disorders accompanied by systemic mast cell activation, anaphylactic shock, bronchoconstriction, urticaria, eczema, acne, allergic bronchial pulmonary aspergillosis, sinusitis, migraine, nasal polyps, anaphylactic vasculitis, eosinophilic syndrome, contact dermatitis, diseases accompanied by itch (e.g., atopic dermatitis, urticaria, allergic conjunctivitis, allergic rhinitis and contact dermatitis), diseases (e.g., cataract, retinal detachment, inflammation, infection and sleeping disorders) which are generated secondarily as a result of behavior accompanied by itch (e.g., scratching and beating), inflammation, chronic obstructive pulmonary diseases, ischemic reperfusion injury, cerebrovascular accident, autoimmune disease, traumatic brain disorder, hepatopathy, graft rejection, chronic rheumatoid arthritis, pleurisy, osteoarthritis, Crohn's disease, ulcerative colitis, irritable bowel syndrome, etc. It also participates in sleep and platelet aggregation and is believed to be useful for those diseases as well.

For example, in the specification of WO 86/05779, compounds represented by formula (T) are useful as antagonists for SRS-A (slow reacting substance of anaphylaxis):

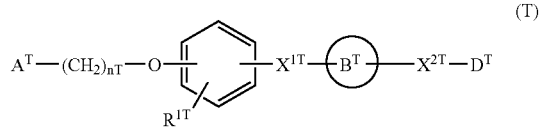

(in the formula, $A^T$ is a hydrogen atom, phenyl or phenoxy; nT is an integer from 3 to 10; $R^{1T}$ is a hydrogen atom or a lower alkoxy; $X^{1T}$ is —$CH_2$—$Y^{1T}$— (in the group, $Y^{1T}$ is —O—, —S— or —NH—), —CO—$Y^{2T}$— (in the group, $Y^{2T}$ is —O—, —S— or —NH—), etc.;

is a group represented by the formula

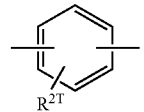

etc.; $R^{2T}$ is a hydrogen atom, a halogen atom, nitro, hydroxyl, lower alkoxy, cyano, lower alkyl, lower alkoxy lower alkyl, halo lower alkyl or a group represented by —$NR^{4T}R^{5T}$—, etc.;
$X^{2T}$ is a formula —$Y^{3T}$-$Y^{4T}$— (in the group, $Y^{3T}$ is a single bond, —O—, —S— or —NH— and $Y^{4T}$ is a $C_{1-6}$ alkylene which may be interrupted by sulfur atom), etc.; and
$D^T$ is carboxyl or a lower alkoxycarbonyl and the like).

In prostaglandin receptors, there are many receptors including subtypes and each of them has a different pharmacological action. Now, if novel compounds which specifically binds to a DP receptor and binds weakly to other prostaglandin receptors are able to be found, they can be pharmaceuticals having little side effect since no other functions are not exerted. Therefore, there has been a demand for finding such pharmaceuticals.

DISCLOSURE OF THE INVENTION

The inventors of the present invention have carried out intensive studies for finding compounds which specifically binds to DP receptors and exerts antagonistic activity and, as a result, they have found that carboxylic acid compounds represented by formula (I) achieve the problem to accomplish the present invention.

Thus, the present invention relates to:

(1) a carboxylic acid compound represented by formula (I):

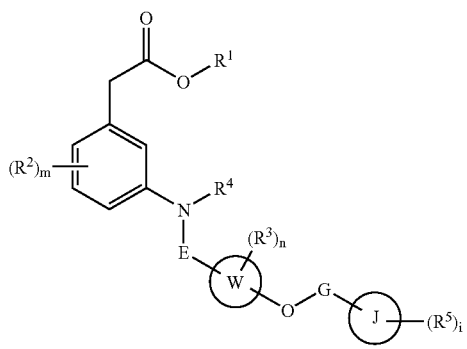

(in the formula, $R^1$ represents (1) hydrogen atom, (2) a $C_{1-4}$ alkyl, (3) a $C_{2-4}$ alkenyl or (4) benzyl;

E represents —C(=O)—, —SO$_2$— or —CH$_2$—;

$R^2$ represents (1) a halogen atom, (2) $C_{1-6}$ alkyl, (3) $C_{1-6}$ alkoxy, (4) hydroxyl, (5) trihalomethyl, (6) cyano, (7) phenyl, (8) pyridyl, (9) nitro, (10) —NR$^6$R$^7$ or (11) $C_{1-4}$ alkyl substituted with —OR$^8$;

$R^3$ represents (1) a halogen atom, (2) $C_{1-6}$ alkyl, (3) $C_{1-6}$ alkoxy, (4) hydroxyl, (5) trihalomethyl, (6) cyano, (7) phenyl, (8) pyridyl, (9) nitro, (10) —NR$^6$R$^7$ or (11) $C_{1-4}$ alkyl substituted with —OR$^8$;

$R^6$ and $R^7$ each independently represents a hydrogen atom or $C_{1-4}$ alkyl;

$R^8$ represents $C_{1-4}$ alkyl, phenyl or pyridyl;

$R^4$ represents (1) a hydrogen atom, (2) $C_{1-6}$ alkyl or (3) benzyl;

$R^5$ represents (1) $C_{1-6}$ alkyl, (2) $C_{1-10}$ alkoxy, (3) $C_{1-6}$ alkyl substituted with $C_{1-6}$ alkoxy, (4) a halogen atom, (5) hydroxyl, (6) trihalomethyl, (7) nitro, (8) —NR$^9$R$^{10}$, (9) phenyl, (10) phenoxy, (11) oxo, (12) a $C_{2-6}$ acyl, (13) cyano or (14) —SO$_2$R$^{11}$;

$R^9$ and $R^{10}$ each independently represents a hydrogen atom or $C_{1-4}$ alkyl;

$R^{11}$ represents $C_{1-6}$ alkyl;

represents a $C_{5-12}$ monocyclic or bicyclic carbon ring or a 5- to 12-membered monocyclic or bicyclic hetero ring;

G represents (1) $C_{1-6}$ alkylene having 0 to 2 hetero atom(s) selected from an nitrogen atom, an oxygen atom and a sulfur atom, (2) $C_{2-6}$ alkenylene having 0 to 2 hetero atom(s) selected from an nitrogen atom, an oxygen atom and a sulfur atom or (3) $C_{2-6}$ alkynylene having 0 to 2 hetero atom(s) selected from an nitrogen atom, an oxygen atom and a sulfur atom;

represents a $C_{5-12}$ monocyclic or bicyclic carbon ring or a 5- to 12-membered monocyclic or bicyclic hetero ring;

m represents 0 or an integer of 1 to 4;
n represents 0 or an integer of 1 to 4; and
i represents 0 or an integer of 1 to 11;
wherein when m is 2 or more, $R^2$ are the same or different; when n is 2 or more, $R^3$ are the same or different; and i is 2 or more, $R^5$ are the same or different, or a pharmaceutically acceptable salt thereof (2) a process for producing the same and (3) a pharmaceutical comprising the same as an active ingredient.

DETAILED DESCRIPTION OF THE INVENTION

In the present specification, $C_{1-4}$ alkyl includes linear and branched $C_{1-4}$ alkyl such as methyl, ethyl, propyl, isopropyl, butyl, isobutyl, sec-butyl and tert-butyl.

In the present specification, $C_{1-6}$ alkyl includes linear and branched $C_{1-6}$ alkyl such as methyl, ethyl, propyl, isopropyl, butyl, isobutyl, sec-butyl, tert-butyl, pentyl, isopentyl, neopentyl, hexyl and isohexyl.

In the present specification, $C_{1-6}$ alkoxy includes linear and branched $C_{1-6}$ alkoxy such as methoxy, ethoxy, propoxy, isopropoxy, butoxy, isobutoxy, sec-butoxy, tert-butoxy, pentyloxy, isopentyloxy, neopentyloxy, hexyloxy and isohexyloxy.

In the present specification, $C_{1-10}$ alkoxy includes linear and branched $C_{1-10}$ alkoxy selected from methoxy, ethoxy, propoxy, isopropoxy, butoxy, isobutoxy, sec-butoxy, tert-butoxy, pentyloxy, isopentyloxy, neopentyloxy, hexyloxy, isohexyloxy, heptyloxy, octyloxy, nonyloxy and decyloxy.

In the present specification, $C_{2-6}$ acyl includes linear and branched $C_{1-6}$ acyl such as ethanoyl, propanoyl, butanoyl, 2-methylpropanoyl, pentanoyl, 2-methylbutanoyl, 3-methylbutanoyl, hexanoyl, 2-methylpentanoyl, 3-methylpentanoyl, 4-methylpentanoyl, 2-ethylbutanoyl and 2,3-dimethylbutanoyl.

In the present specification, a halogen atom includes such as a fluorine, chlorine, bromine and iodine atom.

In the present specification, examples of the trihalomethyl are methyl which are substituted with three halogen atoms.

In the present specification, $C_{1-4}$ alkylene includes linear or branched $C_{1-4}$ alkylene such as methylene, ethylene, propylene, isopropylene, butylene and isobutylene.

In the present specification, $C_{2-4}$ alkenylene includes linear or branched $C_{2-4}$ alkenylene such as vinylene, propenylene, 1- or 2-butenylene and butadienylene.

In the present specification, $C_{2-4}$ alkynylene includes linear or branched $C_{2-4}$ alkynylene such as ethynylene, 1- or 2-propynylene and 1- or 2-butynylene.

In the present specification, $C_{1-6}$ alkylene having 0 to 2 hetero atom(s) selected from an nitrogen atom, an oxygen atom and a sulfur atom includes linear or branched $C_{1-6}$ alkylene such as methylene, ethylene, propylene, isopropylene, butylene, isobutylene, pentylene and hexylene or linear or branched $C_{1-6}$ alkylene in which one or two carbon atom(s) in methylene, ethylene, propylene, isopropylene, butylene, isobutylene, pentylene and hexylene is/are substituted with one or two hetero atom(s) selected from an nitrogen atom, an oxygen atom and a sulfur atom such as linear or branched $C_{1-6}$ alkylene having one or two hetero atom(s) selected from an nitrogen atom, an oxygen atom and a sulfur atom, e.g. —$(CH_2)_2$—NH—, —$(CH_2)_2$—N$(CH_3)$—, —$(CH_2)_2$—O—, —$(CH_2)_2$—S—, —$(CH_2)_3$—NH—, —$(CH_2)_3$—N$(CH_3)$—, —$CH_2$—CH$(CH_3)$—$CH_2$—NH—, —$CH_2$—CH$(CH_3)$—$CH_2$—N$(CH_3)$—, —$(CH_2)_3$—O— and —$(CH_2)_3$—S— wherein only a carbon atom in the alkylene binds to an adjacent —O—.

In the present specification, $C_{2-6}$ alkenylene having 0 to 2 hetero atom(s) selected from an nitrogen atom, an oxygen atom and a sulfur atom includes linear or branched $C_{2-6}$ alkenylene such as vinylene, propenylene, 1- or 2-butenylene, butadienylene, pentenylene and hexenylene or $C_{2-6}$ alkenylene in which one or two carbon atom(s) in vinylene, propenylene, 1- or 2-butenylene, butadienylene, pentenylene and hexenylene is/are substituted with one or two hetero atom(s) selected from an nitrogen atom, an oxygen atom and a sulfur atom such as linear or branched $C_{2-6}$ alkenylene having one or two hetero atom(s) selected from an nitrogen atom, an oxygen atom and a sulfur atom, e.g. —CH=CH—NH—, —CH=CH—N$(CH_3)$—, —CH=CH—O—, —CH=CH—S—, —CH=CH—$CH_2$—NH—, —CH=CH—$CH_2$—N$(CH_3)$—, —CH=CH—$CH_2$—O— and —CH=CH—$CH_2$—S— wherein only a carbon atom in the alkenylene binds to an adjacent —O—.

In the present specification, $C_{2-6}$ alkynylene having 0 to 2 hetero atom(s) selected from an nitrogen atom, an oxygen atom and a sulfur atom includes such as linear or branched $C_{2-6}$ alkynylene such as ethynylene, 1- or 2-propynylene, 1- or 2-butynylene, pentynylene and hexynylene or $C_{2-6}$ alkynylene in which one or two carbon atom(s) in ethynylene, 1- or 2-propynylene, 1- or 2-butynylene, pentynylene, hexynylene and hexenylene is/are substituted with one or two hetero atom(s) selected from an nitrogen atom, an oxygen atom and a sulfur atom such as linear or branched $C_{2-6}$ alkynylene having one or two hetero atom(s) selected from an nitrogen atom, an oxygen atom and a sulfur atom, e.g. —C≡C—NH—, —C≡C—N$(CH_3)$—, —C≡C—O—, —C≡C—S—, —C≡C—$CH_2$—NH—, —C≡C—$CH_2$—N$(CH_3)$—, —C≡C—$CH_2$—O— and —C≡C—$CH_2$—S— wherein only a carbon atom in the alkenylene binds to an adjacent —O—.

In the present specification, examples of the $C_{5-12}$ monocyclic or bicyclic carbon ring includes a monocyclic or bicyclic $C_{5-12}$ carbon ring aryl or carbon ring which is saturated either partially or wholly such as cyclopentane, cyclohexane, cycloheptane, cyclopentene, cyclohexene, cycloheptene, cyclopentadiene, cyclohexadiene, cycloheptadiene, benzene, pentalene, perhydropentalene, azulene, perhydroazulene, indene, perhydroindene, indane, naphthalene, dihydronaphthalene, tetrahydronaphthalene and perhydronaphthalene.

In the present specification, a 5- to 12-membered monocyclic or bicyclic hetero ring includes a 5- to 12-membered monocyclic or bicyclic hetero ring aryl having hetero atom(s) selected from one to four nitrogen atom(s), one to two oxygen atom(s) and/or one to two sulfur atom(s) and such as a hetero ring which is saturated either partially or wholly. They are, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, oxazine, thiazine, indole, isoindole, benzofuran, isobenzofuran, benzothiophene, isobenzothiophene, dithianaphthalene, indazole, quinoline, isoquinoline, quinolidine, phthalazine, naphthylidine, quinoxaline, quinazoline, cinnoline, benzoxazole, benzothiazole, benzimidazole, chromene, benzoxepine, benzoxazepine, benzothiepine, benzothiazepine, benzoazepine, benzodiazepine, pyrroline, pyrrolidine, imidazoline, imidazolidine, triazoline, triazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrooxazine, tetrahydrooxazine, dihydrooxazepine, tetrahydrooxazepine, perhydrooxazepine, dihydrothiazine, tetrahydrothiazine, dihydrothiazepine, tetrahydrothiazepine, perhydrothiazepine, morpholine, thiomorpholine, oxathiane, dioxolane, dioxane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathian, dihydrobenzoxazine, dihydrobenzothiazine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepan, dihydrobenzoxazepine and tetrahydrobenzoxazepine.

In the present specification, a $C_{5-6}$ saturated carbon ring includes such as cyclopentane and cyclohexane rings.

In the present specification, the 5- to 6-membered saturated hetero ring having one to two nitrogen atom(s), one to two oxygen atom(s) and/or one sulfur atom includes such as pyrrolidine, imidazolidine, pyrazolidine, piperidine, piperazine, perhydropyrimidine, perhydropyridazine, tetrahydrofuran, tetrahydropyran, tetrahydrothiophene, tetrahydrothiopyran, tetrahydrooxazole (oxazolidine), tetrahydroisoxazole (isoxazolidine), tetrahydrothiazole (thiazolidine), tetrahydroisothiazole (isothiazolidine), tetrahydrooxazine, tetrahydrothiazine, morpholine, thiomorpholine, oxathiane, dioxolane and dioxane ring.

In the present specification, a $C_{5-6}$ carbon ring includes such as cyclopentane, cyclohexane, cyclopentene, cyclohexene, cyclopentadiene, cyclohexadiene and benzene ring.

In the present specification, examples of 5- to 6-membered hetero ring having one to two nitrogen atom(s), one to two oxygen atom(s) and/or one sulfur atom includes such as pyrrole, imidazole, pyrazole, pyridine, pyrazine, pyrimidine, pyridazine, furan, pyran, thiophene, thiopyran, oxazole, isoxazole, thiazole, isothiazole, oxazine, thiazine, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydroxazine, tetrahydroxazine, dihydrothiazine, tetrahydrothiazine, morpholine, thiomorpholine, oxathiane, dioxolane and dioxane ring.

Unless otherwise specifically mentioned, all isomers are included in the present specification. For example, alkyl, alkoxy and alkylene include linear and branched ones. Moreover, all of isomers due to double bond, ring and fused ring (E-, Z-, cis- and trans-substances), isomers due to presence of asymmetric carbon, etc. (R-, S-, α- and β-substances, enantiomer and diastereomer), optically active substances having optical rotation (D-, L-, d- and l-substances), polar substances by chromatographic separation (high-polar substance and low-polar substance), equilibrium compounds, rotational isomers, a mixture thereof in any proportion and a racemic mixture are included in the present invention.

Unless otherwise specifically mentioned in the present specification, a symbol

means a bond to the opposite side of the paper (i.e., α-configuration),

means a bond to this side of the paper (i.e., β-configuration) and

means a mixture of α- and β-configurations as will be obvious for persons skilled in the art.

The compounds of the present invention are converted to pharmaceutically acceptable salts by known methods. With regard to the pharmaceutically acceptable salts, those which are non-toxic and soluble in water are preferred. Examples of appropriate salts are salt with alkaline metal (such as potassium, sodium and lithium), salt with alkaline earth metal (such as calcium and magnesium), ammonium salt (such as tetramethylammonium salt and tetrabutylammonium salt), salt with organic amine (such as triethylamine, methylamine, dimethylamine, cyclopentylamine, benzylamine, phenethylamine, piperidine, monoethanolamine, diethanolamine, tris(hydroxymethyl) methylamine, lysine, arginine and N-methyl-D-glucamine) and acid addition salt (such as inorganic acid salt (e.g., hydrochloride, hydrobromide, hydroiodide, sulfate, phosphate and nitrate) and organic acid salt (e.g., acetate, trifluoroacetate, lactate, tartrate, oxalate, fumarate, maleate, benzoate, citrate, methanesulfonate, ethanesulfonate, benzenesulfonate, toluenesulfonate, isothionate, glucuronate and gluconate)).

The salt of the compound of the present invention also includes solvates and also solvates with the above-mentioned alkaline (earth) metal salt, ammonium salt, organic amine salt and acid addition salt.

The solvate is preferably non-toxic and water-soluble. Examples of an appropriate solvate are solvates with water and with alcoholic solvent (such as ethanol).

$R^1$ in formula (I) is preferably a hydrogen atom, $C_{1-4}$ alkyl or benzyl and, more preferably, a hydrogen atom or $C_{1-4}$ alkyl.

$R^2$ in formula (I) is preferably a halogen atom, $C_{1-6}$ alkyl, $C_{1-6}$ alkoxy, hydroxyl, trihalomethyl, cyano, phenyl, pyridyl, nitro or $NR^6R^7$ and, more preferably, a halogen atom, $C_{1-6}$ alkyl, $C_{1-6}$ alkoxy or hydroxyl.

$R^3$ in formula (I) is preferably a halogen atom, $C_{1-6}$ alkyl, $C_{1-6}$ alkoxy, hydroxyl, trihalomethyl or cyano and, more preferably, a halogen atom, $C_{1-6}$ alkyl, $C_{1-6}$ alkoxy or hydroxyl.

$R^8$ in formula (I) is preferably $C_{1-4}$ alkyl or phenyl.

$R^4$ in formula (I) is preferably a hydrogen atom, $C_{1-4}$ alkyl or benzyl and, more preferably, a hydrogen atom or $C_{1-4}$ alkyl.

$R^5$ in formula (I) is preferably $C_{1-6}$ alkyl, $C_{1-10}$ alkoxy, a halogen atom, hydroxyl, trihalomethyl, phenyl or cyano and, more preferably, $C_{1-6}$ alkyl, $C_{1-10}$ alkoxy or a halogen atom.

A ring

in formula (I) are preferably a $C_{5-6}$ monocyclic carbon ring or a 5- to 6-membered monocyclic hetero ring having one or two nitrogen atom(s), one or two oxygen atom(s) and/or one sulfur atom. More specifically, cyclopentane, cyclohexane, benzene, pyrrole, imidazole, pyrazole, pyridine, pyrazine, pyrimidine, pyridazine, furan, pyran, thiophene, thiopyran, oxazole, isoxazole, thiazole, isothiazole, pyrrolidine, imidazolidine, piperidine or piperaizne ring is preferable ring and benzene or pyridine ring is more preferable. A $C_{5-6}$ monocyclic carbon ring is particularly preferable and, to be more specific, it is a benzene ring represented by

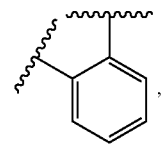 , 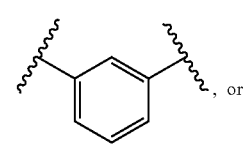 , or

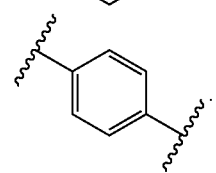 .

With regard to G in formula (I), it is preferably (1) $C_{1-6}$ alkylene having 0 to 2 hetero atom(s) selected from an nitrogen atom, an oxygen atom and a sulfur atom, (2) $C_{2-6}$ alkenylene or (3) $C_{2-6}$ alkynylene, more preferably, (1) $C_{1-6}$ alkylene having 0 to 2 hetero atom(s) selected from an nitrogen atom, an oxygen atom and a sulfur atom, (2) $C_{2-4}$ alkenylene group or (3) $C_{2-4}$ alkynylene and, particularly preferably, (1) $C_{1-4}$ alkylene, (2) $C_{2-4}$ alkenylene or (3) $C_{2-4}$ alkynylene.

A ring

in formula (I) is preferably

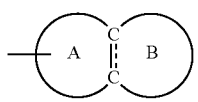

(in the formula,

is a $C_{5-6}$ saturated carbon ring or a 5- to 6-membered saturated hetero ring having one or two nitrogen atom(s), one or two oxygen atom(s) and/or one sulfur atom; and

is a $C_{5-6}$ carbon ring or a 5- to 6-membered hetero ring having one or two nitrogen atom(s), one or two oxygen atom(s) and/or one sulfur atom).

A ring

is preferably a 5- to 6-membered saturated hetero ring having one or two nitrogen atom(s), one or two oxygen atom(s) and/or one sulfur atom and, more preferably, a 5- to 6-membered saturated hetero ring having one or two nitrogen atom(s) and/or one or two oxygen atom(s). For example, morpholine, dioxane, oxathiane, tetrahydrofuran, pyrrolidine, tetrahydrooxazole (oxazolidine) and an imidazolidine ring are preferable, and morpholine, tetrahydrofuran and a pyrrolidine ring are particularly preferable.

is preferably a $C_{5-6}$ carbon ring or a 5- to 6-membered hetero ring having one or two nitrogen atom(s) and/or one or two oxygen atom(s) and more preferably, a $C_{5-6}$ carbon ring or a 5- to 6-membered hetero ring having one or two nitrogen atom(s). For example, cyclopentane, cyclohexane, cyclopentadiene, benzene, pyridine, pyrazine, pyrimidine, pyridazine, oxazine, piperidine and piperazine rings are preferable and cyclohexane, benzene, pyridine, pyrazine and a pyrimidine ring are more preferable and a benzene ring is particularly preferable.

is preferably dihydrobenzoxazine, benzodioxane, benzoxathiane, dihydrobenzofuran or an indoline ring, more preferably dihydrobenzoxazine, dihydrobenzofuran or an indoline ring and particularly preferably dihydrobenzoxazine.

With regard to m, 0, 1 or 2 is preferable.
With regard to n, 0, 1 or 2 is preferable.
With regard to i, 0 or an integer of 1 to 5 is preferable.
With regard to the compound represented by formula (I), a preferred compound is a compound represented by formula (I-a)

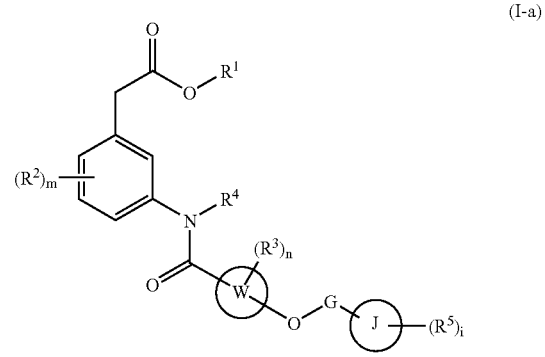

(I-a)

(in the formula, all symbols have the same meanings as those defined above), a compound represented by formula (I-b)

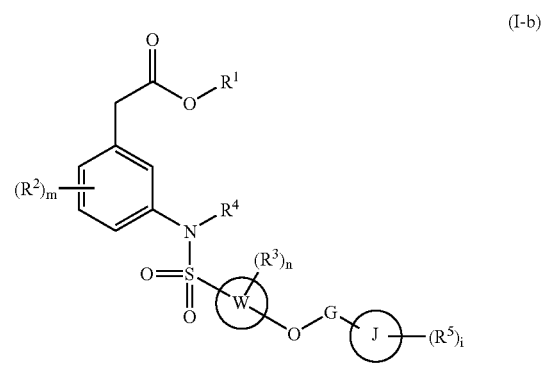

(I-b)

(in the formula, all symbols have the same meanings as those defined above) or a compound represented by formula (I-c)

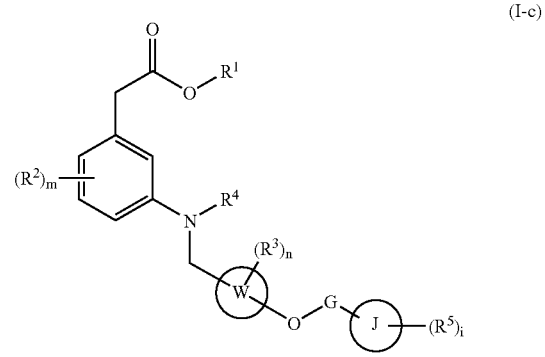

(I-c)

(in the formula, all symbols have the same meanings as those defined above).

Specific compounds of the present invention are the compounds mentioned in Table 1 to Table 35, the compounds mentioned in Examples and pharmaceutically acceptable salts thereof.

Figure 1

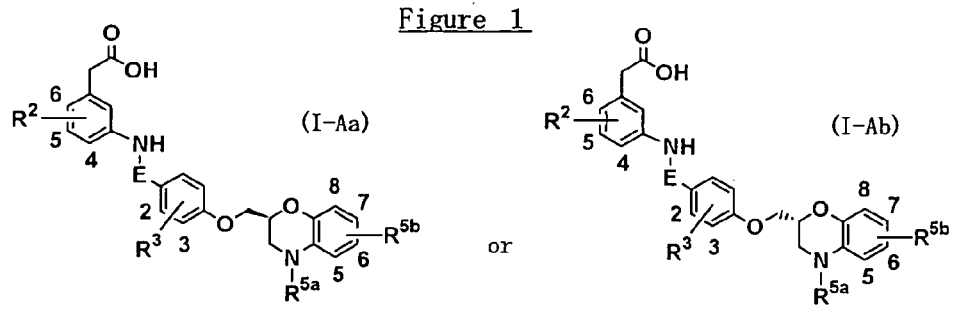

| No. | $R^2$ | E | $R^3$ | $R^{5a}$ | $R^{5b}$ | No. | $R^2$ | E | $R^3$ | $R^{5a}$ | $R^{5b}$ |
|---|---|---|---|---|---|---|---|---|---|---|---|
| 1 | H | -CO- | 2-CH$_3$ | CH$_3$ | H | 37 | H | -CO- | 2-CH$_3$ | CH$_3$ | 8-CH$_3$ |
| 2 | H | -SO$_2$- | 2-CH$_3$ | CH$_3$ | H | 38 | H | -SO$_2$- | 2-CH$_3$ | CH$_3$ | 8-CH$_3$ |
| 3 | H | -CH$_2$- | 2-CH$_3$ | CH$_3$ | H | 39 | H | -CH$_2$- | 2-CH$_3$ | CH$_3$ | 8-CH$_3$ |
| 4 | 4-CH$_3$ | -CO- | 2-CH$_3$ | CH$_3$ | H | 40 | 4-CH$_3$ | -CO- | 2-CH$_3$ | CH$_3$ | 8-CH$_3$ |
| 5 | 4-CH$_3$ | -SO$_2$- | 2-CH$_3$ | CH$_3$ | H | 41 | 4-CH$_3$ | -SO$_2$- | 2-CH$_3$ | CH$_3$ | 8-CH$_3$ |
| 6 | 4-CH$_3$ | -CH$_2$- | 2-CH$_3$ | CH$_3$ | H | 42 | 4-CH$_3$ | -CH$_2$- | 2-CH$_3$ | CH$_3$ | 8-CH$_3$ |
| 7 | 4-Cl | -CO- | 2-CH$_3$ | CH$_3$ | H | 43 | 4-Cl | -CO- | 2-CH$_3$ | CH$_3$ | 8-CH$_3$ |
| 8 | 4-Cl | -SO$_2$- | 2-CH$_3$ | CH$_3$ | H | 44 | 4-Cl | -SO$_2$- | 2-CH$_3$ | CH$_3$ | 8-CH$_3$ |
| 9 | 4-Cl | -CH$_2$- | 2-CH$_3$ | CH$_3$ | H | 45 | 4-Cl | -CH$_2$- | 2-CH$_3$ | CH$_3$ | 8-CH$_3$ |
| 10 | 4-F | -CO- | 2-CH$_3$ | CH$_3$ | H | 46 | 4-F | -CO- | 2-CH$_3$ | CH$_3$ | 8-CH$_3$ |
| 11 | 4-F | -SO$_2$- | 2-CH$_3$ | CH$_3$ | H | 47 | 4-F | -SO$_2$- | 2-CH$_3$ | CH$_3$ | 8-CH$_3$ |
| 12 | 4-F | -CH$_2$- | 2-CH$_3$ | CH$_3$ | H | 48 | 4-F | -CH$_2$- | 2-CH$_3$ | CH$_3$ | 8-CH$_3$ |
| 13 | H | -CO- | 2-Cl | CH$_3$ | H | 49 | H | -CO- | 2-Cl | CH$_3$ | 8-CH$_3$ |
| 14 | H | -SO$_2$- | 2-Cl | CH$_3$ | H | 50 | H | -SO$_2$- | 2-Cl | CH$_3$ | 8-CH$_3$ |
| 15 | H | -CH$_2$- | 2-Cl | CH$_3$ | H | 51 | H | -CH$_2$- | 2-Cl | CH$_3$ | 8-CH$_3$ |
| 16 | 4-CH$_3$ | -CO- | 2-Cl | CH$_3$ | H | 52 | 4-CH$_3$ | -CO- | 2-Cl | CH$_3$ | 8-CH$_3$ |
| 17 | 4-CH$_3$ | -SO$_2$- | 2-Cl | CH$_3$ | H | 53 | 4-CH$_3$ | -SO$_2$- | 2-Cl | CH$_3$ | 8-CH$_3$ |
| 18 | 4-CH$_3$ | -CH$_2$- | 2-Cl | CH$_3$ | H | 54 | 4-CH$_3$ | -CH$_2$- | 2-Cl | CH$_3$ | 8-CH$_3$ |
| 19 | 4-Cl | -CO- | 2-Cl | CH$_3$ | H | 55 | 4-Cl | -CO- | 2-Cl | CH$_3$ | 8-CH$_3$ |
| 20 | 4-Cl | -SO$_2$- | 2-Cl | CH$_3$ | H | 56 | 4-Cl | -SO$_2$- | 2-Cl | CH$_3$ | 8-CH$_3$ |
| 21 | 4-Cl | -CH$_2$- | 2-Cl | CH$_3$ | H | 57 | 4-Cl | -CH$_2$- | 2-Cl | CH$_3$ | 8-CH$_3$ |
| 22 | 4-F | -CO- | 2-Cl | CH$_3$ | H | 58 | 4-F | -CO- | 2-Cl | CH$_3$ | 8-CH$_3$ |
| 23 | 4-F | -SO$_2$- | 2-Cl | CH$_3$ | H | 59 | 4-F | -SO$_2$- | 2-Cl | CH$_3$ | 8-CH$_3$ |
| 24 | 4-F | -CH$_2$- | 2-Cl | CH$_3$ | H | 60 | 4-F | -CH$_2$- | 2-Cl | CH$_3$ | 8-CH$_3$ |
| 25 | H | -CO- | 2-F | CH$_3$ | H | 61 | H | -CO- | 2-F | CH$_3$ | 8-CH$_3$ |
| 26 | H | -SO$_2$- | 2-F | CH$_3$ | H | 62 | H | -SO$_2$- | 2-F | CH$_3$ | 8-CH$_3$ |
| 27 | H | -CH$_2$- | 2-F | CH$_3$ | H | 63 | H | -CH$_2$- | 2-F | CH$_3$ | 8-CH$_3$ |
| 28 | 4-CH$_3$ | -CO- | 2-F | CH$_3$ | H | 64 | 4-CH$_3$ | -CO- | 2-F | CH$_3$ | 8-CH$_3$ |
| 29 | 4-CH$_3$ | -SO$_2$- | 2-F | CH$_3$ | H | 65 | 4-CH$_3$ | -SO$_2$- | 2-F | CH$_3$ | 8-CH$_3$ |
| 30 | 4-CH$_3$ | -CH$_2$- | 2-F | CH$_3$ | H | 66 | 4-CH$_3$ | -CH$_2$- | 2-F | CH$_3$ | 8-CH$_3$ |
| 31 | 4-Cl | -CO- | 2-F | CH$_3$ | H | 67 | 4-Cl | -CO- | 2-F | CH$_3$ | 8-CH$_3$ |
| 32 | 4-Cl | -SO$_2$- | 2-F | CH$_3$ | H | 68 | 4-Cl | -SO$_2$- | 2-F | CH$_3$ | 8-CH$_3$ |
| 33 | 4-Cl | -CH$_2$- | 2-F | CH$_3$ | H | 69 | 4-Cl | -CH$_2$- | 2-F | CH$_3$ | 8-CH$_3$ |
| 34 | 4-F | -CO- | 2-F | CH$_3$ | H | 70 | 4-F | -CO- | 2-F | CH$_3$ | 8-CH$_3$ |
| 35 | 4-F | -SO$_2$- | 2-F | CH$_3$ | H | 71 | 4-F | -SO$_2$- | 2-F | CH$_3$ | 8-CH$_3$ |
| 36 | 4-F | -CH$_2$- | 2-F | CH$_3$ | H | 72 | 4-F | -CH$_2$- | 2-F | CH$_3$ | 8-CH$_3$ |

Figure 2

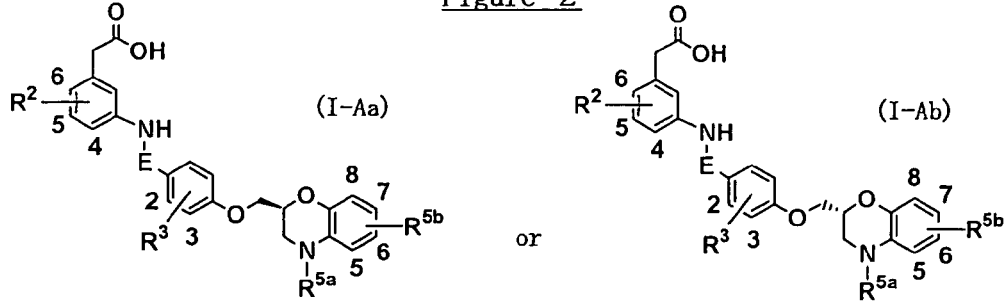

| No. | $R^2$ | E | $R^3$ | $R^{5a}$ | $R^{5b}$ | No. | $R^2$ | E | $R^3$ | $R^{5a}$ | $R^{5b}$ |
|---|---|---|---|---|---|---|---|---|---|---|---|
| 1 | H | -CO- | 2-CH$_3$ | CH$_3$ | 8-F | 37 | H | -CO- | 2-CH$_3$ | CH$_3$ | 7-CH$_3$ |
| 2 | H | -SO$_2$- | 2-CH$_3$ | CH$_3$ | 8-F | 38 | H | -SO$_2$- | 2-CH$_3$ | CH$_3$ | 7-CH$_3$ |
| 3 | H | -CH$_2$- | 2-CH$_3$ | CH$_3$ | 8-F | 39 | H | -CH$_2$- | 2-CH$_3$ | CH$_3$ | 7-CH$_3$ |
| 4 | 4-CH$_3$ | -CO- | 2-CH$_3$ | CH$_3$ | 8-F | 40 | 4-CH$_3$ | -CO- | 2-CH$_3$ | CH$_3$ | 7-CH$_3$ |
| 5 | 4-CH$_3$ | -SO$_2$- | 2-CH$_3$ | CH$_3$ | 8-F | 41 | 4-CH$_3$ | -SO$_2$- | 2-CH$_3$ | CH$_3$ | 7-CH$_3$ |
| 6 | 4-CH$_3$ | -CH$_2$- | 2-CH$_3$ | CH$_3$ | 8-F | 42 | 4-CH$_3$ | -CH$_2$- | 2-CH$_3$ | CH$_3$ | 7-CH$_3$ |
| 7 | 4-Cl | -CO- | 2-CH$_3$ | CH$_3$ | 8-F | 43 | 4-Cl | -CO- | 2-CH$_3$ | CH$_3$ | 7-CH$_3$ |
| 8 | 4-Cl | -SO$_2$- | 2-CH$_3$ | CH$_3$ | 8-F | 44 | 4-Cl | -SO$_2$- | 2-CH$_3$ | CH$_3$ | 7-CH$_3$ |
| 9 | 4-Cl | -CH$_2$- | 2-CH$_3$ | CH$_3$ | 8-F | 45 | 4-Cl | -CH$_2$- | 2-CH$_3$ | CH$_3$ | 7-CH$_3$ |
| 10 | 4-F | -CO- | 2-CH$_3$ | CH$_3$ | 8-F | 46 | 4-F | -CO- | 2-CH$_3$ | CH$_3$ | 7-CH$_3$ |
| 11 | 4-F | -SO$_2$- | 2-CH$_3$ | CH$_3$ | 8-F | 47 | 4-F | -SO$_2$- | 2-CH$_3$ | CH$_3$ | 7-CH$_3$ |
| 12 | 4-F | -CH$_2$- | 2-CH$_3$ | CH$_3$ | 8-F | 48 | 4-F | -CH$_2$- | 2-CH$_3$ | CH$_3$ | 7-CH$_3$ |
| 13 | H | -CO- | 2-Cl | CH$_3$ | 8-F | 49 | H | -CO- | 2-Cl | CH$_3$ | 7-CH$_3$ |
| 14 | H | -SO$_2$- | 2-Cl | CH$_3$ | 8-F | 50 | H | -SO$_2$- | 2-Cl | CH$_3$ | 7-CH$_3$ |
| 15 | H | -CH$_2$- | 2-Cl | CH$_3$ | 8-F | 51 | H | -CH$_2$- | 2-Cl | CH$_3$ | 7-CH$_3$ |
| 16 | 4-CH$_3$ | -CO- | 2-Cl | CH$_3$ | 8-F | 52 | 4-CH$_3$ | -CO- | 2-Cl | CH$_3$ | 7-CH$_3$ |
| 17 | 4-CH$_3$ | -SO$_2$- | 2-Cl | CH$_3$ | 8-F | 53 | 4-CH$_3$ | -SO$_2$- | 2-Cl | CH$_3$ | 7-CH$_3$ |
| 18 | 4-CH$_3$ | -CH$_2$- | 2-Cl | CH$_3$ | 8-F | 54 | 4-CH$_3$ | -CH$_2$- | 2-Cl | CH$_3$ | 7-CH$_3$ |
| 19 | 4-Cl | -CO- | 2-Cl | CH$_3$ | 8-F | 55 | 4-Cl | -CO- | 2-Cl | CH$_3$ | 7-CH$_3$ |
| 20 | 4-Cl | -SO$_2$- | 2-Cl | CH$_3$ | 8-F | 56 | 4-Cl | -SO$_2$- | 2-Cl | CH$_3$ | 7-CH$_3$ |
| 21 | 4-Cl | -CH$_2$- | 2-Cl | CH$_3$ | 8-F | 57 | 4-Cl | -CH$_2$- | 2-Cl | CH$_3$ | 7-CH$_3$ |
| 22 | 4-F | -CO- | 2-Cl | CH$_3$ | 8-F | 58 | 4-F | -CO- | 2-Cl | CH$_3$ | 7-CH$_3$ |
| 23 | 4-F | -SO$_2$- | 2-Cl | CH$_3$ | 8-F | 59 | 4-F | -SO$_2$- | 2-Cl | CH$_3$ | 7-CH$_3$ |
| 24 | 4-F | -CH$_2$- | 2-Cl | CH$_3$ | 8-F | 60 | 4-F | -CH$_2$- | 2-Cl | CH$_3$ | 7-CH$_3$ |
| 25 | H | -CO- | 2-F | CH$_3$ | 8-F | 61 | H | -CO- | 2-F | CH$_3$ | 7-CH$_3$ |
| 26 | H | -SO$_2$- | 2-F | CH$_3$ | 8-F | 62 | H | -SO$_2$- | 2-F | CH$_3$ | 7-CH$_3$ |
| 27 | H | -CH$_2$- | 2-F | CH$_3$ | 8-F | 63 | H | -CH$_2$- | 2-F | CH$_3$ | 7-CH$_3$ |
| 28 | 4-CH$_3$ | -CO- | 2-F | CH$_3$ | 8-F | 64 | 4-CH$_3$ | -CO- | 2-F | CH$_3$ | 7-CH$_3$ |
| 29 | 4-CH$_3$ | -SO$_2$- | 2-F | CH$_3$ | 8-F | 65 | 4-CH$_3$ | -SO$_2$- | 2-F | CH$_3$ | 7-CH$_3$ |
| 30 | 4-CH$_3$ | -CH$_2$- | 2-F | CH$_3$ | 8-F | 66 | 4-CH$_3$ | -CH$_2$- | 2-F | CH$_3$ | 7-CH$_3$ |
| 31 | 4-Cl | -CO- | 2-F | CH$_3$ | 8-F | 67 | 4-Cl | -CO- | 2-F | CH$_3$ | 7-CH$_3$ |
| 32 | 4-Cl | -SO$_2$- | 2-F | CH$_3$ | 8-F | 68 | 4-Cl | -SO$_2$- | 2-F | CH$_3$ | 7-CH$_3$ |
| 33 | 4-Cl | -CH$_2$- | 2-F | CH$_3$ | 8-F | 69 | 4-Cl | -CH$_2$- | 2-F | CH$_3$ | 7-CH$_3$ |
| 34 | 4-F | -CO- | 2-F | CH$_3$ | 8-F | 70 | 4-F | -CO- | 2-F | CH$_3$ | 7-CH$_3$ |
| 35 | 4-F | -SO$_2$- | 2-F | CH$_3$ | 8-F | 71 | 4-F | -SO$_2$- | 2-F | CH$_3$ | 7-CH$_3$ |
| 36 | 4-F | -CH$_2$- | 2-F | CH$_3$ | 8-F | 72 | 4-F | -CH$_2$- | 2-F | CH$_3$ | 7-CH$_3$ |

Figure 3

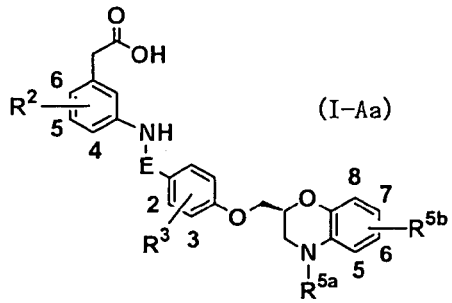
(I-Aa)

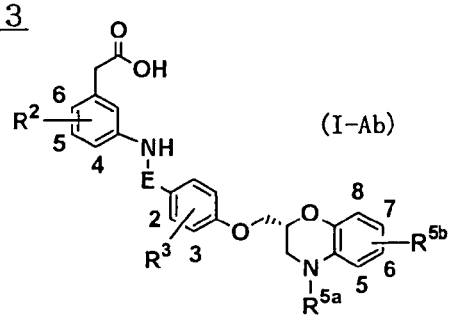
(I-Ab)

| No. | R² | E | R³ | R⁵ᵃ | R⁵ᵇ | No. | R² | E | R³ | R⁵ᵃ | R⁵ᵇ |
|---|---|---|---|---|---|---|---|---|---|---|---|
| 1 | H | -CO- | 2-CH₃ | CH₃ | 7-F | 37 | H | -CO- | 2-CH₃ | CH₃ | 7-OCH₃ |
| 2 | H | -SO₂- | 2-CH₃ | CH₃ | 7-F | 38 | H | -SO₂- | 2-CH₃ | CH₃ | 7-OCH₃ |
| 3 | H | -CH₂- | 2-CH₃ | CH₃ | 7-F | 39 | H | -CH₂- | 2-CH₃ | CH₃ | 7-OCH₃ |
| 4 | 4-CH₃ | -CO- | 2-CH₃ | CH₃ | 7-F | 40 | 4-CH₃ | -CO- | 2-CH₃ | CH₃ | 7-OCH₃ |
| 5 | 4-CH₃ | -SO₂- | 2-CH₃ | CH₃ | 7-F | 41 | 4-CH₃ | -SO₂- | 2-CH₃ | CH₃ | 7-OCH₃ |
| 6 | 4-CH₃ | -CH₂- | 2-CH₃ | CH₃ | 7-F | 42 | 4-CH₃ | -CH₂- | 2-CH₃ | CH₃ | 7-OCH₃ |
| 7 | 4-Cl | -CO- | 2-CH₃ | CH₃ | 7-F | 43 | 4-Cl | -CO- | 2-CH₃ | CH₃ | 7-OCH₃ |
| 8 | 4-Cl | -SO₂- | 2-CH₃ | CH₃ | 7-F | 44 | 4-Cl | -SO₂- | 2-CH₃ | CH₃ | 7-OCH₃ |
| 9 | 4-Cl | -CH₂- | 2-CH₃ | CH₃ | 7-F | 45 | 4-Cl | -CH₂- | 2-CH₃ | CH₃ | 7-OCH₃ |
| 10 | 4-F | -CO- | 2-CH₃ | CH₃ | 7-F | 46 | 4-F | -CO- | 2-CH₃ | CH₃ | 7-OCH₃ |
| 11 | 4-F | -SO₂- | 2-CH₃ | CH₃ | 7-F | 47 | 4-F | -SO₂- | 2-CH₃ | CH₃ | 7-OCH₃ |
| 12 | 4-F | -CH₂- | 2-CH₃ | CH₃ | 7-F | 48 | 4-F | -CH₂- | 2-CH₃ | CH₃ | 7-OCH₃ |
| 13 | H | -CO- | 2-Cl | CH₃ | 7-F | 49 | H | -CO- | 2-Cl | CH₃ | 7-OCH₃ |
| 14 | H | -SO₂- | 2-Cl | CH₃ | 7-F | 50 | H | -SO₂- | 2-Cl | CH₃ | 7-OCH₃ |
| 15 | H | -CH₂- | 2-Cl | CH₃ | 7-F | 51 | H | -CH₂- | 2-Cl | CH₃ | 7-OCH₃ |
| 16 | 4-CH₃ | -CO- | 2-Cl | CH₃ | 7-F | 52 | 4-CH₃ | -CO- | 2-Cl | CH₃ | 7-OCH₃ |
| 17 | 4-CH₃ | -SO₂- | 2-Cl | CH₃ | 7-F | 53 | 4-CH₃ | -SO₂- | 2-Cl | CH₃ | 7-OCH₃ |
| 18 | 4-CH₃ | -CH₂- | 2-Cl | CH₃ | 7-F | 54 | 4-CH₃ | -CH₂- | 2-Cl | CH₃ | 7-OCH₃ |
| 19 | 4-Cl | -CO- | 2-Cl | CH₃ | 7-F | 55 | 4-Cl | -CO- | 2-Cl | CH₃ | 7-OCH₃ |
| 20 | 4-Cl | -SO₂- | 2-Cl | CH₃ | 7-F | 56 | 4-Cl | -SO₂- | 2-Cl | CH₃ | 7-OCH₃ |
| 21 | 4-Cl | -CH₂- | 2-Cl | CH₃ | 7-F | 57 | 4-Cl | -CH₂- | 2-Cl | CH₃ | 7-OCH₃ |
| 22 | 4-F | -CO- | 2-Cl | CH₃ | 7-F | 58 | 4-F | -CO- | 2-Cl | CH₃ | 7-OCH₃ |
| 23 | 4-F | -SO₂- | 2-Cl | CH₃ | 7-F | 59 | 4-F | -SO₂- | 2-Cl | CH₃ | 7-OCH₃ |
| 24 | 4-F | -CH₂- | 2-Cl | CH₃ | 7-F | 60 | 4-F | -CH₂- | 2-Cl | CH₃ | 7-OCH₃ |
| 25 | H | -CO- | 2-F | CH₃ | 7-F | 61 | H | -CO- | 2-F | CH₃ | 7-OCH₃ |
| 26 | H | -SO₂- | 2-F | CH₃ | 7-F | 62 | H | -SO₂- | 2-F | CH₃ | 7-OCH₃ |
| 27 | H | -CH₂- | 2-F | CH₃ | 7-F | 63 | H | -CH₂- | 2-F | CH₃ | 7-OCH₃ |
| 28 | 4-CH₃ | -CO- | 2-F | CH₃ | 7-F | 64 | 4-CH₃ | -CO- | 2-F | CH₃ | 7-OCH₃ |
| 29 | 4-CH₃ | -SO₂- | 2-F | CH₃ | 7-F | 65 | 4-CH₃ | -SO₂- | 2-F | CH₃ | 7-OCH₃ |
| 30 | 4-CH₃ | -CH₂- | 2-F | CH₃ | 7-F | 66 | 4-CH₃ | -CH₂- | 2-F | CH₃ | 7-OCH₃ |
| 31 | 4-Cl | -CO- | 2-F | CH₃ | 7-F | 67 | 4-Cl | -CO- | 2-F | CH₃ | 7-OCH₃ |
| 32 | 4-Cl | -SO₂- | 2-F | CH₃ | 7-F | 68 | 4-Cl | -SO₂- | 2-F | CH₃ | 7-OCH₃ |
| 33 | 4-Cl | -CH₂- | 2-F | CH₃ | 7-F | 69 | 4-Cl | -CH₂- | 2-F | CH₃ | 7-OCH₃ |
| 34 | 4-F | -CO- | 2-F | CH₃ | 7-F | 70 | 4-F | -CO- | 2-F | CH₃ | 7-OCH₃ |
| 35 | 4-F | -SO₂- | 2-F | CH₃ | 7-F | 71 | 4-F | -SO₂- | 2-F | CH₃ | 7-OCH₃ |
| 36 | 4-F | -CH₂- | 2-F | CH₃ | 7-F | 72 | 4-F | -CH₂- | 2-F | CH₃ | 7-OCH₃ |

Figure 4

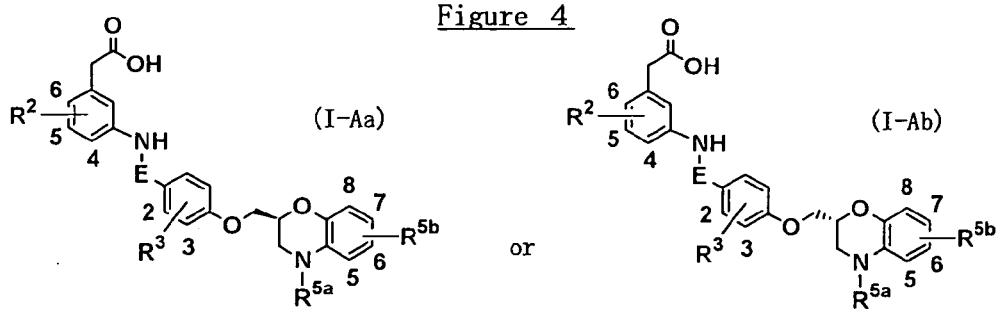

| No. | $R^2$ | E | $R^3$ | $R^{5a}$ | $R^{5b}$ | No. | $R^2$ | E | $R^3$ | $R^{5a}$ | $R^{5b}$ |
|---|---|---|---|---|---|---|---|---|---|---|---|
| 1 | H | -CO- | 2-CH$_3$ | CH$_3$ | 6-CH$_3$ | 37 | H | -CO- | 2-CH$_3$ | CH$_3$ | 6-F |
| 2 | H | -SO$_2$- | 2-CH$_3$ | CH$_3$ | 6-CH$_3$ | 38 | H | -SO$_2$- | 2-CH$_3$ | CH$_3$ | 6-F |
| 3 | H | -CH$_2$- | 2-CH$_3$ | CH$_3$ | 6-CH$_3$ | 39 | H | -CH$_2$- | 2-CH$_3$ | CH$_3$ | 6-F |
| 4 | 4-CH$_3$ | -CO- | 2-CH$_3$ | CH$_3$ | 6-CH$_3$ | 40 | 4-CH$_3$ | -CO- | 2-CH$_3$ | CH$_3$ | 6-F |
| 5 | 4-CH$_3$ | -SO$_2$- | 2-CH$_3$ | CH$_3$ | 6-CH$_3$ | 41 | 4-CH$_3$ | -SO$_2$- | 2-CH$_3$ | CH$_3$ | 6-F |
| 6 | 4-CH$_3$ | -CH$_2$- | 2-CH$_3$ | CH$_3$ | 6-CH$_3$ | 42 | 4-CH$_3$ | -CH$_2$- | 2-CH$_3$ | CH$_3$ | 6-F |
| 7 | 4-Cl | -CO- | 2-CH$_3$ | CH$_3$ | 6-CH$_3$ | 43 | 4-Cl | -CO- | 2-CH$_3$ | CH$_3$ | 6-F |
| 8 | 4-Cl | -SO$_2$- | 2-CH$_3$ | CH$_3$ | 6-CH$_3$ | 44 | 4-Cl | -SO$_2$- | 2-CH$_3$ | CH$_3$ | 6-F |
| 9 | 4-Cl | -CH$_2$- | 2-CH$_3$ | CH$_3$ | 6-CH$_3$ | 45 | 4-Cl | -CH$_2$- | 2-CH$_3$ | CH$_3$ | 6-F |
| 10 | 4-F | -CO- | 2-CH$_3$ | CH$_3$ | 6-CH$_3$ | 46 | 4-F | -CO- | 2-CH$_3$ | CH$_3$ | 6-F |
| 11 | 4-F | -SO$_2$- | 2-CH$_3$ | CH$_3$ | 6-CH$_3$ | 47 | 4-F | -SO$_2$- | 2-CH$_3$ | CH$_3$ | 6-F |
| 12 | 4-F | -CH$_2$- | 2-CH$_3$ | CH$_3$ | 6-CH$_3$ | 48 | 4-F | -CH$_2$- | 2-CH$_3$ | CH$_3$ | 6-F |
| 13 | H | -CO- | 2-Cl | CH$_3$ | 6-CH$_3$ | 49 | H | -CO- | 2-Cl | CH$_3$ | 6-F |
| 14 | H | -SO$_2$- | 2-Cl | CH$_3$ | 6-CH$_3$ | 50 | H | -SO$_2$- | 2-Cl | CH$_3$ | 6-F |
| 15 | H | -CH$_2$- | 2-Cl | CH$_3$ | 6-CH$_3$ | 51 | H | -CH$_2$- | 2-Cl | CH$_3$ | 6-F |
| 16 | 4-CH$_3$ | -CO- | 2-Cl | CH$_3$ | 6-CH$_3$ | 52 | 4-CH$_3$ | -CO- | 2-Cl | CH$_3$ | 6-F |
| 17 | 4-CH$_3$ | -SO$_2$- | 2-Cl | CH$_3$ | 6-CH$_3$ | 53 | 4-CH$_3$ | -SO$_2$- | 2-Cl | CH$_3$ | 6-F |
| 18 | 4-CH$_3$ | -CH$_2$- | 2-Cl | CH$_3$ | 6-CH$_3$ | 54 | 4-CH$_3$ | -CH$_2$- | 2-Cl | CH$_3$ | 6-F |
| 19 | 4-Cl | -CO- | 2-Cl | CH$_3$ | 6-CH$_3$ | 55 | 4-Cl | -CO- | 2-Cl | CH$_3$ | 6-F |
| 20 | 4-Cl | -SO$_2$- | 2-Cl | CH$_3$ | 6-CH$_3$ | 56 | 4-Cl | -SO$_2$- | 2-Cl | CH$_3$ | 6-F |
| 21 | 4-Cl | -CH$_2$- | 2-Cl | CH$_3$ | 6-CH$_3$ | 57 | 4-Cl | -CH$_2$- | 2-Cl | CH$_3$ | 6-F |
| 22 | 4-F | -CO- | 2-Cl | CH$_3$ | 6-CH$_3$ | 58 | 4-F | -CO- | 2-Cl | CH$_3$ | 6-F |
| 23 | 4-F | -SO$_2$- | 2-Cl | CH$_3$ | 6-CH$_3$ | 59 | 4-F | -SO$_2$- | 2-Cl | CH$_3$ | 6-F |
| 24 | 4-F | -CH$_2$- | 2-Cl | CH$_3$ | 6-CH$_3$ | 60 | 4-F | -CH$_2$- | 2-Cl | CH$_3$ | 6-F |
| 25 | H | -CO- | 2-F | CH$_3$ | 6-CH$_3$ | 61 | H | -CO- | 2-F | CH$_3$ | 6-F |
| 26 | H | -SO$_2$- | 2-F | CH$_3$ | 6-CH$_3$ | 62 | H | -SO$_2$- | 2-F | CH$_3$ | 6-F |
| 27 | H | -CH$_2$- | 2-F | CH$_3$ | 6-CH$_3$ | 63 | H | -CH$_2$- | 2-F | CH$_3$ | 6-F |
| 28 | 4-CH$_3$ | -CO- | 2-F | CH$_3$ | 6-CH$_3$ | 64 | 4-CH$_3$ | -CO- | 2-F | CH$_3$ | 6-F |
| 29 | 4-CH$_3$ | -SO$_2$- | 2-F | CH$_3$ | 6-CH$_3$ | 65 | 4-CH$_3$ | -SO$_2$- | 2-F | CH$_3$ | 6-F |
| 30 | 4-CH$_3$ | -CH$_2$- | 2-F | CH$_3$ | 6-CH$_3$ | 66 | 4-CH$_3$ | -CH$_2$- | 2-F | CH$_3$ | 6-F |
| 31 | 4-Cl | -CO- | 2-F | CH$_3$ | 6-CH$_3$ | 67 | 4-Cl | -CO- | 2-F | CH$_3$ | 6-F |
| 32 | 4-Cl | -SO$_2$- | 2-F | CH$_3$ | 6-CH$_3$ | 68 | 4-Cl | -SO$_2$- | 2-F | CH$_3$ | 6-F |
| 33 | 4-Cl | -CH$_2$- | 2-F | CH$_3$ | 6-CH$_3$ | 69 | 4-Cl | -CH$_2$- | 2-F | CH$_3$ | 6-F |
| 34 | 4-F | -CO- | 2-F | CH$_3$ | 6-CH$_3$ | 70 | 4-F | -CO- | 2-F | CH$_3$ | 6-F |
| 35 | 4-F | -SO$_2$- | 2-F | CH$_3$ | 6-CH$_3$ | 71 | 4-F | -SO$_2$- | 2-F | CH$_3$ | 6-F |
| 36 | 4-F | -CH$_2$- | 2-F | CH$_3$ | 6-CH$_3$ | 72 | 4-F | -CH$_2$- | 2-F | CH$_3$ | 6-F |

Figure 5

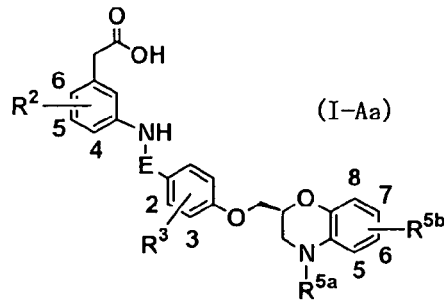
(I-Aa)

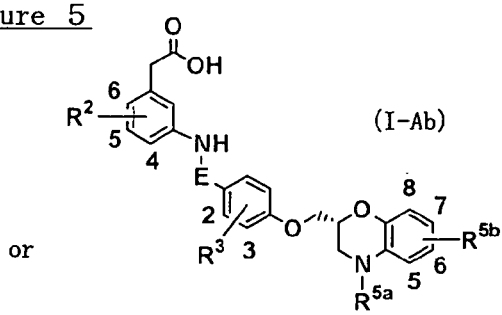
(I-Ab)

| No. | R² | E | R³ | R⁵ᵃ | R⁵ᵇ | No. | R² | E | R³ | R⁵ᵃ | R⁵ᵇ |
|---|---|---|---|---|---|---|---|---|---|---|---|
| 1 | H | -CO- | 2-CH₃ | CH₃ | 6-OCH₃ | 37 | H | -CO- | 2-CH₃ | CH₃ | 5-F |
| 2 | H | -SO₂- | 2-CH₃ | CH₃ | 6-OCH₃ | 38 | H | -SO₂- | 2-CH₃ | CH₃ | 5-F |
| 3 | H | -CH₂- | 2-CH₃ | CH₃ | 6-OCH₃ | 39 | H | -CH₂- | 2-CH₃ | CH₃ | 5-F |
| 4 | 4-CH₃ | -CO- | 2-CH₃ | CH₃ | 6-OCH₃ | 40 | 4-CH₃ | -CO- | 2-CH₃ | CH₃ | 5-F |
| 5 | 4-CH₃ | -SO₂- | 2-CH₃ | CH₃ | 6-OCH₃ | 41 | 4-CH₃ | -SO₂- | 2-CH₃ | CH₃ | 5-F |
| 6 | 4-CH₃ | -CH₂- | 2-CH₃ | CH₃ | 6-OCH₃ | 42 | 4-CH₃ | -CH₂- | 2-CH₃ | CH₃ | 5-F |
| 7 | 4-Cl | -CO- | 2-CH₃ | CH₃ | 6-OCH₃ | 43 | 4-Cl | -CO- | 2-CH₃ | CH₃ | 5-F |
| 8 | 4-Cl | -SO₂- | 2-CH₃ | CH₃ | 6-OCH₃ | 44 | 4-Cl | -SO₂- | 2-CH₃ | CH₃ | 5-F |
| 9 | 4-Cl | -CH₂- | 2-CH₃ | CH₃ | 6-OCH₃ | 45 | 4-Cl | -CH₂- | 2-CH₃ | CH₃ | 5-F |
| 10 | 4-F | -CO- | 2-CH₃ | CH₃ | 6-OCH₃ | 46 | 4-F | -CO- | 2-CH₃ | CH₃ | 5-F |
| 11 | 4-F | -SO₂- | 2-CH₃ | CH₃ | 6-OCH₃ | 47 | 4-F | -SO₂- | 2-CH₃ | CH₃ | 5-F |
| 12 | 4-F | -CH₂- | 2-CH₃ | CH₃ | 6-OCH₃ | 48 | 4-F | -CH₂- | 2-CH₃ | CH₃ | 5-F |
| 13 | H | -CO- | 2-Cl | CH₃ | 6-OCH₃ | 49 | H | -CO- | 2-Cl | CH₃ | 5-F |
| 14 | H | -SO₂- | 2-Cl | CH₃ | 6-OCH₃ | 50 | H | -SO₂- | 2-Cl | CH₃ | 5-F |
| 15 | H | -CH₂- | 2-Cl | CH₃ | 6-OCH₃ | 51 | H | -CH₂- | 2-Cl | CH₃ | 5-F |
| 16 | 4-CH₃ | -CO- | 2-Cl | CH₃ | 6-OCH₃ | 52 | 4-CH₃ | -CO- | 2-Cl | CH₃ | 5-F |
| 17 | 4-CH₃ | -SO₂- | 2-Cl | CH₃ | 6-OCH₃ | 53 | 4-CH₃ | -SO₂- | 2-Cl | CH₃ | 5-F |
| 18 | 4-CH₃ | -CH₂- | 2-Cl | CH₃ | 6-OCH₃ | 54 | 4-CH₃ | -CH₂- | 2-Cl | CH₃ | 5-F |
| 19 | 4-Cl | -CO- | 2-Cl | CH₃ | 6-OCH₃ | 55 | 4-Cl | -CO- | 2-Cl | CH₃ | 5-F |
| 20 | 4-Cl | -SO₂- | 2-Cl | CH₃ | 6-OCH₃ | 56 | 4-Cl | -SO₂- | 2-Cl | CH₃ | 5-F |
| 21 | 4-Cl | -CH₂- | 2-Cl | CH₃ | 6-OCH₃ | 57 | 4-Cl | -CH₂- | 2-Cl | CH₃ | 5-F |
| 22 | 4-F | -CO- | 2-Cl | CH₃ | 6-OCH₃ | 58 | 4-F | -CO- | 2-Cl | CH₃ | 5-F |
| 23 | 4-F | -SO₂- | 2-Cl | CH₃ | 6-OCH₃ | 59 | 4-F | -SO₂- | 2-Cl | CH₃ | 5-F |
| 24 | 4-F | -CH₂- | 2-Cl | CH₃ | 6-OCH₃ | 60 | 4-F | -CH₂- | 2-Cl | CH₃ | 5-F |
| 25 | H | -CO- | 2-F | CH₃ | 6-OCH₃ | 61 | H | -CO- | 2-F | CH₃ | 5-F |
| 26 | H | -SO₂- | 2-F | CH₃ | 6-OCH₃ | 62 | H | -SO₂- | 2-F | CH₃ | 5-F |
| 27 | H | -CH₂- | 2-F | CH₃ | 6-OCH₃ | 63 | H | -CH₂- | 2-F | CH₃ | 5-F |
| 28 | 4-CH₃ | -CO- | 2-F | CH₃ | 6-OCH₃ | 64 | 4-CH₃ | -CO- | 2-F | CH₃ | 5-F |
| 29 | 4-CH₃ | -SO₂- | 2-F | CH₃ | 6-OCH₃ | 65 | 4-CH₃ | -SO₂- | 2-F | CH₃ | 5-F |
| 30 | 4-CH₃ | -CH₂- | 2-F | CH₃ | 6-OCH₃ | 66 | 4-CH₃ | -CH₂- | 2-F | CH₃ | 5-F |
| 31 | 4-Cl | -CO- | 2-F | CH₃ | 6-OCH₃ | 67 | 4-Cl | -CO- | 2-F | CH₃ | 5-F |
| 32 | 4-Cl | -SO₂- | 2-F | CH₃ | 6-OCH₃ | 68 | 4-Cl | -SO₂- | 2-F | CH₃ | 5-F |
| 33 | 4-Cl | -CH₂- | 2-F | CH₃ | 6-OCH₃ | 69 | 4-Cl | -CH₂- | 2-F | CH₃ | 5-F |
| 34 | 4-F | -CO- | 2-F | CH₃ | 6-OCH₃ | 70 | 4-F | -CO- | 2-F | CH₃ | 5-F |
| 35 | 4-F | -SO₂- | 2-F | CH₃ | 6-OCH₃ | 71 | 4-F | -SO₂- | 2-F | CH₃ | 5-F |
| 36 | 4-F | -CH₂- | 2-F | CH₃ | 6-OCH₃ | 72 | 4-F | -CH₂- | 2-F | CH₃ | 5-F |

Figure 6

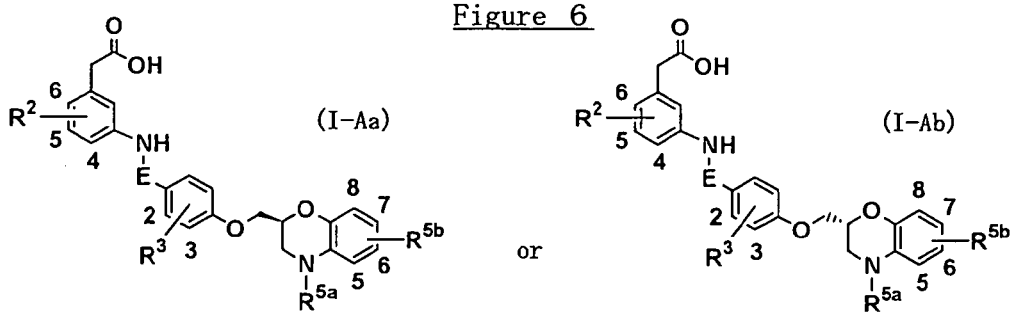

| No. | $R^2$ | E | $R^3$ | $R^{5a}$ | $R^{5b}$ | No. | $R^2$ | E | $R^3$ | $R^{5a}$ | $R^{5b}$ |
|---|---|---|---|---|---|---|---|---|---|---|---|
| 1 | H | -CO- | 2-CH$_3$ | CH$_3$ | 5-CH$_3$ | 37 | H | -CO- | 2-CH$_3$ | CH$_3$ | 5-OCH$_3$ |
| 2 | H | -SO$_2$- | 2-CH$_3$ | CH$_3$ | 5-CH$_3$ | 38 | H | -SO$_2$- | 2-CH$_3$ | CH$_3$ | 5-OCH$_3$ |
| 3 | H | -CH$_2$- | 2-CH$_3$ | CH$_3$ | 5-CH$_3$ | 39 | H | -CH$_2$- | 2-CH$_3$ | CH$_3$ | 5-OCH$_3$ |
| 4 | 4-CH$_3$ | -CO- | 2-CH$_3$ | CH$_3$ | 5-CH$_3$ | 40 | 4-CH$_3$ | -CO- | 2-CH$_3$ | CH$_3$ | 5-OCH$_3$ |
| 5 | 4-CH$_3$ | -SO$_2$- | 2-CH$_3$ | CH$_3$ | 5-CH$_3$ | 41 | 4-CH$_3$ | -SO$_2$- | 2-CH$_3$ | CH$_3$ | 5-OCH$_3$ |
| 6 | 4-CH$_3$ | -CH$_2$- | 2-CH$_3$ | CH$_3$ | 5-CH$_3$ | 42 | 4-CH$_3$ | -CH$_2$- | 2-CH$_3$ | CH$_3$ | 5-OCH$_3$ |
| 7 | 4-Cl | -CO- | 2-CH$_3$ | CH$_3$ | 5-CH$_3$ | 43 | 4-Cl | -CO- | 2-CH$_3$ | CH$_3$ | 5-OCH$_3$ |
| 8 | 4-Cl | -SO$_2$- | 2-CH$_3$ | CH$_3$ | 5-CH$_3$ | 44 | 4-Cl | -SO$_2$- | 2-CH$_3$ | CH$_3$ | 5-OCH$_3$ |
| 9 | 4-Cl | -CH$_2$- | 2-CH$_3$ | CH$_3$ | 5-CH$_3$ | 45 | 4-Cl | -CH$_2$- | 2-CH$_3$ | CH$_3$ | 5-OCH$_3$ |
| 10 | 4-F | -CO- | 2-CH$_3$ | CH$_3$ | 5-CH$_3$ | 46 | 4-F | -CO- | 2-CH$_3$ | CH$_3$ | 5-OCH$_3$ |
| 11 | 4-F | -SO$_2$- | 2-CH$_3$ | CH$_3$ | 5-CH$_3$ | 47 | 4-F | -SO$_2$- | 2-CH$_3$ | CH$_3$ | 5-OCH$_3$ |
| 12 | 4-F | -CH$_2$- | 2-CH$_3$ | CH$_3$ | 5-CH$_3$ | 48 | 4-F | -CH$_2$- | 2-CH$_3$ | CH$_3$ | 5-OCH$_3$ |
| 13 | H | -CO- | 2-Cl | CH$_3$ | 5-CH$_3$ | 49 | H | -CO- | 2-Cl | CH$_3$ | 5-OCH$_3$ |
| 14 | H | -SO$_2$- | 2-Cl | CH$_3$ | 5-CH$_3$ | 50 | H | -SO$_2$- | 2-Cl | CH$_3$ | 5-OCH$_3$ |
| 15 | H | -CH$_2$- | 2-Cl | CH$_3$ | 5-CH$_3$ | 51 | H | -CH$_2$- | 2-Cl | CH$_3$ | 5-OCH$_3$ |
| 16 | 4-CH$_3$ | -CO- | 2-Cl | CH$_3$ | 5-CH$_3$ | 52 | 4-CH$_3$ | -CO- | 2-Cl | CH$_3$ | 5-OCH$_3$ |
| 17 | 4-CH$_3$ | -SO$_2$- | 2-Cl | CH$_3$ | 5-CH$_3$ | 53 | 4-CH$_3$ | -SO$_2$- | 2-Cl | CH$_3$ | 5-OCH$_3$ |
| 18 | 4-CH$_3$ | -CH$_2$- | 2-Cl | CH$_3$ | 5-CH$_3$ | 54 | 4-CH$_3$ | -CH$_2$- | 2-Cl | CH$_3$ | 5-OCH$_3$ |
| 19 | 4-Cl | -CO- | 2-Cl | CH$_3$ | 5-CH$_3$ | 55 | 4-Cl | -CO- | 2-Cl | CH$_3$ | 5-OCH$_3$ |
| 20 | 4-Cl | -SO$_2$- | 2-Cl | CH$_3$ | 5-CH$_3$ | 56 | 4-Cl | -SO$_2$- | 2-Cl | CH$_3$ | 5-OCH$_3$ |
| 21 | 4-Cl | -CH$_2$- | 2-Cl | CH$_3$ | 5-CH$_3$ | 57 | 4-Cl | -CH$_2$- | 2-Cl | CH$_3$ | 5-OCH$_3$ |
| 22 | 4-F | -CO- | 2-Cl | CH$_3$ | 5-CH$_3$ | 58 | 4-F | -CO- | 2-Cl | CH$_3$ | 5-OCH$_3$ |
| 23 | 4-F | -SO$_2$- | 2-Cl | CH$_3$ | 5-CH$_3$ | 59 | 4-F | -SO$_2$- | 2-Cl | CH$_3$ | 5-OCH$_3$ |
| 24 | 4-F | -CH$_2$- | 2-Cl | CH$_3$ | 5-CH$_3$ | 60 | 4-F | -CH$_2$- | 2-Cl | CH$_3$ | 5-OCH$_3$ |
| 25 | H | -CO- | 2-F | CH$_3$ | 5-CH$_3$ | 61 | H | -CO- | 2-F | CH$_3$ | 5-OCH$_3$ |
| 26 | H | -SO$_2$- | 2-F | CH$_3$ | 5-CH$_3$ | 62 | H | -SO$_2$- | 2-F | CH$_3$ | 5-OCH$_3$ |
| 27 | H | -CH$_2$- | 2-F | CH$_3$ | 5-CH$_3$ | 63 | H | -CH$_2$- | 2-F | CH$_3$ | 5-OCH$_3$ |
| 28 | 4-CH$_3$ | -CO- | 2-F | CH$_3$ | 5-CH$_3$ | 64 | 4-CH$_3$ | -CO- | 2-F | CH$_3$ | 5-OCH$_3$ |
| 29 | 4-CH$_3$ | -SO$_2$- | 2-F | CH$_3$ | 5-CH$_3$ | 65 | 4-CH$_3$ | -SO$_2$- | 2-F | CH$_3$ | 5-OCH$_3$ |
| 30 | 4-CH$_3$ | -CH$_2$- | 2-F | CH$_3$ | 5-CH$_3$ | 66 | 4-CH$_3$ | -CH$_2$- | 2-F | CH$_3$ | 5-OCH$_3$ |
| 31 | 4-Cl | -CO- | 2-F | CH$_3$ | 5-CH$_3$ | 67 | 4-Cl | -CO- | 2-F | CH$_3$ | 5-OCH$_3$ |
| 32 | 4-Cl | -SO$_2$- | 2-F | CH$_3$ | 5-CH$_3$ | 68 | 4-Cl | -SO$_2$- | 2-F | CH$_3$ | 5-OCH$_3$ |
| 33 | 4-Cl | -CH$_2$- | 2-F | CH$_3$ | 5-CH$_3$ | 69 | 4-Cl | -CH$_2$- | 2-F | CH$_3$ | 5-OCH$_3$ |
| 34 | 4-F | -CO- | 2-F | CH$_3$ | 5-CH$_3$ | 70 | 4-F | -CO- | 2-F | CH$_3$ | 5-OCH$_3$ |
| 35 | 4-F | -SO$_2$- | 2-F | CH$_3$ | 5-CH$_3$ | 71 | 4-F | -SO$_2$- | 2-F | CH$_3$ | 5-OCH$_3$ |
| 36 | 4-F | -CH$_2$- | 2-F | CH$_3$ | 5-CH$_3$ | 72 | 4-F | -CH$_2$- | 2-F | CH$_3$ | 5-OCH$_3$ |

Figure 7

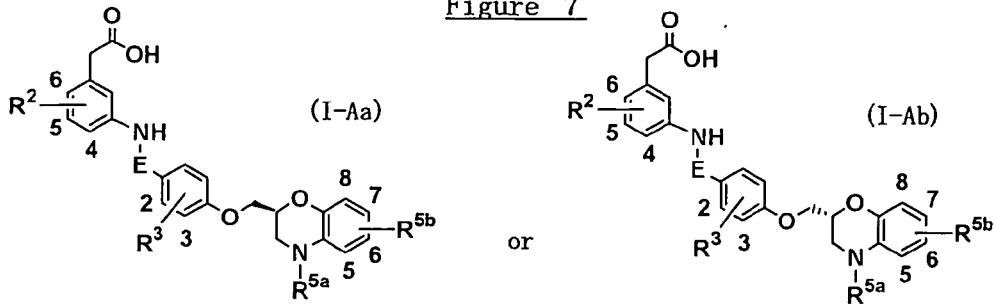

| No. | $R^2$ | E | $R^3$ | $R^{5a}$ | $R^{5b}$ | No. | $R^2$ | E | $R^3$ | $R^{5a}$ | $R^{5b}$ |
|---|---|---|---|---|---|---|---|---|---|---|---|
| 1 | 5-CH$_3$ | -CO- | 2-CH$_3$ | CH$_3$ | H | 37 | 5-CH$_3$ | -CO- | 2-CH$_3$ | CH$_3$ | 7-CH$_3$ |
| 2 | 5-CH$_3$ | -SO$_2$- | 2-CH$_3$ | CH$_3$ | H | 38 | 5-CH$_3$ | -SO$_2$- | 2-CH$_3$ | CH$_3$ | 7-CH$_3$ |
| 3 | 5-CH$_3$ | -CH$_2$- | 2-CH$_3$ | CH$_3$ | H | 39 | 5-CH$_3$ | -CH$_2$- | 2-CH$_3$ | CH$_3$ | 7-CH$_3$ |
| 4 | 5-Cl | -CO- | 2-Cl | CH$_3$ | H | 40 | 5-Cl | -CO- | 2-Cl | CH$_3$ | 7-CH$_3$ |
| 5 | 5-Cl | -SO$_2$- | 2-Cl | CH$_3$ | H | 41 | 5-Cl | -SO$_2$- | 2-Cl | CH$_3$ | 7-CH$_3$ |
| 6 | 5-Cl | -CH$_2$- | 2-Cl | CH$_3$ | H | 42 | 5-Cl | -CH$_2$- | 2-Cl | CH$_3$ | 7-CH$_3$ |
| 7 | 5-CH$_3$ | -CO- | 2-Cl | CH$_3$ | H | 43 | 5-CH$_3$ | -CO- | 2-Cl | CH$_3$ | 7-CH$_3$ |
| 8 | 5-CH$_3$ | -SO$_2$- | 2-Cl | CH$_3$ | H | 44 | 5-CH$_3$ | -SO$_2$- | 2-Cl | CH$_3$ | 7-CH$_3$ |
| 9 | 5-CH$_3$ | -CH$_2$- | 2-Cl | CH$_3$ | H | 45 | 5-CH$_3$ | -CH$_2$- | 2-Cl | CH$_3$ | 7-CH$_3$ |
| 10 | 5-F | -CO- | 2-Cl | CH$_3$ | H | 46 | 5-F | -CO- | 2-Cl | CH$_3$ | 7-CH$_3$ |
| 11 | 5-F | -SO$_2$- | 2-Cl | CH$_3$ | H | 47 | 5-F | -SO$_2$- | 2-Cl | CH$_3$ | 7-CH$_3$ |
| 12 | 5-F | -CH$_2$- | 2-Cl | CH$_3$ | H | 48 | 5-F | -CH$_2$- | 2-Cl | CH$_3$ | 7-CH$_3$ |
| 13 | 5-CH$_3$ | -CO- | 2-CH$_3$ | CH$_3$ | 8-CH$_3$ | 49 | 5-CH$_3$ | -CO- | 2-CH$_3$ | CH$_3$ | 7-F |
| 14 | 5-CH$_3$ | -SO$_2$- | 2-CH$_3$ | CH$_3$ | 8-CH$_3$ | 50 | 5-CH$_3$ | -SO$_2$- | 2-CH$_3$ | CH$_3$ | 7-F |
| 15 | 5-CH$_3$ | -CH$_2$- | 2-CH$_3$ | CH$_3$ | 8-CH$_3$ | 51 | 5-CH$_3$ | -CH$_2$- | 2-CH$_3$ | CH$_3$ | 7-F |
| 16 | 5-Cl | -CO- | 2-Cl | CH$_3$ | 8-CH$_3$ | 52 | 5-Cl | -CO- | 2-Cl | CH$_3$ | 7-F |
| 17 | 5-Cl | -SO$_2$- | 2-Cl | CH$_3$ | 8-CH$_3$ | 53 | 5-Cl | -SO$_2$- | 2-Cl | CH$_3$ | 7-F |
| 18 | 5-Cl | -CH$_2$- | 2-Cl | CH$_3$ | 8-CH$_3$ | 54 | 5-Cl | -CH$_2$- | 2-Cl | CH$_3$ | 7-F |
| 19 | 5-CH$_3$ | -CO- | 2-Cl | CH$_3$ | 8-CH$_3$ | 55 | 5-CH$_3$ | -CO- | 2-Cl | CH$_3$ | 7-F |
| 20 | 5-CH$_3$ | -SO$_2$- | 2-Cl | CH$_3$ | 8-CH$_3$ | 56 | 5-CH$_3$ | -SO$_2$- | 2-Cl | CH$_3$ | 7-F |
| 21 | 5-CH$_3$ | -CH$_2$- | 2-Cl | CH$_3$ | 8-CH$_3$ | 57 | 5-CH$_3$ | -CH$_2$- | 2-Cl | CH$_3$ | 7-F |
| 22 | 5-F | -CO- | 2-Cl | CH$_3$ | 8-CH$_3$ | 58 | 5-F | -CO- | 2-Cl | CH$_3$ | 7-F |
| 23 | 5-F | -SO$_2$- | 2-Cl | CH$_3$ | 8-CH$_3$ | 59 | 5-F | -SO$_2$- | 2-Cl | CH$_3$ | 7-F |
| 24 | 5-F | -CH$_2$- | 2-Cl | CH$_3$ | 8-CH$_3$ | 60 | 5-F | -CH$_2$- | 2-Cl | CH$_3$ | 7-F |
| 25 | 5-CH$_3$ | -CO- | 2-CH$_3$ | CH$_3$ | 8-F | 61 | 5-CH$_3$ | -CO- | 2-CH$_3$ | CH$_3$ | 7-OCH$_3$ |
| 26 | 5-CH$_3$ | -SO$_2$- | 2-CH$_3$ | CH$_3$ | 8-F | 62 | 5-CH$_3$ | -SO$_2$- | 2-CH$_3$ | CH$_3$ | 7-OCH$_3$ |
| 27 | 5-CH$_3$ | -CH$_2$- | 2-CH$_3$ | CH$_3$ | 8-F | 63 | 5-CH$_3$ | -CH$_2$- | 2-CH$_3$ | CH$_3$ | 7-OCH$_3$ |
| 28 | 5-Cl | -CO- | 2-Cl | CH$_3$ | 8-F | 64 | 5-Cl | -CO- | 2-Cl | CH$_3$ | 7-OCH$_3$ |
| 29 | 5-Cl | -SO$_2$- | 2-Cl | CH$_3$ | 8-F | 65 | 5-Cl | -SO$_2$- | 2-Cl | CH$_3$ | 7-OCH$_3$ |
| 30 | 5-Cl | -CH$_2$- | 2-Cl | CH$_3$ | 8-F | 66 | 5-Cl | -CH$_2$- | 2-Cl | CH$_3$ | 7-OCH$_3$ |
| 31 | 5-CH$_3$ | -CO- | 2-Cl | CH$_3$ | 8-F | 67 | 5-CH$_3$ | -CO- | 2-Cl | CH$_3$ | 7-OCH$_3$ |
| 32 | 5-CH$_3$ | -SO$_2$- | 2-Cl | CH$_3$ | 8-F | 68 | 5-CH$_3$ | -SO$_2$- | 2-Cl | CH$_3$ | 7-OCH$_3$ |
| 33 | 5-CH$_3$ | -CH$_2$- | 2-Cl | CH$_3$ | 8-F | 69 | 5-CH$_3$ | -CH$_2$- | 2-Cl | CH$_3$ | 7-OCH$_3$ |
| 34 | 5-F | -CO- | 2-Cl | CH$_3$ | 8-F | 70 | 5-F | -CO- | 2-Cl | CH$_3$ | 7-OCH$_3$ |
| 35 | 5-F | -SO$_2$- | 2-Cl | CH$_3$ | 8-F | 71 | 5-F | -SO$_2$- | 2-Cl | CH$_3$ | 7-OCH$_3$ |
| 36 | 5-F | -CH$_2$- | 2-Cl | CH$_3$ | 8-F | 72 | 5-F | -CH$_2$- | 2-Cl | CH$_3$ | 7-OCH$_3$ |

Figure 8

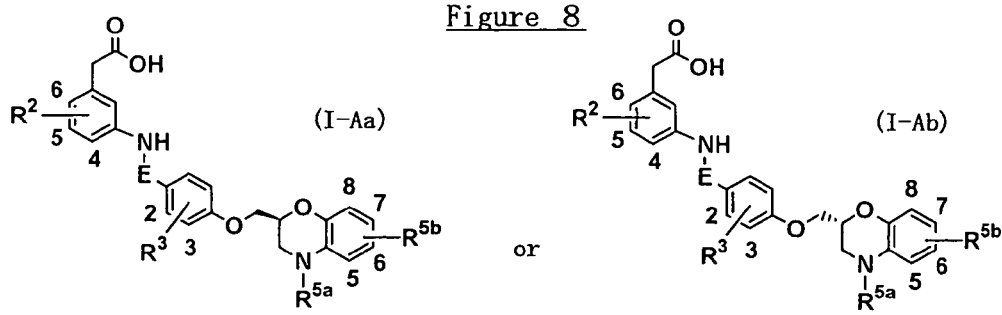

| No. | R² | E | R³ | R⁵ᵃ | R⁵ᵇ | No. | R² | E | R³ | R⁵ᵃ | R⁵ᵇ |
|---|---|---|---|---|---|---|---|---|---|---|---|
| 1 | 5-CH$_3$ | -CO- | 2-CH$_3$ | CH$_3$ | 6-CH$_3$ | 37 | 5-CH$_3$ | -CO- | 2-CH$_3$ | CH$_3$ | 5-F |
| 2 | 5-CH$_3$ | -SO$_2$- | 2-CH$_3$ | CH$_3$ | 6-CH$_3$ | 38 | 5-CH$_3$ | -SO$_2$- | 2-CH$_3$ | CH$_3$ | 5-F |
| 3 | 5-CH$_3$ | -CH$_2$- | 2-CH$_3$ | CH$_3$ | 6-CH$_3$ | 39 | 5-CH$_3$ | -CH$_2$- | 2-CH$_3$ | CH$_3$ | 5-F |
| 4 | 5-Cl | -CO- | 2-Cl | CH$_3$ | 6-CH$_3$ | 40 | 5-Cl | -CO- | 2-Cl | CH$_3$ | 5-F |
| 5 | 5-Cl | -SO$_2$- | 2-Cl | CH$_3$ | 6-CH$_3$ | 41 | 5-Cl | -SO$_2$- | 2-Cl | CH$_3$ | 5-F |
| 6 | 5-Cl | -CH$_2$- | 2-Cl | CH$_3$ | 6-CH$_3$ | 42 | 5-Cl | -CH$_2$- | 2-Cl | CH$_3$ | 5-F |
| 7 | 5-CH$_3$ | -CO- | 2-Cl | CH$_3$ | 6-CH$_3$ | 43 | 5-CH$_3$ | -CO- | 2-Cl | CH$_3$ | 5-F |
| 8 | 5-CH$_3$ | -SO$_2$- | 2-Cl | CH$_3$ | 6-CH$_3$ | 44 | 5-CH$_3$ | -SO$_2$- | 2-Cl | CH$_3$ | 5-F |
| 9 | 5-CH$_3$ | -CH$_2$- | 2-Cl | CH$_3$ | 6-CH$_3$ | 45 | 5-CH$_3$ | -CH$_2$- | 2-Cl | CH$_3$ | 5-F |
| 10 | 5-F | -CO- | 2-Cl | CH$_3$ | 6-CH$_3$ | 46 | 5-F | -CO- | 2-Cl | CH$_3$ | 5-F |
| 11 | 5-F | -SO$_2$- | 2-Cl | CH$_3$ | 6-CH$_3$ | 47 | 5-F | -SO$_2$- | 2-Cl | CH$_3$ | 5-F |
| 12 | 5-F | -CH$_2$- | 2-Cl | CH$_3$ | 6-CH$_3$ | 48 | 5-F | -CH$_2$- | 2-Cl | CH$_3$ | 5-F |
| 13 | 5-CH$_3$ | -CO- | 2-CH$_3$ | CH$_3$ | 6-F | 49 | 5-CH$_3$ | -CO- | 2-CH$_3$ | CH$_3$ | 5-OCH$_3$ |
| 14 | 5-CH$_3$ | -SO$_2$- | 2-CH$_3$ | CH$_3$ | 6-F | 50 | 5-CH$_3$ | -SO$_2$- | 2-CH$_3$ | CH$_3$ | 5-OCH$_3$ |
| 15 | 5-CH$_3$ | -CH$_2$- | 2-CH$_3$ | CH$_3$ | 6-F | 51 | 5-CH$_3$ | -CH$_2$- | 2-CH$_3$ | CH$_3$ | 5-OCH$_3$ |
| 16 | 5-Cl | -CO- | 2-Cl | CH$_3$ | 6-F | 52 | 5-Cl | -CO- | 2-Cl | CH$_3$ | 5-OCH$_3$ |
| 17 | 5-Cl | -SO$_2$- | 2-Cl | CH$_3$ | 6-F | 53 | 5-Cl | -SO$_2$- | 2-Cl | CH$_3$ | 5-OCH$_3$ |
| 18 | 5-Cl | -CH$_2$- | 2-Cl | CH$_3$ | 6-F | 54 | 5-Cl | -CH$_2$- | 2-Cl | CH$_3$ | 5-OCH$_3$ |
| 19 | 5-CH$_3$ | -CO- | 2-Cl | CH$_3$ | 6-F | 55 | 5-CH$_3$ | -CO- | 2-Cl | CH$_3$ | 5-OCH$_3$ |
| 20 | 5-CH$_3$ | -SO$_2$- | 2-Cl | CH$_3$ | 6-F | 56 | 5-CH$_3$ | -SO$_2$- | 2-Cl | CH$_3$ | 5-OCH$_3$ |
| 21 | 5-CH$_3$ | -CH$_2$- | 2-Cl | CH$_3$ | 6-F | 57 | 5-CH$_3$ | -CH$_2$- | 2-Cl | CH$_3$ | 5-OCH$_3$ |
| 22 | 5-F | -CO- | 2-Cl | CH$_3$ | 6-F | 58 | 5-F | -CO- | 2-Cl | CH$_3$ | 5-OCH$_3$ |
| 23 | 5-F | -SO$_2$- | 2-Cl | CH$_3$ | 6-F | 59 | 5-F | -SO$_2$- | 2-Cl | CH$_3$ | 5-OCH$_3$ |
| 24 | 5-F | -CH$_2$- | 2-Cl | CH$_3$ | 6-F | 60 | 5-F | -CH$_2$- | 2-Cl | CH$_3$ | 5-OCH$_3$ |
| 25 | 5-CH$_3$ | -CO- | 2-CH$_3$ | CH$_3$ | 6-OCH$_3$ | 61 | 5-CH$_3$ | -CO- | 2-CH$_3$ | CH$_3$ | 5-CH$_3$ |
| 26 | 5-CH$_3$ | -SO$_2$- | 2-CH$_3$ | CH$_3$ | 6-OCH$_3$ | 62 | 5-CH$_3$ | -SO$_2$- | 2-CH$_3$ | CH$_3$ | 5-CH$_3$ |
| 27 | 5-CH$_3$ | -CH$_2$- | 2-CH$_3$ | CH$_3$ | 6-OCH$_3$ | 63 | 5-CH$_3$ | -CH$_2$- | 2-CH$_3$ | CH$_3$ | 5-CH$_3$ |
| 28 | 5-Cl | -CO- | 2-Cl | CH$_3$ | 6-OCH$_3$ | 64 | 5-Cl | -CO- | 2-Cl | CH$_3$ | 5-CH$_3$ |
| 29 | 5-Cl | -SO$_2$- | 2-Cl | CH$_3$ | 6-OCH$_3$ | 65 | 5-Cl | -SO$_2$- | 2-Cl | CH$_3$ | 5-CH$_3$ |
| 30 | 5-Cl | -CH$_2$- | 2-Cl | CH$_3$ | 6-OCH$_3$ | 66 | 5-Cl | -CH$_2$- | 2-Cl | CH$_3$ | 5-CH$_3$ |
| 31 | 5-CH$_3$ | -CO- | 2-Cl | CH$_3$ | 6-OCH$_3$ | 67 | 5-CH$_3$ | -CO- | 2-Cl | CH$_3$ | 5-CH$_3$ |
| 32 | 5-CH$_3$ | -SO$_2$- | 2-Cl | CH$_3$ | 6-OCH$_3$ | 68 | 5-CH$_3$ | -SO$_2$- | 2-Cl | CH$_3$ | 5-CH$_3$ |
| 33 | 5-CH$_3$ | -CH$_2$- | 2-Cl | CH$_3$ | 6-OCH$_3$ | 69 | 5-CH$_3$ | -CH$_2$- | 2-Cl | CH$_3$ | 5-CH$_3$ |
| 34 | 5-F | -CO- | 2-Cl | CH$_3$ | 6-OCH$_3$ | 70 | 5-F | -CO- | 2-Cl | CH$_3$ | 5-CH$_3$ |
| 35 | 5-F | -SO$_2$- | 2-Cl | CH$_3$ | 6-OCH$_3$ | 71 | 5-F | -SO$_2$- | 2-Cl | CH$_3$ | 5-CH$_3$ |
| 36 | 5-F | -CH$_2$- | 2-Cl | CH$_3$ | 6-OCH$_3$ | 72 | 5-F | -CH$_2$- | 2-Cl | CH$_3$ | 5-CH$_3$ |

Figure 9

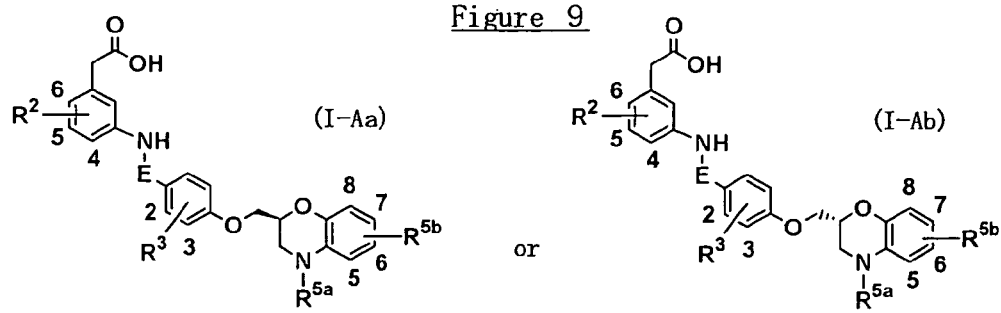

| No. | $R^2$ | E | $R^3$ | $R^{5a}$ | $R^{5b}$ | No. | $R^2$ | E | $R^3$ | $R^{5a}$ | $R^{5b}$ |
|---|---|---|---|---|---|---|---|---|---|---|---|
| 1 | 4-CH₃ | -CO- | 3-CH₃ | CH₃ | H | 37 | 4-CH₃ | -CO- | 3-CH₃ | CH₃ | 7-CH₃ |
| 2 | 4-CH₃ | -SO₂- | 3-CH₃ | CH₃ | H | 38 | 4-CH₃ | -SO₂- | 3-CH₃ | CH₃ | 7-CH₃ |
| 3 | 4-CH₃ | -CH₂- | 3-CH₃ | CH₃ | H | 39 | 4-CH₃ | -CH₂- | 3-CH₃ | CH₃ | 7-CH₃ |
| 4 | 4-Cl | -CO- | 3-CH₃ | CH₃ | H | 40 | 4-Cl | -CO- | 3-CH₃ | CH₃ | 7-CH₃ |
| 5 | 4-Cl | -SO₂- | 3-CH₃ | CH₃ | H | 41 | 4-Cl | -SO₂- | 3-CH₃ | CH₃ | 7-CH₃ |
| 6 | 4-Cl | -CH₂- | 3-CH₃ | CH₃ | H | 42 | 4-Cl | -CH₂- | 3-CH₃ | CH₃ | 7-CH₃ |
| 7 | 4-Cl | -CO- | 3-Cl | CH₃ | H | 43 | 4-Cl | -CO- | 3-Cl | CH₃ | 7-CH₃ |
| 8 | 4-Cl | -SO₂- | 3-Cl | CH₃ | H | 44 | 4-Cl | -SO₂- | 3-Cl | CH₃ | 7-CH₃ |
| 9 | 4-Cl | -CH₂- | 3-Cl | CH₃ | H | 45 | 4-Cl | -CH₂- | 3-Cl | CH₃ | 7-CH₃ |
| 10 | 4-CH₃ | -CO- | 3-Cl | CH₃ | H | 46 | 4-CH₃ | -CO- | 3-Cl | CH₃ | 7-CH₃ |
| 11 | 4-CH₃ | -SO₂- | 3-Cl | CH₃ | H | 47 | 4-CH₃ | -SO₂- | 3-Cl | CH₃ | 7-CH₃ |
| 12 | 4-CH₃ | -CH₂- | 3-Cl | CH₃ | H | 48 | 4-CH₃ | -CH₂- | 3-Cl | CH₃ | 7-CH₃ |
| 13 | 4-CH₃ | -CO- | 3-CH₃ | CH₃ | 8-CH₃ | 49 | 4-CH₃ | -CO- | 3-CH₃ | CH₃ | 7-F |
| 14 | 4-CH₃ | -SO₂- | 3-CH₃ | CH₃ | 8-CH₃ | 50 | 4-CH₃ | -SO₂- | 3-CH₃ | CH₃ | 7-F |
| 15 | 4-CH₃ | -CH₂- | 3-CH₃ | CH₃ | 8-CH₃ | 51 | 4-CH₃ | -CH₂- | 3-CH₃ | CH₃ | 7-F |
| 16 | 4-Cl | -CO- | 3-CH₃ | CH₃ | 8-CH₃ | 52 | 4-Cl | -CO- | 3-CH₃ | CH₃ | 7-F |
| 17 | 4-Cl | -SO₂- | 3-CH₃ | CH₃ | 8-CH₃ | 53 | 4-Cl | -SO₂- | 3-CH₃ | CH₃ | 7-F |
| 18 | 4-Cl | -CH₂- | 3-CH₃ | CH₃ | 8-CH₃ | 54 | 4-Cl | -CH₂- | 3-CH₃ | CH₃ | 7-F |
| 19 | 4-Cl | -CO- | 3-Cl | CH₃ | 8-CH₃ | 55 | 4-Cl | -CO- | 3-Cl | CH₃ | 7-F |
| 20 | 4-Cl | -SO₂- | 3-Cl | CH₃ | 8-CH₃ | 56 | 4-Cl | -SO₂- | 3-Cl | CH₃ | 7-F |
| 21 | 4-Cl | -CH₂- | 3-Cl | CH₃ | 8-CH₃ | 57 | 4-Cl | -CH₂- | 3-Cl | CH₃ | 7-F |
| 22 | 4-CH₃ | -CO- | 3-Cl | CH₃ | 8-CH₃ | 58 | 4-CH₃ | -CO- | 3-Cl | CH₃ | 7-F |
| 23 | 4-CH₃ | -SO₂- | 3-Cl | CH₃ | 8-CH₃ | 59 | 4-CH₃ | -SO₂- | 3-Cl | CH₃ | 7-F |
| 24 | 4-CH₃ | -CH₂- | 3-Cl | CH₃ | 8-CH₃ | 60 | 4-CH₃ | -CH₂- | 3-Cl | CH₃ | 7-F |
| 25 | 4-CH₃ | -CO- | 3-CH₃ | CH₃ | 8-F | 61 | 4-CH₃ | -CO- | 3-CH₃ | CH₃ | 7-OCH₃ |
| 26 | 4-CH₃ | -SO₂- | 3-CH₃ | CH₃ | 8-F | 62 | 4-CH₃ | -SO₂- | 3-CH₃ | CH₃ | 7-OCH₃ |
| 27 | 4-CH₃ | -CH₂- | 3-CH₃ | CH₃ | 8-F | 63 | 4-CH₃ | -CH₂- | 3-CH₃ | CH₃ | 7-OCH₃ |
| 28 | 4-Cl | -CO- | 3-CH₃ | CH₃ | 8-F | 64 | 4-Cl | -CO- | 3-CH₃ | CH₃ | 7-OCH₃ |
| 29 | 4-Cl | -SO₂- | 3-CH₃ | CH₃ | 8-F | 65 | 4-Cl | -SO₂- | 3-CH₃ | CH₃ | 7-OCH₃ |
| 30 | 4-Cl | -CH₂- | 3-CH₃ | CH₃ | 8-F | 66 | 4-Cl | -CH₂- | 3-CH₃ | CH₃ | 7-OCH₃ |
| 31 | 4-Cl | -CO- | 3-Cl | CH₃ | 8-F | 67 | 4-Cl | -CO- | 3-Cl | CH₃ | 7-OCH₃ |
| 32 | 4-Cl | -SO₂- | 3-Cl | CH₃ | 8-F | 68 | 4-Cl | -SO₂- | 3-Cl | CH₃ | 7-OCH₃ |
| 33 | 4-Cl | -CH₂- | 3-Cl | CH₃ | 8-F | 69 | 4-Cl | -CH₂- | 3-Cl | CH₃ | 7-OCH₃ |
| 34 | 4-CH₃ | -CO- | 3-Cl | CH₃ | 8-F | 70 | 4-CH₃ | -CO- | 3-Cl | CH₃ | 7-OCH₃ |
| 35 | 4-CH₃ | -SO₂- | 3-Cl | CH₃ | 8-F | 71 | 4-CH₃ | -SO₂- | 3-Cl | CH₃ | 7-OCH₃ |
| 36 | 4-CH₃ | -CH₂- | 3-Cl | CH₃ | 8-F | 72 | 4-CH₃ | -CH₂- | 3-Cl | CH₃ | 7-OCH₃ |

Figure 10

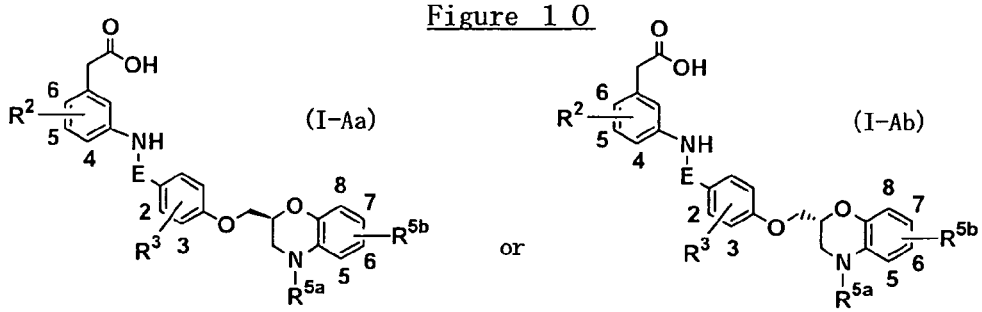

| No. | R² | E | R³ | R⁵ᵃ | R⁵ᵇ | No. | R² | E | R³ | R⁵ᵃ | R⁵ᵇ |
|---|---|---|---|---|---|---|---|---|---|---|---|
| 1 | 4-CH₃ | -CO- | 3-CH₃ | CH₃ | 6-CH₃ | 37 | 4-CH₃ | -CO- | 3-CH₃ | CH₃ | 5-F |
| 2 | 4-CH₃ | -SO₂- | 3-CH₃ | CH₃ | 6-CH₃ | 38 | 4-CH₃ | -SO₂- | 3-CH₃ | CH₃ | 5-F |
| 3 | 4-CH₃ | -CH₂- | 3-CH₃ | CH₃ | 6-CH₃ | 39 | 4-CH₃ | -CH₂- | 3-CH₃ | CH₃ | 5-F |
| 4 | 4-Cl | -CO- | 3-CH₃ | CH₃ | 6-CH₃ | 40 | 4-Cl | -CO- | 3-CH₃ | CH₃ | 5-F |
| 5 | 4-Cl | -SO₂- | 3-CH₃ | CH₃ | 6-CH₃ | 41 | 4-Cl | -SO₂- | 3-CH₃ | CH₃ | 5-F |
| 6 | 4-Cl | -CH₂- | 3-CH₃ | CH₃ | 6-CH₃ | 42 | 4-Cl | -CH₂- | 3-CH₃ | CH₃ | 5-F |
| 7 | 4-Cl | -CO- | 3-Cl | CH₃ | 6-CH₃ | 43 | 4-Cl | -CO- | 3-Cl | CH₃ | 5-F |
| 8 | 4-Cl | -SO₂- | 3-Cl | CH₃ | 6-CH₃ | 44 | 4-Cl | -SO₂- | 3-Cl | CH₃ | 5-F |
| 9 | 4-Cl | -CH₂- | 3-Cl | CH₃ | 6-CH₃ | 45 | 4-Cl | -CH₂- | 3-Cl | CH₃ | 5-F |
| 10 | 4-CH₃ | -CO- | 3-Cl | CH₃ | 6-CH₃ | 46 | 4-CH₃ | -CO- | 3-Cl | CH₃ | 5-F |
| 11 | 4-CH₃ | -SO₂- | 3-Cl | CH₃ | 6-CH₃ | 47 | 4-CH₃ | -SO₂- | 3-Cl | CH₃ | 5-F |
| 12 | 4-CH₃ | -CH₂- | 3-Cl | CH₃ | 6-CH₃ | 48 | 4-CH₃ | -CH₂- | 3-Cl | CH₃ | 5-F |
| 13 | 4-CH₃ | -CO- | 3-CH₃ | CH₃ | 6-F | 49 | 4-CH₃ | -CO- | 3-CH₃ | CH₃ | 5-OCH₃ |
| 14 | 4-CH₃ | -SO₂- | 3-CH₃ | CH₃ | 6-F | 50 | 4-CH₃ | -SO₂- | 3-CH₃ | CH₃ | 5-OCH₃ |
| 15 | 4-CH₃ | -CH₂- | 3-CH₃ | CH₃ | 6-F | 51 | 4-CH₃ | -CH₂- | 3-CH₃ | CH₃ | 5-OCH₃ |
| 16 | 4-Cl | -CO- | 3-CH₃ | CH₃ | 6-F | 52 | 4-Cl | -CO- | 3-CH₃ | CH₃ | 5-OCH₃ |
| 17 | 4-Cl | -SO₂- | 3-CH₃ | CH₃ | 6-F | 53 | 4-Cl | -SO₂- | 3-CH₃ | CH₃ | 5-OCH₃ |
| 18 | 4-Cl | -CH₂- | 3-CH₃ | CH₃ | 6-F | 54 | 4-Cl | -CH₂- | 3-CH₃ | CH₃ | 5-OCH₃ |
| 19 | 4-Cl | -CO- | 3-Cl | CH₃ | 6-F | 55 | 4-Cl | -CO- | 3-Cl | CH₃ | 5-OCH₃ |
| 20 | 4-Cl | -SO₂- | 3-Cl | CH₃ | 6-F | 56 | 4-Cl | -SO₂- | 3-Cl | CH₃ | 5-OCH₃ |
| 21 | 4-Cl | -CH₂- | 3-Cl | CH₃ | 6-F | 57 | 4-Cl | -CH₂- | 3-Cl | CH₃ | 5-OCH₃ |
| 22 | 4-CH₃ | -CO- | 3-Cl | CH₃ | 6-F | 58 | 4-CH₃ | -CO- | 3-Cl | CH₃ | 5-OCH₃ |
| 23 | 4-CH₃ | -SO₂- | 3-Cl | CH₃ | 6-F | 59 | 4-CH₃ | -SO₂- | 3-Cl | CH₃ | 5-OCH₃ |
| 24 | 4-CH₃ | -CH₂- | 3-Cl | CH₃ | 6-F | 60 | 4-CH₃ | -CH₂- | 3-Cl | CH₃ | 5-OCH₃ |
| 25 | 4-CH₃ | -CO- | 3-CH₃ | CH₃ | 6-OCH₃ | 61 | 4-CH₃ | -CO- | 3-CH₃ | CH₃ | 5-CH₃ |
| 26 | 4-CH₃ | -SO₂- | 3-CH₃ | CH₃ | 6-OCH₃ | 62 | 4-CH₃ | -SO₂- | 3-CH₃ | CH₃ | 5-CH₃ |
| 27 | 4-CH₃ | -CH₂- | 3-CH₃ | CH₃ | 6-OCH₃ | 63 | 4-CH₃ | -CH₂- | 3-CH₃ | CH₃ | 5-CH₃ |
| 28 | 4-Cl | -CO- | 3-CH₃ | CH₃ | 6-OCH₃ | 64 | 4-Cl | -CO- | 3-CH₃ | CH₃ | 5-CH₃ |
| 29 | 4-Cl | -SO₂- | 3-CH₃ | CH₃ | 6-OCH₃ | 65 | 4-Cl | -SO₂- | 3-CH₃ | CH₃ | 5-CH₃ |
| 30 | 4-Cl | -CH₂- | 3-CH₃ | CH₃ | 6-OCH₃ | 66 | 4-Cl | -CH₂- | 3-CH₃ | CH₃ | 5-CH₃ |
| 31 | 4-Cl | -CO- | 3-Cl | CH₃ | 6-OCH₃ | 67 | 4-Cl | -CO- | 3-Cl | CH₃ | 5-CH₃ |
| 32 | 4-Cl | -SO₂- | 3-Cl | CH₃ | 6-OCH₃ | 68 | 4-Cl | -SO₂- | 3-Cl | CH₃ | 5-CH₃ |
| 33 | 4-Cl | -CH₂- | 3-Cl | CH₃ | 6-OCH₃ | 69 | 4-Cl | -CH₂- | 3-Cl | CH₃ | 5-CH₃ |
| 34 | 4-CH₃ | -CO- | 3-Cl | CH₃ | 6-OCH₃ | 70 | 4-CH₃ | -CO- | 3-Cl | CH₃ | 5-CH₃ |
| 35 | 4-CH₃ | -SO₂- | 3-Cl | CH₃ | 6-OCH₃ | 71 | 4-CH₃ | -SO₂- | 3-Cl | CH₃ | 5-CH₃ |
| 36 | 4-CH₃ | -CH₂- | 3-Cl | CH₃ | 6-OCH₃ | 72 | 4-CH₃ | -CH₂- | 3-Cl | CH₃ | 5-CH₃ |

Figure 11

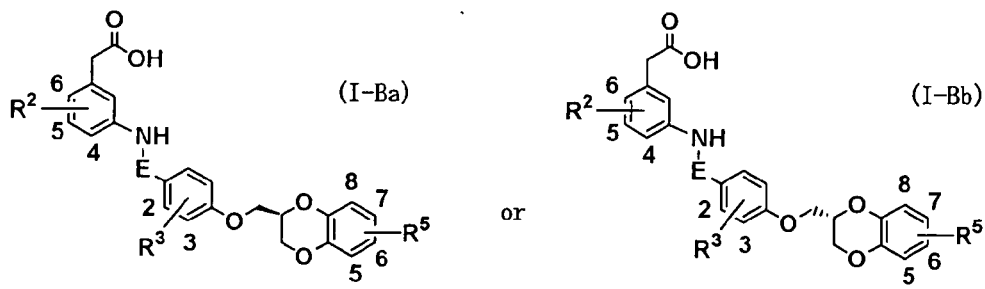

| No. | R² | E | R³ | R⁵ | No. | R² | E | R³ | R⁵ |
|---|---|---|---|---|---|---|---|---|---|
| 1 | H | -CO- | 2-CH₃ | H | 37 | H | -CO- | 2-CH₃ | 8-F |
| 2 | H | -SO₂- | 2-CH₃ | H | 38 | H | -SO₂- | 2-CH₃ | 8-F |
| 3 | H | -CH₂- | 2-CH₃ | H | 39 | H | -CH₂- | 2-CH₃ | 8-F |
| 4 | 4-CH₃ | -CO- | 2-CH₃ | H | 40 | 4-CH₃ | -CO- | 2-CH₃ | 8-F |
| 5 | 4-CH₃ | -SO₂- | 2-CH₃ | H | 41 | 4-CH₃ | -SO₂- | 2-CH₃ | 8-F |
| 6 | 4-CH₃ | -CH₂- | 2-CH₃ | H | 42 | 4-CH₃ | -CH₂- | 2-CH₃ | 8-F |
| 7 | 4-Cl | -CO- | 2-CH₃ | H | 43 | 4-Cl | -CO- | 2-CH₃ | 8-F |
| 8 | 4-Cl | -SO₂- | 2-CH₃ | H | 44 | 4-Cl | -SO₂- | 2-CH₃ | 8-F |
| 9 | 4-Cl | -CH₂- | 2-CH₃ | H | 45 | 4-Cl | -CH₂- | 2-CH₃ | 8-F |
| 10 | 4-F | -CO- | 2-CH₃ | H | 46 | 4-F | -CO- | 2-CH₃ | 8-F |
| 11 | 4-F | -SO₂- | 2-CH₃ | H | 47 | 4-F | -SO₂- | 2-CH₃ | 8-F |
| 12 | 4-F | -CH₂- | 2-CH₃ | H | 48 | 4-F | -CH₂- | 2-CH₃ | 8-F |
| 13 | H | -CO- | 2-Cl | H | 49 | H | -CO- | 2-Cl | 8-F |
| 14 | H | -SO₂- | 2-Cl | H | 50 | H | -SO₂- | 2-Cl | 8-F |
| 15 | H | -CH₂- | 2-Cl | H | 51 | H | -CH₂- | 2-Cl | 8-F |
| 16 | 4-CH₃ | -CO- | 2-Cl | H | 52 | 4-CH₃ | -CO- | 2-Cl | 8-F |
| 17 | 4-CH₃ | -SO₂- | 2-Cl | H | 53 | 4-CH₃ | -SO₂- | 2-Cl | 8-F |
| 18 | 4-CH₃ | -CH₂- | 2-Cl | H | 54 | 4-CH₃ | -CH₂- | 2-Cl | 8-F |
| 19 | 4-Cl | -CO- | 2-Cl | H | 55 | 4-Cl | -CO- | 2-Cl | 8-F |
| 20 | 4-Cl | -SO₂- | 2-Cl | H | 56 | 4-Cl | -SO₂- | 2-Cl | 8-F |
| 21 | 4-Cl | -CH₂- | 2-Cl | H | 57 | 4-Cl | -CH₂- | 2-Cl | 8-F |
| 22 | 4-F | -CO- | 2-Cl | H | 58 | 4-F | -CO- | 2-Cl | 8-F |
| 23 | 4-F | -SO₂- | 2-Cl | H | 59 | 4-F | -SO₂- | 2-Cl | 8-F |
| 24 | 4-F | -CH₂- | 2-Cl | H | 60 | 4-F | -CH₂- | 2-Cl | 8-F |
| 25 | H | -CO- | 2-F | H | 61 | H | -CO- | 2-F | 8-F |
| 26 | H | -SO₂- | 2-F | H | 62 | H | -SO₂- | 2-F | 8-F |
| 27 | H | -CH₂- | 2-F | H | 63 | H | -CH₂- | 2-F | 8-F |
| 28 | 4-CH₃ | -CO- | 2-F | H | 64 | 4-CH₃ | -CO- | 2-F | 8-F |
| 29 | 4-CH₃ | -SO₂- | 2-F | H | 65 | 4-CH₃ | -SO₂- | 2-F | 8-F |
| 30 | 4-CH₃ | -CH₂- | 2-F | H | 66 | 4-CH₃ | -CH₂- | 2-F | 8-F |
| 31 | 4-Cl | -CO- | 2-F | H | 67 | 4-Cl | -CO- | 2-F | 8-F |
| 32 | 4-Cl | -SO₂- | 2-F | H | 68 | 4-Cl | -SO₂- | 2-F | 8-F |
| 33 | 4-Cl | -CH₂- | 2-F | H | 69 | 4-Cl | -CH₂- | 2-F | 8-F |
| 34 | 4-F | -CO- | 2-F | H | 70 | 4-F | -CO- | 2-F | 8-F |
| 35 | 4-F | -SO₂- | 2-F | H | 71 | 4-F | -SO₂- | 2-F | 8-F |
| 36 | 4-F | -CH₂- | 2-F | H | 72 | 4-F | -CH₂- | 2-F | 8-F |

Figure 12

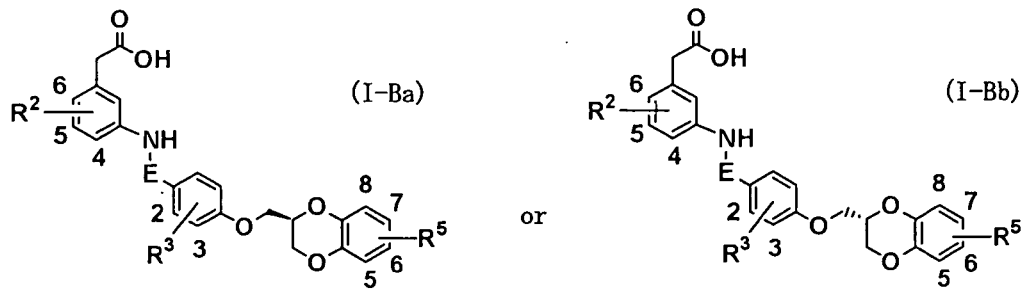

| No. | R² | E | R³ | R⁵ | No. | R² | E | R³ | R⁵ |
|---|---|---|---|---|---|---|---|---|---|
| 1 | H | -CO- | 2-CH₃ | 5-F | 37 | H | -CO- | 2-CH₃ | 7-F |
| 2 | H | -SO₂- | 2-CH₃ | 5-F | 38 | H | -SO₂- | 2-CH₃ | 7-F |
| 3 | H | -CH₂- | 2-CH₃ | 5-F | 39 | H | -CH₂- | 2-CH₃ | 7-F |
| 4 | 4-CH₃ | -CO- | 2-CH₃ | 5-F | 40 | 4-CH₃ | -CO- | 2-CH₃ | 7-F |
| 5 | 4-CH₃ | -SO₂- | 2-CH₃ | 5-F | 41 | 4-CH₃ | -SO₂- | 2-CH₃ | 7-F |
| 6 | 4-CH₃ | -CH₂- | 2-CH₃ | 5-F | 42 | 4-CH₃ | -CH₂- | 2-CH₃ | 7-F |
| 7 | 4-Cl | -CO- | 2-CH₃ | 5-F | 43 | 4-Cl | -CO- | 2-CH₃ | 7-F |
| 8 | 4-Cl | -SO₂- | 2-CH₃ | 5-F | 44 | 4-Cl | -SO₂- | 2-CH₃ | 7-F |
| 9 | 4-Cl | -CH₂- | 2-CH₃ | 5-F | 45 | 4-Cl | -CH₂- | 2-CH₃ | 7-F |
| 10 | 4-F | -CO- | 2-CH₃ | 5-F | 46 | 4-F | -CO- | 2-CH₃ | 7-F |
| 11 | 4-F | -SO₂- | 2-CH₃ | 5-F | 47 | 4-F | -SO₂- | 2-CH₃ | 7-F |
| 12 | 4-F | -CH₂- | 2-CH₃ | 5-F | 48 | 4-F | -CH₂- | 2-CH₃ | 7-F |
| 13 | H | -CO- | 2-Cl | 5-F | 49 | H | -CO- | 2-Cl | 7-F |
| 14 | H | -SO₂- | 2-Cl | 5-F | 50 | H | -SO₂- | 2-Cl | 7-F |
| 15 | H | -CH₂- | 2-Cl | 5-F | 51 | H | -CH₂- | 2-Cl | 7-F |
| 16 | 4-CH₃ | -CO- | 2-Cl | 5-F | 52 | 4-CH₃ | -CO- | 2-Cl | 7-F |
| 17 | 4-CH₃ | -SO₂- | 2-Cl | 5-F | 53 | 4-CH₃ | -SO₂- | 2-Cl | 7-F |
| 18 | 4-CH₃ | -CH₂- | 2-Cl | 5-F | 54 | 4-CH₃ | -CH₂- | 2-Cl | 7-F |
| 19 | 4-Cl | -CO- | 2-Cl | 5-F | 55 | 4-Cl | -CO- | 2-Cl | 7-F |
| 20 | 4-Cl | -SO₂- | 2-Cl | 5-F | 56 | 4-Cl | -SO₂- | 2-Cl | 7-F |
| 21 | 4-Cl | -CH₂- | 2-Cl | 5-F | 57 | 4-Cl | -CH₂- | 2-Cl | 7-F |
| 22 | 4-F | -CO- | 2-Cl | 5-F | 58 | 4-F | -CO- | 2-Cl | 7-F |
| 23 | 4-F | -SO₂- | 2-Cl | 5-F | 59 | 4-F | -SO₂- | 2-Cl | 7-F |
| 24 | 4-F | -CH₂- | 2-Cl | 5-F | 60 | 4-F | -CH₂- | 2-Cl | 7-F |
| 25 | H | -CO- | 2-F | 5-F | 61 | H | -CO- | 2-F | 7-F |
| 26 | H | -SO₂- | 2-F | 5-F | 62 | H | -SO₂- | 2-F | 7-F |
| 27 | H | -CH₂- | 2-F | 5-F | 63 | H | -CH₂- | 2-F | 7-F |
| 28 | 4-CH₃ | -CO- | 2-F | 5-F | 64 | 4-CH₃ | -CO- | 2-F | 7-F |
| 29 | 4-CH₃ | -SO₂- | 2-F | 5-F | 65 | 4-CH₃ | -SO₂- | 2-F | 7-F |
| 30 | 4-CH₃ | -CH₂- | 2-F | 5-F | 66 | 4-CH₃ | -CH₂- | 2-F | 7-F |
| 31 | 4-Cl | -CO- | 2-F | 5-F | 67 | 4-Cl | -CO- | 2-F | 7-F |
| 32 | 4-Cl | -SO₂- | 2-F | 5-F | 68 | 4-Cl | -SO₂- | 2-F | 7-F |
| 33 | 4-Cl | -CH₂- | 2-F | 5-F | 69 | 4-Cl | -CH₂- | 2-F | 7-F |
| 34 | 4-F | -CO- | 2-F | 5-F | 70 | 4-F | -CO- | 2-F | 7-F |
| 35 | 4-F | -SO₂- | 2-F | 5-F | 71 | 4-F | -SO₂- | 2-F | 7-F |
| 36 | 4-F | -CH₂- | 2-F | 5-F | 72 | 4-F | -CH₂- | 2-F | 7-F |

Figure 13

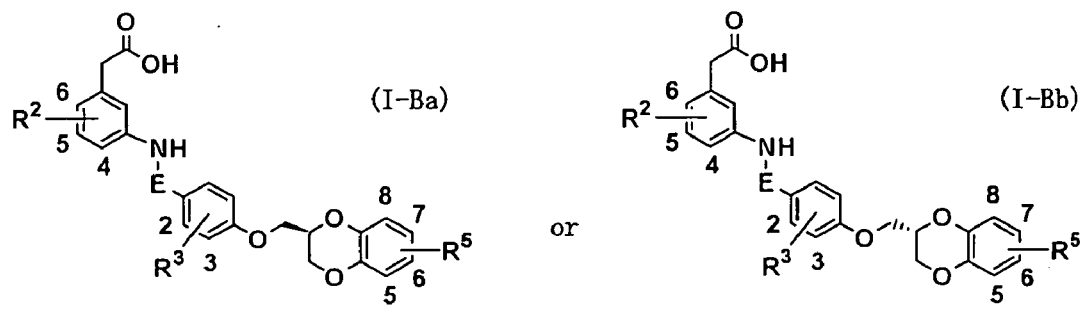

| No. | R² | E | R³ | R⁵ | No. | R² | E | R³ | R⁵ |
|---|---|---|---|---|---|---|---|---|---|
| 1 | 5-CH₃ | -CO- | 2-CH₃ | H | 25 | 5-CH₃ | -CO- | 2-CH₃ | 5-F |
| 2 | 5-CH₃ | -SO₂- | 2-CH₃ | H | 26 | 5-CH₃ | -SO₂- | 2-CH₃ | 5-F |
| 3 | 5-CH₃ | -CH₂- | 2-CH₃ | H | 27 | 5-CH₃ | -CH₂- | 2-CH₃ | 5-F |
| 4 | 5-Cl | -CO- | 2-Cl | H | 28 | 5-Cl | -CO- | 2-Cl | 5-F |
| 5 | 5-Cl | -SO₂- | 2-Cl | H | 29 | 5-Cl | -SO₂- | 2-Cl | 5-F |
| 6 | 5-Cl | -CH₂- | 2-Cl | H | 30 | 5-Cl | -CH₂- | 2-Cl | 5-F |
| 7 | 5-CH₃ | -CO- | 2-Cl | H | 31 | 5-CH₃ | -CO- | 2-Cl | 5-F |
| 8 | 5-CH₃ | -SO₂- | 2-Cl | H | 32 | 5-CH₃ | -SO₂- | 2-Cl | 5-F |
| 9 | 5-CH₃ | -CH₂- | 2-Cl | H | 33 | 5-CH₃ | -CH₂- | 2-Cl | 5-F |
| 10 | 5-F | -CO- | 2-Cl | H | 34 | 5-F | -CO- | 2-Cl | 5-F |
| 11 | 5-F | -SO₂- | 2-Cl | H | 35 | 5-F | -SO₂- | 2-Cl | 5-F |
| 12 | 5-F | -CH₂- | 2-Cl | H | 36 | 5-F | -CH₂- | 2-Cl | 5-F |
| 13 | 5-CH₃ | -CO- | 2-CH₃ | 8-F | 37 | 5-CH₃ | -CO- | 2-CH₃ | 7-F |
| 14 | 5-CH₃ | -SO₂- | 2-CH₃ | 8-F | 38 | 5-CH₃ | -SO₂- | 2-CH₃ | 7-F |
| 15 | 5-CH₃ | -CH₂- | 2-CH₃ | 8-F | 39 | 5-CH₃ | -CH₂- | 2-CH₃ | 7-F |
| 16 | 5-Cl | -CO- | 2-Cl | 8-F | 40 | 5-Cl | -CO- | 2-Cl | 7-F |
| 17 | 5-Cl | -SO₂- | 2-Cl | 8-F | 41 | 5-Cl | -SO₂- | 2-Cl | 7-F |
| 18 | 5-Cl | -CH₂- | 2-Cl | 8-F | 42 | 5-Cl | -CH₂- | 2-Cl | 7-F |
| 19 | 5-CH₃ | -CO- | 2-Cl | 8-F | 43 | 5-CH₃ | -CO- | 2-Cl | 7-F |
| 20 | 5-CH₃ | -SO₂- | 2-Cl | 8-F | 44 | 5-CH₃ | -SO₂- | 2-Cl | 7-F |
| 21 | 5-CH₃ | -CH₂- | 2-Cl | 8-F | 45 | 5-CH₃ | -CH₂- | 2-Cl | 7-F |
| 22 | 5-F | -CO- | 2-Cl | 8-F | 46 | 5-F | -CO- | 2-Cl | 7-F |
| 23 | 5-F | -SO₂- | 2-Cl | 8-F | 47 | 5-F | -SO₂- | 2-Cl | 7-F |
| 24 | 5-F | -CH₂- | 2-Cl | 8-F | 48 | 5-F | -CH₂- | 2-Cl | 7-F |

Figure 14

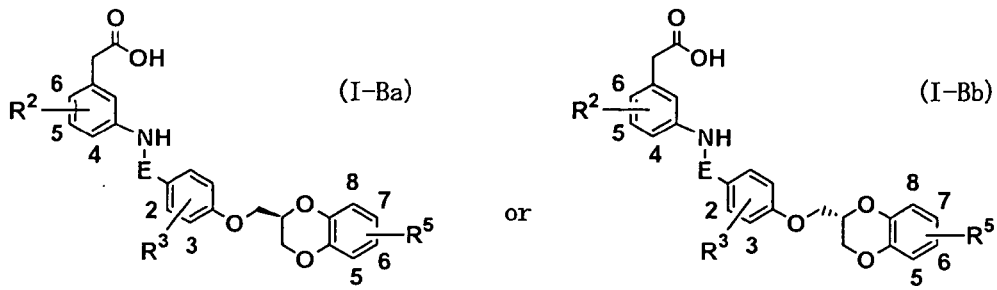

| No. | R² | E | R³ | R⁵ | No. | R² | E | R³ | R⁵ |
|---|---|---|---|---|---|---|---|---|---|
| 1 | 4-CH₃ | -CO- | 3-CH₃ | H | 25 | 4-CH₃ | -CO- | 3-CH₃ | 5-F |
| 2 | 4-CH₃ | -SO₂- | 3-CH₃ | H | 26 | 4-CH₃ | -SO₂- | 3-CH₃ | 5-F |
| 3 | 4-CH₃ | -CH₂- | 3-CH₃ | H | 27 | 4-CH₃ | -CH₂- | 3-CH₃ | 5-F |
| 4 | 4-Cl | -CO- | 3-CH₃ | H | 28 | 4-Cl | -CO- | 3-CH₃ | 5-F |
| 5 | 4-Cl | -SO₂- | 3-CH₃ | H | 29 | 4-Cl | -SO₂- | 3-CH₃ | 5-F |
| 6 | 4-Cl | -CH₂- | 3-CH₃ | H | 30 | 4-Cl | -CH₂- | 3-CH₃ | 5-F |
| 7 | 4-Cl | -CO- | 3-Cl | H | 31 | 4-Cl | -CO- | 3-Cl | 5-F |
| 8 | 4-Cl | -SO₂- | 3-Cl | H | 32 | 4-Cl | -SO₂- | 3-Cl | 5-F |
| 9 | 4-Cl | -CH₂- | 3-Cl | H | 33 | 4-Cl | -CH₂- | 3-Cl | 5-F |
| 10 | 4-CH₃ | -CO- | 3-Cl | H | 34 | 4-CH₃ | -CO- | 3-Cl | 5-F |
| 11 | 4-CH₃ | -SO₂- | 3-Cl | H | 35 | 4-CH₃ | -SO₂- | 3-Cl | 5-F |
| 12 | 4-CH₃ | -CH₂- | 3-Cl | H | 36 | 4-CH₃ | -CH₂- | 3-Cl | 5-F |
| 13 | 4-CH₃ | -CO- | 3-CH₃ | 8-F | 37 | 4-CH₃ | -CO- | 3-CH₃ | 7-F |
| 14 | 4-CH₃ | -SO₂- | 3-CH₃ | 8-F | 38 | 4-CH₃ | -SO₂- | 3-CH₃ | 7-F |
| 15 | 4-CH₃ | -CH₂- | 3-CH₃ | 8-F | 39 | 4-CH₃ | -CH₂- | 3-CH₃ | 7-F |
| 16 | 4-Cl | -CO- | 3-CH₃ | 8-F | 40 | 4-Cl | -CO- | 3-CH₃ | 7-F |
| 17 | 4-Cl | -SO₂- | 3-CH₃ | 8-F | 41 | 4-Cl | -SO₂- | 3-CH₃ | 7-F |
| 18 | 4-Cl | -CH₂- | 3-CH₃ | 8-F | 42 | 4-Cl | -CH₂- | 3-CH₃ | 7-F |
| 19 | 4-Cl | -CO- | 3-Cl | 8-F | 43 | 4-Cl | -CO- | 3-Cl | 7-F |
| 20 | 4-Cl | -SO₂- | 3-Cl | 8-F | 44 | 4-Cl | -SO₂- | 3-Cl | 7-F |
| 21 | 4-Cl | -CH₂- | 3-Cl | 8-F | 45 | 4-Cl | -CH₂- | 3-Cl | 7-F |
| 22 | 4-CH₃ | -CO- | 3-Cl | 8-F | 46 | 4-CH₃ | -CO- | 3-Cl | 7-F |
| 23 | 4-CH₃ | -SO₂- | 3-Cl | 8-F | 47 | 4-CH₃ | -SO₂- | 3-Cl | 7-F |
| 24 | 4-CH₃ | -CH₂- | 3-Cl | 8-F | 48 | 4-CH₃ | -CH₂- | 3-Cl | 7-F |

Figure 15

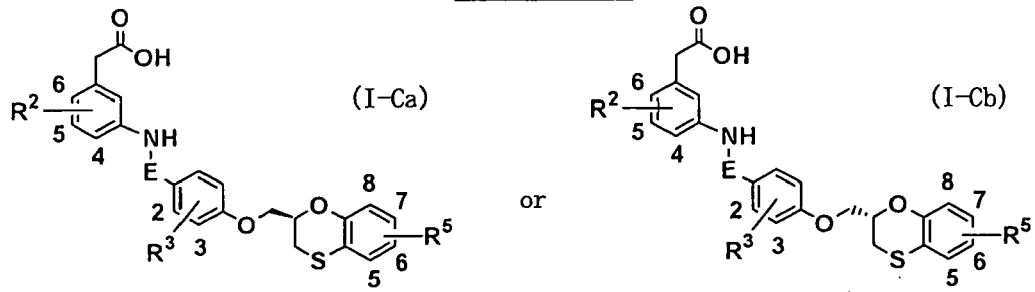

| No. | R² | E | R³ | R⁵ | | No. | R² | E | R³ | R⁵ |
|---|---|---|---|---|---|---|---|---|---|---|
| 1 | H | -CO- | 2-CH₃ | H | | 37 | H | -CO- | 2-CH₃ | 8-F |
| 2 | H | -SO₂- | 2-CH₃ | H | | 38 | H | -SO₂- | 2-CH₃ | 8-F |
| 3 | H | -CH₂- | 2-CH₃ | H | | 39 | H | -CH₂- | 2-CH₃ | 8-F |
| 4 | 4-CH₃ | -CO- | 2-CH₃ | H | | 40 | 4-CH₃ | -CO- | 2-CH₃ | 8-F |
| 5 | 4-CH₃ | -SO₂- | 2-CH₃ | H | | 41 | 4-CH₃ | -SO₂- | 2-CH₃ | 8-F |
| 6 | 4-CH₃ | -CH₂- | 2-CH₃ | H | | 42 | 4-CH₃ | -CH₂- | 2-CH₃ | 8-F |
| 7 | 4-Cl | -CO- | 2-CH₃ | H | | 43 | 4-Cl | -CO- | 2-CH₃ | 8-F |
| 8 | 4-Cl | -SO₂- | 2-CH₃ | H | | 44 | 4-Cl | -SO₂- | 2-CH₃ | 8-F |
| 9 | 4-Cl | -CH₂- | 2-CH₃ | H | | 45 | 4-Cl | -CH₂- | 2-CH₃ | 8-F |
| 10 | 4-F | -CO- | 2-CH₃ | H | | 46 | 4-F | -CO- | 2-CH₃ | 8-F |
| 11 | 4-F | -SO₂- | 2-CH₃ | H | | 47 | 4-F | -SO₂- | 2-CH₃ | 8-F |
| 12 | 4-F | -CH₂- | 2-CH₃ | H | | 48 | 4-F | -CH₂- | 2-CH₃ | 8-F |
| 13 | H | -CO- | 2-Cl | H | | 49 | H | -CO- | 2-Cl | 8-F |
| 14 | H | -SO₂- | 2-Cl | H | | 50 | H | -SO₂- | 2-Cl | 8-F |
| 15 | H | -CH₂- | 2-Cl | H | | 51 | H | -CH₂- | 2-Cl | 8-F |
| 16 | 4-CH₃ | -CO- | 2-Cl | H | | 52 | 4-CH₃ | -CO- | 2-Cl | 8-F |
| 17 | 4-CH₃ | -SO₂- | 2-Cl | H | | 53 | 4-CH₃ | -SO₂- | 2-Cl | 8-F |
| 18 | 4-CH₃ | -CH₂- | 2-Cl | H | | 54 | 4-CH₃ | -CH₂- | 2-Cl | 8-F |
| 19 | 4-Cl | -CO- | 2-Cl | H | | 55 | 4-Cl | -CO- | 2-Cl | 8-F |
| 20 | 4-Cl | -SO₂- | 2-Cl | H | | 56 | 4-Cl | -SO₂- | 2-Cl | 8-F |
| 21 | 4-Cl | -CH₂- | 2-Cl | H | | 57 | 4-Cl | -CH₂- | 2-Cl | 8-F |
| 22 | 4-F | -CO- | 2-Cl | H | | 58 | 4-F | -CO- | 2-Cl | 8-F |
| 23 | 4-F | -SO₂- | 2-Cl | H | | 59 | 4-F | -SO₂- | 2-Cl | 8-F |
| 24 | 4-F | -CH₂- | 2-Cl | H | | 60 | 4-F | -CH₂- | 2-Cl | 8-F |
| 25 | H | -CO- | 2-F | H | | 61 | H | -CO- | 2-F | 8-F |
| 26 | H | -SO₂- | 2-F | H | | 62 | H | -SO₂- | 2-F | 8-F |
| 27 | H | -CH₂- | 2-F | H | | 63 | H | -CH₂- | 2-F | 8-F |
| 28 | 4-CH₃ | -CO- | 2-F | H | | 64 | 4-CH₃ | -CO- | 2-F | 8-F |
| 29 | 4-CH₃ | -SO₂- | 2-F | H | | 65 | 4-CH₃ | -SO₂- | 2-F | 8-F |
| 30 | 4-CH₃ | -CH₂- | 2-F | H | | 66 | 4-CH₃ | -CH₂- | 2-F | 8-F |
| 31 | 4-Cl | -CO- | 2-F | H | | 67 | 4-Cl | -CO- | 2-F | 8-F |
| 32 | 4-Cl | -SO₂- | 2-F | H | | 68 | 4-Cl | -SO₂- | 2-F | 8-F |
| 33 | 4-Cl | -CH₂- | 2-F | H | | 69 | 4-Cl | -CH₂- | 2-F | 8-F |
| 34 | 4-F | -CO- | 2-F | H | | 70 | 4-F | -CO- | 2-F | 8-F |
| 35 | 4-F | -SO₂- | 2-F | H | | 71 | 4-F | -SO₂- | 2-F | 8-F |
| 36 | 4-F | -CH₂- | 2-F | H | | 72 | 4-F | -CH₂- | 2-F | 8-F |

Figure 16

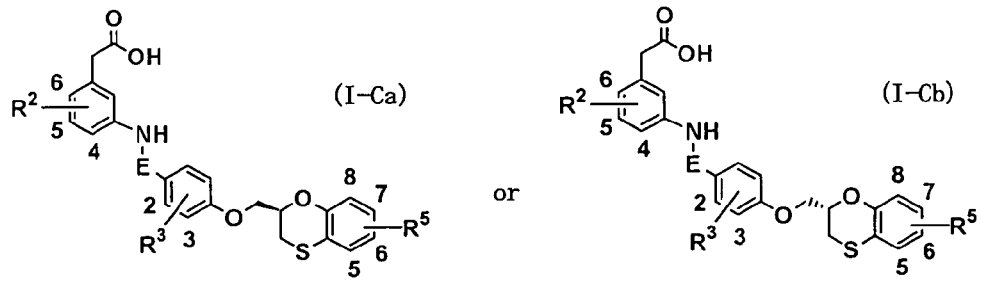

| No. | $R^2$ | E | $R^3$ | $R^5$ | No. | $R^2$ | E | $R^3$ | $R^5$ |
|---|---|---|---|---|---|---|---|---|---|
| 1 | H | -CO- | 2-CH$_3$ | 5-F | 37 | H | -CO- | 2-CH$_3$ | 7-F |
| 2 | H | -SO$_2$- | 2-CH$_3$ | 5-F | 38 | H | -SO$_2$- | 2-CH$_3$ | 7-F |
| 3 | H | -CH$_2$- | 2-CH$_3$ | 5-F | 39 | H | -CH$_2$- | 2-CH$_3$ | 7-F |
| 4 | 4-CH$_3$ | -CO- | 2-CH$_3$ | 5-F | 40 | 4-CH$_3$ | -CO- | 2-CH$_3$ | 7-F |
| 5 | 4-CH$_3$ | -SO$_2$- | 2-CH$_3$ | 5-F | 41 | 4-CH$_3$ | -SO$_2$- | 2-CH$_3$ | 7-F |
| 6 | 4-CH$_3$ | -CH$_2$- | 2-CH$_3$ | 5-F | 42 | 4-CH$_3$ | -CH$_2$- | 2-CH$_3$ | 7-F |
| 7 | 4-Cl | -CO- | 2-CH$_3$ | 5-F | 43 | 4-Cl | -CO- | 2-CH$_3$ | 7-F |
| 8 | 4-Cl | -SO$_2$- | 2-CH$_3$ | 5-F | 44 | 4-Cl | -SO$_2$- | 2-CH$_3$ | 7-F |
| 9 | 4-Cl | -CH$_2$- | 2-CH$_3$ | 5-F | 45 | 4-Cl | -CH$_2$- | 2-CH$_3$ | 7-F |
| 10 | 4-F | -CO- | 2-CH$_3$ | 5-F | 46 | 4-F | -CO- | 2-CH$_3$ | 7-F |
| 11 | 4-F | -SO$_2$- | 2-CH$_3$ | 5-F | 47 | 4-F | -SO$_2$- | 2-CH$_3$ | 7-F |
| 12 | 4-F | -CH$_2$- | 2-CH$_3$ | 5-F | 48 | 4-F | -CH$_2$- | 2-CH$_3$ | 7-F |
| 13 | H | -CO- | 2-Cl | 5-F | 49 | H | -CO- | 2-Cl | 7-F |
| 14 | H | -SO$_2$- | 2-Cl | 5-F | 50 | H | -SO$_2$- | 2-Cl | 7-F |
| 15 | H | -CH$_2$- | 2-Cl | 5-F | 51 | H | -CH$_2$- | 2-Cl | 7-F |
| 16 | 4-CH$_3$ | -CO- | 2-Cl | 5-F | 52 | 4-CH$_3$ | -CO- | 2-Cl | 7-F |
| 17 | 4-CH$_3$ | -SO$_2$- | 2-Cl | 5-F | 53 | 4-CH$_3$ | -SO$_2$- | 2-Cl | 7-F |
| 18 | 4-CH$_3$ | -CH$_2$- | 2-Cl | 5-F | 54 | 4-CH$_3$ | -CH$_2$- | 2-Cl | 7-F |
| 19 | 4-Cl | -CO- | 2-Cl | 5-F | 55 | 4-Cl | -CO- | 2-Cl | 7-F |
| 20 | 4-Cl | -SO$_2$- | 2-Cl | 5-F | 56 | 4-Cl | -SO$_2$- | 2-Cl | 7-F |
| 21 | 4-Cl | -CH$_2$- | 2-Cl | 5-F | 57 | 4-Cl | -CH$_2$- | 2-Cl | 7-F |
| 22 | 4-F | -CO- | 2-Cl | 5-F | 58 | 4-F | -CO- | 2-Cl | 7-F |
| 23 | 4-F | -SO$_2$- | 2-Cl | 5-F | 59 | 4-F | -SO$_2$- | 2-Cl | 7-F |
| 24 | 4-F | -CH$_2$- | 2-Cl | 5-F | 60 | 4-F | -CH$_2$- | 2-Cl | 7-F |
| 25 | H | -CO- | 2-F | 5-F | 61 | H | -CO- | 2-F | 7-F |
| 26 | H | -SO$_2$- | 2-F | 5-F | 62 | H | -SO$_2$- | 2-F | 7-F |
| 27 | H | -CH$_2$- | 2-F | 5-F | 63 | H | -CH$_2$- | 2-F | 7-F |
| 28 | 4-CH$_3$ | -CO- | 2-F | 5-F | 64 | 4-CH$_3$ | -CO- | 2-F | 7-F |
| 29 | 4-CH$_3$ | -SO$_2$- | 2-F | 5-F | 65 | 4-CH$_3$ | -SO$_2$- | 2-F | 7-F |
| 30 | 4-CH$_3$ | -CH$_2$- | 2-F | 5-F | 66 | 4-CH$_3$ | -CH$_2$- | 2-F | 7-F |
| 31 | 4-Cl | -CO- | 2-F | 5-F | 67 | 4-Cl | -CO- | 2-F | 7-F |
| 32 | 4-Cl | -SO$_2$- | 2-F | 5-F | 68 | 4-Cl | -SO$_2$- | 2-F | 7-F |
| 33 | 4-Cl | -CH$_2$- | 2-F | 5-F | 69 | 4-Cl | -CH$_2$- | 2-F | 7-F |
| 34 | 4-F | -CO- | 2-F | 5-F | 70 | 4-F | -CO- | 2-F | 7-F |
| 35 | 4-F | -SO$_2$- | 2-F | 5-F | 71 | 4-F | -SO$_2$- | 2-F | 7-F |
| 36 | 4-F | -CH$_2$- | 2-F | 5-F | 72 | 4-F | -CH$_2$- | 2-F | 7-F |

Figure 17

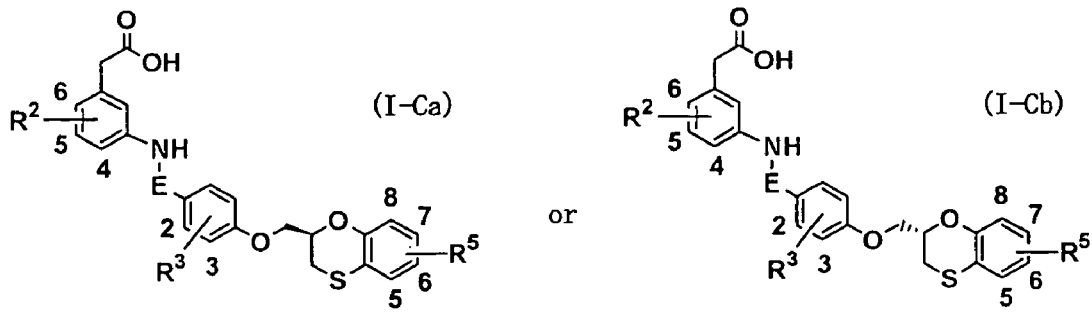

| No. | R² | E | R³ | R⁵ | No. | R² | E | R³ | R⁵ |
|---|---|---|---|---|---|---|---|---|---|
| 1 | 5-CH₃ | -CO- | 2-CH₃ | H | 25 | 5-CH₃ | -CO- | 2-CH₃ | 5-F |
| 2 | 5-CH₃ | -SO₂- | 2-CH₃ | H | 26 | 5-CH₃ | -SO₂- | 2-CH₃ | 5-F |
| 3 | 5-CH₃ | -CH₂- | 2-CH₃ | H | 27 | 5-CH₃ | -CH₂- | 2-CH₃ | 5-F |
| 4 | 5-Cl | -CO- | 2-Cl | H | 28 | 5-Cl | -CO- | 2-Cl | 5-F |
| 5 | 5-Cl | -SO₂- | 2-Cl | H | 29 | 5-Cl | -SO₂- | 2-Cl | 5-F |
| 6 | 5-Cl | -CH₂- | 2-Cl | H | 30 | 5-Cl | -CH₂- | 2-Cl | 5-F |
| 7 | 5-CH₃ | -CO- | 2-Cl | H | 31 | 5-CH₃ | -CO- | 2-Cl | 5-F |
| 8 | 5-CH₃ | -SO₂- | 2-Cl | H | 32 | 5-CH₃ | -SO₂- | 2-Cl | 5-F |
| 9 | 5-CH₃ | -CH₂- | 2-Cl | H | 33 | 5-CH₃ | -CH₂- | 2-Cl | 5-F |
| 10 | 5-F | -CO- | 2-Cl | H | 34 | 5-F | -CO- | 2-Cl | 5-F |
| 11 | 5-F | -SO₂- | 2-Cl | H | 35 | 5-F | -SO₂- | 2-Cl | 5-F |
| 12 | 5-F | -CH₂- | 2-Cl | H | 36 | 5-F | -CH₂- | 2-Cl | 5-F |
| 13 | 5-CH₃ | -CO- | 2-CH₃ | 8-F | 37 | 5-CH₃ | -CO- | 2-CH₃ | 7-F |
| 14 | 5-CH₃ | -SO₂- | 2-CH₃ | 8-F | 38 | 5-CH₃ | -SO₂- | 2-CH₃ | 7-F |
| 15 | 5-CH₃ | -CH₂- | 2-CH₃ | 8-F | 39 | 5-CH₃ | -CH₂- | 2-CH₃ | 7-F |
| 16 | 5-Cl | -CO- | 2-Cl | 8-F | 40 | 5-Cl | -CO- | 2-Cl | 7-F |
| 17 | 5-Cl | -SO₂- | 2-Cl | 8-F | 41 | 5-Cl | -SO₂- | 2-Cl | 7-F |
| 18 | 5-Cl | -CH₂- | 2-Cl | 8-F | 42 | 5-Cl | -CH₂- | 2-Cl | 7-F |
| 19 | 5-CH₃ | -CO- | 2-Cl | 8-F | 43 | 5-CH₃ | -CO- | 2-Cl | 7-F |
| 20 | 5-CH₃ | -SO₂- | 2-Cl | 8-F | 44 | 5-CH₃ | -SO₂- | 2-Cl | 7-F |
| 21 | 5-CH₃ | -CH₂- | 2-Cl | 8-F | 45 | 5-CH₃ | -CH₂- | 2-Cl | 7-F |
| 22 | 5-F | -CO- | 2-Cl | 8-F | 46 | 5-F | -CO- | 2-Cl | 7-F |
| 23 | 5-F | -SO₂- | 2-Cl | 8-F | 47 | 5-F | -SO₂- | 2-Cl | 7-F |
| 24 | 5-F | -CH₂- | 2-Cl | 8-F | 48 | 5-F | -CH₂- | 2-Cl | 7-F |

Figure 1 8

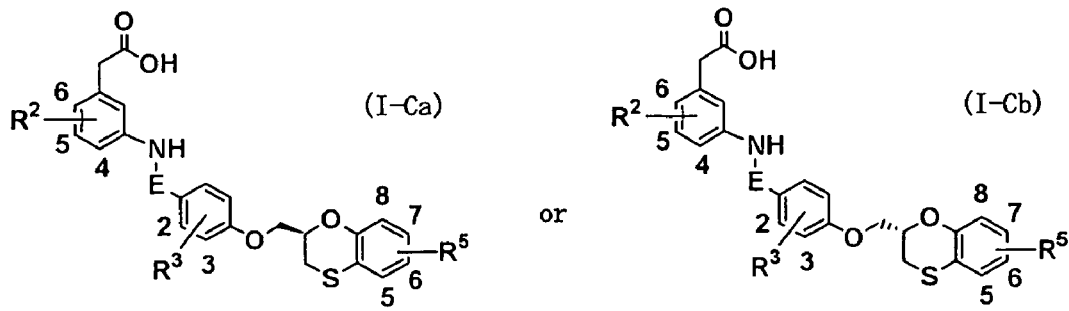

(I-Ca) or (I-Cb)

| No. | R² | E | R³ | R⁵ | No. | R² | E | R³ | R⁵ |
|---|---|---|---|---|---|---|---|---|---|
| 1 | 4-CH₃ | -CO- | 3-CH₃ | H | 25 | 4-CH₃ | -CO- | 3-CH₃ | 5-F |
| 2 | 4-CH₃ | -SO₂- | 3-CH₃ | H | 26 | 4-CH₃ | -SO₂- | 3-CH₃ | 5-F |
| 3 | 4-CH₃ | -CH₂- | 3-CH₃ | H | 27 | 4-CH₃ | -CH₂- | 3-CH₃ | 5-F |
| 4 | 4-Cl | -CO- | 3-CH₃ | H | 28 | 4-Cl | -CO- | 3-CH₃ | 5-F |
| 5 | 4-Cl | -SO₂- | 3-CH₃ | H | 29 | 4-Cl | -SO₂- | 3-CH₃ | 5-F |
| 6 | 4-Cl | -CH₂- | 3-CH₃ | H | 30 | 4-Cl | -CH₂- | 3-CH₃ | 5-F |
| 7 | 4-Cl | -CO- | 3-Cl | H | 31 | 4-Cl | -CO- | 3-Cl | 5-F |
| 8 | 4-Cl | -SO₂- | 3-Cl | H | 32 | 4-Cl | -SO₂- | 3-Cl | 5-F |
| 9 | 4-Cl | -CH₂- | 3-Cl | H | 33 | 4-Cl | -CH₂- | 3-Cl | 5-F |
| 10 | 4-CH₃ | -CO- | 3-Cl | H | 34 | 4-CH₃ | -CO- | 3-Cl | 5-F |
| 11 | 4-CH₃ | -SO₂- | 3-Cl | H | 35 | 4-CH₃ | -SO₂- | 3-Cl | 5-F |
| 12 | 4-CH₃ | -CH₂- | 3-Cl | H | 36 | 4-CH₃ | -CH₂- | 3-Cl | 5-F |
| 13 | 4-CH₃ | -CO- | 3-CH₃ | 8-F | 37 | 4-CH₃ | -CO- | 3-CH₃ | 7-F |
| 14 | 4-CH₃ | -SO₂- | 3-CH₃ | 8-F | 38 | 4-CH₃ | -SO₂- | 3-CH₃ | 7-F |
| 15 | 4-CH₃ | -CH₂- | 3-CH₃ | 8-F | 39 | 4-CH₃ | -CH₂- | 3-CH₃ | 7-F |
| 16 | 4-Cl | -CO- | 3-CH₃ | 8-F | 40 | 4-Cl | -CO- | 3-CH₃ | 7-F |
| 17 | 4-Cl | -SO₂- | 3-CH₃ | 8-F | 41 | 4-Cl | -SO₂- | 3-CH₃ | 7-F |
| 18 | 4-Cl | -CH₂- | 3-CH₃ | 8-F | 42 | 4-Cl | -CH₂- | 3-CH₃ | 7-F |
| 19 | 4-Cl | -CO- | 3-Cl | 8-F | 43 | 4-Cl | -CO- | 3-Cl | 7-F |
| 20 | 4-Cl | -SO₂- | 3-Cl | 8-F | 44 | 4-Cl | -SO₂- | 3-Cl | 7-F |
| 21 | 4-Cl | -CH₂- | 3-Cl | 8-F | 45 | 4-Cl | -CH₂- | 3-Cl | 7-F |
| 22 | 4-CH₃ | -CO- | 3-Cl | 8-F | 46 | 4-CH₃ | -CO- | 3-Cl | 7-F |
| 23 | 4-CH₃ | -SO₂- | 3-Cl | 8-F | 47 | 4-CH₃ | -SO₂- | 3-Cl | 7-F |
| 24 | 4-CH₃ | -CH₂- | 3-Cl | 8-F | 48 | 4-CH₃ | -CH₂- | 3-Cl | 7-F |

Figure 19

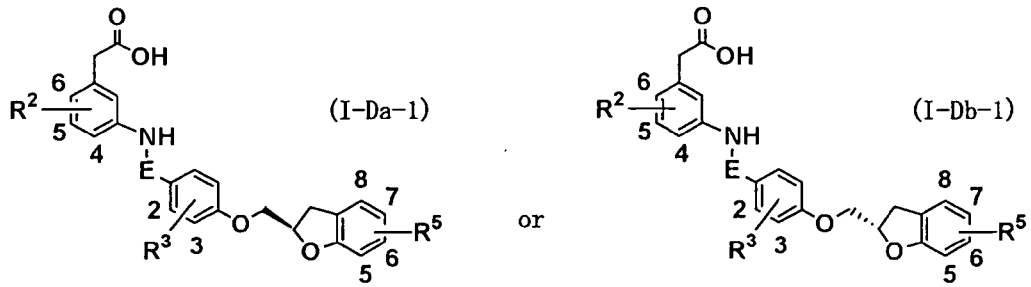

| No. | R² | E | R³ | R⁵ | No. | R² | E | R³ | R⁵ |
|---|---|---|---|---|---|---|---|---|---|
| 1 | H | -CO- | 2-CH₃ | H | 37 | H | -CO- | 2-CH₃ | 7-F |
| 2 | H | -SO₂- | 2-CH₃ | H | 38 | H | -SO₂- | 2-CH₃ | 7-F |
| 3 | H | -CH₂- | 2-CH₃ | H | 39 | H | -CH₂- | 2-CH₃ | 7-F |
| 4 | 4-CH₃ | -CO- | 2-CH₃ | H | 40 | 4-CH₃ | -CO- | 2-CH₃ | 7-F |
| 5 | 4-CH₃ | -SO₂- | 2-CH₃ | H | 41 | 4-CH₃ | -SO₂- | 2-CH₃ | 7-F |
| 6 | 4-CH₃ | -CH₂- | 2-CH₃ | H | 42 | 4-CH₃ | -CH₂- | 2-CH₃ | 7-F |
| 7 | 4-Cl | -CO- | 2-CH₃ | H | 43 | 4-Cl | -CO- | 2-CH₃ | 7-F |
| 8 | 4-Cl | -SO₂- | 2-CH₃ | H | 44 | 4-Cl | -SO₂- | 2-CH₃ | 7-F |
| 9 | 4-Cl | -CH₂- | 2-CH₃ | H | 45 | 4-Cl | -CH₂- | 2-CH₃ | 7-F |
| 10 | 4-F | -CO- | 2-CH₃ | H | 46 | 4-F | -CO- | 2-CH₃ | 7-F |
| 11 | 4-F | -SO₂- | 2-CH₃ | H | 47 | 4-F | -SO₂- | 2-CH₃ | 7-F |
| 12 | 4-F | -CH₂- | 2-CH₃ | H | 48 | 4-F | -CH₂- | 2-CH₃ | 7-F |
| 13 | H | -CO- | 2-Cl | H | 49 | H | -CO- | 2-Cl | 7-F |
| 14 | H | -SO₂- | 2-Cl | H | 50 | H | -SO₂- | 2-Cl | 7-F |
| 15 | H | -CH₂- | 2-Cl | H | 51 | H | -CH₂- | 2-Cl | 7-F |
| 16 | 4-CH₃ | -CO- | 2-Cl | H | 52 | 4-CH₃ | -CO- | 2-Cl | 7-F |
| 17 | 4-CH₃ | -SO₂- | 2-Cl | H | 53 | 4-CH₃ | -SO₂- | 2-Cl | 7-F |
| 18 | 4-CH₃ | -CH₂- | 2-Cl | H | 54 | 4-CH₃ | -CH₂- | 2-Cl | 7-F |
| 19 | 4-Cl | -CO- | 2-Cl | H | 55 | 4-Cl | -CO- | 2-Cl | 7-F |
| 20 | 4-Cl | -SO₂- | 2-Cl | H | 56 | 4-Cl | -SO₂- | 2-Cl | 7-F |
| 21 | 4-Cl | -CH₂- | 2-Cl | H | 57 | 4-Cl | -CH₂- | 2-Cl | 7-F |
| 22 | 4-F | -CO- | 2-Cl | H | 58 | 4-F | -CO- | 2-Cl | 7-F |
| 23 | 4-F | -SO₂- | 2-Cl | H | 59 | 4-F | -SO₂- | 2-Cl | 7-F |
| 24 | 4-F | -CH₂- | 2-Cl | H | 60 | 4-F | -CH₂- | 2-Cl | 7-F |
| 25 | H | -CO- | 2-F | H | 61 | H | -CO- | 2-F | 7-F |
| 26 | H | -SO₂- | 2-F | H | 62 | H | -SO₂- | 2-F | 7-F |
| 27 | H | -CH₂- | 2-F | H | 63 | H | -CH₂- | 2-F | 7-F |
| 28 | 4-CH₃ | -CO- | 2-F | H | 64 | 4-CH₃ | -CO- | 2-F | 7-F |
| 29 | 4-CH₃ | -SO₂- | 2-F | H | 65 | 4-CH₃ | -SO₂- | 2-F | 7-F |
| 30 | 4-CH₃ | -CH₂- | 2-F | H | 66 | 4-CH₃ | -CH₂- | 2-F | 7-F |
| 31 | 4-Cl | -CO- | 2-F | H | 67 | 4-Cl | -CO- | 2-F | 7-F |
| 32 | 4-Cl | -SO₂- | 2-F | H | 68 | 4-Cl | -SO₂- | 2-F | 7-F |
| 33 | 4-Cl | -CH₂- | 2-F | H | 69 | 4-Cl | -CH₂- | 2-F | 7-F |
| 34 | 4-F | -CO- | 2-F | H | 70 | 4-F | -CO- | 2-F | 7-F |
| 35 | 4-F | -SO₂- | 2-F | H | 71 | 4-F | -SO₂- | 2-F | 7-F |
| 36 | 4-F | -CH₂- | 2-F | H | 72 | 4-F | -CH₂- | 2-F | 7-F |

Figure 2 0

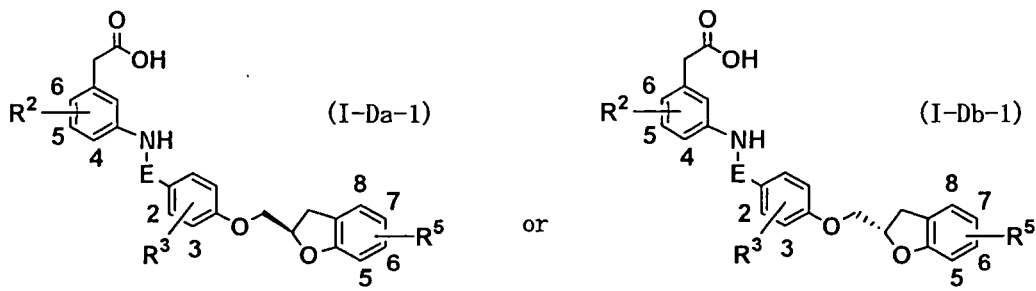

| No. | R² | E | R³ | R⁵ | No. | R² | E | R³ | R⁵ |
|---|---|---|---|---|---|---|---|---|---|
| 1 | H | -CO- | 2-CH₃ | 6-F | 37 | H | -CO- | 2-CH₃ | 5-F |
| 2 | H | -SO₂- | 2-CH₃ | 6-F | 38 | H | -SO₂- | 2-CH₃ | 5-F |
| 3 | H | -CH₂- | 2-CH₃ | 6-F | 39 | H | -CH₂- | 2-CH₃ | 5-F |
| 4 | 4-CH₃ | -CO- | 2-CH₃ | 6-F | 40 | 4-CH₃ | -CO- | 2-CH₃ | 5-F |
| 5 | 4-CH₃ | -SO₂- | 2-CH₃ | 6-F | 41 | 4-CH₃ | -SO₂- | 2-CH₃ | 5-F |
| 6 | 4-CH₃ | -CH₂- | 2-CH₃ | 6-F | 42 | 4-CH₃ | -CH₂- | 2-CH₃ | 5-F |
| 7 | 4-Cl | -CO- | 2-CH₃ | 6-F | 43 | 4-Cl | -CO- | 2-CH₃ | 5-F |
| 8 | 4-Cl | -SO₂- | 2-CH₃ | 6-F | 44 | 4-Cl | -SO₂- | 2-CH₃ | 5-F |
| 9 | 4-Cl | -CH₂- | 2-CH₃ | 6-F | 45 | 4-Cl | -CH₂- | 2-CH₃ | 5-F |
| 10 | 4-F | -CO- | 2-CH₃ | 6-F | 46 | 4-F | -CO- | 2-CH₃ | 5-F |
| 11 | 4-F | -SO₂- | 2-CH₃ | 6-F | 47 | 4-F | -SO₂- | 2-CH₃ | 5-F |
| 12 | 4-F | -CH₂- | 2-CH₃ | 6-F | 48 | 4-F | -CH₂- | 2-CH₃ | 5-F |
| 13 | H | -CO- | 2-Cl | 6-F | 49 | H | -CO- | 2-Cl | 5-F |
| 14 | H | -SO₂- | 2-Cl | 6-F | 50 | H | -SO₂- | 2-Cl | 5-F |
| 15 | H | -CH₂- | 2-Cl | 6-F | 51 | H | -CH₂- | 2-Cl | 5-F |
| 16 | 4-CH₃ | -CO- | 2-Cl | 6-F | 52 | 4-CH₃ | -CO- | 2-Cl | 5-F |
| 17 | 4-CH₃ | -SO₂- | 2-Cl | 6-F | 53 | 4-CH₃ | -SO₂- | 2-Cl | 5-F |
| 18 | 4-CH₃ | -CH₂- | 2-Cl | 6-F | 54 | 4-CH₃ | -CH₂- | 2-Cl | 5-F |
| 19 | 4-Cl | -CO- | 2-Cl | 6-F | 55 | 4-Cl | -CO- | 2-Cl | 5-F |
| 20 | 4-Cl | -SO₂- | 2-Cl | 6-F | 56 | 4-Cl | -SO₂- | 2-Cl | 5-F |
| 21 | 4-Cl | -CH₂- | 2-Cl | 6-F | 57 | 4-Cl | -CH₂- | 2-Cl | 5-F |
| 22 | 4-F | -CO- | 2-Cl | 6-F | 58 | 4-F | -CO- | 2-Cl | 5-F |
| 23 | 4-F | -SO₂- | 2-Cl | 6-F | 59 | 4-F | -SO₂- | 2-Cl | 5-F |
| 24 | 4-F | -CH₂- | 2-Cl | 6-F | 60 | 4-F | -CH₂- | 2-Cl | 5-F |
| 25 | H | -CO- | 2-F | 6-F | 61 | H | -CO- | 2-F | 5-F |
| 26 | H | -SO₂- | 2-F | 6-F | 62 | H | -SO₂- | 2-F | 5-F |
| 27 | H | -CH₂- | 2-F | 6-F | 63 | H | -CH₂- | 2-F | 5-F |
| 28 | 4-CH₃ | -CO- | 2-F | 6-F | 64 | 4-CH₃ | -CO- | 2-F | 5-F |
| 29 | 4-CH₃ | -SO₂- | 2-F | 6-F | 65 | 4-CH₃ | -SO₂- | 2-F | 5-F |
| 30 | 4-CH₃ | -CH₂- | 2-F | 6-F | 66 | 4-CH₃ | -CH₂- | 2-F | 5-F |
| 31 | 4-Cl | -CO- | 2-F | 6-F | 67 | 4-Cl | -CO- | 2-F | 5-F |
| 32 | 4-Cl | -SO₂- | 2-F | 6-F | 68 | 4-Cl | -SO₂- | 2-F | 5-F |
| 33 | 4-Cl | -CH₂- | 2-F | 6-F | 69 | 4-Cl | -CH₂- | 2-F | 5-F |
| 34 | 4-F | -CO- | 2-F | 6-F | 70 | 4-F | -CO- | 2-F | 5-F |
| 35 | 4-F | -SO₂- | 2-F | 6-F | 71 | 4-F | -SO₂- | 2-F | 5-F |
| 36 | 4-F | -CH₂- | 2-F | 6-F | 72 | 4-F | -CH₂- | 2-F | 5-F |

Figure 21

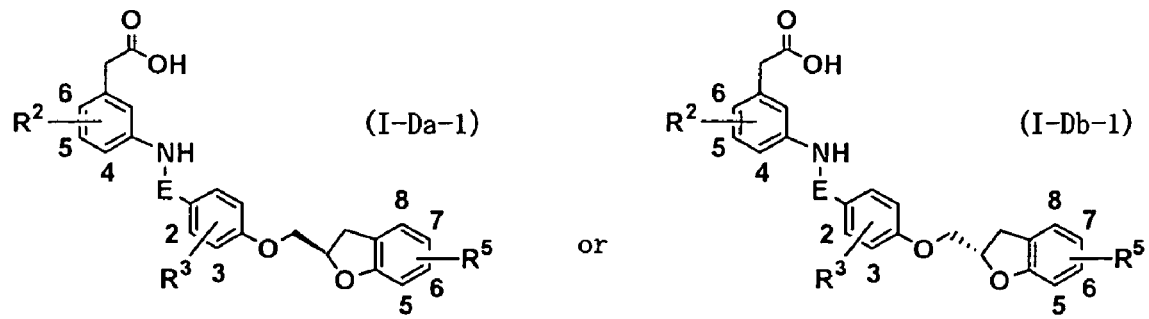

| No. | R² | E | R³ | R⁵ | No. | R² | E | R³ | R⁵ |
|---|---|---|---|---|---|---|---|---|---|
| 1 | 5-CH₃ | -CO- | 2-CH₃ | H | 25 | 5-CH₃ | -CO- | 2-CH₃ | 6-F |
| 2 | 5-CH₃ | -SO₂- | 2-CH₃ | H | 26 | 5-CH₃ | -SO₂- | 2-CH₃ | 6-F |
| 3 | 5-CH₃ | -CH₂- | 2-CH₃ | H | 27 | 5-CH₃ | -CH₂- | 2-CH₃ | 6-F |
| 4 | 5-Cl | -CO- | 2-Cl | H | 28 | 5-Cl | -CO- | 2-Cl | 6-F |
| 5 | 5-Cl | -SO₂- | 2-Cl | H | 29 | 5-Cl | -SO₂- | 2-Cl | 6-F |
| 6 | 5-Cl | -CH₂- | 2-Cl | H | 30 | 5-Cl | -CH₂- | 2-Cl | 6-F |
| 7 | 5-CH₃ | -CO- | 2-Cl | H | 31 | 5-CH₃ | -CO- | 2-Cl | 6-F |
| 8 | 5-CH₃ | -SO₂- | 2-Cl | H | 32 | 5-CH₃ | -SO₂- | 2-Cl | 6-F |
| 9 | 5-CH₃ | -CH₂- | 2-Cl | H | 33 | 5-CH₃ | -CH₂- | 2-Cl | 6-F |
| 10 | 5-F | -CO- | 2-Cl | H | 34 | 5-F | -CO- | 2-Cl | 6-F |
| 11 | 5-F | -SO₂- | 2-Cl | H | 35 | 5-F | -SO₂- | 2-Cl | 6-F |
| 12 | 5-F | -CH₂- | 2-Cl | H | 36 | 5-F | -CH₂- | 2-Cl | 6-F |
| 13 | 5-CH₃ | -CO- | 2-CH₃ | 7-F | 37 | 5-CH₃ | -CO- | 2-CH₃ | 5-F |
| 14 | 5-CH₃ | -SO₂- | 2-CH₃ | 7-F | 38 | 5-CH₃ | -SO₂- | 2-CH₃ | 5-F |
| 15 | 5-CH₃ | -CH₂- | 2-CH₃ | 7-F | 39 | 5-CH₃ | -CH₂- | 2-CH₃ | 5-F |
| 16 | 5-Cl | -CO- | 2-Cl | 7-F | 40 | 5-Cl | -CO- | 2-Cl | 5-F |
| 17 | 5-Cl | -SO₂- | 2-Cl | 7-F | 41 | 5-Cl | -SO₂- | 2-Cl | 5-F |
| 18 | 5-Cl | -CH₂- | 2-Cl | 7-F | 42 | 5-Cl | -CH₂- | 2-Cl | 5-F |
| 19 | 5-CH₃ | -CO- | 2-Cl | 7-F | 43 | 5-CH₃ | -CO- | 2-Cl | 5-F |
| 20 | 5-CH₃ | -SO₂- | 2-Cl | 7-F | 44 | 5-CH₃ | -SO₂- | 2-Cl | 5-F |
| 21 | 5-CH₃ | -CH₂- | 2-Cl | 7-F | 45 | 5-CH₃ | -CH₂- | 2-Cl | 5-F |
| 22 | 5-F | -CO- | 2-Cl | 7-F | 46 | 5-F | -CO- | 2-Cl | 5-F |
| 23 | 5-F | -SO₂- | 2-Cl | 7-F | 47 | 5-F | -SO₂- | 2-Cl | 5-F |
| 24 | 5-F | -CH₂- | 2-Cl | 7-F | 48 | 5-F | -CH₂- | 2-Cl | 5-F |

Figure 2 2

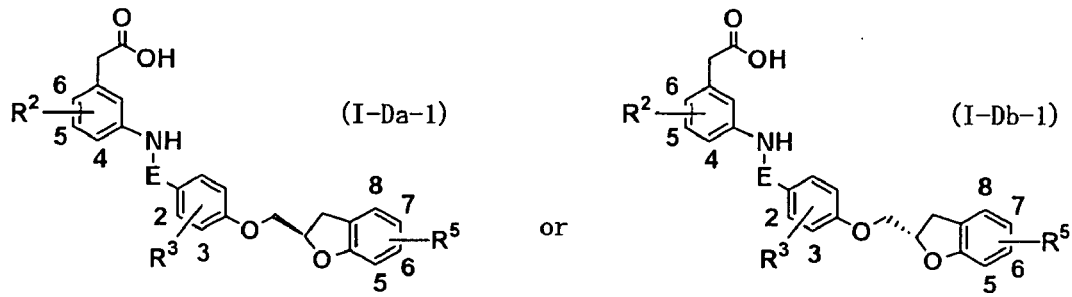

| No. | $R^2$ | E | $R^3$ | $R^5$ | No. | $R^2$ | E | $R^3$ | $R^5$ |
|---|---|---|---|---|---|---|---|---|---|
| 1 | 4-$CH_3$ | -CO- | 3-$CH_3$ | H | 25 | 4-$CH_3$ | -CO- | 3-$CH_3$ | 6-F |
| 2 | 4-$CH_3$ | -$SO_2$- | 3-$CH_3$ | H | 26 | 4-$CH_3$ | -$SO_2$- | 3-$CH_3$ | 6-F |
| 3 | 4-$CH_3$ | -$CH_2$- | 3-$CH_3$ | H | 27 | 4-$CH_3$ | -$CH_2$- | 3-$CH_3$ | 6-F |
| 4 | 4-Cl | -CO- | 3-$CH_3$ | H | 28 | 4-Cl | -CO- | 3-$CH_3$ | 6-F |
| 5 | 4-Cl | -$SO_2$- | 3-$CH_3$ | H | 29 | 4-Cl | -$SO_2$- | 3-$CH_3$ | 6-F |
| 6 | 4-Cl | -$CH_2$- | 3-$CH_3$ | H | 30 | 4-Cl | -$CH_2$- | 3-$CH_3$ | 6-F |
| 7 | 4-Cl | -CO- | 3-Cl | H | 31 | 4-Cl | -CO- | 3-Cl | 6-F |
| 8 | 4-Cl | -$SO_2$- | 3-Cl | H | 32 | 4-Cl | -$SO_2$- | 3-Cl | 6-F |
| 9 | 4-Cl | -$CH_2$- | 3-Cl | H | 33 | 4-Cl | -$CH_2$- | 3-Cl | 6-F |
| 10 | 4-$CH_3$ | -CO- | 3-Cl | H | 34 | 4-$CH_3$ | -CO- | 3-Cl | 6-F |
| 11 | 4-$CH_3$ | -$SO_2$- | 3-Cl | H | 35 | 4-$CH_3$ | -$SO_2$- | 3-Cl | 6-F |
| 12 | 4-$CH_3$ | -$CH_2$- | 3-Cl | H | 36 | 4-$CH_3$ | -$CH_2$- | 3-Cl | 6-F |
| 13 | 4-$CH_3$ | -CO- | 3-$CH_3$ | 7-F | 37 | 4-$CH_3$ | -CO- | 3-$CH_3$ | 5-F |
| 14 | 4-$CH_3$ | -$SO_2$- | 3-$CH_3$ | 7-F | 38 | 4-$CH_3$ | -$SO_2$- | 3-$CH_3$ | 5-F |
| 15 | 4-$CH_3$ | -$CH_2$- | 3-$CH_3$ | 7-F | 39 | 4-$CH_3$ | -$CH_2$- | 3-$CH_3$ | 5-F |
| 16 | 4-Cl | -CO- | 3-$CH_3$ | 7-F | 40 | 4-Cl | -CO- | 3-$CH_3$ | 5-F |
| 17 | 4-Cl | -$SO_2$- | 3-$CH_3$ | 7-F | 41 | 4-Cl | -$SO_2$- | 3-$CH_3$ | 5-F |
| 18 | 4-Cl | -$CH_2$- | 3-$CH_3$ | 7-F | 42 | 4-Cl | -$CH_2$- | 3-$CH_3$ | 5-F |
| 19 | 4-Cl | -CO- | 3-Cl | 7-F | 43 | 4-Cl | -CO- | 3-Cl | 5-F |
| 20 | 4-Cl | -$SO_2$- | 3-Cl | 7-F | 44 | 4-Cl | -$SO_2$- | 3-Cl | 5-F |
| 21 | 4-Cl | -$CH_2$- | 3-Cl | 7-F | 45 | 4-Cl | -$CH_2$- | 3-Cl | 5-F |
| 22 | 4-$CH_3$ | -CO- | 3-Cl | 7-F | 46 | 4-$CH_3$ | -CO- | 3-Cl | 5-F |
| 23 | 4-$CH_3$ | -$SO_2$- | 3-Cl | 7-F | 47 | 4-$CH_3$ | -$SO_2$- | 3-Cl | 5-F |
| 24 | 4-$CH_3$ | -$CH_2$- | 3-Cl | 7-F | 48 | 4-$CH_3$ | -$CH_2$- | 3-Cl | 5-F |

Figure 23

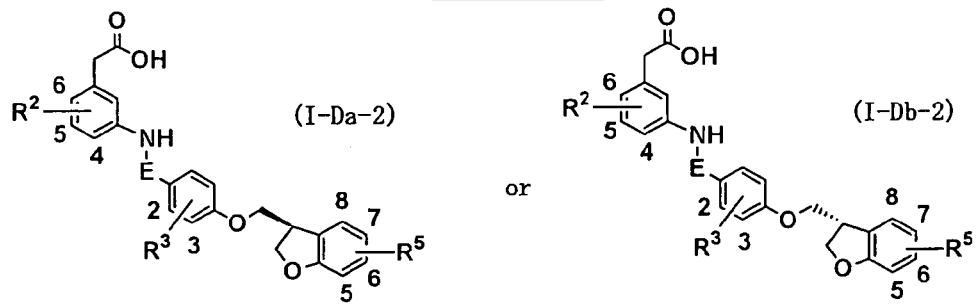

| No. | R² | E | R³ | R⁵ | No. | R² | E | R³ | R⁵ |
|---|---|---|---|---|---|---|---|---|---|
| 1 | H | -CO- | 2-CH₃ | H | 37 | H | -CO- | 2-CH₃ | 7-F |
| 2 | H | -SO₂- | 2-CH₃ | H | 38 | H | -SO₂- | 2-CH₃ | 7-F |
| 3 | H | -CH₂- | 2-CH₃ | H | 39 | H | -CH₂- | 2-CH₃ | 7-F |
| 4 | 4-CH₃ | -CO- | 2-CH₃ | H | 40 | 4-CH₃ | -CO- | 2-CH₃ | 7-F |
| 5 | 4-CH₃ | -SO₂- | 2-CH₃ | H | 41 | 4-CH₃ | -SO₂- | 2-CH₃ | 7-F |
| 6 | 4-CH₃ | -CH₂- | 2-CH₃ | H | 42 | 4-CH₃ | -CH₂- | 2-CH₃ | 7-F |
| 7 | 4-Cl | -CO- | 2-CH₃ | H | 43 | 4-Cl | -CO- | 2-CH₃ | 7-F |
| 8 | 4-Cl | -SO₂- | 2-CH₃ | H | 44 | 4-Cl | -SO₂- | 2-CH₃ | 7-F |
| 9 | 4-Cl | -CH₂- | 2-CH₃ | H | 45 | 4-Cl | -CH₂- | 2-CH₃ | 7-F |
| 10 | 4-F | -CO- | 2-CH₃ | H | 46 | 4-F | -CO- | 2-CH₃ | 7-F |
| 11 | 4-F | -SO₂- | 2-CH₃ | H | 47 | 4-F | -SO₂- | 2-CH₃ | 7-F |
| 12 | 4-F | -CH₂- | 2-CH₃ | H | 48 | 4-F | -CH₂- | 2-CH₃ | 7-F |
| 13 | H | -CO- | 2-Cl | H | 49 | H | -CO- | 2-Cl | 7-F |
| 14 | H | -SO₂- | 2-Cl | H | 50 | H | -SO₂- | 2-Cl | 7-F |
| 15 | H | -CH₂- | 2-Cl | H | 51 | H | -CH₂- | 2-Cl | 7-F |
| 16 | 4-CH₃ | -CO- | 2-Cl | H | 52 | 4-CH₃ | -CO- | 2-Cl | 7-F |
| 17 | 4-CH₃ | -SO₂- | 2-Cl | H | 53 | 4-CH₃ | -SO₂- | 2-Cl | 7-F |
| 18 | 4-CH₃ | -CH₂- | 2-Cl | H | 54 | 4-CH₃ | -CH₂- | 2-Cl | 7-F |
| 19 | 4-Cl | -CO- | 2-Cl | H | 55 | 4-Cl | -CO- | 2-Cl | 7-F |
| 20 | 4-Cl | -SO₂- | 2-Cl | H | 56 | 4-Cl | -SO₂- | 2-Cl | 7-F |
| 21 | 4-Cl | -CH₂- | 2-Cl | H | 57 | 4-Cl | -CH₂- | 2-Cl | 7-F |
| 22 | 4-F | -CO- | 2-Cl | H | 58 | 4-F | -CO- | 2-Cl | 7-F |
| 23 | 4-F | -SO₂- | 2-Cl | H | 59 | 4-F | -SO₂- | 2-Cl | 7-F |
| 24 | 4-F | -CH₂- | 2-Cl | H | 60 | 4-F | -CH₂- | 2-Cl | 7-F |
| 25 | H | -CO- | 2-F | H | 61 | H | -CO- | 2-F | 7-F |
| 26 | H | -SO₂- | 2-F | H | 62 | H | -SO₂- | 2-F | 7-F |
| 27 | H | -CH₂- | 2-F | H | 63 | H | -CH₂- | 2-F | 7-F |
| 28 | 4-CH₃ | -CO- | 2-F | H | 64 | 4-CH₃ | -CO- | 2-F | 7-F |
| 29 | 4-CH₃ | -SO₂- | 2-F | H | 65 | 4-CH₃ | -SO₂- | 2-F | 7-F |
| 30 | 4-CH₃ | -CH₂- | 2-F | H | 66 | 4-CH₃ | -CH₂- | 2-F | 7-F |
| 31 | 4-Cl | -CO- | 2-F | H | 67 | 4-Cl | -CO- | 2-F | 7-F |
| 32 | 4-Cl | -SO₂- | 2-F | H | 68 | 4-Cl | -SO₂- | 2-F | 7-F |
| 33 | 4-Cl | -CH₂- | 2-F | H | 69 | 4-Cl | -CH₂- | 2-F | 7-F |
| 34 | 4-F | -CO- | 2-F | H | 70 | 4-F | -CO- | 2-F | 7-F |
| 35 | 4-F | -SO₂- | 2-F | H | 71 | 4-F | -SO₂- | 2-F | 7-F |
| 36 | 4-F | -CH₂- | 2-F | H | 72 | 4-F | -CH₂- | 2-F | 7-F |

Figure 24

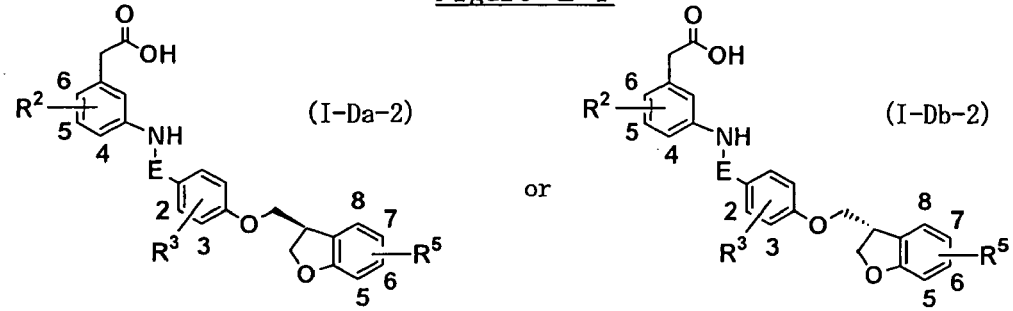

| No. | R² | E | R³ | R⁵ | No. | R² | E | R³ | R⁵ |
|---|---|---|---|---|---|---|---|---|---|
| 1 | H | -CO- | 2-CH₃ | 6-F | 37 | H | -CO- | 2-CH₃ | 5-F |
| 2 | H | -SO₂- | 2-CH₃ | 6-F | 38 | H | -SO₂- | 2-CH₃ | 5-F |
| 3 | H | -CH₂- | 2-CH₃ | 6-F | 39 | H | -CH₂- | 2-CH₃ | 5-F |
| 4 | 4-CH₃ | -CO- | 2-CH₃ | 6-F | 40 | 4-CH₃ | -CO- | 2-CH₃ | 5-F |
| 5 | 4-CH₃ | -SO₂- | 2-CH₃ | 6-F | 41 | 4-CH₃ | -SO₂- | 2-CH₃ | 5-F |
| 6 | 4-CH₃ | -CH₂- | 2-CH₃ | 6-F | 42 | 4-CH₃ | -CH₂- | 2-CH₃ | 5-F |
| 7 | 4-Cl | -CO- | 2-CH₃ | 6-F | 43 | 4-Cl | -CO- | 2-CH₃ | 5-F |
| 8 | 4-Cl | -SO₂- | 2-CH₃ | 6-F | 44 | 4-Cl | -SO₂- | 2-CH₃ | 5-F |
| 9 | 4-Cl | -CH₂- | 2-CH₃ | 6-F | 45 | 4-Cl | -CH₂- | 2-CH₃ | 5-F |
| 10 | 4-F | -CO- | 2-CH₃ | 6-F | 46 | 4-F | -CO- | 2-CH₃ | 5-F |
| 11 | 4-F | -SO₂- | 2-CH₃ | 6-F | 47 | 4-F | -SO₂- | 2-CH₃ | 5-F |
| 12 | 4-F | -CH₂- | 2-CH₃ | 6-F | 48 | 4-F | -CH₂- | 2-CH₃ | 5-F |
| 13 | H | -CO- | 2-Cl | 6-F | 49 | H | -CO- | 2-Cl | 5-F |
| 14 | H | -SO₂- | 2-Cl | 6-F | 50 | H | -SO₂- | 2-Cl | 5-F |
| 15 | H | -CH₂- | 2-Cl | 6-F | 51 | H | -CH₂- | 2-Cl | 5-F |
| 16 | 4-CH₃ | -CO- | 2-Cl | 6-F | 52 | 4-CH₃ | -CO- | 2-Cl | 5-F |
| 17 | 4-CH₃ | -SO₂- | 2-Cl | 6-F | 53 | 4-CH₃ | -SO₂- | 2-Cl | 5-F |
| 18 | 4-CH₃ | -CH₂- | 2-Cl | 6-F | 54 | 4-CH₃ | -CH₂- | 2-Cl | 5-F |
| 19 | 4-Cl | -CO- | 2-Cl | 6-F | 55 | 4-Cl | -CO- | 2-Cl | 5-F |
| 20 | 4-Cl | -SO₂- | 2-Cl | 6-F | 56 | 4-Cl | -SO₂- | 2-Cl | 5-F |
| 21 | 4-Cl | -CH₂- | 2-Cl | 6-F | 57 | 4-Cl | -CH₂- | 2-Cl | 5-F |
| 22 | 4-F | -CO- | 2-Cl | 6-F | 58 | 4-F | -CO- | 2-Cl | 5-F |
| 23 | 4-F | -SO₂- | 2-Cl | 6-F | 59 | 4-F | -SO₂- | 2-Cl | 5-F |
| 24 | 4-F | -CH₂- | 2-Cl | 6-F | 60 | 4-F | -CH₂- | 2-Cl | 5-F |
| 25 | H | -CO- | 2-F | 6-F | 61 | H | -CO- | 2-F | 5-F |
| 26 | H | -SO₂- | 2-F | 6-F | 62 | H | -SO₂- | 2-F | 5-F |
| 27 | H | -CH₂- | 2-F | 6-F | 63 | H | -CH₂- | 2-F | 5-F |
| 28 | 4-CH₃ | -CO- | 2-F | 6-F | 64 | 4-CH₃ | -CO- | 2-F | 5-F |
| 29 | 4-CH₃ | -SO₂- | 2-F | 6-F | 65 | 4-CH₃ | -SO₂- | 2-F | 5-F |
| 30 | 4-CH₃ | -CH₂- | 2-F | 6-F | 66 | 4-CH₃ | -CH₂- | 2-F | 5-F |
| 31 | 4-Cl | -CO- | 2-F | 6-F | 67 | 4-Cl | -CO- | 2-F | 5-F |
| 32 | 4-Cl | -SO₂- | 2-F | 6-F | 68 | 4-Cl | -SO₂- | 2-F | 5-F |
| 33 | 4-Cl | -CH₂- | 2-F | 6-F | 69 | 4-Cl | -CH₂- | 2-F | 5-F |
| 34 | 4-F | -CO- | 2-F | 6-F | 70 | 4-F | -CO- | 2-F | 5-F |
| 35 | 4-F | -SO₂- | 2-F | 6-F | 71 | 4-F | -SO₂- | 2-F | 5-F |
| 36 | 4-F | -CH₂- | 2-F | 6-F | 72 | 4-F | -CH₂- | 2-F | 5-F |

Figure 25

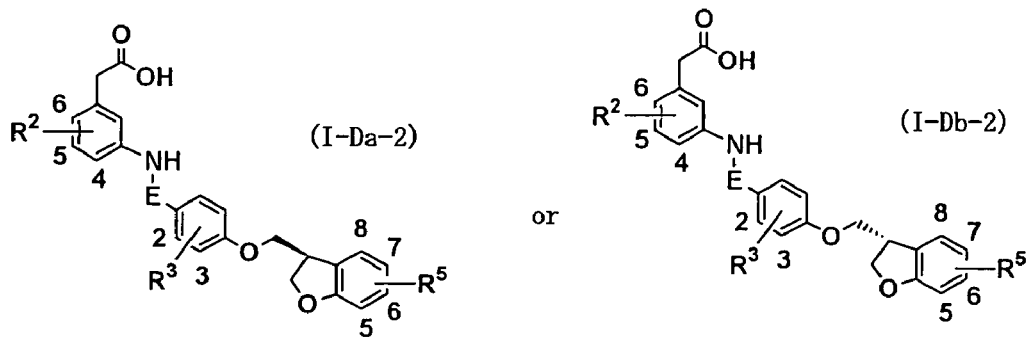

| No. | R² | E | R³ | R⁵ | No. | R² | E | R³ | R⁵ |
|---|---|---|---|---|---|---|---|---|---|
| 1 | 5-CH₃ | -CO- | 2-CH₃ | H | 25 | 5-CH₃ | -CO- | 2-CH₃ | 6-F |
| 2 | 5-CH₃ | -SO₂- | 2-CH₃ | H | 26 | 5-CH₃ | -SO₂- | 2-CH₃ | 6-F |
| 3 | 5-CH₃ | -CH₂- | 2-CH₃ | H | 27 | 5-CH₃ | -CH₂- | 2-CH₃ | 6-F |
| 4 | 5-Cl | -CO- | 2-Cl | H | 28 | 5-Cl | -CO- | 2-Cl | 6-F |
| 5 | 5-Cl | -SO₂- | 2-Cl | H | 29 | 5-Cl | -SO₂- | 2-Cl | 6-F |
| 6 | 5-Cl | -CH₂- | 2-Cl | H | 30 | 5-Cl | -CH₂- | 2-Cl | 6-F |
| 7 | 5-CH₃ | -CO- | 2-Cl | H | 31 | 5-CH₃ | -CO- | 2-Cl | 6-F |
| 8 | 5-CH₃ | -SO₂- | 2-Cl | H | 32 | 5-CH₃ | -SO₂- | 2-Cl | 6-F |
| 9 | 5-CH₃ | -CH₂- | 2-Cl | H | 33 | 5-CH₃ | -CH₂- | 2-Cl | 6-F |
| 10 | 5-F | -CO- | 2-Cl | H | 34 | 5-F | -CO- | 2-Cl | 6-F |
| 11 | 5-F | -SO₂- | 2-Cl | H | 35 | 5-F | -SO₂- | 2-Cl | 6-F |
| 12 | 5-F | -CH₂- | 2-Cl | H | 36 | 5-F | -CH₂- | 2-Cl | 6-F |
| 13 | 5-CH₃ | -CO- | 2-CH₃ | 7-F | 37 | 5-CH₃ | -CO- | 2-CH₃ | 5-F |
| 14 | 5-CH₃ | -SO₂- | 2-CH₃ | 7-F | 38 | 5-CH₃ | -SO₂- | 2-CH₃ | 5-F |
| 15 | 5-CH₃ | -CH₂- | 2-CH₃ | 7-F | 39 | 5-CH₃ | -CH₂- | 2-CH₃ | 5-F |
| 16 | 5-Cl | -CO- | 2-Cl | 7-F | 40 | 5-Cl | -CO- | 2-Cl | 5-F |
| 17 | 5-Cl | -SO₂- | 2-Cl | 7-F | 41 | 5-Cl | -SO₂- | 2-Cl | 5-F |
| 18 | 5-Cl | -CH₂- | 2-Cl | 7-F | 42 | 5-Cl | -CH₂- | 2-Cl | 5-F |
| 19 | 5-CH₃ | -CO- | 2-Cl | 7-F | 43 | 5-CH₃ | -CO- | 2-Cl | 5-F |
| 20 | 5-CH₃ | -SO₂- | 2-Cl | 7-F | 44 | 5-CH₃ | -SO₂- | 2-Cl | 5-F |
| 21 | 5-CH₃ | -CH₂- | 2-Cl | 7-F | 45 | 5-CH₃ | -CH₂- | 2-Cl | 5-F |
| 22 | 5-F | -CO- | 2-Cl | 7-F | 46 | 5-F | -CO- | 2-Cl | 5-F |
| 23 | 5-F | -SO₂- | 2-Cl | 7-F | 47 | 5-F | -SO₂- | 2-Cl | 5-F |
| 24 | 5-F | -CH₂- | 2-Cl | 7-F | 48 | 5-F | -CH₂- | 2-Cl | 5-F |

Figure 26

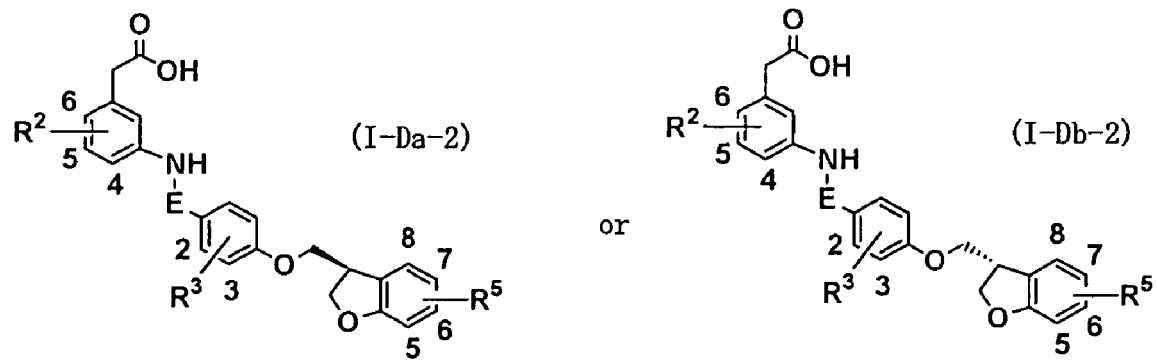

| No. | $R^2$ | E | $R^3$ | $R^5$ | No. | $R^2$ | E | $R^3$ | $R^5$ |
|---|---|---|---|---|---|---|---|---|---|
| 1 | 4-$CH_3$ | -CO- | 3-$CH_3$ | H | 25 | 4-$CH_3$ | -CO- | 3-$CH_3$ | 6-F |
| 2 | 4-$CH_3$ | -$SO_2$- | 3-$CH_3$ | H | 26 | 4-$CH_3$ | -$SO_2$- | 3-$CH_3$ | 6-F |
| 3 | 4-$CH_3$ | -$CH_2$- | 3-$CH_3$ | H | 27 | 4-$CH_3$ | -$CH_2$- | 3-$CH_3$ | 6-F |
| 4 | 4-Cl | -CO- | 3-$CH_3$ | H | 28 | 4-Cl | -CO- | 3-$CH_3$ | 6-F |
| 5 | 4-Cl | -$SO_2$- | 3-$CH_3$ | H | 29 | 4-Cl | -$SO_2$- | 3-$CH_3$ | 6-F |
| 6 | 4-Cl | -$CH_2$- | 3-$CH_3$ | H | 30 | 4-Cl | -$CH_2$- | 3-$CH_3$ | 6-F |
| 7 | 4-Cl | -CO- | 3-Cl | H | 31 | 4-Cl | -CO- | 3-Cl | 6-F |
| 8 | 4-Cl | -$SO_2$- | 3-Cl | H | 32 | 4-Cl | -$SO_2$- | 3-Cl | 6-F |
| 9 | 4-Cl | -$CH_2$- | 3-Cl | H | 33 | 4-Cl | -$CH_2$- | 3-Cl | 6-F |
| 10 | 4-$CH_3$ | -CO- | 3-Cl | H | 34 | 4-$CH_3$ | -CO- | 3-Cl | 6-F |
| 11 | 4-$CH_3$ | -$SO_2$- | 3-Cl | H | 35 | 4-$CH_3$ | -$SO_2$- | 3-Cl | 6-F |
| 12 | 4-$CH_3$ | -$CH_2$- | 3-Cl | H | 36 | 4-$CH_3$ | -$CH_2$- | 3-Cl | 6-F |
| 13 | 4-$CH_3$ | -CO- | 3-$CH_3$ | 7-F | 37 | 4-$CH_3$ | -CO- | 3-$CH_3$ | 5-F |
| 14 | 4-$CH_3$ | -$SO_2$- | 3-$CH_3$ | 7-F | 38 | 4-$CH_3$ | -$SO_2$- | 3-$CH_3$ | 5-F |
| 15 | 4-$CH_3$ | -$CH_2$- | 3-$CH_3$ | 7-F | 39 | 4-$CH_3$ | -$CH_2$- | 3-$CH_3$ | 5-F |
| 16 | 4-Cl | -CO- | 3-$CH_3$ | 7-F | 40 | 4-Cl | -CO- | 3-$CH_3$ | 5-F |
| 17 | 4-Cl | -$SO_2$- | 3-$CH_3$ | 7-F | 41 | 4-Cl | -$SO_2$- | 3-$CH_3$ | 5-F |
| 18 | 4-Cl | -$CH_2$- | 3-$CH_3$ | 7-F | 42 | 4-Cl | -$CH_2$- | 3-$CH_3$ | 5-F |
| 19 | 4-Cl | -CO- | 3-Cl | 7-F | 43 | 4-Cl | -CO- | 3-Cl | 5-F |
| 20 | 4-Cl | -$SO_2$- | 3-Cl | 7-F | 44 | 4-Cl | -$SO_2$- | 3-Cl | 5-F |
| 21 | 4-Cl | -$CH_2$- | 3-Cl | 7-F | 45 | 4-Cl | -$CH_2$- | 3-Cl | 5-F |
| 22 | 4-$CH_3$ | -CO- | 3-Cl | 7-F | 46 | 4-$CH_3$ | -CO- | 3-Cl | 5-F |
| 23 | 4-$CH_3$ | -$SO_2$- | 3-Cl | 7-F | 47 | 4-$CH_3$ | -$SO_2$- | 3-Cl | 5-F |
| 24 | 4-$CH_3$ | -$CH_2$- | 3-Cl | 7-F | 48 | 4-$CH_3$ | -$CH_2$- | 3-Cl | 5-F |

Figure 27

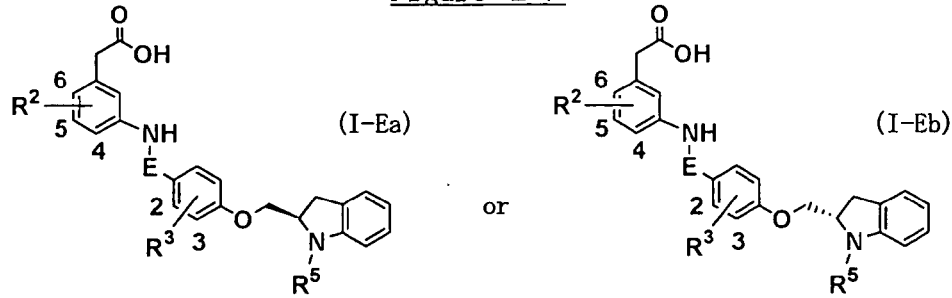

| No. | $R^2$ | E | $R^3$ | $R^5$ | No. | $R^2$ | E | $R^3$ | $R^5$ |
|---|---|---|---|---|---|---|---|---|---|
| 1 | H | -CO- | 2-$CH_3$ | $CH_3$ | 37 | H | -CO- | 2-$CH_3$ | $CH_2CH_3$ |
| 2 | H | -$SO_2$- | 2-$CH_3$ | $CH_3$ | 38 | H | -$SO_2$- | 2-$CH_3$ | $CH_2CH_3$ |
| 3 | H | -$CH_2$- | 2-$CH_3$ | $CH_3$ | 39 | H | -$CH_2$- | 2-$CH_3$ | $CH_2CH_3$ |
| 4 | 4-$CH_3$ | -CO- | 2-$CH_3$ | $CH_3$ | 40 | 4-$CH_3$ | -CO- | 2-$CH_3$ | $CH_2CH_3$ |
| 5 | 4-$CH_3$ | -$SO_2$- | 2-$CH_3$ | $CH_3$ | 41 | 4-$CH_3$ | -$SO_2$- | 2-$CH_3$ | $CH_2CH_3$ |
| 6 | 4-$CH_3$ | -$CH_2$- | 2-$CH_3$ | $CH_3$ | 42 | 4-$CH_3$ | -$CH_2$- | 2-$CH_3$ | $CH_2CH_3$ |
| 7 | 4-Cl | -CO- | 2-$CH_3$ | $CH_3$ | 43 | 4-Cl | -CO- | 2-$CH_3$ | $CH_2CH_3$ |
| 8 | 4-Cl | -$SO_2$- | 2-$CH_3$ | $CH_3$ | 44 | 4-Cl | -$SO_2$- | 2-$CH_3$ | $CH_2CH_3$ |
| 9 | 4-Cl | -$CH_2$- | 2-$CH_3$ | $CH_3$ | 45 | 4-Cl | -$CH_2$- | 2-$CH_3$ | $CH_2CH_3$ |
| 10 | 4-F | -CO- | 2-$CH_3$ | $CH_3$ | 46 | 4-F | -CO- | 2-$CH_3$ | $CH_2CH_3$ |
| 11 | 4-F | -$SO_2$- | 2-$CH_3$ | $CH_3$ | 47 | 4-F | -$SO_2$- | 2-$CH_3$ | $CH_2CH_3$ |
| 12 | 4-F | -$CH_2$- | 2-$CH_3$ | $CH_3$ | 48 | 4-F | -$CH_2$- | 2-$CH_3$ | $CH_2CH_3$ |
| 13 | H | -CO- | 2-Cl | $CH_3$ | 49 | H | -CO- | 2-Cl | $CH_2CH_3$ |
| 14 | H | -$SO_2$- | 2-Cl | $CH_3$ | 50 | H | -$SO_2$- | 2-Cl | $CH_2CH_3$ |
| 15 | H | -$CH_2$- | 2-Cl | $CH_3$ | 51 | H | -$CH_2$- | 2-Cl | $CH_2CH_3$ |
| 16 | 4-$CH_3$ | -CO- | 2-Cl | $CH_3$ | 52 | 4-$CH_3$ | -CO- | 2-Cl | $CH_2CH_3$ |
| 17 | 4-$CH_3$ | -$SO_2$- | 2-Cl | $CH_3$ | 53 | 4-$CH_3$ | -$SO_2$- | 2-Cl | $CH_2CH_3$ |
| 18 | 4-$CH_3$ | -$CH_2$- | 2-Cl | $CH_3$ | 54 | 4-$CH_3$ | -$CH_2$- | 2-Cl | $CH_2CH_3$ |
| 19 | 4-Cl | -CO- | 2-Cl | $CH_3$ | 55 | 4-Cl | -CO- | 2-Cl | $CH_2CH_3$ |
| 20 | 4-Cl | -$SO_2$- | 2-Cl | $CH_3$ | 56 | 4-Cl | -$SO_2$- | 2-Cl | $CH_2CH_3$ |
| 21 | 4-Cl | -$CH_2$- | 2-Cl | $CH_3$ | 57 | 4-Cl | -$CH_2$- | 2-Cl | $CH_2CH_3$ |
| 22 | 4-F | -CO- | 2-Cl | $CH_3$ | 58 | 4-F | -CO- | 2-Cl | $CH_2CH_3$ |
| 23 | 4-F | -$SO_2$- | 2-Cl | $CH_3$ | 59 | 4-F | -$SO_2$- | 2-Cl | $CH_2CH_3$ |
| 24 | 4-F | -$CH_2$- | 2-Cl | $CH_3$ | 60 | 4-F | -$CH_2$- | 2-Cl | $CH_2CH_3$ |
| 25 | H | -CO- | 2-F | $CH_3$ | 61 | H | -CO- | 2-F | $CH_2CH_3$ |
| 26 | H | -$SO_2$- | 2-F | $CH_3$ | 62 | H | -$SO_2$- | 2-F | $CH_2CH_3$ |
| 27 | H | -$CH_2$- | 2-F | $CH_3$ | 63 | H | -$CH_2$- | 2-F | $CH_2CH_3$ |
| 28 | 4-$CH_3$ | -CO- | 2-F | $CH_3$ | 64 | 4-$CH_3$ | -CO- | 2-F | $CH_2CH_3$ |
| 29 | 4-$CH_3$ | -$SO_2$- | 2-F | $CH_3$ | 65 | 4-$CH_3$ | -$SO_2$- | 2-F | $CH_2CH_3$ |
| 30 | 4-$CH_3$ | -$CH_2$- | 2-F | $CH_3$ | 66 | 4-$CH_3$ | -$CH_2$- | 2-F | $CH_2CH_3$ |
| 31 | 4-Cl | -CO- | 2-F | $CH_3$ | 67 | 4-Cl | -CO- | 2-F | $CH_2CH_3$ |
| 32 | 4-Cl | -$SO_2$- | 2-F | $CH_3$ | 68 | 4-Cl | -$SO_2$- | 2-F | $CH_2CH_3$ |
| 33 | 4-Cl | -$CH_2$- | 2-F | $CH_3$ | 69 | 4-Cl | -$CH_2$- | 2-F | $CH_2CH_3$ |
| 34 | 4-F | -CO- | 2-F | $CH_3$ | 70 | 4-F | -CO- | 2-F | $CH_2CH_3$ |
| 35 | 4-F | -$SO_2$- | 2-F | $CH_3$ | 71 | 4-F | -$SO_2$- | 2-F | $CH_2CH_3$ |
| 36 | 4-F | -$CH_2$- | 2-F | $CH_3$ | 72 | 4-F | -$CH_2$- | 2-F | $CH_2CH_3$ |

Figure 28

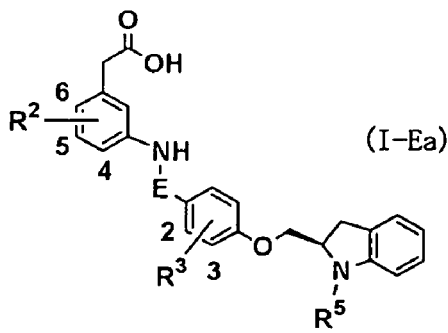 (I-Ea) or 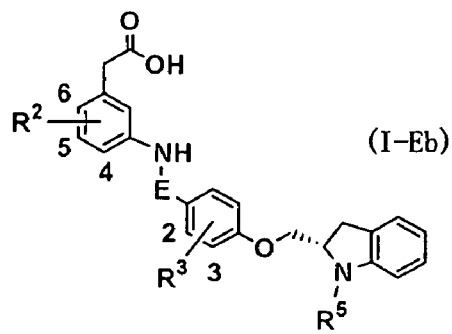 (I-Eb)

| No. | R² | E | R³ | R⁵ | No. | R² | E | R³ | R⁵ |
|---|---|---|---|---|---|---|---|---|---|
| 1 | 5-CH₃ | -CO- | 2-CH₃ | CH₃ | 25 | 4-CH₃ | -CO- | 3-CH₃ | CH₃ |
| 2 | 5-CH₃ | -SO₂- | 2-CH₃ | CH₃ | 26 | 4-CH₃ | -SO₂- | 3-CH₃ | CH₃ |
| 3 | 5-CH₃ | -CH₂- | 2-CH₃ | CH₃ | 27 | 4-CH₃ | -CH₂- | 3-CH₃ | CH₃ |
| 4 | 5-Cl | -CO- | 2-Cl | CH₃ | 28 | 4-Cl | -CO- | 3-CH₃ | CH₃ |
| 5 | 5-Cl | -SO₂- | 2-Cl | CH₃ | 29 | 4-Cl | -SO₂- | 3-CH₃ | CH₃ |
| 6 | 5-Cl | -CH₂- | 2-Cl | CH₃ | 30 | 4-Cl | -CH₂- | 3-CH₃ | CH₃ |
| 7 | 5-CH₃ | -CO- | 2-Cl | CH₃ | 31 | 4-Cl | -CO- | 3-Cl | CH₃ |
| 8 | 5-CH₃ | -SO₂- | 2-Cl | CH₃ | 32 | 4-Cl | -SO₂- | 3-Cl | CH₃ |
| 9 | 5-CH₃ | -CH₂- | 2-Cl | CH₃ | 33 | 4-Cl | -CH₂- | 3-Cl | CH₃ |
| 10 | 5-F | -CO- | 2-Cl | CH₃ | 34 | 4-CH₃ | -CO- | 3-Cl | CH₃ |
| 11 | 5-F | -SO₂- | 2-Cl | CH₃ | 35 | 4-CH₃ | -SO₂- | 3-Cl | CH₃ |
| 12 | 5-F | -CH₂- | 2-Cl | CH₃ | 36 | 4-CH₃ | -CH₂- | 3-Cl | CH₃ |
| 13 | 5-CH₃ | -CO- | 2-CH₃ | CH₂CH₃ | 37 | 4-CH₃ | -CO- | 3-CH₃ | CH₂CH₃ |
| 14 | 5-CH₃ | -SO₂- | 2-CH₃ | CH₂CH₃ | 38 | 4-CH₃ | -SO₂- | 3-CH₃ | CH₂CH₃ |
| 15 | 5-CH₃ | -CH₂- | 2-CH₃ | CH₂CH₃ | 39 | 4-CH₃ | -CH₂- | 3-CH₃ | CH₂CH₃ |
| 16 | 5-Cl | -CO- | 2-Cl | CH₂CH₃ | 40 | 4-Cl | -CO- | 3-CH₃ | CH₂CH₃ |
| 17 | 5-Cl | -SO₂- | 2-Cl | CH₂CH₃ | 41 | 4-Cl | -SO₂- | 3-CH₃ | CH₂CH₃ |
| 18 | 5-Cl | -CH₂- | 2-Cl | CH₂CH₃ | 42 | 4-Cl | -CH₂- | 3-CH₃ | CH₂CH₃ |
| 19 | 5-CH₃ | -CO- | 2-Cl | CH₂CH₃ | 43 | 4-Cl | -CO- | 3-Cl | CH₂CH₃ |
| 20 | 5-CH₃ | -SO₂- | 2-Cl | CH₂CH₃ | 44 | 4-Cl | -SO₂- | 3-Cl | CH₂CH₃ |
| 21 | 5-CH₃ | -CH₂- | 2-Cl | CH₂CH₃ | 45 | 4-Cl | -CH₂- | 3-Cl | CH₂CH₃ |
| 22 | 5-F | -CO- | 2-Cl | CH₂CH₃ | 46 | 4-CH₃ | -CO- | 3-Cl | CH₂CH₃ |
| 23 | 5-F | -SO₂- | 2-Cl | CH₂CH₃ | 47 | 4-CH₃ | -SO₂- | 3-Cl | CH₂CH₃ |
| 24 | 5-F | -CH₂- | 2-Cl | CH₂CH₃ | 48 | 4-CH₃ | -CH₂- | 3-Cl | CH₂CH₃ |

Figure 29

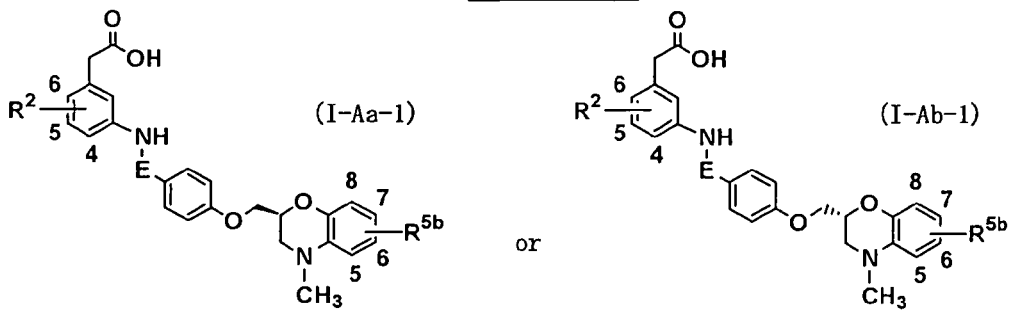

| No. | R² | E | R⁵ᵇ | No. | R² | E | R⁵ᵇ | No. | R² | E | R⁵ᵇ |
|---|---|---|---|---|---|---|---|---|---|---|---|
| 1 | H | -CO- | H | 43 | H | -CO- | 8-F | 85 | H | -CO- | 7-F |
| 2 | H | -SO₂- | H | 44 | H | -SO₂- | 8-F | 86 | H | -SO₂- | 7-F |
| 3 | H | -CH₂- | H | 45 | H | -CH₂- | 8-F | 87 | H | -CH₂- | 7-F |
| 4 | 4-CH₃ | -CO- | H | 46 | 4-CH₃ | -CO- | 8-F | 88 | 4-CH₃ | -CO- | 7-F |
| 5 | 4-CH₃ | -SO₂- | H | 47 | 4-CH₃ | -SO₂- | 8-F | 89 | 4-CH₃ | -SO₂- | 7-F |
| 6 | 4-CH₃ | -CH₂- | H | 48 | 4-CH₃ | -CH₂- | 8-F | 90 | 4-CH₃ | -CH₂- | 7-F |
| 7 | 4-Cl | -CO- | H | 49 | 4-Cl | -CO- | 8-F | 91 | 4-Cl | -CO- | 7-F |
| 8 | 4-Cl | -SO₂- | H | 50 | 4-Cl | -SO₂- | 8-F | 92 | 4-Cl | -SO₂- | 7-F |
| 9 | 4-Cl | -CH₂- | H | 51 | 4-Cl | -CH₂- | 8-F | 93 | 4-Cl | -CH₂- | 7-F |
| 10 | 4-F | -CO- | H | 52 | 4-F | -CO- | 8-F | 94 | 4-F | -CO- | 7-F |
| 11 | 4-F | -SO₂- | H | 53 | 4-F | -SO₂- | 8-F | 95 | 4-F | -SO₂- | 7-F |
| 12 | 4-F | -CH₂- | H | 54 | 4-F | -CH₂- | 8-F | 96 | 4-F | -CH₂- | 7-F |
| 13 | 5-CH₃ | -CO- | H | 55 | 5-CH₃ | -CO- | 8-F | 97 | 5-CH₃ | -CO- | 7-F |
| 14 | 5-CH₃ | -SO₂- | H | 56 | 5-CH₃ | -SO₂- | 8-F | 98 | 5-CH₃ | -SO₂- | 7-F |
| 15 | 5-CH₃ | -CH₂- | H | 57 | 5-CH₃ | -CH₂- | 8-F | 99 | 5-CH₃ | -CH₂- | 7-F |
| 16 | 5-Cl | -CO- | H | 58 | 5-Cl | -CO- | 8-F | 100 | 5-Cl | -CO- | 7-F |
| 17 | 5-Cl | -SO₂- | H | 59 | 5-Cl | -SO₂- | 8-F | 101 | 5-Cl | -SO₂- | 7-F |
| 18 | 5-Cl | -CH₂- | H | 60 | 5-Cl | -CH₂- | 8-F | 102 | 5-Cl | -CH₂- | 7-F |
| 19 | 5-F | -CO- | H | 61 | 5-F | -CO- | 8-F | 103 | 5-F | -CO- | 7-F |
| 20 | 5-F | -SO₂- | H | 62 | 5-F | -SO₂- | 8-F | 104 | 5-F | -SO₂- | 7-F |
| 21 | 5-F | -CH₂- | H | 63 | 5-F | -CH₂- | 8-F | 105 | 5-F | -CH₂- | 7-F |
| 22 | H | -CO- | 8-CH₃ | 64 | H | -CO- | 7-CH₃ | 106 | H | -CO- | 7-OCH₃ |
| 23 | H | -SO₂- | 8-CH₃ | 65 | H | -SO₂- | 7-CH₃ | 107 | H | -SO₂- | 7-OCH₃ |
| 24 | H | -CH₂- | 8-CH₃ | 66 | H | -CH₂- | 7-CH₃ | 108 | H | -CH₂- | 7-OCH₃ |
| 25 | 4-CH₃ | -CO- | 8-CH₃ | 67 | 4-CH₃ | -CO- | 7-CH₃ | 109 | 4-CH₃ | -CO- | 7-OCH₃ |
| 26 | 4-CH₃ | -SO₂- | 8-CH₃ | 68 | 4-CH₃ | -SO₂- | 7-CH₃ | 110 | 4-CH₃ | -SO₂- | 7-OCH₃ |
| 27 | 4-CH₃ | -CH₂- | 8-CH₃ | 69 | 4-CH₃ | -CH₂- | 7-CH₃ | 111 | 4-CH₃ | -CH₂- | 7-OCH₃ |
| 28 | 4-Cl | -CO- | 8-CH₃ | 70 | 4-Cl | -CO- | 7-CH₃ | 112 | 4-Cl | -CO- | 7-OCH₃ |
| 29 | 4-Cl | -SO₂- | 8-CH₃ | 71 | 4-Cl | -SO₂- | 7-CH₃ | 113 | 4-Cl | -SO₂- | 7-OCH₃ |
| 30 | 4-Cl | -CH₂- | 8-CH₃ | 72 | 4-Cl | -CH₂- | 7-CH₃ | 114 | 4-Cl | -CH₂- | 7-OCH₃ |
| 31 | 4-F | -CO- | 8-CH₃ | 73 | 4-F | -CO- | 7-CH₃ | 115 | 4-F | -CO- | 7-OCH₃ |
| 32 | 4-F | -SO₂- | 8-CH₃ | 74 | 4-F | -SO₂- | 7-CH₃ | 116 | 4-F | -SO₂- | 7-OCH₃ |
| 33 | 4-F | -CH₂- | 8-CH₃ | 75 | 4-F | -CH₂- | 7-CH₃ | 117 | 4-F | -CH₂- | 7-OCH₃ |
| 34 | 5-CH₃ | -CO- | 8-CH₃ | 76 | 5-CH₃ | -CO- | 7-CH₃ | 118 | 5-CH₃ | -CO- | 7-OCH₃ |
| 35 | 5-CH₃ | -SO₂- | 8-CH₃ | 77 | 5-CH₃ | -SO₂- | 7-CH₃ | 119 | 5-CH₃ | -SO₂- | 7-OCH₃ |
| 36 | 5-CH₃ | -CH₂- | 8-CH₃ | 78 | 5-CH₃ | -CH₂- | 7-CH₃ | 120 | 5-CH₃ | -CH₂- | 7-OCH₃ |
| 37 | 5-Cl | -CO- | 8-CH₃ | 79 | 5-Cl | -CO- | 7-CH₃ | 121 | 5-Cl | -CO- | 7-OCH₃ |
| 38 | 5-Cl | -SO₂- | 8-CH₃ | 80 | 5-Cl | -SO₂- | 7-CH₃ | 122 | 5-Cl | -SO₂- | 7-OCH₃ |
| 39 | 5-Cl | -CH₂- | 8-CH₃ | 81 | 5-Cl | -CH₂- | 7-CH₃ | 123 | 5-Cl | -CH₂- | 7-OCH₃ |
| 40 | 5-F | -CO- | 8-CH₃ | 82 | 5-F | -CO- | 7-CH₃ | 124 | 5-F | -CO- | 7-OCH₃ |
| 41 | 5-F | -SO₂- | 8-CH₃ | 83 | 5-F | -SO₂- | 7-CH₃ | 125 | 5-F | -SO₂- | 7-OCH₃ |
| 42 | 5-F | -CH₂- | 8-CH₃ | 84 | 5-F | -CH₂- | 7-CH₃ | 126 | 5-F | -CH₂- | 7-OCH₃ |

Figure 30

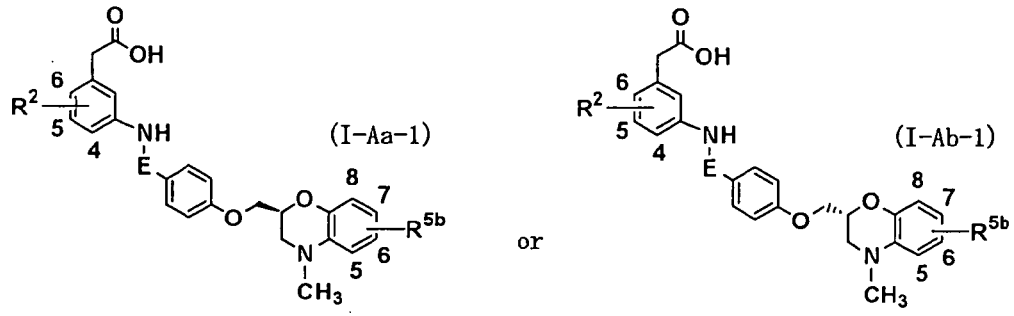

| No. | R² | E | R⁵ᵇ | No. | R² | E | R⁵ᵇ | No. | R² | E | R⁵ᵇ |
|---|---|---|---|---|---|---|---|---|---|---|---|
| 1 | H | -CO- | 6-CH₃ | 43 | H | -CO- | 6-OCH₃ | 85 | H | -CO- | 5-CH₃ |
| 2 | H | -SO₂- | 6-CH₃ | 44 | H | -SO₂- | 6-OCH₃ | 86 | H | -SO₂- | 5-CH₃ |
| 3 | H | -CH₂- | 6-CH₃ | 45 | H | -CH₂- | 6-OCH₃ | 87 | H | -CH₂- | 5-CH₃ |
| 4 | 4-CH₃ | -CO- | 6-CH₃ | 46 | 4-CH₃ | -CO- | 6-OCH₃ | 88 | 4-CH₃ | -CO- | 5-CH₃ |
| 5 | 4-CH₃ | -SO₂- | 6-CH₃ | 47 | 4-CH₃ | -SO₂- | 6-OCH₃ | 89 | 4-CH₃ | -SO₂- | 5-CH₃ |
| 6 | 4-CH₃ | -CH₂- | 6-CH₃ | 48 | 4-CH₃ | -CH₂- | 6-OCH₃ | 90 | 4-CH₃ | -CH₂- | 5-CH₃ |
| 7 | 4-Cl | -CO- | 6-CH₃ | 49 | 4-Cl | -CO- | 6-OCH₃ | 91 | 4-Cl | -CO- | 5-CH₃ |
| 8 | 4-Cl | -SO₂- | 6-CH₃ | 50 | 4-Cl | -SO₂- | 6-OCH₃ | 92 | 4-Cl | -SO₂- | 5-CH₃ |
| 9 | 4-Cl | -CH₂- | 6-CH₃ | 51 | 4-Cl | -CH₂- | 6-OCH₃ | 93 | 4-Cl | -CH₂- | 5-CH₃ |
| 10 | 4-F | -CO- | 6-CH₃ | 52 | 4-F | -CO- | 6-OCH₃ | 94 | 4-F | -CO- | 5-CH₃ |
| 11 | 4-F | -SO₂- | 6-CH₃ | 53 | 4-F | -SO₂- | 6-OCH₃ | 95 | 4-F | -SO₂- | 5-CH₃ |
| 12 | 4-F | -CH₂- | 6-CH₃ | 54 | 4-F | -CH₂- | 6-OCH₃ | 96 | 4-F | -CH₂- | 5-CH₃ |
| 13 | 5-CH₃ | -CO- | 6-CH₃ | 55 | 5-CH₃ | -CO- | 6-OCH₃ | 97 | 5-CH₃ | -CO- | 5-CH₃ |
| 14 | 5-CH₃ | -SO₂- | 6-CH₃ | 56 | 5-CH₃ | -SO₂- | 6-OCH₃ | 98 | 5-CH₃ | -SO₂- | 5-CH₃ |
| 15 | 5-CH₃ | -CH₂- | 6-CH₃ | 57 | 5-CH₃ | -CH₂- | 6-OCH₃ | 99 | 5-CH₃ | -CH₂- | 5-CH₃ |
| 16 | 5-Cl | -CO- | 6-CH₃ | 58 | 5-Cl | -CO- | 6-OCH₃ | 100 | 5-Cl | -CO- | 5-CH₃ |
| 17 | 5-Cl | -SO₂- | 6-CH₃ | 59 | 5-Cl | -SO₂- | 6-OCH₃ | 101 | 5-Cl | -SO₂- | 5-CH₃ |
| 18 | 5-Cl | -CH₂- | 6-CH₃ | 60 | 5-Cl | -CH₂- | 6-OCH₃ | 102 | 5-Cl | -CH₂- | 5-CH₃ |
| 19 | 5-F | -CO- | 6-CH₃ | 61 | 5-F | -CO- | 6-OCH₃ | 103 | 5-F | -CO- | 5-CH₃ |
| 20 | 5-F | -SO₂- | 6-CH₃ | 62 | 5-F | -SO₂- | 6-OCH₃ | 104 | 5-F | -SO₂- | 5-CH₃ |
| 21 | 5-F | -CH₂- | 6-CH₃ | 63 | 5-F | -CH₂- | 6-OCH₃ | 105 | 5-F | -CH₂- | 5-CH₃ |
| 22 | H | -CO- | 6-F | 64 | H | -CO- | 5-F | 106 | H | -CO- | 5-OCH₃ |
| 23 | H | -SO₂- | 6-F | 65 | H | -SO₂- | 5-F | 107 | H | -SO₂- | 5-OCH₃ |
| 24 | H | -CH₂- | 6-F | 66 | H | -CH₂- | 5-F | 108 | H | -CH₂- | 5-OCH₃ |
| 25 | 4-CH₃ | -CO- | 6-F | 67 | 4-CH₃ | -CO- | 5-F | 109 | 4-CH₃ | -CO- | 5-OCH₃ |
| 26 | 4-CH₃ | -SO₂- | 6-F | 68 | 4-CH₃ | -SO₂- | 5-F | 110 | 4-CH₃ | -SO₂- | 5-OCH₃ |
| 27 | 4-CH₃ | -CH₂- | 6-F | 69 | 4-CH₃ | -CH₂- | 5-F | 111 | 4-CH₃ | -CH₂- | 5-OCH₃ |
| 28 | 4-Cl | -CO- | 6-F | 70 | 4-Cl | -CO- | 5-F | 112 | 4-Cl | -CO- | 5-OCH₃ |
| 29 | 4-Cl | -SO₂- | 6-F | 71 | 4-Cl | -SO₂- | 5-F | 113 | 4-Cl | -SO₂- | 5-OCH₃ |
| 30 | 4-Cl | -CH₂- | 6-F | 72 | 4-Cl | -CH₂- | 5-F | 114 | 4-Cl | -CH₂- | 5-OCH₃ |
| 31 | 4-F | -CO- | 6-F | 73 | 4-F | -CO- | 5-F | 115 | 4-F | -CO- | 5-OCH₃ |
| 32 | 4-F | -SO₂- | 6-F | 74 | 4-F | -SO₂- | 5-F | 116 | 4-F | -SO₂- | 5-OCH₃ |
| 33 | 4-F | -CH₂- | 6-F | 75 | 4-F | -CH₂- | 5-F | 117 | 4-F | -CH₂- | 5-OCH₃ |
| 34 | 5-CH₃ | -CO- | 6-F | 76 | 5-CH₃ | -CO- | 5-F | 118 | 5-CH₃ | -CO- | 5-OCH₃ |
| 35 | 5-CH₃ | -SO₂- | 6-F | 77 | 5-CH₃ | -SO₂- | 5-F | 119 | 5-CH₃ | -SO₂- | 5-OCH₃ |
| 36 | 5-CH₃ | -CH₂- | 6-F | 78 | 5-CH₃ | -CH₂- | 5-F | 120 | 5-CH₃ | -CH₂- | 5-OCH₃ |
| 37 | 5-Cl | -CO- | 6-F | 79 | 5-Cl | -CO- | 5-F | 121 | 5-Cl | -CO- | 5-OCH₃ |
| 38 | 5-Cl | -SO₂- | 6-F | 80 | 5-Cl | -SO₂- | 5-F | 122 | 5-Cl | -SO₂- | 5-OCH₃ |
| 39 | 5-Cl | -CH₂- | 6-F | 81 | 5-Cl | -CH₂- | 5-F | 123 | 5-Cl | -CH₂- | 5-OCH₃ |
| 40 | 5-F | -CO- | 6-F | 82 | 5-F | -CO- | 5-F | 124 | 5-F | -CO- | 5-OCH₃ |
| 41 | 5-F | -SO₂- | 6-F | 83 | 5-F | -SO₂- | 5-F | 125 | 5-F | -SO₂- | 5-OCH₃ |
| 42 | 5-F | -CH₂- | 6-F | 84 | 5-F | -CH₂- | 5-F | 126 | 5-F | -CH₂- | 5-OCH₃ |

Figure 31

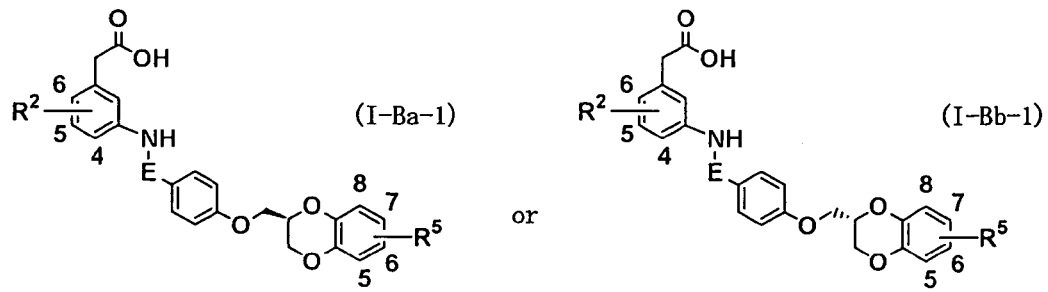

| No. | $R^2$ | E | $R^5$ | No. | $R^2$ | E | $R^5$ |
|---|---|---|---|---|---|---|---|
| 1 | H | -CO- | H | 43 | H | -CO- | 5-F |
| 2 | H | -SO$_2$- | H | 44 | H | -SO$_2$- | 5-F |
| 3 | H | -CH$_2$- | H | 45 | H | -CH$_2$- | 5-F |
| 4 | 4-CH$_3$ | -CO- | H | 46 | 4-CH$_3$ | -CO- | 5-F |
| 5 | 4-CH$_3$ | -SO$_2$- | H | 47 | 4-CH$_3$ | -SO$_2$- | 5-F |
| 6 | 4-CH$_3$ | -CH$_2$- | H | 48 | 4-CH$_3$ | -CH$_2$- | 5-F |
| 7 | 4-Cl | -CO- | H | 49 | 4-Cl | -CO- | 5-F |
| 8 | 4-Cl | -SO$_2$- | H | 50 | 4-Cl | -SO$_2$- | 5-F |
| 9 | 4-Cl | -CH$_2$- | H | 51 | 4-Cl | -CH$_2$- | 5-F |
| 10 | 4-F | -CO- | H | 52 | 4-F | -CO- | 5-F |
| 11 | 4-F | -SO$_2$- | H | 53 | 4-F | -SO$_2$- | 5-F |
| 12 | 4-F | -CH$_2$- | H | 54 | 4-F | -CH$_2$- | 5-F |
| 13 | 5-CH$_3$ | -CO- | H | 55 | 5-CH$_3$ | -CO- | 5-F |
| 14 | 5-CH$_3$ | -SO$_2$- | H | 56 | 5-CH$_3$ | -SO$_2$- | 5-F |
| 15 | 5-CH$_3$ | -CH$_2$- | H | 57 | 5-CH$_3$ | -CH$_2$- | 5-F |
| 16 | 5-Cl | -CO- | H | 58 | 5-Cl | -CO- | 5-F |
| 17 | 5-Cl | -SO$_2$- | H | 59 | 5-Cl | -SO$_2$- | 5-F |
| 18 | 5-Cl | -CH$_2$- | H | 60 | 5-Cl | -CH$_2$- | 5-F |
| 19 | 5-F | -CO- | H | 61 | 5-F | -CO- | 5-F |
| 20 | 5-F | -SO$_2$- | H | 62 | 5-F | -SO$_2$- | 5-F |
| 21 | 5-F | -CH$_2$- | H | 63 | 5-F | -CH$_2$- | 5-F |
| 22 | H | -CO- | 8-F | 64 | H | -CO- | 7-F |
| 23 | H | -SO$_2$- | 8-F | 65 | H | -SO$_2$- | 7-F |
| 24 | H | -CH$_2$- | 8-F | 66 | H | -CH$_2$- | 7-F |
| 25 | 4-CH$_3$ | -CO- | 8-F | 67 | 4-CH$_3$ | -CO- | 7-F |
| 26 | 4-CH$_3$ | -SO$_2$- | 8-F | 68 | 4-CH$_3$ | -SO$_2$- | 7-F |
| 27 | 4-CH$_3$ | -CH$_2$- | 8-F | 69 | 4-CH$_3$ | -CH$_2$- | 7-F |
| 28 | 4-Cl | -CO- | 8-F | 70 | 4-Cl | -CO- | 7-F |
| 29 | 4-Cl | -SO$_2$- | 8-F | 71 | 4-Cl | -SO$_2$- | 7-F |
| 30 | 4-Cl | -CH$_2$- | 8-F | 72 | 4-Cl | -CH$_2$- | 7-F |
| 31 | 4-F | -CO- | 8-F | 73 | 4-F | -CO- | 7-F |
| 32 | 4-F | -SO$_2$- | 8-F | 74 | 4-F | -SO$_2$- | 7-F |
| 33 | 4-F | -CH$_2$- | 8-F | 75 | 4-F | -CH$_2$- | 7-F |
| 34 | 5-CH$_3$ | -CO- | 8-F | 76 | 5-CH$_3$ | -CO- | 7-F |
| 35 | 5-CH$_3$ | -SO$_2$- | 8-F | 77 | 5-CH$_3$ | -SO$_2$- | 7-F |
| 36 | 5-CH$_3$ | -CH$_2$- | 8-F | 78 | 5-CH$_3$ | -CH$_2$- | 7-F |
| 37 | 5-Cl | -CO- | 8-F | 79 | 5-Cl | -CO- | 7-F |
| 38 | 5-Cl | -SO$_2$- | 8-F | 80 | 5-Cl | -SO$_2$- | 7-F |
| 39 | 5-Cl | -CH$_2$- | 8-F | 81 | 5-Cl | -CH$_2$- | 7-F |
| 40 | 5-F | -CO- | 8-F | 82 | 5-F | -CO- | 7-F |
| 41 | 5-F | -SO$_2$- | 8-F | 83 | 5-F | -SO$_2$- | 7-F |
| 42 | 5-F | -CH$_2$- | 8-F | 84 | 5-F | -CH$_2$- | 7-F |

Figure 32

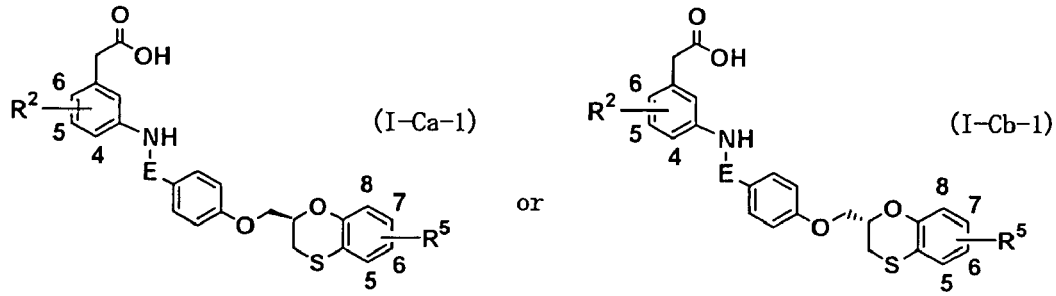

| No. | R² | E | R⁵ | No. | R² | E | R⁵ |
|---|---|---|---|---|---|---|---|
| 1 | H | -CO- | H | 43 | H | -CO- | 5-F |
| 2 | H | -SO₂- | H | 44 | H | -SO₂- | 5-F |
| 3 | H | -CH₂- | H | 45 | H | -CH₂- | 5-F |
| 4 | 4-CH₃ | -CO- | H | 46 | 4-CH₃ | -CO- | 5-F |
| 5 | 4-CH₃ | -SO₂- | H | 47 | 4-CH₃ | -SO₂- | 5-F |
| 6 | 4-CH₃ | -CH₂- | H | 48 | 4-CH₃ | -CH₂- | 5-F |
| 7 | 4-Cl | -CO- | H | 49 | 4-Cl | -CO- | 5-F |
| 8 | 4-Cl | -SO₂- | H | 50 | 4-Cl | -SO₂- | 5-F |
| 9 | 4-Cl | -CH₂- | H | 51 | 4-Cl | -CH₂- | 5-F |
| 10 | 4-F | -CO- | H | 52 | 4-F | -CO- | 5-F |
| 11 | 4-F | -SO₂- | H | 53 | 4-F | -SO₂- | 5-F |
| 12 | 4-F | -CH₂- | H | 54 | 4-F | -CH₂- | 5-F |
| 13 | 5-CH₃ | -CO- | H | 55 | 5-CH₃ | -CO- | 5-F |
| 14 | 5-CH₃ | -SO₂- | H | 56 | 5-CH₃ | -SO₂- | 5-F |
| 15 | 5-CH₃ | -CH₂- | H | 57 | 5-CH₃ | -CH₂- | 5-F |
| 16 | 5-Cl | -CO- | H | 58 | 5-Cl | -CO- | 5-F |
| 17 | 5-Cl | -SO₂- | H | 59 | 5-Cl | -SO₂- | 5-F |
| 18 | 5-Cl | -CH₂- | H | 60 | 5-Cl | -CH₂- | 5-F |
| 19 | 5-F | -CO- | H | 61 | 5-F | -CO- | 5-F |
| 20 | 5-F | -SO₂- | H | 62 | 5-F | -SO₂- | 5-F |
| 21 | 5-F | -CH₂- | H | 63 | 5-F | -CH₂- | 5-F |
| 22 | H | -CO- | 8-F | 64 | H | -CO- | 7-F |
| 23 | H | -SO₂- | 8-F | 65 | H | -SO₂- | 7-F |
| 24 | H | -CH₂- | 8-F | 66 | H | -CH₂- | 7-F |
| 25 | 4-CH₃ | -CO- | 8-F | 67 | 4-CH₃ | -CO- | 7-F |
| 26 | 4-CH₃ | -SO₂- | 8-F | 68 | 4-CH₃ | -SO₂- | 7-F |
| 27 | 4-CH₃ | -CH₂- | 8-F | 69 | 4-CH₃ | -CH₂- | 7-F |
| 28 | 4-Cl | -CO- | 8-F | 70 | 4-Cl | -CO- | 7-F |
| 29 | 4-Cl | -SO₂- | 8-F | 71 | 4-Cl | -SO₂- | 7-F |
| 30 | 4-Cl | -CH₂- | 8-F | 72 | 4-Cl | -CH₂- | 7-F |
| 31 | 4-F | -CO- | 8-F | 73 | 4-F | -CO- | 7-F |
| 32 | 4-F | -SO₂- | 8-F | 74 | 4-F | -SO₂- | 7-F |
| 33 | 4-F | -CH₂- | 8-F | 75 | 4-F | -CH₂- | 7-F |
| 34 | 5-CH₃ | -CO- | 8-F | 76 | 5-CH₃ | -CO- | 7-F |
| 35 | 5-CH₃ | -SO₂- | 8-F | 77 | 5-CH₃ | -SO₂- | 7-F |
| 36 | 5-CH₃ | -CH₂- | 8-F | 78 | 5-CH₃ | -CH₂- | 7-F |
| 37 | 5-Cl | -CO- | 8-F | 79 | 5-Cl | -CO- | 7-F |
| 38 | 5-Cl | -SO₂- | 8-F | 80 | 5-Cl | -SO₂- | 7-F |
| 39 | 5-Cl | -CH₂- | 8-F | 81 | 5-Cl | -CH₂- | 7-F |
| 40 | 5-F | -CO- | 8-F | 82 | 5-F | -CO- | 7-F |
| 41 | 5-F | -SO₂- | 8-F | 83 | 5-F | -SO₂- | 7-F |
| 42 | 5-F | -CH₂- | 8-F | 84 | 5-F | -CH₂- | 7-F |

Figure 33

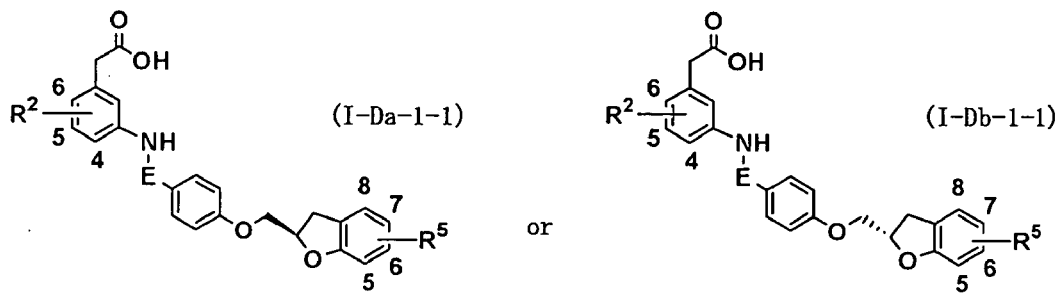

| No. | R² | E | R⁵ | No. | R² | E | R⁵ |
|---|---|---|---|---|---|---|---|
| 1 | H | -CO- | H | 43 | H | -CO- | 6-F |
| 2 | H | -SO₂- | H | 44 | H | -SO₂- | 6-F |
| 3 | H | -CH₂- | H | 45 | H | -CH₂- | 6-F |
| 4 | 4-CH₃ | -CO- | H | 46 | 4-CH₃ | -CO- | 6-F |
| 5 | 4-CH₃ | -SO₂- | H | 47 | 4-CH₃ | -SO₂- | 6-F |
| 6 | 4-CH₃ | -CH₂- | H | 48 | 4-CH₃ | -CH₂- | 6-F |
| 7 | 4-Cl | -CO- | H | 49 | 4-Cl | -CO- | 6-F |
| 8 | 4-Cl | -SO₂- | H | 50 | 4-Cl | -SO₂- | 6-F |
| 9 | 4-Cl | -CH₂- | H | 51 | 4-Cl | -CH₂- | 6-F |
| 10 | 4-F | -CO- | H | 52 | 4-F | -CO- | 6-F |
| 11 | 4-F | -SO₂- | H | 53 | 4-F | -SO₂- | 6-F |
| 12 | 4-F | -CH₂- | H | 54 | 4-F | -CH₂- | 6-F |
| 13 | 5-CH₃ | -CO- | H | 55 | 5-CH₃ | -CO- | 6-F |
| 14 | 5-CH₃ | -SO₂- | H | 56 | 5-CH₃ | -SO₂- | 6-F |
| 15 | 5-CH₃ | -CH₂- | H | 57 | 5-CH₃ | -CH₂- | 6-F |
| 16 | 5-Cl | -CO- | H | 58 | 5-Cl | -CO- | 6-F |
| 17 | 5-Cl | -SO₂- | H | 59 | 5-Cl | -SO₂- | 6-F |
| 18 | 5-Cl | -CH₂- | H | 60 | 5-Cl | -CH₂- | 6-F |
| 19 | 5-F | -CO- | H | 61 | 5-F | -CO- | 6-F |
| 20 | 5-F | -SO₂- | H | 62 | 5-F | -SO₂- | 6-F |
| 21 | 5-F | -CH₂- | H | 63 | 5-F | -CH₂- | 6-F |
| 22 | H | -CO- | 7-F | 64 | H | -CO- | 5-F |
| 23 | H | -SO₂- | 7-F | 65 | H | -SO₂- | 5-F |
| 24 | H | -CH₂- | 7-F | 66 | H | -CH₂- | 5-F |
| 25 | 4-CH₃ | -CO- | 7-F | 67 | 4-CH₃ | -CO- | 5-F |
| 26 | 4-CH₃ | -SO₂- | 7-F | 68 | 4-CH₃ | -SO₂- | 5-F |
| 27 | 4-CH₃ | -CH₂- | 7-F | 69 | 4-CH₃ | -CH₂- | 5-F |
| 28 | 4-Cl | -CO- | 7-F | 70 | 4-Cl | -CO- | 5-F |
| 29 | 4-Cl | -SO₂- | 7-F | 71 | 4-Cl | -SO₂- | 5-F |
| 30 | 4-Cl | -CH₂- | 7-F | 72 | 4-Cl | -CH₂- | 5-F |
| 31 | 4-F | -CO- | 7-F | 73 | 4-F | -CO- | 5-F |
| 32 | 4-F | -SO₂- | 7-F | 74 | 4-F | -SO₂- | 5-F |
| 33 | 4-F | -CH₂- | 7-F | 75 | 4-F | -CH₂- | 5-F |
| 34 | 5-CH₃ | -CO- | 7-F | 76 | 5-CH₃ | -CO- | 5-F |
| 35 | 5-CH₃ | -SO₂- | 7-F | 77 | 5-CH₃ | -SO₂- | 5-F |
| 36 | 5-CH₃ | -CH₂- | 7-F | 78 | 5-CH₃ | -CH₂- | 5-F |
| 37 | 5-Cl | -CO- | 7-F | 79 | 5-Cl | -CO- | 5-F |
| 38 | 5-Cl | -SO₂- | 7-F | 80 | 5-Cl | -SO₂- | 5-F |
| 39 | 5-Cl | -CH₂- | 7-F | 81 | 5-Cl | -CH₂- | 5-F |
| 40 | 5-F | -CO- | 7-F | 82 | 5-F | -CO- | 5-F |
| 41 | 5-F | -SO₂- | 7-F | 83 | 5-F | -SO₂- | 5-F |
| 42 | 5-F | -CH₂- | 7-F | 84 | 5-F | -CH₂- | 5-F |

Figure 34

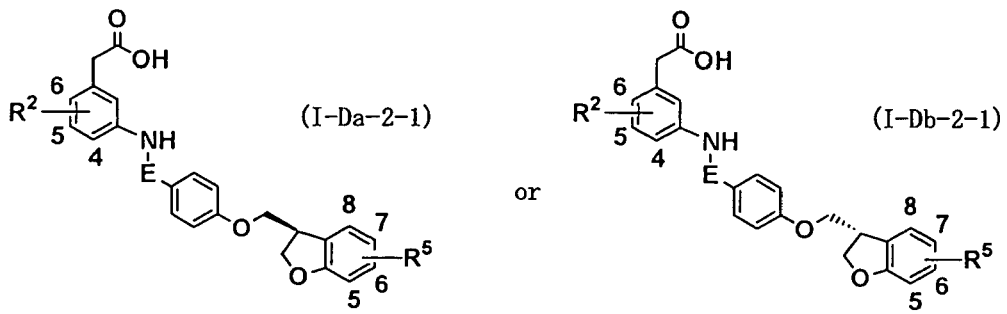

| No. | R² | E | R⁵ | No. | R² | E | R⁵ |
|---|---|---|---|---|---|---|---|
| 1 | H | -CO- | H | 43 | H | -CO- | 6-F |
| 2 | H | -SO₂- | H | 44 | H | -SO₂- | 6-F |
| 3 | H | -CH₂- | H | 45 | H | -CH₂- | 6-F |
| 4 | 4-CH₃ | -CO- | H | 46 | 4-CH₃ | -CO- | 6-F |
| 5 | 4-CH₃ | -SO₂- | H | 47 | 4-CH₃ | -SO₂- | 6-F |
| 6 | 4-CH₃ | -CH₂- | H | 48 | 4-CH₃ | -CH₂- | 6-F |
| 7 | 4-Cl | -CO- | H | 49 | 4-Cl | -CO- | 6-F |
| 8 | 4-Cl | -SO₂- | H | 50 | 4-Cl | -SO₂- | 6-F |
| 9 | 4-Cl | -CH₂- | H | 51 | 4-Cl | -CH₂- | 6-F |
| 10 | 4-F | -CO- | H | 52 | 4-F | -CO- | 6-F |
| 11 | 4-F | -SO₂- | H | 53 | 4-F | -SO₂- | 6-F |
| 12 | 4-F | -CH₂- | H | 54 | 4-F | -CH₂- | 6-F |
| 13 | 5-CH₃ | -CO- | H | 55 | 5-CH₃ | -CO- | 6-F |
| 14 | 5-CH₃ | -SO₂- | H | 56 | 5-CH₃ | -SO₂- | 6-F |
| 15 | 5-CH₃ | -CH₂- | H | 57 | 5-CH₃ | -CH₂- | 6-F |
| 16 | 5-Cl | -CO- | H | 58 | 5-Cl | -CO- | 6-F |
| 17 | 5-Cl | -SO₂- | H | 59 | 5-Cl | -SO₂- | 6-F |
| 18 | 5-Cl | -CH₂- | H | 60 | 5-Cl | -CH₂- | 6-F |
| 19 | 5-F | -CO- | H | 61 | 5-F | -CO- | 6-F |
| 20 | 5-F | -SO₂- | H | 62 | 5-F | -SO₂- | 6-F |
| 21 | 5-F | -CH₂- | H | 63 | 5-F | -CH₂- | 6-F |
| 22 | H | -CO- | 7-F | 64 | H | -CO- | 5-F |
| 23 | H | -SO₂- | 7-F | 65 | H | -SO₂- | 5-F |
| 24 | H | -CH₂- | 7-F | 66 | H | -CH₂- | 5-F |
| 25 | 4-CH₃ | -CO- | 7-F | 67 | 4-CH₃ | -CO- | 5-F |
| 26 | 4-CH₃ | -SO₂- | 7-F | 68 | 4-CH₃ | -SO₂- | 5-F |
| 27 | 4-CH₃ | -CH₂- | 7-F | 69 | 4-CH₃ | -CH₂- | 5-F |
| 28 | 4-Cl | -CO- | 7-F | 70 | 4-Cl | -CO- | 5-F |
| 29 | 4-Cl | -SO₂- | 7-F | 71 | 4-Cl | -SO₂- | 5-F |
| 30 | 4-Cl | -CH₂- | 7-F | 72 | 4-Cl | -CH₂- | 5-F |
| 31 | 4-F | -CO- | 7-F | 73 | 4-F | -CO- | 5-F |
| 32 | 4-F | -SO₂- | 7-F | 74 | 4-F | -SO₂- | 5-F |
| 33 | 4-F | -CH₂- | 7-F | 75 | 4-F | -CH₂- | 5-F |
| 34 | 5-CH₃ | -CO- | 7-F | 76 | 5-CH₃ | -CO- | 5-F |
| 35 | 5-CH₃ | -SO₂- | 7-F | 77 | 5-CH₃ | -SO₂- | 5-F |
| 36 | 5-CH₃ | -CH₂- | 7-F | 78 | 5-CH₃ | -CH₂- | 5-F |
| 37 | 5-Cl | -CO- | 7-F | 79 | 5-Cl | -CO- | 5-F |
| 38 | 5-Cl | -SO₂- | 7-F | 80 | 5-Cl | -SO₂- | 5-F |
| 39 | 5-Cl | -CH₂- | 7-F | 81 | 5-Cl | -CH₂- | 5-F |
| 40 | 5-F | -CO- | 7-F | 82 | 5-F | -CO- | 5-F |
| 41 | 5-F | -SO₂- | 7-F | 83 | 5-F | -SO₂- | 5-F |
| 42 | 5-F | -CH₂- | 7-F | 84 | 5-F | -CH₂- | 5-F |

Figure 35

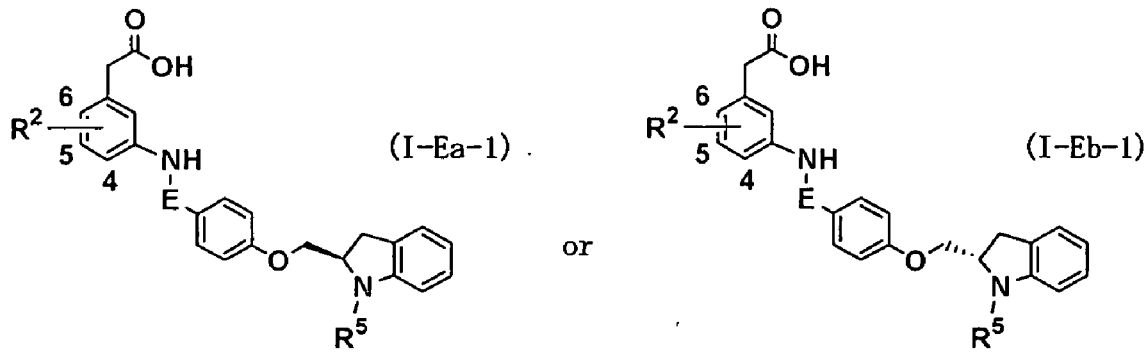

| No. | R² | E | R⁵ | No. | R² | E | R⁵ |
|---|---|---|---|---|---|---|---|
| 1 | H | -CO- | $CH_3$ | 22 | H | -CO- | $CH_2CH_3$ |
| 2 | H | -$SO_2$- | $CH_3$ | 23 | H | -$SO_2$- | $CH_2CH_3$ |
| 3 | H | -$CH_2$- | $CH_3$ | 24 | H | -$CH_2$- | $CH_2CH_3$ |
| 4 | 4-$CH_3$ | -CO- | $CH_3$ | 25 | 4-$CH_3$ | -CO- | $CH_2CH_3$ |
| 5 | 4-$CH_3$ | -$SO_2$- | $CH_3$ | 26 | 4-$CH_3$ | -$SO_2$- | $CH_2CH_3$ |
| 6 | 4-$CH_3$ | -$CH_2$- | $CH_3$ | 27 | 4-$CH_3$ | -$CH_2$- | $CH_2CH_3$ |
| 7 | 4-Cl | -CO- | $CH_3$ | 28 | 4-Cl | -CO- | $CH_2CH_3$ |
| 8 | 4-Cl | -$SO_2$- | $CH_3$ | 29 | 4-Cl | -$SO_2$- | $CH_2CH_3$ |
| 9 | 4-Cl | -$CH_2$- | $CH_3$ | 30 | 4-Cl | -$CH_2$- | $CH_2CH_3$ |
| 10 | 4-F | -CO- | $CH_3$ | 31 | 4-F | -CO- | $CH_2CH_3$ |
| 11 | 4-F | -$SO_2$- | $CH_3$ | 32 | 4-F | -$SO_2$- | $CH_2CH_3$ |
| 12 | 4-F | -$CH_2$- | $CH_3$ | 33 | 4-F | -$CH_2$- | $CH_2CH_3$ |
| 13 | 5-$CH_3$ | -CO- | $CH_3$ | 34 | 5-$CH_3$ | -CO- | $CH_2CH_3$ |
| 14 | 5-$CH_3$ | -$SO_2$- | $CH_3$ | 35 | 5-$CH_3$ | -$SO_2$- | $CH_2CH_3$ |
| 15 | 5-$CH_3$ | -$CH_2$- | $CH_3$ | 36 | 5-$CH_3$ | -$CH_2$- | $CH_2CH_3$ |
| 16 | 5-Cl | -CO- | $CH_3$ | 37 | 5-Cl | -CO- | $CH_2CH_3$ |
| 17 | 5-Cl | -$SO_2$- | $CH_3$ | 38 | 5-Cl | -$SO_2$- | $CH_2CH_3$ |
| 18 | 5-Cl | -$CH_2$- | $CH_3$ | 39 | 5-Cl | -$CH_2$- | $CH_2CH_3$ |
| 19 | 5-F | -CO- | $CH_3$ | 40 | 5-F | -CO- | $CH_2CH_3$ |
| 20 | 5-F | -$SO_2$- | $CH_3$ | 41 | 5-F | -$SO_2$- | $CH_2CH_3$ |
| 21 | 5-F | -$CH_2$- | $CH_3$ | 42 | 5-F | -$CH_2$- | $CH_2CH_3$ |

The compound of the present invention specifically binds to DP receptors and binds weakly to other prostaglandins receptors. Additionally, the compounds of the present invention are the compounds having excellent solubility. Such properties are important for developing as pharmaceuticals and it is believed that the compounds of the present invention have requirements for very useful pharmaceuticals [*The Merck Manual of Diagnosis and Therapy* (17th Ed.), published by Merck & Co.].

[Process for Production of the Compounds of the Present Invention]

The compound of the present invention represented by formula (I) are able to be produced by, for example, the method as shown below.

[I] Among the compounds represented by formula (I), the compound in which $R^1$ represents $C_{1-4}$ alkyl, $C_{2-4}$ alkenyl or benzyl, i.e. those represented by formula (IA)

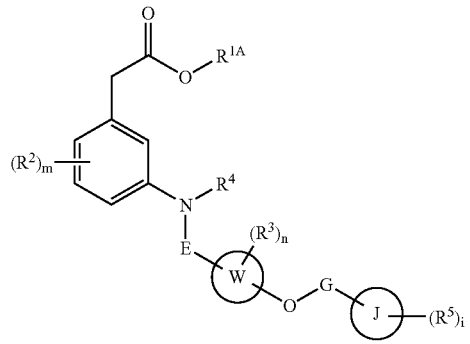

(IA)

(in the formula, $R^{1A}$ is $C_{1-4}$ alkyl, $C_{2-4}$ alkenyl or benzyl and other symbols have the same meanings as those defined already), is able to be produced according to the process as mentioned below.

(a) The compound in which E represents —C(=O)— or —S(O)$_2$— in formula (IA), i.e. the compound represented by formula (IA-1)

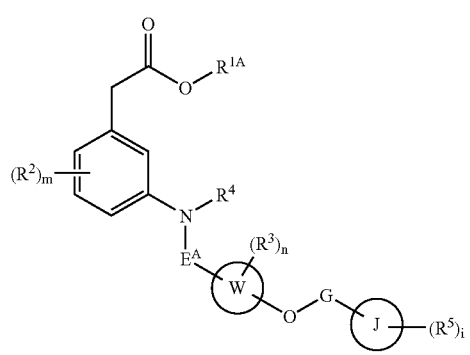

(IA-1)

(in the formula, $E^A$ is —C(=O)— or —S(O)$_2$— and other symbols have the same meanings as those defined above) is able to be produced subjecting the compound represented by formula (II-1)

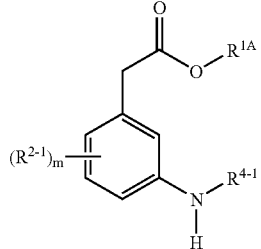

(II-1)

(in the formula, $R^{2-1}$ has the same meaning as $R^2$ and hydroxyl or amino in the group represented by $R^{2-1}$ is protected, if necessary; $R^{4-1}$ is a hydrogen atom; and other symbols have the same meanings as defined above) or the compound represented by formula (II-2)

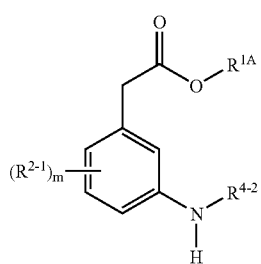

(II-2)

(in the formula, $R^{4-2}$ is a $C_{1-6}$ alkyl or benzyl and other symbols have the same meanings as those defined already) to an amidation reaction with a compound represented by formula (III)

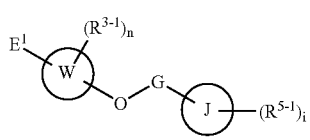

(III)

(in the formula, $E^1$ is —COOH or —SO$_3$H; $R^{3-1}$ and $R^{5-1}$ have the same meanings as $R^3$ and $R^5$, respectively and hydroxyl or amino in the group represented by $R^{3-1}$ and $R^{5-1}$ is protected, that is protected, if necessary; and other symbols have the same meanings as those defined already) followed, by subjecting to deprotection, if necessary.

Amidation reaction has been known and its examples are
(1) a process using an acid halide,
(2) a process using a mixed acid anhydride and
(3) a process using a condensing agent.

Such processes will be specifically illustrated as follows.
(1) A process using an acid halide is carried out, for example, in such a manner that carboxylic acid reacts with an agent for producing an acid halide (such as oxalyl chloride and thionyl chloride) in an organic solvent (such as chloroform, dichloromethane, diethyl ether, tetrahydrofuran, dimethoxyethane and toluene) or without solvent at −20° C. to refluxing temperature and the resulting acid halide reacts with an amine in the presence of a base (such as pyridine, triethylamine, dimethylaniline, dimethylaminopyridine and diisopropylethylamine) in an inert organic solvent (such as chloroform, dichloromethane, diethyl ether and tetrahydrofuran) at the temperature of 0 to 40° C. It is also possible to conduct the reaction with an acid halide at 0 to 40° C. in an organic solvent (such as dioxane, tetrahydrofuran, dichloromethane and toluene) in the presence or absence of a phase-transfer catalyst (such as a quaternary ammonium salt, e.g. tetrabutylammonium chloride, triethylbenzylammonium chloride, tri-n-octylmethylammonium chloride, trimethyldecylammonium chloride and tetramethylammonium bromide) using an aqueous solution of alkali (such as aqueous solution of sodium bicarbonate and an aqueous solution of sodium hydroxide).

(2) A process using a mixed acid anhydride is carried out, for example, in such a manner that carboxylic acid is made to react with an acid halide (such as pivaloyl chloride, tosyl chloride or mesyl chloride) or with an acid derivative (such as ethyl chloroformate and isobutyl chloroformate) at 0 to 40° C. in the presence or absence of an organic solvent (such as chloroform, dichloromethane, diethyl ether and tetrahydrofuran) or without a solvent in the presence of a base (such as pyridine, triethylamine, dimethylaniline, dimethylaminopyridine and diisopropylethylamine) and the resulting mixed acid anhydride is made to react with an amine at 0 to 40° C. in an organic solvent (such as chloroform, dichloromethane, diethyl ether and tetrahydrofuran).

(3) A process using a condensing agent is carried out, for example, in such a manner that carboxylic acid and an amine are subjected to a reaction at 0 to 40° C. with or without 1-hydroxybenztriazole (HOBt) using a condensing agent (such as 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide and 1-propylphosphonic acid cyclic anhydride in the presence or absence of a base (such as pyridine, triethylamine, dimethylanilin and dimethylaminopyridine) in an organic solvent (such as chloroform, dichloromethane, dimethylformamide, diethyl ether and tetrahydrofuran) or without a solvent.

It is preferred that all of the reactions (1), (2) and (3) are carried out in an atmosphere of inert gas (such as argon and nitrogen) under an anhydrous condition.

Deprotection reaction of a protective group for hydroxyl or amino is known and its examples are as follows.

(1) a hydrolyzing reaction with an alkali;
(2) a deprotection reaction under an acidic condition;
(3) a deprotection reaction by hydrogenolysis;
(4) a deprotection reaction of silyl;
(5) a deprotection reaction using metal; and
(6) a deprotection reaction using an organic metal.

Those methods will be specifically illustrated as follows.

(1) A deprotection reaction using an alkali is carried out, for example, at the temperature of 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and dioxane).

(2) A deprotection reaction under an acidic condition is carried out, for example, at the temperature of 0 to 100° C. in an organic acid (such as acetic acid, trifluoroacetic acid, methanesulfonic acid and p-tosylic acid), an inorganic acid (hydrochloric acid and sulfuric acid) or a mixture thereof (such as hydrogen bromide/acetic acid) in an organic solvent (such as dichloromethane, chloroform, dioxane, ethyl acetate and anisole).

(3) A deprotection reaction by hydrogenolysis is carried out, for example, at the temperature of 0 to 200° C. in a hydrogen atmosphere of ordinary pressure or high pressure or in the presence of ammonium formate in the presence of a catalyst [such as palladium-carbon, palladium black, palladium hydroxide, platinum hydroxide, platinum oxide and Raney nickel) in a solvent (such as an ether type (such as tetrahydrofuran, dioxane, dimethoxyethane and diethyl ether), an alcohol type (such as methanol and ethanol), a benzene type (such as benzene and toluene), a ketone type (such as acetone and methyl ethyl ketone), a nitrile type (such as acetonitrile), an amide type (such as dimethylformamide), water, ethyl acetate, acetic acid or a mixed solvent comprising two or more thereof].

(4) A deprotection reaction of silyl is carried out, for example, at the temperature of 0 to 40° C. using tetrabutylammonium fluoride in an organic solvent miscible with water (such as tetrahydrofuran and acetonitrile).

(5) A deprotection reaction using metal is carried out, for example, at the temperature of 0 to 40° C. with or without ultrasonic wave in the presence of powdery zinc in an acidic solvent (such as acetic acid, a buffer of pH 4.2 to 7.2 and a mixed solution of a solution thereof with an organic solvent such as tetrahydrofuran).

(6) A deprotection reaction using a metal complex is carried out, for example, at the temperature of 0 to 40° C. using a metal complex such as tetrakistriphenylphosphine palladium (0), bis(triphenylphosphine) palladium (II) dichloride, palladium (II) acetate and tris(triphenylphosphine) rhodium (I) chloride) in the presence or absence of a phosphine agent (such as triphenyl phosphine) in the presence of a trap reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhexanoate and potassium 2-ethylhexanoate) in an organic solvent (such as dichloromethane, dimethylformamide, tetrahydrofuran, ethyl acetate, acetonitrile, dioxane and ethanol), water or a mixed solvent thereof.

The protective group for hydroxyl includes such as methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc) and 2,2,2-trichloroethoxycarbonyl (Troc).

The protective group of amino includes such as benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM) and 2-(trimethylsilyl)ethoxymethyl (SEM) and the like.

With regard to the protective group for hydroxyl and for amino, there is no particular limitation to the above ones so far as it is a group which is able to be easily and selectively detached. For example, a deprotection reaction may be carried out by a method mentioned in "T. W. Greene, *Protective Groups in Organic Synthesis*, Wiley, New York, 1999".

As persons skilled in the art can easily understand it, the aimed compound of the present invention is able to be easily produced by using appropriate ones among those deprotection reactions.

(b) A compound of formula (IA) in which E represents —$CH_2$— or, in other words, a compound represented by formula (IA-2)

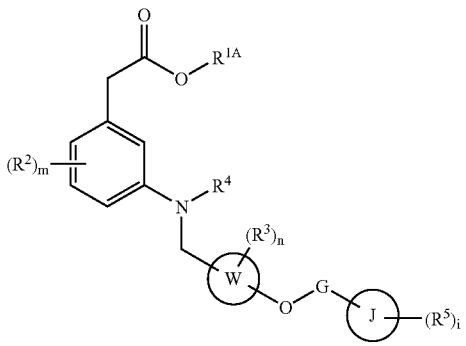

(IA-2)

(in the formula, all symbols have the same meanings as those defined above) is able to be produced by subjecting a compound represented by formula (II-1) or formula (II-2) and a compound represented by formula (IV)

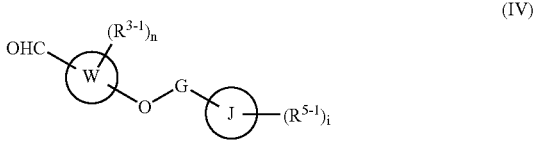

(IV)

(in the formula, all symbols have the same meanings as those defined above) to a reductive amination reaction.

Reductive amination reaction has been known and, for example, it is carried out at the temperature of 0 to 40° C. in the presence of a reducing agent (such as sodium triacetoxyborohydride, sodium cyanoborohydride and sodium borohydride) in an organic solvent (such as dichloroethane, dichloromethane, dimethylformamide, acetic acid and mixture thereof).

(c) A compound represented by formula (IA) is also able to be produced by subjecting a compound represented by formula (V)

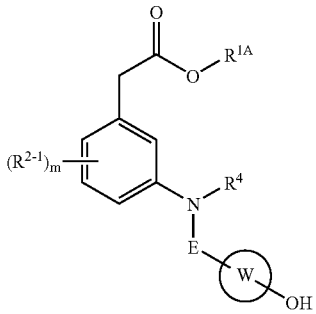

(V)

(in the formula, all symbols have the same meanings as those defined above) and a compound represented by formula (VI)

(VI)

(in the formula, Z is a leaving group or a hydrogen atom and all other symbols have the same meanings as those defined above) to an etherification reaction.

An etherification reaction has been known and, when a compound represented by formula (VI) in which Z is a leaving group is used, it is carried out, for example, at 0° C. to a refluxing temperature in the presence of an alkaline metal hydroxide (such as sodium hydroxide, potassium hydroxide and lithium hydroxide), an alkaline earth metal hydroxide (such as barium hydroxide and calcium hydroxide) a carbonate (such as cesium carbonate, sodium carbonate and potassium carbonate), an alkaline metal hydride (such as sodium hydride and potassium hydride), an aqueous solution thereof or a mixture thereof in an organic solvent (such as dimethylformamide, dimethyl sulfoxide, chloroform, dichloromethane, diethyl ether, tetrahydrofuran and methyl tert-butyl ether).

When a compound represented by formula (VI) in which Z is a hydrogen atom is used, it is carried out, for example, at 0 to 60° C. in the presence of an azo compound (such as diethyl azodicarboxylate, diisopropyl azodicarboxylate, 1,1'-(azodicarbonyl)-dipiperidine and 1,1'-azobis(N,N-dimethylformamide) and a phosphine compound (such as triphenyl phosphine, tributyl phosphine, trimethyl phosphine and polymer-supported triphenyl phosphine) in an organic solvent (such as dichloromethane, diethyl ether, tetrahydrofuran, acetonitrile, benzene and toluene).

(d) A compound in which $R^4$ is $R^{4-2}$ or, in other words, a compound represented by formula (IA-3)

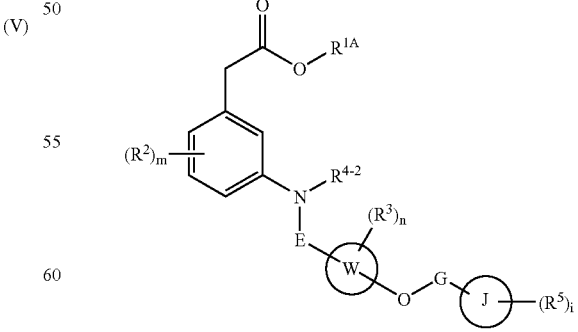

(IA-3)

(in the formula, all symbols have the same meanings as those defined above) is also able to be produced by subjecting a compound represented by formula (IA-4)

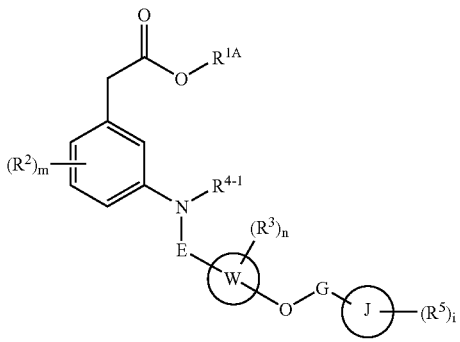

(in the formula, all symbols have the same meanings as those defined above) to an N-alkylation reaction.

An N-alkylation reaction has been known and it is able to be carried out by the reaction of, for example, at 0 to 40° C. using an alkyl ($C_{1-6}$) halide or a benzyl halide in the presence of a carbonate (such as cesium carbonate, sodium carbonate and potassium carbonate) in an organic solvent (such as dimethylformamide, dimethyl sulfoxide, chloroform, dichloromethane, diethyl ether and tetrahydrofuran).

In the case of a compound in which E in formula (IA-4) is —$SO_2$—, it is also able to be carried out, for example, at 0 to 60° C. using a $C_{1-6}$ alkyl alcohol or benzyl alcohol in the presence of an azo compound (such as diethyl azodicarboxylate, diisopropyl azodicarboxylate, 1,1'-(azodicarbonyl)dipiperidine and 1,1'-azobis(N,N-dimethylformamide) and a phosphine compound (such as triphenyl phosphine, tributyl phosphine, trimethyl phosphoine and polymer-supported triphenyl phosphine) in an organic solvent (such as dichloromethane, diethyl ether, tetrahydrofuran, acetonitrile, benzene and toluene).

[II] In the case of a compound in which $R^1$ in formula (I) represents a hydrogen atom or, in other words, a compound represented by formula (IB)

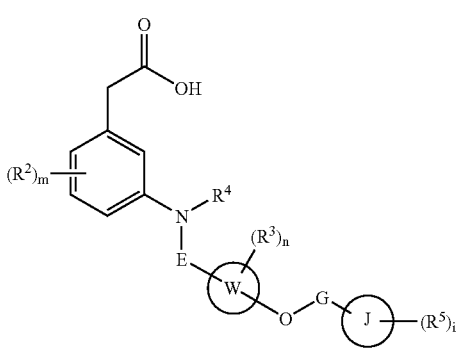

(in the formula, all symbols have the same meanings as those defined above) is able to be produced by subjecting a compound represented by formula (IA) to a deprotection reaction of a protective group for a carboxyl followed, by subjecting to a deprotection reaction of a protective group for hydroxyl or amino, if necessary.

Deprotection reaction of carboxyl has been well known and its examples are as follows.

(1) Hydrolysis with an alkali, (2) a deprotection reaction under an acidic condition, (3) a deprotection reaction by hydrogenolysis and (4) a deprotection reaction using metal.

Those methods will be specifically illustrated as follows.

(1) A deprotection reaction using an alkali is carried out, for example, at the temperature of 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and dioxane).

(2) A deprotection reaction under an acidic condition is carried out, for example, at the temperature of 0 to 100° C. in an organic acid (such as acetic acid, trifluoroacetic acid, methanesulfonic acid and p-tosylic acid), an inorganic acid (hydrochloric acid and sulfuric acid) or a mixture thereof (such as hydrogen bromide/acetic acid) in an organic solvent (such as dichloromethane, chloroform, dioxane, ethyl acetate and anisole).

(3) A deprotection reaction by hydrogenolysis is carried out, for example, at the temperature of 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel), in a solvent (such as an ether type (e.g., tetrahydrofuran, dioxane, dimethoxyethane and diethyl ether), an alcohol type (e.g., methanol and ethanol), a benzene type (e.g., benzene and toluene), a ketone type (e.g., acetone and methyl ethyl ketone), a nitrile type (e.g., acetonitrile), an amide type (such as dimethylformamide), water, ethyl acetate, acetic acid or a mixed solvent comprising two or more thereof).

(4) A deprotection reaction using metal is carried out, for example, at the temperature of 0 to 40° C., with or without ultrasonic wave in the presence of powdery zinc in an acidic solvent (such as buffer of acetic acid of pH 4.2 to 7.2 or mixture of the buffer and an organic solvent such as tetrahydrofuran).

As persons skilled in the art can easily understand that the aimed compound of the present invention is able to be easily produced by using appropriate ones among those deprotection reactions.

A deprotection reaction of hydroxyl or amino is able to be carried out by the same methods as those mentioned above.

Compounds represented by formulae (II-1), (II-2), (III), (IV), (V) and (VI) have been known per se or are able to be easily produced by known methods.

For example, the compounds represented by formulae (II-1) and (II-2) are able to be produced by the process shown in the following reaction step formula 1.

In the reaction step, X represents a halogen atom, $R^{4-3}$ represents $C_{1-5}$ alkyl or phenyl and other symbols have the same meanings as those defined above.

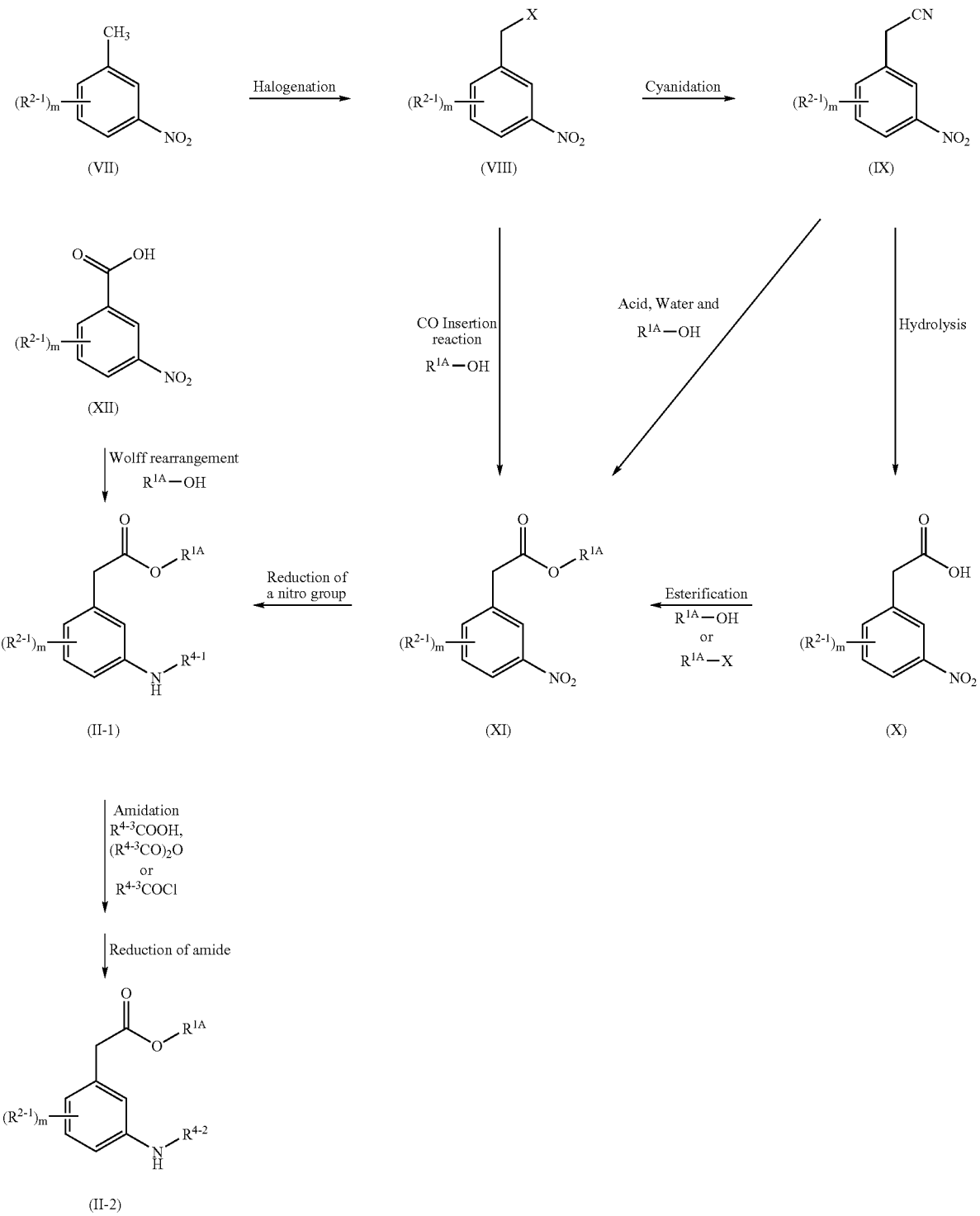

Reaction Step Formula 1

In the above reaction step formula 1, the compounds represented by formulae (VII) and (XII) used as starting materials have been known or able to be easily produced by known methods.

In each of the reactions mentioned in the present specification, the reaction product is able to be purified by a conventional purifying method such as distillation under ordinary pressure, or high performance liquid chromatography, thin-layer chromatography or column chromatography using silica gel or magnesium silicate and recrystallization. Purification may be carried out for each reaction or after completion of some reactions.

[Pharmacological Activity of the Compound of the Present Invention]

Hereinafter, experimental examples evaluating the activity of the compounds of the present invention for the DP receptor will be explained. Although method for the measurement is mentioned, for example, in the specification of WO 96/23066, the inventors of the present invention made several improvements in order to measure the activity of the test substances to the DP receptor easily and accurately. To be more specific, as is shown in the following experimental examples, it was conducted using Chinese hamster ovary (CHO) cells stably expressing the human DP receptor.

(i) Ligand Binding Using Cells Expressing the Prostanoid DP Receptor

Chinese hamster ovary (CHO) cells expressing the human DP receptor were cultivated and, according to a common method, membrane fraction was prepared.

The membrane fraction (50 μL) (protein content: 40 to 150 μg), 100 μL of an assay buffer (25 mmol/L HEPES-NaOH containing 1 mmol/L EDTA, 5 mmol/L $Mg^{2+}$ and 10 mmol/L $Mn^{2+}$; pH 7.4), 1 μL of a vehicle (dimethyl sulfoxide; DMSO) or the compound of the present invention (final concentration of DMSO: 0.5%) and 50 μL of 10 nmol/L [3H]-$PGD_2$ (final concentration: 2.5 nmol/L) were added to a polyethylene tube, and an incubation mixture was incubated at the room temperature. In a non-specific binding group, 2 mmol/L $PGD_2$ was added instead of the vehicle (final concentration of $PGD_2$: 10 μmol/L). Twenty minutes later, 1 mL of ice-cold wash buffer (10 mmol/L Tris-HCl buffer containing 0.01% bovine serum albumin (BSA) and 100 mmol/L NaCl; pH 7.4) was added to the tube to terminate the reaction. Immediately, the membrane fraction was collected on a glass fiber filter (GF/B) by filtration under reduced pressure. The membrane fraction on the glass fiber filter was washed once with approximately 2 mL of wash buffer and the glass fiber filter was dried. The dried glass fiber filter was place in a glass vial, a liquid scintillation cocktail was added thereto and radioactivity was measured by a liquid scintillation counter.

A specific binding of [$^3$H]-$PGD_2$ to the DP receptor was calculated by subtracting the radioactivity in the non-specific binding group from those in the groups other than the non-specific binding group. An inhibition by the compound of the present invention was calculated base on the specific binding of [$^3$H]-$PGD_2$ in the vehicle and the present invention groups. The $K_i$ value (dissociation constant of the compound of the present invention) was calculated according to the following formula using the estimated $IC_{50}$ value (concentration of the compound of the present invention required to inhibit the specific binding in the vehicle group by 50%).

$K_i = IC_{50}/(1+([L]*/K_d))$

[L]*: Concentration of [$^3$H]-$PGD_2$ (2.5 nmol/L)
$K_d$: Dissociation constant of [$^3$H]-$PGD_2$ The $K_d$ value of [$^3$H]-$PGD_2$ was estimated from a non-linear regression analysis after calculating the specific bindings of [$^3$H]-$PGD_2$ upon addition of various concentrations of [$^3$H]-$PGD_2$ in accordance with the above-mentioned method.

From the results of the above measurement, it was found that the compounds of the present invention strongly bound to the DP receptor at the $K_i$ values of not more than 10 μmol/L.

(ii) Measurement of Antagonistic Activity Against the DP Receptor Using Cells Expressing the Prostanoid DP Receptor CHO cells stably expressing the human DP receptor was constructed; seeded on a 24-well culture plate at a cell density of $1\times10^5$ cells/well and incubated at 37° C. for 2 days in 5% $CO_2$. Each well was washed with 500 μL of MEM (minimum essential medium) and the cells were incubated at 37° C. for 10 minutes after adding 500 μL of MEM containing 2 μmol/L of diclofenac. After removal of the supernatant by aspiration, 450 μL of an MEM containing 1 mmol/L 3-isobutyl-1-methylxanthine, 2 μmol/L diclofenac and 1% BSA (assay medium) was added, followed by incubation at 37° C. for 10 minutes. Reaction was initiated by addition of 50 μL of an assay medium containing $PGD_2$ and vehicle or an assay medium containing $PGD_2$ and the compound of the present invention (final concentration of $PGD_2$: 10 nmol/L), followed by incubation at 37° C. Ten minutes later, 500 μL of ice-cold trichloroacetic acid (TCA, 10% w/v) was added to terminate the reaction. After freezing (−80° C.) and thawing the reaction mixture once, the cells were detached therefrom using a cell scraper followed by centrifugation at 13,000 rpm for 3 minutes. The resultant supernatant was collected and cAMP concentration in the supernatant was determined by a radioimmunoassay using a cAMP assay kit (manufactured by Amersham). Thus, a buffer from the [$^{125}$I]cAMP assay kit was added to a 125 μL aliquot of the above-prepared supernatant to be the volume of 500 μL and the resultant solution was mixed with 1 mL of 0.5 mol/L tri-n-octylamine in chloroform. After extraction of TCA into a chloroform layer, the amount of cAMP in an aqueous layer was quantified according to the procedure mentioned in the [$^{125}$I]cAMP assay kit.

Potency of the antagonistic activity of the compound of the present invention for the DP receptor was expressed as an $IC_{50}$ value (a concentration of the compound of the present invention which is necessary to suppress the cAMP production in the absence of the compound of the present invention by 50%). The $IC_{50}$ value was calculated from inhibitory percentage to the cAMP production obtained by 10 nmol/L $PGD_2$, at which $PGD_2$ elicited a submaximum cAMP production.

From the above-mentioned measuring results, it was found that the compounds of the present invention strongly antagonized the DP receptor at the $IC_{50}$ values of not more than 10 μmol/L.

[Toxicity]

Toxicity of the compound of the present invention represented by formula (I) is sufficiently low and it was confirmed to be sufficiently safe to be used as pharmaceuticals.

INDUSTRIAL APPLICABILITY

[Application to Pharmaceuticals]

Since the compounds of the present invention represented by formula (I) binds to DP receptors and shows antagonistic activity, they are believed to be useful for prevention and/or treatment of diseases caused by activation of DP receptor such as allergic disease (such as allergic rhinitis, allergic conjunctivitis, atopic dermatitis, bronchial asthma and food allergy), systemic mastocytosis, disorders accompanied by systemic mast cell activation, anaphylaxis shock, bronchoconstriction, urticaria, eczema, pimples, allergic bronchial pulmonary aspergillosis, sinusitis, migraine, nasal polypus, anaphylactic vasculitis, eosinophilic syndrome, contact dermatitis, diseases accompanied by itch (such as atopic dermatitis, urticaria, allergic conjunctivitis, allergic rhinitis and contact dermatitis), diseases (such as cataract, retinal detachment, inflammation, infection and sleeping disorders) which are generated secondarily as a result of behavior accompanied by itch (such as scratching and beating), inflammation, chronic obstructive pulmonary diseases, ischemic reperfusion injury, cerebrovascular accident, autoimmune disease, traumatic brain disorder, hepatopathy, graft rejection, chronic rheumatoid arthritis, pleurisy, osteoarthritis, Crohn's disease, ulcerative colitis and irritable bowel syndrome. They also participate in sleep and platelet aggregation and are believed to be useful for those diseases as well.

Among the compound of the present invention represented by formula (I), since compounds which binds weakly to substances other than DP receptors do not express other activity, they can be pharmaceuticals having little side effects.

The compound of the present invention represented by formula (I) may be administered as a combined preparation by combining with other pharmaceuticals for the purpose of 1) supplementing and/or enhancing of prevention and/or treatment effect of the compound, 2) improvement in pharmacokinetics and absorption and reduction of dose of the compound and/or 3) reduction of side effect of the compound.

The combined preparation of the compound of the present invention represented by formula (I) with other pharmaceuticals may be administered in a form of a compounded agent in which both components are compounded in a preparation or may be in a form in which they are administered by means of separate preparations. The case of administration by means of separate preparations includes a simultaneous administration and administrations with time difference. In the case of administrations with time difference, the compound of the present invention represented by formula (I) may be firstly administered followed by administering the other pharmaceutical or the other pharmaceutical may be administered firstly followed by administering the compound of the present invention represented by formula (I). Methods for each of the administration are the same or different.

There is no particular limitation for the diseases showing prevention and/or treatment effect by the above-mentioned combined preparation, so far as it is a disease in which the prevention and/or treatment effect of the compound of present invention represented by formula (I) are supplemented and/or enhanced.

The other pharmaceutical for supplementing and/or enhancing the prevention and/or treatment effect of the compound of the present invention represented by formula (I) for allergic rhinitis includes such as antihistaminic agent, suppressor for mediator liberation, inhibitor for thromboxane synthase, antagonist for thromboxane A2 receptor, antagonist for leukotriene receptor, steroid, stimulant for α-adrenaline receptor, xanthine derivative, anticholinergic agent and suppressor for nitrogen monoxide synthase.

The other pharmaceutical for supplementing and/or enhancing the prevention and/or treatment effect of the compound of the present invention represented by formula (I) for allergic conjunctivitis includes such as antagonist to leukotriene receptor, antihistaminic agent, suppressor for mediator liberation, non-steroid anti-inflammatory agent, prostaglandins, steroid and inhibitor for nitrogen monoxide synthase.

The antihistaminic agent includes such as ketotifen fumarate, mequitazine, azelastine hydrochloride, oxatomide, terfenadine, emedastine fumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andrast, auranofin and acrivastine.

The suppressor for mediator liberation includes such as tranilast, sodium cromoglicate, amlexanox, repirinast, ibudilast, tazanolast and pemirolast potassium.

Examples of the suppressor for enzymes for synthesis of thromboxane are ozagrel hydrochloride and imitorodast sodium.

The antagonist for thromboxane $A_2$ receptor includes such as seratrodast, ramatroban, domitroban calcium hydrate and KT-2-962.

The antagonist for leukotriene receptor includes such as pranlukast hydrate, montelukast, zafirlukast, MCC-847, KCA-757, CS-615, YM-158, L-740515, CP-195494, LM-1484, RS-635, A-93178, S-36496, BIIL-284 and ONO-4057.

The steroid agent, as its external application, includes such as clobetasol propionate, diflorasone acetate, fluocinonide, mometasone furancarboxylate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate propionate, fluocinolone acetonide, beclomethasone propionate, triamcinolone acetonide, flumethasone pivalate, alclometasone propionate, clobetasone valerate, prednisolone, beclomethasone propionate and fludroxycortide.

The agent for oral use and for injection includes such as cortisone acetate, hydrocortisone, hydrocortisone sodium phosphate, hydrocortisone sodium succinate, fludrocortisone acetate, prednisolone, prednisolone acetate, prednisolone sodium succinate, prednisolone butyl acetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate and betamethasone.

The inhalation agent includes such as beclomethasone propionate, fluticasone propionate, budesonide, flunisolide, triamcinolone, ST-126P, ciclesonide, dexamethasone palomithioate, mometasone furancarbonate, prasterone sulfonate, deflazacort, methylprednisolone suleptanate and methylprednisolone sodium succinate.

The xanthine derivative includes such as aminophylline, theophylline, doxophylline, cipamfylline and diprophylline.

The anticholinergic agent includes such as ipratropium bromide, oxitropium bromide, flutropium bromide, cimetropium bromide, temiberin, tiotropium bromide and levatropate (UK-112166).

The non-steroid anti-inflammatory agent includes such as sasapyrine, sodium salicylate, aspirin, aspirin dialuminate compounding, diflunisal, indomethacin, suprofen, ufenamate, dimethylisopropylazulene, bufexamac, felbinac, diclofenac, tolmetin sodium, clinoril, fenbufen, nabumetone, proglumetacin, indomethacin farnesyl, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranoprofen, loxoprofen sodium, aluminoprofen, zaltoprofen, mefenamic acid, aluminum mefenamate, tolfenamic acid, floctafenine, ketophenylbutazone, oxyphenbutazone, piroxicam, tenoxicam, ampiroxicam, Napageln ointment, epirizole, tiaramide hydrochloride, tinoridine hydrochloride, emorfazone, sulpyrine, migrenin, salidon, Sedes G, Amipylo-N, Solbon, pyrazolone-type remedy for common cold, acetaminophen, phenacetin, dimethothiazine mesylate, simetride-compounded agent and non-pyrazolone-type remedy for common cold.

The prostaglandins (hereinafter, abbreviated as PG) includes such as an agonist for PG receptor and an antagonist for PG receptor.

The PG receptor includes such as PGE receptors (EP1, EP2, EP3 and EP4), PGD receptors (DP and CRTH2), PGF receptor (FP), PGI receptor (IP) and TX receptor (TP).

There is no particular limitation for the ratio by weight of the compound represented by formula (I) to other pharmaceuticals.

With regard to other pharmaceuticals, any two or more may be compounded and administered.

With regard to other pharmaceuticals which supplement and/or enhance the prevention and/or treatment effect of the compound represented by formula (I), not only that which has been found up to now but also that which will be found in future on the basis of the above-mentioned mechanism are included.

When the compound represented by formula (I) or non-toxic salt thereof used in the present invention or a combined preparation of the compound represented by formula (I) with other pharmaceutical is used for the above-mentioned purpose, it is usually administered systemically or topically in an oral or parenteral form.

Although the dose varies depending upon age, body weight, symptom, therapeutic effect, administering method, treating time and the like, it is usually administered orally within a range of 1 mg to 1,000 mg for one administration to an adult from once to several times a day; parenterally (preferably, as a nasal agent, eye drops or ointment) within a range of 1 mg to 100 mg for one administration to an adult from one to several times a day; or intravenously within a range of 1 to 24 hour(s) a day in a sustained manner.

It goes without saying that the dose varies under various conditions as described above and accordingly that, in some cases, less dose than the above may be sufficient while, in some other cases, more dose than the above range may be necessary.

In administering the compound represented by formula (I) or a non-toxic salt thereof or a combined preparation of the compound represented by formula (I) with other pharmaceutical, it is used as a solid composition, liquid composition and other composition for oral administration or as injection, agent for external application, suppository, and the like for parenteral administration.

The solid composition for oral administration includes such as tablets, pills, capsules, diluted powder and granules.

The capsules include hard capsules and soft capsules.

In such a solid composition, one or more active substance(s) is mixed with at least one inert diluent such as lactose, mannitol, glucose, hydroxypropyl cellulose, microcrystalline cellulose, starch, polyvinylpyrrolidone and magnesium metasilicate aluminate. The composition may contain an additive which is other than the inert diluent by a conventional method such as a lubricant such as magnesium stearate, a disintegrating agent such as calcium cellulose glycolate, a stabilizer such as lactose and a solubilizing agent such as glutamic acid and aspartic acid. Tablet or pill may, if necessary, be coated with film of an intragastrically soluble or enteric substance such as sugar, gelatin, hydroxypropyl cellulose and hydroxypropyl methylcellulose phthalate or may be coated with two or more layers. Capsule of a substance which is able to be absorbed such as gelatin is also included.

Liquid composition for oral administration includes such as pharmaceutically acceptable emulsion/suspension, solution, syrup and elixir. In such a liquid composition, one or more active substance(s) is included in a commonly used inert diluent (such as pure water and ethanol). Besides the inert diluent, the composition may contain an adjuvant such as moisturizer and suspending agent, sweetener, flavor, aromatic agent and antiseptic agent.

Other composition for oral administration includes spray agent which contains one or more active substance(s) and is formulated by a known method per se. Besides the inert diluent, the composition may contain a stabilizer such as sodium hydrogen sulfite and a buffer giving isotonicity such as isotonizing agent (such as sodium chloride, sodium citrate and citric acid). Method for the manufacture of spray agents is described, for example, in U.S. Pat. Nos. 2,868,691 and 3,095,355 in detail.

Parenteral injection according to the present invention includes aseptic aqueous and/or non-aqueous solution, suspension and emulsion. Aqueous solution and suspension includes such as distilled water for injection and physiological saline solution. Non-aqueous solution and suspension includes such as propylene glycol, polyethylene glycol, vegetable oil such as olive oil, alcohol such as ethanol and Polysorbate 80 (Registered Trademark). It is also possible that aseptic and aqueous or non-aqueous solution, suspension and emulsion may be mixed and used. Such a composition may further contain adjuvants such as antiseptic, moisturizer, emulsifier, dispersing agent, stabilizer (such as lactose) and solubilizing agent (such as glutamic acid and aspartic acid). They are sterilized by, for example, filtration passing through a bacteria-fixing filter, compounding of a disinfectant or irradiation. They may be also used in such a manner that, an aseptic solid composition is manufactured and, before using as a freeze-dried product for example, they are dissolved in sterilized or aseptic distilled water for injection or in other solvents.

An administration form of eye drop for parenteral administration includes eye drops, eye drops of a suspension type, eye drops of an emulsion type, eye drops which is dissolved upon actual use and eye ointment.

Such eye drops may be manufactured according to a known method. For example, in the case of the eye drops, an isotonizing agent (such as sodium chloride and concentrated glycerol), a buffering agent (such as sodium phosphate and sodium acetate), a surfactant (such as Polysorbate 80 (trade name), polyoxyl stearate 40 and polyoxyethylene hydrogenated castor oil), stabilizer (such as sodium citrate and sodium edetate), antiseptic agent (such as benzalkonium chloride and paraben), and the like are appropriately selected and prepared upon necessity. They are sterilized in the final step or prepared by an aseptic operation.

Inhalation agent for parenteral administration includes aerosol preparation, powder for inhalation and liquid for inhalation. The liquid for inhalation may be such a form that, in actual use, the ingredient is dissolved or suspended in water or in other appropriate medium.

Those inhalation agents are prepared according to a known method.

For example, in the case of liquid for inhalation, antiseptic agent (such as benzalkonium chloride and paraben), coloring agent, buffer (such as sodium phosphate and sodium acetate), isotonizing agent (such as sodium chloride and concentrated glycerol), thickener (such as carboxyvinyl polymer), absorption promoter, and the like are appropriately selected and prepared upon necessity.

In the case of powder for inhalation, lubricant (such as stearic acid and salt thereof), binder (such as starch and dextrin), excipient (such as lactose and cellulose), coloring agent, antiseptic (such as benzalkonium chloride and paraben), absorption promoter, and the like are appropriately selected and prepared upon necessity.

In the administration of the liquid for inhalation, a spraying device (such as atomizer and nebulizer) are usually used while, in the administration of the powder for inhalation, an administering device for inhalation of powdery pharmaceutical is usually used.

Other composition for parenteral administration includes one or more active substance(s) and outer solution, ointment, liniment, suppository for intrarectal administration, pessary for intravaginal administration, and the like which are formulated by a conventional method.

BEST MODE FOR CARRYING OUT THE INVENTION

The following reference examples and examples illustrate the present invention, but do not limit the present invention.

The solvents in the parentheses show the developing or eluting solvents and the ratios of the solvents used are by volume in chromatographic separations or TLC. The solvents in the parentheses in NMR show the solvents for measurement.

REFERENCE EXAMPLE 1

N-formyl-2-fluoroaniline

To an acetic anhydride (15.5 mL) was added dropwise formic acid (6.1 mL) at 0 degrees under an atmosphere of argon. The mixture was stirred at 50 degrees for 2 hours. After the reaction mixture was cooled to room temperature, it was diluted with tetrahydrofuran (THF; 10 mL). To the diluted solution was added 2-fluoroaniline (5.56 g) in THF (20 mL) at room temperature and then the mixture was stirred at room temperature for 1 hour. The reaction mixture was concentrated to give the title compound having the following physical data. The obtained title compound was used to next reaction without further purification.

TLC: Rf 0.70 (hexane:ethyl acetate=2:1).

REFERENCE EXAMPLE 2

N-methyl-2-fluoroaniline

To a solution of the compound prepared in Reference Example 1 in anhydrous THF (25 mL) was added borane-tetrahydrofuran complex (1M THF solution; 125 mL) under an atmosphere of argon, and the mixture was stirred at 50 degrees for 2 hours. The reaction mixture was cooled to room temperature. To the reaction mixture were added methanol (30 mL) and 4N hydrogen chloride in dioxane (10 mL) under ice cooling and the mixture was stirred at 60 degrees for 1 hour. The reaction mixture was concentrated, added 2N aqueous solution of sodium hydroxide, and then extracted with ethyl acetate. The organic layer was washed with a saturated aqueous solution of sodium chloride, dried over anhydrous sodium sulfate. The solution was filtered through Celite (trade mark) and the filtrate was concentrated. To the residue was added mixed solvent (hexane:ethyl acetate=10:1) and then filtered through silica gel. The filtrate was concentrated to give the title compound (6.45 g) having the following physical data.

TLC: Rf 0.85 (hexane:ethyl acetate=5:1); NMR (CDCl$_3$): δ 7.00-6.91 (m, 2H), 6.80-6.55 (m, 2H), 3.90 (br.s, 1H), 2.82 (s, 3H).

REFERENCE EXAMPLE 3

(2S)-3-(N-(2-fluorophenyl)-N-methylamino)-1,2-propanediol

A mixture of the compound prepared in Reference Example 2 (1.24 g), (R)-(+)-glycidol (1.11 g, Aldrich, 98% ee) and ethanol (1 mL) was stirred at 50 degrees for 12 hours under an atmosphere of argon. The reaction mixture was concentrated to give the title compound having the following physical data. The obtained compound was used to next reaction without further purification.

TLC: Rf 0.40 (hexane:ethyl acetate=1:1).

REFERENCE EXAMPLE 4

(2S)-2-hydroxymethyl-4-methyl-3,4-dihydro-2H-1,4-benzoxazine

To a solution of the compound prepared in Reference Example 3 in anhydrous dimethylformamide (DMF; 10 mL) was added potassium t-butoxide (1.68 g) in water bath, the mixture was stirred at 80 degrees for 3 hours. The reaction mixture was poured into water and extracted with ethyl acetate. The organic layer was washed with a saturated aqueous solution of sodium chloride, dried over anhydrous sodium sulfate, and then concentrated. The residue was purified by column chromatography on silica gel (hexane:ethyl acetate=3:1) to give the title compound (1.55 g, 97.6% ee) having the following physical data.

TLC: Rf 0.35 (hexane:ethyl acetate=2:1); NMR (CDCl$_3$): δ 7.90-6.79 (m, 2H), 6.70-6.60 (m, 2H), 4.33 (m, 1H), 3.82 (dd, J=13.0, 4.2 Hz, 1H), 3.79 (dd, J=13.0, 4.2 Hz, 1H), 3.19 (dd, J=10.2, 2.1 Hz, 1H), 3.17 (dd, J=11.4, 5.4 Hz, 1H), 2.86 (s, 3H).

The optical purity of the title compound was determined by high performance liquid chromatography (HPLC).
Column: CHIRALCEL OD (Daicel Chemical Industries Ltd.), 0.46 cmφ×25 cm,
Flow rate: 1 mL/minute
Solvent: hexane:2-propanol=93:7,
Detected wave-length: 254 nm,
Retention time: 30.70 minutes,
Temperature: 24 degrees.

REFERENCE EXAMPLE 5

(2S)-2-mesyloxymethyl-4-methyl-3,4-dihydro-2H-1,4-benzoxazine

To a solution of the compound prepared in Reference Example 4 (20 g) in toluene (80 mL) was added triethylamine (23 mL). The mixture was cooled to 5 degrees. To the mixture was added dropwise methanesulfonyl chloride (9.5 mL) and the mixture was stirred at 5 degrees for 30 minutes. To the reaction mixture was added water and then the mixture was extracted with ethyl acetate. The organic layer was washed with water and a saturated aqueous solution of sodium chloride, successively, dried over anhydrous sodium sulfate. The solution was filtered through Celite (trade mark). The filtrate was concentrated to give the title compound having the following physical data. The compound was used to next reaction without further purification.

TLC: Rf 0.55 (hexane:ethyl acetate=1:1); NMR (CDCl$_3$): δ 6.88 (m, 1H), 6.81 (dd, J=8.4, 1.5 Hz, 1H), 6.75-6.65 (m, 2H), 4.54 (m, 1H), 4.40 (d, J=5.4 Hz, 2H), 3.27 (dd, J=11.7, 2.7 Hz, 1H), 3.17 (dd, J=11.7, 6.3 Hz, 1H), 3.07 (s, 3H), 2.88 (s, 3H).

REFERENCE EXAMPLE 6

4-((2S)-4-methyl-3,4-dihydro-2H-1,4-benzoxazin-2-ylmethoxy)benzoic acid methyl ester To a solution of the compound prepared in Reference Example 5 and 4-hydroxybenzoic acid methyl ester (23.2 g) in DMF (200 mL) was added potassium carbonate (38.3 g) at room temperature, and the mixture was stirred at 80 degrees for 15 hours. The reaction mixture was poured into water and then extracted with mixed solvent (ethyl acetate:hexane=1:2). The organic layer was washed with 1N aqueous solution of sodium hydroxide, water and a saturated aqueous solution of sodium chloride, successively, and dried over anhydrous sodium sulfate. The solution was filtered through Celite (trade mark). The filtrate was concentrated to give the title compound having the following physical data. The compound was used to next reaction without further purification.

TLC: Rf 0.62 (hexane:ethyl acetate=2:1); NMR (CDCl$_3$): δ 7.99 (d, J=9.0 Hz, 2H), 6.96 (d, J=9.0 Hz, 2H), 6.94-6.79 (m, 2H), 6.70 (d, J=7.5 Hz, 1H), 6.68 (t, J=7.5 Hz, 1H), 4.65 (m, 1H), 4.27 (dd, J=9.9, 4.8 Hz, 1H), 4.17 (dd, J=9.9, 6.6 Hz, 1H), 3.89 (s, 3H), 3.39 (dd, J=11.7, 2.7 Hz, 1H), 3.25 (dd, J=11.7, 6.6 Hz, 1H), 2.90 (s, 3H).

REFERENCE EXAMPLE 7

4-((2S)-4-methyl-3,4-dihydro-2H-1,4-benzoxazin-2-ylmethoxy)benzoic acid

The compound prepared in Reference Example 6 in methanol (150 mL) and THF (150 mL). To the solution was added 5N aqueous solution of sodium hydroxide (100 mL) at room temperature and the mixture was stirred at room temperature for 15 hours. The reaction mixture was poured into water and washed with mixed solvent (ethyl acetate:hexane=1:2). The aqueous layer was acidified by adding 2N hydrochloric acid (260 mL) and the appeared crystal was collected by filtration. The filtered material was washed with water, dried under reduced pressure for 2 days to give the title compound (39 g) having the following physical data.

TLC: Rf 0.13 (hexane:ethyl acetate=2:1).

REFERENCE EXAMPLE 8

4-((2S)-4-methyl-3,4-dihydro-2H-1,4-benzoxazin-2-ylmethoxy)benzoyl chloride

To a solution of the compound in Reference Example 7 (5 g) in dimethoxyethane (21 mL) was added oxalyl chloride (2.75 mL) under an atmosphere of argon, the mixture was stirred at 40 degrees for 1 hour. The reaction mixture was concentrated to give the title compound (4.7 g) having the following physical data.

NMR (CDCl$_3$): δ 8.12 (d, J=8.7 Hz, 2H), 7.50 (dd, J=8.1, 1.5 Hz, 1H), 7.35 (dt, J=1.5, 8.1 Hz, 1H), 7.16-6.95 (m, 4H), 5.07-4.96 (m, 1H), 4.52-4.40 (m, 2H), 3.87 (dd, J=12.9, 2.1 Hz, 1H), 3.68 (dd, J=12.9, 10.5 Hz, 1H), 3.29 (s, 3H).

REFERENCE EXAMPLE 9

3-aminophenylacetic acid methyl ester

Methanol (20 mL) was cooled to −10 degrees under an atmosphere of argon. To the solvent was added dropwise thionyl chloride (4.31 mL) and a solution of 3-aminophenylacetic acid (3.00 g) in methanol (25 mL) and the mixture was stirred at −10~0 degrees for 1 hour. To the reaction mixture was added saturated aqueous solution of sodium bicarbonate and the mixture was extracted with ethyl acetate. The organic layer was washed with a saturated aqueous solution of sodium chloride, dried over sodium sulfate, and then concentrated. The residue was purified by column chromatography on silica gel (ethyl acetate:hexane=1:1) to give the title compound (3.90 g) having the following physical data.

TLC: Rf 0.43 (hexane:ethyl acetate=1:1); NMR (CDCl$_3$): δ 7.10 (t, J=7.8 Hz, 1H), 6.69-6.57 (m, 3H), 3.69 (s, 3H), 3.53 (s, 2H).

EXAMPLE 1

3-(4-((2S)-4-methyl-3,4-dihydro-2H-1,4-benzoxazin-2-ylmethoxy)benzoylamino)phenylacetic acid methyl ester To a solution of the compound prepared in Reference Example 9 (165 mg) in methylene chloride (2 mL) was added pyridine (161 μl) under an atmosphere of argon. To the mixture was added dropwise a solution of the compound prepared in Reference Example 8 (350 mg) in methylene chloride (2.5 mL) under ice cooling and the mixture was stirred at 0 degrees for 15 minutes. To the mixture was added methanol and water. The mixture was extracted with ethyl acetate. The organic layer was washed with a saturated aqueous solution of ammonium chloride and a saturated aqueous solution of sodium chloride, dried over anhydrous sodium sulfate, and concentrated to give the title compound (447 mg) having the following physical data.

TLC: Rf 0.23 (hexane:ethyl acetate=2:1).

EXAMPLE 1(1)~1(15)

The following compounds were obtained in the same manner as in Example 1 using the corresponding amines instead of the compound prepared in Reference Example 9.

EXAMPLE 1(1)

3-(4-((2S)-4-methyl-3,4-dihydro-2H-1,4-benzoxazin-2-ylmethoxy)benzoylamino)-4-chlorophenylacetic acid methyl ester TLC: Rf 0.27 (ethyl acetate:hexane=3:7); NMR (CDCl$_3$): δ8.51 (s, 1H), 8.36 (s, 1H), 7.88 (d, J=6.9 Hz, 2H), 7.37 (d, J=8.1 Hz, 1H), 7.10-6.98 (m, 3H), 6.94-6.80 (m, 2H), 6.78-6.66 (m, 2H), 4.73-4.63 (m, 1H), 4.30 (dd, J=9.6, 4.8 Hz, 1H), 4.21 (dd, J=9.6, 6.3 Hz, 1H), 3.71 (s, 3H), 3.66 (s, 2H), 3.40 (dd, J=12.0, 3.0 Hz, 1H), 3.27 (dd, J=12.0, 6.6 Hz, 1H), 2.91 (s, 3H).

EXAMPLE 1(2)

3-(4-((2S)-4-methyl-3,4-dihydro-2H-1,4-benzoxazin-2-ylmethoxy)benzoylamino)-2-methylphenylacetic acid methyl ester TLC: Rf 0.15 (ethyl acetate:hexane=3:7); NMR (CDCl$_3$): δ 7.86 (d, J=8.7 Hz, 2H), 7.72 (d, J=8.4 Hz, 1H), 7.59 (s, 1H), 7.22 (t, J=7.8 Hz, 1H), 7.10 (d, J=7.8 Hz, 1H), 7.06-6.96 (m, 2H), 6.93-6.81 (m, 2H), 6.76-6.66 (m, 2H), 4.72-4.62 (m, 1H), 4.30 (dd, J=9.9, 4.8 Hz, 1H), 4.19 (dd, J=9.9, 6.3 Hz, 1H), 3.71 (s, 2H), 3.70 (s, 3H), 3.40 (dd, J=11.4, 2.7 Hz, 1H), 3.27 (dd, J=11.4, 6.6 Hz, 1H), 2.92 (s, 3H), 2.26 (s, 3H).

EXAMPLE 1(3)

3-(4-((2S)-4-methyl-3,4-dihydro-2H-1,4-benzoxazin-2-ylmethoxy)benzoylamino)-4-methylphenylacetic acid methyl ester TLC: Rf 0.17 (ethyl acetate:hexane=3:7); NMR (CDCl$_3$): δ 7.89 (brs, 1H), 7.85 (d, J=8.7 Hz, 2H), 7.58 (s, 1H), 7.19 (d, J=7.8 Hz, 1H), 7.07-6.96 (m, 3H), 6.92-6.80 (m, 2H), 6.75-6.66 (m, 2H), 4.72-4.62 (m, 1H), 4.30 (dd, J=9.6, 4.8 Hz, 1H), 4.19 (dd, J=9.6, 6.3 Hz, 1H), 3.69 (s, 3H), 3.64 (s, 2H), 3.40 (dd, J=11.7, 3.0 Hz, 1H), 3.27 (dd, J=11.7, 6.6 Hz, 1H), 2.91 (s, 3H), 2.31 (s, 3H).

EXAMPLE 1(4)

3-(4-((2S)-4-methyl-3,4-dihydro-2H-1,4-benzoxazin-2-ylmethoxy)benzoylamino)-5-methylphenylacetic acid methyl ester TLC: Rf 0.68 (ethyl acetate:hexane=1:1); NMR (CDCl$_3$): δ 7.83 (d, J=8.7 Hz, 2H), 7.69 (s, 1H), 7.44 (s, 1H), 7.33 (s, 1H), 7.06-6.94 (m, 2H), 6.92-6.80 (m, 3H), 6.75-6.66 (m, 2H), 4.70-4.60 (m, 1H), 4.29 (dd, J=9.0, 4.2 Hz, 1H), 4.18 (dd, J=9.0, 6.6 Hz, 1H), 3.70 (s, 3H), 3.62 (s, 2H), 3.40 (dd, J=12.0, 2.7 Hz, 1H), 3.27 (dd, J=12.0, 6.3 Hz, 1H), 2.91 (s, 3H), 2.35 (s, 3H).

EXAMPLE 1(5)

3-(4-((2S)-4-methyl-3,4-dihydro-2H-1,4-benzoxazin-2-ylmethoxy)benzoylamino)-2-chlorophenylacetic acid methyl ester TLC: Rf 0.29 (ethyl acetate:toluene=1:9); NMR (CDCl$_3$): δ 8.50 (dd, J=8.7, 1.8 Hz, 1H), 8.42 (s, 1H), 7.89 (d, J=9.0 Hz, 2H), 7.31 (t, J=8.1 Hz, 1H), 7.10-7.00 (m, 3H), 6.92-6.81 (m, 2H), 6.76-6.66 (m, 2H), 4.72-4.62 (m, 1H), 4.30 (dd, J=9.9, 4.8 Hz, 1H), 4.20 (dd, J=9.9, 6.3 Hz, 1H), 3.82 (s, 2H), 3.72 (s, 3H), 3.40 (dd, J=11.4, 2.7 Hz, 1H), 3.27 (dd, J=11.4, 6.6 Hz, 1H), 2.91 (s, 3H).

EXAMPLE 1(6)

3-(4-((2S)-4-methyl-3,4-dihydro-2H-1,4-benzoxazin-2-ylmethoxy)benzoylamino)-4-hydroxyphenylacetic acid methyl ester TLC: Rf 0.56 (ethyl acetate:hexane=1:1); NMR (CDCl$_3$): δ 8.05 (s, 1H), 7.88 (d, J=8.7 Hz, 2H), 7.13 (d, J=1.8 Hz, 1H), 7.08-7.00 (m, 4H), 6.96-6.80 (m, 2H), 6.75-6.66 (m, 2H), 4.72-4.62 (m, 1H), 4.30 (dd, J=9.6, 4.8 Hz, 1H), 4.20 (dd, J=9.6, 6.3 Hz, 1H), 3.70 (s, 3H), 3.56 (s, 2H), 3.40 (dd, J=11.7, 2.7 Hz, 1H), 3.27 (dd, J=11.7, 6.3 Hz, 1H), 2.92 (s, 3H).

EXAMPLE 1(7)

3-(4-((2S)-4-methyl-3,4-dihydro-2H-1,4-benzoxazin-2-ylmethoxy)benzoylamino)-4-methoxyphenylacetic acid methyl ester TLC: Rf 0.55 (ethyl acetate:hexane=1:1); NMR (CDCl$_3$): δ 8.50-8.42 (m, 2H), 7.86 (d, J=8.7 Hz, 2H), 7.06-6.96 (m, 3H), 6.92-6.81 (m, 3H), 6.76-6.68 (m, 2H), 4.72-4.62 (m, 1H), 4.30 (dd, J=9.9, 5.4 Hz, 1H), 4.19 (dd, J=9.9, 6.3 Hz, 1H), 3.92 (s, 3H), 3.70 (s, 3H), 3.63 (s, 2H), 3.40 (dd, J=11.4, 2.7 Hz, 1H), 3.27 (dd, J=11.4, 6.6 Hz, 1H), 2.91 (s, 3H).

EXAMPLE 1(8)

5-(4-((2S)-4-methyl-3,4-dihydro-2H-1,4-benzoxazin-2-ylmethoxy)benzoylamino)-2-chlorophenylacetic acid methyl ester TLC: Rf 0.61 (ethyl acetate:hexane=1:1); NMR (CDCl$_3$): δ 7.83 (d, J=9.0 Hz, 2H), 7.75 (s, 1H), 7.62 (d, J=2.7 Hz, 1H), 7.54 (dd, J=9.0, 2.4 Hz, 1H), 7.37 (d, J=9.0 Hz, 1H), 7.02 (d, J=9.0 Hz, 2H), 6.93-6.80 (m, 2H), 6.75-6.66 (m, 2H), 4.72-4.62 (m, 1H), 4.29 (dd J=9.9, 5.1 Hz, 1H), 4.19 (dd, J=9.9, 6.3 Hz, 1H), 3.79 (s, 2H), 3.73 (s, 3H), 3.40 (dd, J=11.7, 6.3 Hz, 1H), 3.27 (dd, J=11.7, 6.6 Hz, 1H), 2.91 (s, 3H).

EXAMPLE 1(9)

5-(4-((2S)-4-methyl-3,4-dihydro-2H-1,4-benzoxazin-2-ylmethoxy)benzoylamino)-2-methoxy-3-methylphenylacetic acid methyl ester TLC: Rf 0.50 (ethyl acetate:hexane=1:1); NMR (CDCl$_3$): δ 7.82 (d, J=8.7 Hz, 2H), 7.65 (s, 1H), 7.45 (d, J=2.7 Hz, 1H), 7.30 (d, J=2.7 Hz, 1H), 7.01 (d, J=9.0 Hz, 2H), 6.92-6.81 (m, 2H), 6.75-6.66 (m, 2H), 4.72-4.62 (m, 1H), 4.29 (dd, J=9.6, 4.8 Hz, 1H), 4.18 (dd, J=9.6, 6.3 Hz, 1H), 3.72 (s, 3H), 3.71 (s, 3H), 3.70 (s, 2H), 3.40 (dd, J=11.7, 2.7 Hz, 1H), 3.27 (dd, J=11.7, 6.6 Hz, 1H), 2.91 (s, 3H), 2.32 (s, 3H).

EXAMPLE 1(10)

5-(4-((2S)-4-methyl-3,4-dihydro-2H-1,4-benzoxazin-2-ylmethoxy)benzoylamino)-2-hydroxy-3-methylphenylacetic acid methyl ester TLC: Rf 0.21 (ethyl acetate:hexane=1:1); NMR (CDCl$_3$): δ 8.66-8.58 (m, 1H), 7.81 (d, J=9.0 Hz, 2H), 7.58 (s, 1H), 7.38 (d, J=2.4 Hz, 1H), 7.21 (d, J=2.4 Hz, 1H), 7.07-6.96 (m, 2H), 6.93-6.80 (m, 2H), 6.76-6.66 (m, 2H), 4.72-4.62 (m, 1H), 4.29 (dd, J=9.9, 5.4 Hz, 1H), 4.18 (dd, J=9.9, 6.3 Hz, 1H), 3.75 (s, 3H), 3.68 (s, 2H), 3.40 (dd, J=11.4, 2.7 Hz, 1H), 3.27 (dd, J=11.4, 6.3 Hz, 1H), 2.91 (s, 3H), 2.29 (s, 3H).

EXAMPLE 1(11)

3-(4-((2S)-4-methyl-3,4-dihydro-2H-1,4-benzox-azin-2-ylmethoxy)benzoylamino)-5-phenoxymeth-ylphenylacetic acid methyl ester TLC: Rf 0.59 (ethyl acetate:hexane=1:1);

EXAMPLE 1(12)

5-(4-((2S)-4-methyl-3,4-dihydro-2H-1,4-benzox-azin-2-ylmethoxy)benzoylamino)-4-chloro-2-fluo-rophenylacetic acid methyl ester TLC: Rf 0.71 (ethyl acetate:hexane=1:1); NMR (CDCl$_3$): δ 8.50 (d, J=7.2 Hz, 1H), 8.21 (s, 1H), 7.87 (d, J=9.0 Hz, 2H), 7.18 (d, J=9.0 Hz, 1H), 7.08-6.98 (m, 2H), 6.92-6.80 (m, 2H), 6.76-6.64 (m, 2H), 4.72-4.62 (m, 1H), 4.31 (dd, J=9.9, 5.1 Hz, 1H), 4.21 (dd, J=9.9, 6.6 Hz, 1H), 3.73 (s, 2H), 3.40 (dd, J=11.7, 3.0 Hz, 1H), 3.27 (dd, J=11.7, 6.6 Hz, 1H), 2.91 (s, 3H).

EXAMPLE 1(13)

5-(4-((2S)-4-methyl-3,4-dihydro-2H-1,4-benzox-azin-2-ylmethoxy)benzoylamino)-2-fluoropheny-lacetic acid methyl ester TLC: Rf 0.47 (ethyl acetate:hexane=1:1); NMR (CDCl$_3$): δ 7.83 (d, J=8.4 Hz, 2H), 7.70 (s, 1H), 7.60-7.48 (m, 2H), 7.10-6.98 (m, 3H), 6.92-6.80 (m, 2H), 6.75-6.65 (m, 2H), 4.72-4.62 (m, 1H), 4.29 (dd, J=9.6, 5.4 Hz, 1H), 4.19 (dd, J=9.6, 6.3 Hz, 1H), 3.72 (s, 3H), 3.69 (s, 2H), 3.40 (dd, J=12.0, 2.7 Hz, 1H), 3.27 (dd, J=12.0, 6.6 Hz, 1H), 2.91 (s, 3H).

EXAMPLE 1(14)

3-(4-((2S)-4-methyl-3,4-dihydro-2H-1,4-benzox-azin-2-ylmethoxy)benzoylamino)-5-fluoropheny-lacetic acid methyl ester TLC: Rf 0.21 (ethyl acetate:hexane=3:7); NMR (CDCl$_3$): δ 7.83 (d, J=8.4 Hz, 2H), 7.76 (s, 1H), 7.60-7.52 (m, 1H), 7.20 (s, 1H), 7.02 (d, J=8.4 Hz, 2H), 6.92-6.75 (m, 3H), 6.75-6.66 (m, 2H), 4.72-4.62 (m, 1H), 4.29 (dd, J=9.6, 4.8 Hz, 1H), 4.19 (dd, J=9.6, 6.6 Hz, 1H), 3.72 (s, 3H), 3.62 (s, 2H), 3.40 (dd, J=11.4, 2.7 Hz, 1H), 3.27 (dd, J=11.4, 6.6 Hz, 1H), 2.91 (s, 3H).

EXAMPLE 1(15)

3-(4-((2S)-4-methyl-3,4-dihydro-2H-1,4-benzox-azin-2-ylmethoxy)benzoylamino)-5-methoxymeth-ylphenylacetic acid methyl ester TLC: Rf 0.26 (ethyl acetate:hexane=1:1); NMR (CDCl$_3$): δ 7.83 (d, J=8.7 Hz, 2H), 7.74 (s, 1H), 7.54 (s, 2H), 7.08-6.97 (m, 3H), 6.93-6.80 (m, 2H), 6.75-6.66 (m, 2H), 4.72-4.62 (m, 1H), 4.46 (s, 2H), 4.29 (dd, J=9.9, 5.1 Hz, 1H), 4.19 (dd, J=9.9, 6.3 Hz, 1H), 3.70 (s, 3H), 3.64 (s, 2H), 3.44-3.33 (m, 4H), 3.27 (dd, J=11.7, 6.3 Hz, 1H), 2.91 (s, 3H).

EXAMPLE 2

3-(4-((2S)-4-methyl-3,4-dihydro-2H-1,4-benzox-azin-2-ylmethoxy)benzoylamino)phenylacetic acid

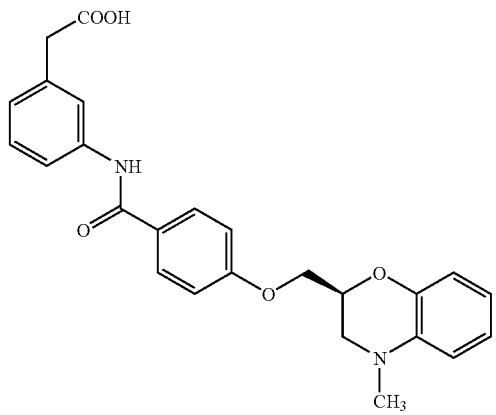

To a solution of the compound prepared in Example 1 (224 mg) in a mixed solvent of tetrahydrofuran (2.5 mL) and methanol (2.5 mL) was added 2N aqueous solution of sodium hydroxide (2 mL). The mixture was stirred at room temperature for 30 minutes. The reaction mixture was concentrated under reduced pressure and then washed with t-butyl methyl ether. The aqueous layer was acidified by adding 1N hydrochloric acid and then extracted with ethyl acetate. The organic layer was washed with a saturated aqueous solution of sodium chloride, dried over anhydrous sodium sulfate, and concentrated. The residue was purified by column chromatography on silica gel (ethyl acetate:hexane=1:1~ethyl acetate:methanol=10:1) to give the title compound (123 mg) having the following physical data.

TLC: Rf 0.52 (ethyl acetate:methanol=19:1); NMR (CDCl$_3$): δ 7.90-7.78 (m, 3H), 7.57 (s, 1H), 7.54 (d, J=8.1 Hz, 1H), 7.29 (m, 1H), 7.06-6.95 (m, 3H), 6.91-6.82 (m, 2H), 6.75-6.66 (m, 2H), 4.65 (m, 1H), 4.27 (dd, J=9.6, 4.8 Hz, 1H), 4.16 (dd, J=9.6, 6.6 Hz, 1H), 3.63 (s, 2H), 3.38 (dd, J=11.4, 2.7 Hz, 1H), 3.25 (dd, J=11.4, 6.6 Hz, 1H), 2.90 (s, 3H).

EXAMPLE 2(1)~2(15)

The following compounds were obtained in the same manner as in Example 2 using the compounds prepared in Example 1(1)~1(15).

EXAMPLE 2(1)

3-(4-((2S)-4-methyl-3,4-dihydro-2H-1,4-benzox-azin-2-ylmethoxy)benzoylamino)-4-chloropheny-lacetic acid TLC: Rf 0.38 (chloroform:methanol=9:1); NMR (CDCl$_3$): δ 8.53 (d, J=1.8 Hz, 1H), 8.36 (s, 1H), 7.88 (d, J=8.7 Hz, 2H), 7.37 (d, J=8.1 Hz, 1H), 7.08-6.98 (m, 3H), 6.92-6.82 (m, 2H), 6.76-6.66 (m, 2H), 4.72-4.62 (m, 1H), 4.30 (dd, J=9.6, 4.8 Hz, 1H), 4.19 (dd, J=9.6, 6.3 Hz, 1H), 3.69 (s, 2H), 3.40 (dd, J=12.0, 3.0 Hz, 1H), 3.27 (dd, J=12.0, 6.9 Hz, 1H), 2.91 (s, 3H).

EXAMPLE 2(2)

3-(4-((2S)-4-methyl-3,4-dihydro-2H-1,4-benzoxazin-2-ylmethoxy)benzoylamino)-2-methylphenylacetic acid TLC: Rf 0.37 (chloroform:methanol=9:1); NMR (CDCl$_3$): δ 7.85 (d, J=8.7 Hz, 2H), 7.71 (d, J=8.4 Hz, 1H), 7.61 (s, 1H), 7.28-7.19 (m, 1H), 7.11 (d, J=7.5 Hz, 1H), 7.02 (d, J=8.7 Hz, 2H), 6.92-6.80 (m, 2H), 6.76-6.66 (m, 2H), 4.72-4.62 (m, 1H), 4.30 (dd, J=9.6, 5.1 Hz, 1H), 4.19 (dd, J=9.6, 6.3 Hz, 1H), 3.74 (s, 2H), 3.40 (dd, J=11.4, 3.3 Hz, 1H), 3.27 (dd, J=11.4, 6.6 Hz, 1H), 2.91 (s, 3H), 2.26 (s, 3H).

EXAMPLE 2(3)

3-(4-((2S)-4-methyl-3,4-dihydro-2H-1,4-benzoxazin-2-ylmethoxy)benzoylamino)-4-methylphenylacetic acid TLC: Rf 0.34 (chloroform:methanol=9:1); NMR (CDCl$_3$): δ 7.89 (s, 1H), 7.84 (d, J=8.7 Hz, 2H), 7.61 (s, 1H), 7.20 (d, J=7.8 Hz, 1H), 7.07-6.99 (m, 3H), 6.92-6.81 (m, 2H), 6.75-6.66 (m, 2H), 4.72-4.62 (m, 1H), 4.30 (dd, J=9.9, 5.1 Hz, 1H), 4.19 (dd, J=9.9, 6.6 Hz, 1H), 3.66 (s, 2H), 3.40 (dd, J=11.4, 2.7 Hz, 1H), 3.27 (dd, J=11.4, 6.6 Hz, 1H), 2.91 (s, 3H), 2.26 (s, 3H).

EXAMPLE 2(4)

3-(4-((2S)-4-methyl-3,4-dihydro-2H-1,4-benzoxazin-2-ylmethoxy)benzoylamino)-5-methylphenylacetic acid TLC: Rf 0.39 (chloroform:methanol=9:1); NMR (CDCl$_3$): δ 7.82 (d, J=9.0 Hz, 2H), 7.74 (s, 1H), 7.41 (s, 1H), 7.37 (s, 1H), 7.00 (d, J=9.0 Hz, 2H), 6.92-6.81 (m, 3H), 6.76-6.66 (m, 2H), 4.70-4.60 (m, 1H), 4.28 (dd, J=9.9, 5.4 Hz, 1H), 4.18 (dd, J=9.9, 6.6 Hz, 1H), 3.62 (s, 2H), 3.39 (dd, J=11.7, 3.3 Hz, 1H), 3.26 (dd, J=11.7, 6.6 Hz, 1H), 2.91 (s, 3H), 2.34 (s, 3H).

EXAMPLE 2(5)

3-(4-((2S)-4-methyl-3,4-dihydro-2H-1,4-benzoxazin-2-ylmethoxy)benzoylamino)-2-chlorophenylacetic acid TLC: Rf 0.46 (chloroform:methanol=9:1); NMR (CDCl$_3$): δ 8.52 (d, J=8.4 Hz, 1H), 8.42 (s, 1H), 7.89 (d, J=9.0 Hz, 2H), 7.32 (t, J=8.4 Hz, 1H), 7.12-7.00 (m, 3H), 6.93-6.82 (m, 2H), 6.75-6.66 (m, 2H), 4.72-4.62 (m, 1H), 4.30 (dd, J=9.9, 5.4 Hz, 1H), 4.20 (dd, J=9.9, 6.3 Hz, 1H), 3.87 (s, 2H), 3.40 (dd, J=11.4, 2.7 Hz, 1H), 3.27 (dd, J=11.4, 6.6 Hz, 1H), 2.91 (s, 3H).

EXAMPLE 2(6)

3-(4-((2S)-4-methyl-3,4-dihydro-2H-1,4-benzoxazin-2-ylmethoxy)benzoylamino)-4-hydroxyphenylacetic acid TLC: Rf 0.28 (chloroform:methanol=9:1); NMR (CDCl$_3$): δ 8.10 (s, 1H), 7.86 (d, J=9.0 Hz, 2H), 7.14 (d, J=1.8 Hz, 1H), 7.08-6.97 (m, 4H), 6.92-6.82 (m, 2H), 6.76-6.66 (m, 2H), 4.72-4.62 (m, 1H), 4.29 (dd, J=9.6, 5.1 Hz, 1H), 4.19 (dd, J=9.6, 6.3 Hz, 1H), 3.58 (s, 2H), 3.40 (dd, J=11.7, 3.0 Hz, 1H), 3.27 (dd, J=11.7, 6.6 Hz, 1H), 2.91 (s, 3H).

EXAMPLE 2(7)

3-(4-((2S)-4-methyl-3,4-dihydro-2H-1,4-benzoxazin-2-ylmethoxy)benzoylamino)-4-methoxyphenylacetic acid TLC: Rf 0.45 (chloroform:methanol=9:1); NMR (CDCl$_3$): δ 8.51-8.44 (m, 2H), 7.85 (d, J=9.0 Hz, 2H), 7.06-6.97 (m, 3H), 6.92-6.82 (m, 3H), 6.76-6.66 (m, 2H), 4.72-4.62 (m, 1H), 4.30 (dd, J=9.9, 5.1 Hz, 1H), 4.18 (dd, J=9.9, 6.6 Hz, 1H), 3.92 (s, 3H), 3.66 (s, 2H), 3.40 (dd, J=11.7, 2.7 Hz, 1H), 3.27 (dd, J=11.7, 6.6 Hz, 1H), 2.91 (s, 3H).

EXAMPLE 2(8)

5-(4-((2S)-4-methyl-3,4-dihydro-2H-1,4-benzoxazin-2-ylmethoxy)benzoylamino)-2-chlorophenylacetic acid TLC: Rf 0.62 (chloroform:methanol=4:1); NMR (CDCl$_3$): δ 7.86-7.76 (m, 3H), 7.66 (d, J=2.4 Hz, 1H), 7.52 (dd, J=8.4, 2.4 Hz, 1H), 7.36 (d, J=8.4 Hz, 1H), 7.00 (d, J=9.0 Hz, 2H), 6.94-6.80 (m, 2H), 6.76-6.66 (m, 2H), 4.72-4.62 (m, 1H), 4.28 (dd J=9.9, 5.1 Hz, 1H), 4.18 (dd, J=9.9, 6.3 Hz, 1H), 3.81 (s, 2H), 3.39 (dd, J=11.4, 2.7 Hz, 1H), 3.26 (dd, J=11.4, 6.6 Hz, 1H), 2.91 (s, 3H).

EXAMPLE 2(9)

5-(4-((2S)-4-methyl-3,4-dihydro-2H-1,4-benzoxazin-2-ylmethoxy)benzoylamino)-2-methoxy-3-methylphenylacetic acid TLC: Rf 0.70 (chloroform:methanol=4:1); NMR (CDCl$_3$): δ 7.82 (d, J=8.7 Hz, 2H), 7.65 (s, 1H), 7.45 (d, J=2.7 Hz, 1H), 7.34 (d, J=2.7 Hz, 1H), 7.01 (d, J=8.7 Hz, 2H), 6.94-6.82 (m, 2H), 6.76-6.66 (m, 2H), 4.72-4.62 (m, 1H), 4.29 (dd, J=9.9, 5.1 Hz, 1H), 4.18 (dd, J=9.9, 6.3 Hz, 1H), 3.76 (s, 3H), 3.71 (s, 2H), 3.40 (dd, J=11.7, 3.0 Hz, 1H), 3.27 (dd, J=11.7, 6.3 Hz, 1H), 2.91 (s, 3H), 2.33 (s, 3H).

EXAMPLE 2(10)

5-(4-((2S)-4-methyl-3,4-dihydro-2H-1,4-benzoxazin-2-ylmethoxy)benzoylamino)-2-hydroxy-3-methylphenylacetic acid TLC: Rf 0.22 (chloroform:methanol=4:1); NMR (CDCl$_3$): δ 7.81 (d, J=9.0 Hz, 2H), 7.74-7.64 (m, 1H), 7.36-7.26 (m, 1H), 7.20-7.14 (m, 1H), 6.99 (d, J=9.0 Hz, 2H), 6.93-6.82 (m, 2H), 6.76-6.66 (m, 2H), 4.71-4.61 (m, 1H), 4.28 (dd, J=9.9, 5.4 Hz, 1H), 4.17 (dd, J=9.9, 6.3 Hz, 1H), 3.65 (s, 2H), 3.40 (dd, J=11.4, 2.4 Hz, 1H), 3.26 (dd, J=11.4, 6.9 Hz, 1H), 2.91 (s, 3H), 2.28 (s, 3H).

EXAMPLE 2(11)

3-(4-((2S)-4-methyl-3,4-dihydro-2H-1,4-benzoxazin-2-ylmethoxy)benzoylamino)-5-phenoxymethylphenylacetic acid TLC: Rf 0.47 (chloroform:methanol=9:1); NMR (CDCl$_3$): δ 7.83 (d, J=9.3 Hz, 2H), 7.78 (s, 1H), 7.66-7.60 (m, 2H), 7.34-7.20 (m, 2H), 7.15 (s, 1H), 7.05-6.92 (m, 5H), 6.92-6.80 (m, 2H), 6.74-6.66 (m, 2H), 5.07 (s, 2H), 4.72-4.62 (m, 1H), 4.29 (dd, J=9.9, 5.4 Hz, 1H), 4.18 (dd, J=9.9, 6.6 Hz, 1H), 3.70 (s, 2H), 3.40 (dd, J=11.7, 2.7 Hz, 1H), 3.27 (dd, J=11.7, 6.9 Hz, 1H), 2.91 (s, 3H).

EXAMPLE 2(12)

5-(4-((2S)-4-methyl-3,4-dihydro-2H-1,4-benzoxazin-2-ylmethoxy)benzoylamino)-4-chloro-2-fluorophenylacetic acid TLC: Rf 0.37 (chloroform:methanol=9:1); NMR (CDCl$_3$): δ 8.52 (d, J=7.8 Hz, 1H), 8.22 (s, 1H), 7.86 (d, J=8.7 Hz, 2H), 7.19 (d, J=9.0 Hz, 1H), 7.04 (d, J=8.7 Hz, 2H), 6.92-6.80 (m, 2H), 6.75-6.66 (m, 2H), 4.72-4.62 (m, 1H), 4.30 (dd, J=9.6, 5.1 Hz, 1H), 4.20 (dd, J=9.6, 6.6 Hz, 1H), 3.75 (s, 2H), 3.40 (dd, J=11.7, 3.0 Hz, 1H), 3.27 (dd, J=11.7, 6.6 Hz, 1H), 2.91 (s, 3H).

EXAMPLE 2(13)

5-(4-((2S)-4-methyl-3,4-dihydro-2H-1,4-benzoxazin-2-ylmethoxy)benzoylamino)-2-fluorophenylacetic acid TLC: Rf 0.50 (chloroform:methanol=9:1); NMR (CDCl$_3$): δ 7.82 (d, J=8.7 Hz, 2H), 7.76 (s, 1H), 7.63-7.56 (m, 1H), 7.54-7.46 (m, 1H), 7.06 (t, J=8.7 Hz, 1H), 7.01 (d, J=8.7 Hz, 2H), 6.93-6.81 (m, 2H), 6.75-6.66 (m, 2H), 4.71-4.61 (m, 1H), 4.29 (dd, J=9.6, 5.4 Hz, 1H), 4.18 (dd, J=9.6, 6.3 Hz, 1H), 3.72 (s, 2H), 3.40 (dd, J=12.0, 2.7 Hz, 1H), 3.27 (dd, J=12.0, 6.6 Hz, 1H), 2.91 (s, 3H).

EXAMPLE 2(14)

3-(4-((2S)-4-methyl-3,4-dihydro-2H-1,4-benzoxazin-2-ylmethoxy)benzoylamino)-5-fluorophenylacetic acid TLC: Rf 0.28 (chloroform:methanol=9:1); NMR (CDCl$_3$): δ 7.86-7.77 (m, 3H), 7.57-7.50 (m, 1H), 7.28-7.22 (m, 1H), 7.01 (d, J=9.0 Hz, 2H), 6.92-6.76 (m, 3H), 6.74-6.66 (m, 2H), 4.72-4.62 (m, 1H), 4.29 (dd, J=9.9, 4.8 Hz, 1H), 4.18 (dd, J=9.9, 6.3 Hz, 1H), 3.65 (s, 2H), 3.40 (dd, J=11.7, 2.7 Hz, 1H), 3.27 (dd, J=11.7, 6.6 Hz, 1H), 2.91 (s, 3H).

EXAMPLE 2(15)

3-(4-((2S)-4-methyl-3,4-dihydro-2H-1,4-benzoxazin-2-ylmethoxy)benzoylamino)-5-methoxymethylphenylacetic acid TLC: Rf 0.33 (chloroform:methanol=9:1); NMR (CDCl$_3$): δ 7.83 (d, J=8.7 Hz, 2H), 7.78 (s, 1H), 7.58 (s, 1H), 7.53 (s, 1H), 7.07-6.97 (m, 3H), 6.92-6.82 (m, 2H), 6.75-6.66 (m, 2H), 4.72-4.62 (m, 1H), 4.46 (s, 2H), 4.29 (dd, J=9.9, 4.8 Hz, 1H), 4.18 (dd, J=9.9, 6.3 Hz, 1H), 3.67 (s, 2H), 3.44-3.36 (m, 4H), 3.27 (dd, J=11.7, 6.6 Hz, 1H), 2.91 (s, 3H).

REFERENCE EXAMPLE 10

3-(N-ethylamino)phenylacetic acid methyl ester

To a solution of the compound prepared in Reference Example 9 (820 mg) in methylene chloride (5 mL) were added pyridine (802 μl) and acetic anhydride (517 μl) under an atmosphere of argon and the mixture was stirred at room temperature for 30 minutes. To the reaction mixture was added water. The mixture was extracted with ethyl acetate. The organic layer was washed with hydrochloric acid and a saturated aqueous solution of sodium chloride, dried over anhydrous sodium sulfate and concentrated to give the crude acetyl compound.

The solution of the crude acetyl compound in anhydrous THF (3 mL) was cooled with ice cooling under an atmosphere of argon. To the solution was added borane-dimethylsulfide complex (2M THF solution; 4.97 mL) and the mixture was stirred at room temperature for 1 hour and then stirred at 60 degrees for 15 hours. After cooling the reaction mixture by ice, To the reaction mixture were added methanol and hydrogen chloride in dioxane. The mixture was stirred at 60 degrees for 30 minutes. The reaction mixture was neutralized with a saturated aqueous solution of sodium bicarbonate and then extracted with ethyl acetate. The organic layer was washed with saturated aqueous solution of sodium chloride, dried over anhydrous sodium sulfate, and concentrated. The residue was purified by column chromatography on silica gel (hexane:ethyl acetate=8:1) to give the title compound (320 mg) having the following physical data.

TLC: Rf 0.49 (hexane:ethyl acetate=2:1); NMR (CDCl$_3$): δ 7.12 (t, J=7.5 Hz, 1H), 6.59 (d, J=7.5 Hz, 1H), 6.55-6.48 (m, 2H), 3.68 (s, 3H), 3.54 (s, 2H), 3.15 (q, J=7.2 Hz, 2H), 1.25 (t, J=7.2 Hz, 3H).

EXAMPLE 3

3-(N-(4-((2S)-4-methyl-3,4-dihydro-2H-1,4-benzoxazin-2-ylmethoxy)benzoyl)-N-ethylamino)phenylacetic acid methyl ester The title compound having the following physical data was obtained in the same manner as in Example 1 using the compound prepared in Reference Example 10 instead of the compound prepared in Reference Example 9.

TLC: Rf 0.20 (hexane:ethyl acetate=2:1).

EXAMPLE 3(1)

3-(N-(4-((2S)-4-methyl-3,4-dihydro-2H-1,4-benzoxazin-2-ylmethoxy)benzoyl)-N-methylamino)phenylacetic acid methyl ester The title compound having the following physical data was obtained in the same manner as in Example 1 using 3-(N-methylamino)phenylacetic acid methyl ester instead of the compound prepared in Reference Example 9.

TLC: Rf 0.33 (hexane:ethyl acetate=1:1).

EXAMPLE 4

3-(N-(4-((2S)-4-methyl-3,4-dihydro-2H-1,4-benzoxazin-2-ylmethoxy)benzoyl)-N-ethylamino)phenylacetic acid The title compound having the following physical data was obtained in the same manner as in Example 2 using the compound prepared in Example 3 instead of the compound prepared in Example 1.

TLC: Rf 0.63 (ethyl acetate:methanol=19:1); NMR (CDCl$_3$): δ 7.30-7.18 (m, 3H), 7.12-7.02 (m, 2H), 6.92-6.66 (m, 7H), 4.54 (m, 1H), 4.30 (dd, J=10.8, 4.8 Hz, 1H), 4.03 (dd, J=10.8, 7.5 Hz, 1H), 3.99 (dq, J=2.4, 7.2 Hz, 2H), 3.41 (s, 2H), 3.39 (dd, J=11.7, 2.4 Hz, 1H), 3.07 (dd, J=11.7, 7.8 Hz, 1H), 2.86 (s, 3H), 1.22 (t, J=7.2 Hz, 3H).

EXAMPLE 4(1)

3-(N-(4-((2S)-4-methyl-3,4-dihydro-2H-1,4-benzoxazin-2-ylmethoxy)benzoyl)-N-methylamino)phenylacetic acid The title compound having the following physical data was obtained in the same manner as in Example 2 using the compound prepared in Example 3(1) instead of the compound prepared in Example 1.

TLC: Rf 0.49 (ethyl acetate:methanol=19:1); NMR (CDCl$_3$): δ 7.29-7.20 (m, 4H), 7.10-7.02 (m, 2H), 6.91-6.69 (m, 6H), 4.55 (m, 1H), 4.28 (dd, J=10.8, 4.8 Hz, 1H), 4.04 (dd, J=10.8, 7.2 Hz, 1H), 3.49 (s, 3H), 3.43 (s, 2H), 3.38 (dd, J=11.4, 2.4 Hz, 1H), 3.09 (dd, J=11.4, 7.2 Hz, 1H), 2.86 (s, 3H).

EXAMPLE 5

3-(2-methyl-4-((2S)-4-methyl-3,4-dihydro-2H-1,4-benzoxazin-2-ylmethoxy)benzoylamino)phenylacetic acid methyl ester The title compound having the following physical data was obtained in the same manner as in Example 1 using 2-methyl-4-((2S)-4-methyl-3,4-dihydro-2H-1,4-benzoxazin-2-ylmethoxy)benzoyl chloride instead of the compound prepared in Reference Example 8.

TLC: Rf 0.14 (ethyl acetate:hexane=3:7); NMR (CDCl$_3$): δ 7.60-7.38 (m, 4H), 7.32 (t, J=7.8 Hz, 1H), 7.06 (d, J=7.5 Hz, 1H), 6.92-6.77 (m, 4H), 6.74-6.66 (m, 2H), 4.70-4.60 (m, 1H), 4.26 (dd, J=9.6, 5.4 Hz, 1H), 4.14 (dd, J=9.6, 6.6 Hz, 1H), 3.71 (s, 3H), 3.65 (s, 2H), 3.39 (dd, J=11.4, 3.0 Hz, 1H), 3.26 (dd, J=11.4, 7.8 Hz, 1H), 2.91 (s, 3H), 2.51 (s, 3H).

EXAMPLE 5(1)~5(14)

The following compounds of the present invention were obtained in the same manner as in Example 5 using corresponding derivatives instead of the compound prepared in Reference Example 8 and using the compound prepared in Reference Example 9 or corresponding derivatives instead of it.

EXAMPLE 5(1)

3-(2-chloro-4-((2S)-4-methyl-3,4-dihydro-2H-1,4-benzoxazin-2-ylmethoxy)benzoylamino)phenylacetic acid methyl ester TLC: Rf 0.45 (hexane:ethyl acetate=1:1); NMR (CDCl$_3$): δ 8.04 (s, 1H), 7.83 (d, J=8.4 Hz, 1H), 7.62-7.52 (m, 2H), 7.33 (t, J=7.8 Hz, 1H), 7.09 (d, J=7.8 Hz, 1H), 7.02 (d, J=2.4 Hz, 1H), 6.99-6.81 (m, 3H), 6.76-6.66 (m, 2H), 4.71-4.61 (m, 1H), 4.27 (dd, J=9.9, 5.1 Hz, 1H), 4.17 (dd, J=9.9, 6.0 Hz, 1H), 3.71 (s, 3H), 3.65 (s, 2H), 3.38 (dd, J=11.4, 2.7 Hz, 1H), 3.25 (dd, J=11.4, 6.3 Hz, 1H), 2.91 (s, 3H).

EXAMPLE 5(2)

3-(2-methyl-4-((2S)-4-methyl-3,4-dihydro-2H-1,4-benzoxazin-2-ylmethoxy)benzoylamino)-2-methylphenylacetic acid methyl ester TLC: Rf 0.46 (hexane:ethyl acetate=1:1); NMR (CDCl$_3$): δ 7.80-7.70 (m, 1H), 7.50 (d, J=7.8 Hz, 1H), 7.30-7.18 (m, 2H), 7.09 (d, J=7.8 Hz, 1H), 6.92-6.78 (m, 4H), 6.75-6.66 (m, 2H), 4.70-4.60 (m, 1H), 4.26 (dd, J=9.6, 5.1 Hz, 1H), 4.14 (dd, J=9.6, 6.6 Hz, 1H), 3.71 (s, 2H), 3.69 (s, 3H), 3.39 (dd, J=11.4, 2.7 Hz, 1H), 3.26 (dd, J=11.4, 6.6 Hz, 1H), 2.91 (s, 3H), 2.53 (s, 3H), 2.24 (s, 3H).

EXAMPLE 5(3)

3-(2-methyl-4-((2S)-4-methyl-3,4-dihydro-2H-1,4-benzoxazin-2-ylmethoxy)benzoylamino)-4-chlorophenylacetic acid methyl ester TLC: Rf 0.68 (hexane:ethyl acetate=1:1); NMR (CDCl$_3$): δ 8.49 (s, 1H), 7.99 (s, 1H), 7.54 (d, J=8.1 Hz, 1H), 7.36 (d, J=8.1 Hz, 1H), 7.04-6.98 (m, 1H), 6.92-6.80 (m, 4H), 6.74-6.66 (m, 2H), 4.70-4.60 (m, 1H), 4.27 (dd, J=9.6, 5.1 Hz, 1H), 4.15 (dd, J=9.6, 6.9 Hz, 1H), 3.72 (s, 3H), 3.67 (s, 2H), 3.40 (dd, J=11.7, 2.1 Hz, 1H), 3.26 (dd, J=11.7, 6.6 Hz, 1H), 2.91 (s, 3H), 2.56 (s, 3H).

EXAMPLE 5(4)

3-(2-methyl-4-((2S)-4-methyl-3,4-dihydro-2H-1,4-benzoxazin-2-ylmethoxy)benzoylamino)-5-fluorophenylacetic acid methyl ester TLC: Rf 0.54 (hexane:ethyl acetate=1:1); NMR (CDCl$_3$): δ 7.56-7.42 (m, 3H), 7.17 (s, 1H), 6.92-6.76 (m, 5H), 6.75-6.66 (m, 2H), 4.70-4.60 (m, 1H), 4.26 (dd, J=9.6, 4.8 Hz, 1H), 4.15 (dd, J=9.6, 5.4 Hz, 1H), 3.71 (s, 3H), 3.61 (s, 2H), 3.39 (dd, J=11.7, 2.7 Hz, 1H), 3.26 (dd, J=11.7, 6.3 Hz, 1H), 2.91 (s, 3H), 2.51 (s, 3H).

EXAMPLE 5(5)

5-(2-methyl-4-((2S)-4-methyl-3,4-dihydro-2H-1,4-benzoxazin-2-ylmethoxy)benzoylamino)-2-fluorophenylacetic acid methyl ester TLC: Rf 0.47 (hexane:ethyl acetate=1:1); NMR (300 MHz, CDCl$_3$): δ 7.60-7.35 (m, 4H), 7.06 (t, J=9.0 Hz, 1H), 6.93-6.75 (m, 4H), 6.75-6.66 (m, 2H), 4.70-4.60 (m, 1H), 4.26 (dd, J=9.6, 4.8 Hz, 1H), 4.14 (dd, J=9.6, 6.3 Hz, 1H), 3.72 (s, 3H), 3.69 (s, 2H), 3.39 (dd, J=11.4, 2.7 Hz, 1H), 3.25 (dd, J=11.4, 6.6 Hz, 1H), 2.91 (s, 3H), 2.51 (s, 3H).

EXAMPLE 5(6)

5-(2-methyl-4-((2S)-4-methyl-3,4-dihydro-2H-1,4-benzoxazin-2-ylmethoxy)benzoylamino)-2-methoxyphenylacetic acid methyl ester TLC: Rf 0.38 (hexane:ethyl acetate=1:1); NMR (300 MHz, CDCl$_3$): δ 7.57-7.48 (m, 1H), 7.48-7.36 (m, 3H), 7.31 (s, 1H), 6.93-6.76 (m, 5H), 6.74-6.66 (m, 2H), 4.70-4.60 (m, 1H), 4.25 (dd, J=9.9, 4.8 Hz, 1H), 4.14 (dd, J=9.9, 6.6 Hz, 1H), 3.82 (s, 3H), 3.70 (s, 3H), 3.65 (s, 2H), 3.39 (dd, J=11.1, 2.4 Hz, 1H), 3.25 (dd, J=11.1, 6.6 Hz, 1H), 2.91 (s, 3H), 2.50 (s, 3H).

EXAMPLE 5(7)

3-(2-chloro-4-((2S)-4-methyl-3,4-dihydro-2H-1,4-benzoxazin-2-ylmethoxy)benzoylamino)-4-chlorophenylacetic acid methyl ester TLC: Rf 0.53 (hexane:ethyl acetate=1:1); NMR (300 MHz, CDCl$_3$): δ 8.68 (brs, 1H), 8.54 (brs, 1H), 7.87 (d, J=8.4 Hz, 1H), 7.36 (d, J=8.4 Hz, 1H), 7.10-6.80 (m, 5H), 6.76-6.66 (m, 2H), 4.72-4.62 (m, 1H), 4.27 (dd, J=9.6, 5.4 Hz, 1H), 4.18 (dd, J=9.6, 6.0 Hz, 1H), 3.71 (s, 3H), 3.66 (s, 2H), 3.39 (dd, J=12.0, 2.7 Hz, 1H), 3.25 (dd, J=12.0, 6.6 Hz, 1H), 2.91 (s, 3H).

EXAMPLE 5(8)

5-(2-chloro-4-((2S)-4-methyl-3,4-dihydro-2H-1,4-benzoxazin-2-ylmethoxy)benzoylamino)-2-fluorophenylacetic acid methyl ester TLC: Rf 0.44 (hexane:ethyl acetate=1:1); NMR (300 MHz, CDCl$_3$): δ 8.03 (s, 1H), 7.83 (d, J=8.4 Hz, 1H), 7.62-7.56 (m, 1H), 7.56-7.48 (m, 1H), 7.07 (t, J=9.3 Hz, 1H), 7.02 (d, J=2.4 Hz, 1H), 6.98-6.80 (m, 3H), 6.76-6.66 (m, 2H), 4.71-4.61 (m, 1H), 4.27 (dd, J=9.6, 4.8 Hz, 1H), 4.17 (dd, J=9.6, 6.0 Hz, 1H), 3.73 (s, 3H), 3.70 (s, 2H), 3.38 (dd, J=11.4, 2.7 Hz, 1H), 3.25 (dd, J=11.4, 6.3 Hz, 1H), 2.91 (s, 3H).

EXAMPLE 5(9)

5-(2-chloro-4-((2S)-4-methyl-3,4-dihydro-2H-1,4-benzoxazin-2-ylmethoxy)benzoylamino)-2-methoxyphenylacetic acid methyl ester TLC: Rf 0.30 (hexane:ethyl acetate=1:1); NMR (300 MHz, CDCl$_3$): δ 7.93 (s, 1H), 7.82 (d, J=8.7 Hz, 1H), 7.57 (dd, J=8.7, 2.7 Hz, 1H), 7.43 (d, J=2.7 Hz, 1H), 7.01 (d, J=2.7 Hz. 1H), 6.98-6.81 (m, 4H), 6.76-6.66 (m, 2H), 4.70-4.60 (m, 1H), 4.26 (dd, J=9.6, 5.1 Hz, 1H), 4.16 (dd, J=9.6, 6.3 Hz, 1H), 3.82 (s, 3H), 3.70 (s, 3H), 3.65 (s, 2H), 3.38 (dd, J=11.4, 2.7 Hz, 1H), 3.25 (dd, J=11.4, 6.3 Hz, 1H), 2.91 (s, 3H).

EXAMPLE 5(10)

3-(2-methyl-4-((2S)-4-methyl-3,4-dihydro-2H-1,4-benzoxazin-2-ylmethoxy)benzoylamino)-4-methylphenylacetic acid methyl ester TLC: Rf 0.38 (hexane:ethyl acetate=1:1); NMR (300 MHz, CDCl$_3$): δ 7.93 (brs, 1H), 7.49 (d, J=8.1 Hz, 1H), 7.28-7.22 (m, 1H), 7.18 (d, J=8.1 Hz, 1H), 7.06-7.01 (m, 1H), 6.92-6.78 (m, 4H), 6.74-6.66 (m, 2H), 4.70-4.60 (m, 1H), 4.26 (dd, J=9.6, 4.8 Hz, 1H), 4.15 (dd, J=9.6, 6.6 Hz, 1H), 3.70 (s, 3H), 3.64 (s, 2H), 3.40 (dd, J=11.7, 2.7 Hz, 1H), 3.26 (dd, J=11.7, 6.3 Hz, 1H), 2.91 (s, 3H), 2.54 (s, 3H), 2.27 (s, 3H).

EXAMPLE 5(11)

5-(2-methyl-4-((2S)-4-methyl-3,4-dihydro-2H-1,4-benzoxazin-2-ylmethoxy)benzoylamino)-4-chloro-2-fluorophenylacetic acid methyl ester TLC: Rf 0.70 (hexane:ethyl acetate=1:1); NMR (300 MHz, CDCl$_3$): δ 8.48 (d, J=7.5 Hz, 1H), 7.85 (s, 1H), 7.53 (d, J=8.1 Hz, 1H), 7.17 (d, J=9.0 Hz, 1H), 6.92-6.80 (m, 4H), 6.75-6.66 (m, 2H), 4.70-4.60 (m, 1H), 4.27 (dd, J=9.6, 4.8 Hz, 1H), 4.15 (dd, J=9.6, 6.6 Hz, 1H), 3.73 (s, 3H), 3.71 (s, 2H), 3.39 (dd, J=11.7, 2.7 Hz, 1H), 3.26 (dd, J=11.7, 6.6 Hz, 1H), 2.91 (s, 3H), 2.55 (s, 3H).

EXAMPLE 5(12)

3-(2-methyl-4-((2S)-4-methyl-3,4-dihydro-2H-1,4-benzoxazin-2-ylmethoxy)benzoylamino)-5-methylphenylacetic acid methyl ester TLC: Rf 0.51 (hexane:ethyl acetate=1:1); NMR (300 MHz, CDCl$_3$): δ 7.44 (d, J=8.4 Hz, 1H), 7.41 (brs, 1H), 7.36 (brs, 1H), 7.30 (brs, 1H), 6.92-6.76 (m, 5H), 6.74-6.66 (m, 2H), 4.70-4.60 (m, 1H), 4.26 (dd, J=9.6, 4.8 Hz, 1H), 4.14 (dd, J=9.6, 6.6 Hz, 1H), 3.70 (s, 3H), 3.60 (s, 2H), 3.39 (dd, J=11.4, 2.7 Hz, 1H), 3.26 (dd, J=11.4, 6.6 Hz, 1H), 2.91 (s, 3H), 2.51 (s, 3H), 2.35 (s, 3H).

EXAMPLE 5(13)

3-(2-chloro-4-((2S)-4-methyl-3,4-dihydro-2H-1,4-benzoxazin-2-ylmethoxy)benzoylamino)-4-methylphenylacetic acid methyl ester TLC: Rf 0.40 (hexane:ethyl acetate=1:1); NMR (300 MHz, CDCl$_3$): δ 8.00 (s, 2H), 7.90 (d, J=8.4 Hz, 1H), 7.19 (d, J=7.5 Hz, 1H), 7.07-7.01 (m, 2H), 7.00-6.93 (m, 1H), 6.93-6.81 (m, 2H), 6.75-6.67 (m, 2H), 4.71-4.61 (m, 1H), 4.27 (dd, J=9.9, 5.7 Hz, 1H), 4.18 (dd, J=9.9, 6.3 Hz, 1H), 3.70 (s, 3H), 3.65 (s, 2H), 3.39 (dd, J=11.7, 2.7 Hz, 1H), 3.25 (dd, J=11.7, 6.3 Hz, 1H), 2.91 (s, 3H), 2.32 (s, 3H).

EXAMPLE 5(14)

3-(2-chloro-4-((2S)-4-methyl-3,4-dihydro-2H-1,4-benzoxazin-2-ylmethoxy)benzoylamino)-5-methylphenylacetic acid methyl ester TLC: Rf 0.49 (hexane:ethyl acetate=1:1); NMR (300 MHz, CDCl$_3$): δ 7.98 (s, 1H), 7.81 (d, J=9.0 Hz, 1H), 7.41 (s, 1H), 7.36 (s, 1H), 7.02 (d, J=2.4 Hz, 1H), 6.99-6.81 (m, 4H), 6.76-6.67 (m, 2H), 4.71-4.61 (m, 1H), 4.26 (dd, J=9.9, 5.4 Hz, 1H), 4.17 (dd, J=9.9, 6.3 Hz, 1H), 3.70 (s, 3H), 3.60 (s, 2H), 3.38 (dd, J=11.4, 2.4 Hz, 1H), 3.25 (dd, J=11.4, 6.3 Hz, 1H), 2.91 (s, 3H), 2.36 (s, 3H).

EXAMPLE 6

3-(2-methyl-4-((2S)-4-methyl-3,4-dihydro-2H-1,4-benzoxazin-2-ylmethoxy)benzoylamino)phenylacetic acid The title compound having the following physical data was obtained in the same manner as in Example 2 using the compound prepared in Example 5.

TLC: Rf 0.40 (chloroform:methanol=9:1); NMR (CDCl$_3$): δ 7.62-7.40 (m, 4H), 7.33 (t, J=8.1 Hz, 1H), 7.10-7.04 (m, 1H), 6.92-6.76 (m, 4H), 6.74-6.66 (m, 2H), 4.70-4.60 (m, 1H), 4.26 (dd, J=9.6, 4.8 Hz, 1H), 4.14 (dd, J=9.6, 6.6 Hz, 1H), 3.68 (s, 2H), 3.39 (dd, J=11.4, 2.7 Hz, 1H), 3.25 (dd, J=11.4, 6.6 Hz, 1H), 2.91 (s, 3H), 2.50 (s, 3H).

EXAMPLE 6(1)~6(14)

The following compounds were obtained in the same manner as in Example 6 using the compounds prepared in Example 5(1)~5(14).

EXAMPLE 6(1)

3-(2-chloro-4-((2S)-4-methyl-3,4-dihydro-2H-1,4-benzoxazin-2-ylmethoxy)benzoylamino)phenylacetic acid TLC: Rf 0.29 (chloroform:methanol=9:1); NMR (CDCl$_3$): δ 8.06 (s, 1H), 7.82 (d, J=8.4 Hz, 1H), 7.62 (s, 1H), 7.55 (d, J=8.4 Hz, 1H), 7.34 (t, J=7.5 Hz, 1H), 7.09 (d, J=7.5 Hz, 1H), 7.01 (d, J=1.8 Hz, 1H), 6.98-6.80 (m, 3H), 6.76-6.67 (m, 2H), 4.71-4.61 (m, 1H), 4.26 (dd, J=9.9, 5.1 Hz, 1H), 4.17 (dd, J=9.9, 6.0 Hz, 1H), 3.68 (s, 2H), 3.38 (dd, J=11.7, 3.0 Hz, 1H), 3.25 (dd, J=11.7, 6.0 Hz, 1H), 2.91 (s, 3H).

EXAMPLE 6(2)

3-(2-methyl-4-((2S)-4-methyl-3,4-dihydro-2H-1,4-benzoxazin-2-ylmethoxy)benzoylamino)-2-methylphenylacetic acid TLC: Rf 0.38 (chloroform:methanol=9:1); NMR (CDCl$_3$): δ 7.82-7.68 (m, 1H), 7.54-7.44 (m, 1H), 7.38-7.18 (m, 2H), 7.10 (d, J=8.1 Hz, 1H), 6.92-6.77 (m, 4H), 6.75-6.66 (m, 2H), 4.70-4.60 (m, 1H), 4.26 (dd, J=9.9, 5.4 Hz, 1H), 4.14 (dd, J=9.9, 6.3 Hz, 1H), 3.73 (s, 2H), 3.39 (dd, J=11.4, 2.7 Hz, 1H), 3.25 (dd, J=11.4, 6.6 Hz, 1H), 2.91 (s, 3H), 2.52 (s, 3H), 2.24 (s, 3H).

EXAMPLE 6(3)

3-(2-methyl-4-((2S)-4-methyl-3,4-dihydro-2H-1,4-benzoxazin-2-ylmethoxy)benzoylamino)-4-chlorophenylacetic acid TLC: Rf 0.41 (chloroform:methanol=9:1); NMR (CDCl$_3$): δ 8.49 (brs, 1H), 7.99 (s, 1H), 7.53 (d, J=7.8 Hz, 1H), 7.37 (d, J=7.8 Hz, 1H), 7.01 (dd, J=7.8, 1.8 Hz, 1H), 6.93-6.78 (m, 4H), 6.76-6.66 (m, 2H), 4.70-4.60 (m, 1H), 4.27 (dd, J=9.9, 4.8 Hz, 1H), 4.16 (dd, J=9.9, 6.6 Hz, 1H), 3.70 (s, 2H), 3.40 (dd, J=11.7, 2.7 Hz, 1H), 3.25 (dd, J=11.7, 6.6 Hz, 1H), 2.91 (s, 3H), 2.55 (s, 3H).

EXAMPLE 6(4)

3-(2-methyl-4-((2S)-4-methyl-3,4-dihydro-2H-1,4-benzoxazin-2-ylmethoxy)benzoylamino)-5-fluorophenylacetic acid TLC: Rf 0.41 (chloroform:methanol=9:1); NMR (CDCl$_3$): δ 7.56-7.40 (m, 3H), 7.20 (brs, 1H), 6.93-6.75 (m, 5H), 6.76-6.66 (m, 2H), 4.70-4.60 (m, 1H), 4.26 (dd, J=9.6, 5.1 Hz, 1H), 4.14 (dd, J=9.6, 6.6 Hz, 1H), 3.64 (s, 2H), 3.39 (dd, J=11.7, 2.4 Hz, 1H), 3.25 (dd, J=11.7, 6.6 Hz, 1H), 2.91 (s, 3H), 2.49 (s, 3H).

EXAMPLE 6(5)

5-(2-methyl-4-((2S)-4-methyl-3,4-dihydro-2H-1,4-benzoxazin-2-ylmethoxy)benzoylamino)-2-fluorophenylacetic acid TLC: Rf 0.31 (chloroform:methanol=9:1); NMR (300 MHz, CDCl$_3$): δ 7.61 (brs, 1H), 7.52-7.38 (m, 3H), 7.07 (t, J=8.7 Hz, 1H), 6.92-6.76 (m, 4H), 6.76-6.66 (m, 2H), 4.70-4.60 (m, 1H), 4.26 (dd, J=9.3, 5.1 Hz, 1H), 4.14 (dd, J=9.3, 6.3 Hz, 1H), 3.73 (s, 2H), 3.39 (dd, J=11.7, 2.7 Hz, 1H), 3.25 (dd, J=11.7, 6.6 Hz, 1H), 2.91 (s, 3H), 2.50 (s, 3H).

EXAMPLE 6(6)

5-(2-methyl-4-((2S)-4-methyl-3,4-dihydro-2H-1,4-benzoxazin-2-ylmethoxy)benzoylamino)-2-methoxyphenylacetic acid TLC: Rf 0.36 (chloroform:methanol=9:1); NMR (300 MHz, CDCl$_3$): δ 7.58-7.39 (m, 3H), 7.34 (brs, 1H), 6.93-6.76 (m, 5H), 6.74-6.66 (m, 2H), 4.70-4.60 (m, 1H), 4.26 (dd, J=9.3, 4.8 Hz, 1H), 4.14 (dd, J=9.3, 6.3 Hz, 1H), 3.85 (s, 3H), 3.69 (s, 2H), 3.39 (dd, J=11.4, 2.7 Hz, 1H), 3.25 (dd, J=11.4, 6.6 Hz, 1H), 2.91 (s, 3H), 2.50 (s, 3H).

EXAMPLE 6(7)

3-(2-chloro-4-((2S)-4-methyl-3,4-dihydro-2H-1,4-benzoxazin-2-ylmethoxy)benzoylamino)-4-chlorophenylacetic acid TLC: Rf 0.41 (chloroform:methanol=9:1); NMR (300 MHz, CDCl$_3$): δ 8.70 (brs, 1H), 8.56 (brs, 1H), 7.87 (d, J=8.4 Hz, 1H), 7.38 (d, J=8.4 Hz, 1H), 7.07-7.00 (m, 2H), 6.96 (dd, J=9.0, 2.4 Hz, 1H), 6.93-6.80 (m, 2H), 6.76-6.66 (m, 2H), 4.70-4.60 (m, 1H), 4.28 (dd, J=9.9, 5.4 Hz, 1H), 4.18 (dd, J=9.9, 6.3 Hz, 1H), 3.71 (s, 2H), 3.39 (dd, J=11.7, 2.7 Hz, 1H), 3.25 (dd, J=11.7, 6.3 Hz, 1H), 2.91 (s, 3H).

EXAMPLE 6(8)

5-(2-chloro-4-((2S)-4-methyl-3,4-dihydro-2H-1,4-benzoxazin-2-ylmethoxy)benzoylamino)-2-fluorophenylacetic acid TLC: Rf 0.41 (chloroform:methanol=9:1); NMR (300 MHz, CDCl$_3$): δ 8.06 (s, 1H), 7.82 (d, J=8.7 Hz, 1H), 7.67-7.60 (m, 1H), 7.56-7.47 (m, 1H), 7.08 (t, J=9.0 Hz, 1H), 7.02 (d, J=2.1 Hz, 1H), 6.99-6.81 (m, 3H), 6.76-6.67 (m, 2H), 4.70-4.60 (m, 1H), 4.26 (dd, J=9.9, 5.4 Hz, 1H), 4.17 (dd, J=9.9, 6.0 Hz, 1H), 3.74 (s, 2H), 3.38 (dd, J=11.7, 2.7 Hz, 1H), 3.25 (dd, J=11.7, 6.3 Hz, 1H), 2.91 (s, 3H).

EXAMPLE 6(9)

5-(2-chloro-4-((2S)-4-methyl-3,4-dihydro-2H-1,4-benzoxazin-2-ylmethoxy)benzoylamino)-2-methoxyphenylacetic acid TLC: Rf 0.41 (chloroform:methanol=9:1); NMR (300 MHz, CDCl$_3$): δ 7.96 (s, 1H), 7.82 (d, J=8.4 Hz, 1H), 7.57 (dd, J=8.4, 2.7 Hz, 1H), 7.48 (d, J=2.7 Hz, 1H), 7.01 (d, J=2.7 Hz, 1H), 6.97-6.81 (m, 4H), 6.75-6.66 (m, 2H), 4.70-4.60 (m, 1H), 4.26 (dd, J=9.9, 5.4 Hz, 1H), 4.16 (dd, J=9.9, 6.3 Hz, 1H), 3.86 (s, 3H), 3.70 (s, 2H), 3.38 (dd, J=11.7, 3.0 Hz, 1H), 3.25 (dd, J=11.7, 6.6 Hz, 1H), 2.91 (s, 3H).

EXAMPLE 6(10)

3-(2-methyl-4-((2S)-4-methyl-3,4-dihydro-2H-1,4-benzoxazin-2-ylmethoxy)benzoylamino)-4-methylphenylacetic acid TLC: Rf 0.35 (chloroform:methanol=9:1); NMR (300 MHz, CDCl$_3$): δ 8.04-7.86 (br, 1H), 7.53-7.42 (m, 1H), 7.34-7.22 (m, 1H), 7.19 (d, J=7.8 Hz, 1H), 7.07-6.99 (m, 1H), 6.92-6.76 (m, 4H), 6.75-6.66 (m, 2H), 4.70-4.60 (m, 1H), 4.27 (dd, J=9.9, 4.8 Hz, 1H), 4.15 (dd, J=9.9, 6.6 Hz, 1H), 3.66 (s, 2H), 3.39 (dd, J=11.7, 2.7 Hz, 1H), 3.25 (dd, J=11.7, 6.6 Hz, 1H), 2.91 (s, 3H), 2.52 (s, 3H), 2.28 (s, 3H).

EXAMPLE 6(11)

5-(2-methyl-4-((2S)-4-methyl-3,4-dihydro-2H-1,4-benzoxazin-2-ylmethoxy)benzoylamino)-4-chloro-2-fluorophenylacetic acid TLC: Rf 0.35 (chloroform:methanol=9:1); NMR (300 MHz, CDCl$_3$): δ 8.54-8.43 (m, 1H), 7.86 (s, 1H), 7.52 (d, J=8.4 Hz, 1H), 7.18 (d, J=9.0 Hz, 1H), 6.92-6.80 (m, 4H), 6.75-6.66 (m, 2H), 4.70-4.60 (m, 1H), 4.27 (dd, J=9.9, 4.8 Hz, 1H), 4.15 (dd, J=9.9, 6.6 Hz, 1H), 3.75 (s, 2H), 3.38 (dd, J=11.7, 3.0 Hz, 1H), 3.25 (dd, J=11.7, 6.6 Hz, 1H), 2.91 (s, 3H), 2.54 (s, 3H).

EXAMPLE 6(12)

3-(2-methyl-4-((2S)-4-methyl-3,4-dihydro-2H-1,4-benzoxazin-2-ylmethoxy)benzoylamino)-5-methylphenylacetic acid TLC: Rf 0.35 (chloroform:methanol=9:1); NMR (300 MHz, CDCl$_3$): δ 7.48-7.28 (m, 4H), 6.92-6.76 (m, 5H), 6.74-6.66 (m, 2H), 4.70-4.60 (m, 1H), 4.26 (dd, J=9.9, 5.1 Hz, 1H), 4.14 (dd, J=9.9, 6.6 Hz, 1H), 3.63 (s, 2H), 3.39 (dd, J=11.4, 2.7 Hz, 1H), 3.25 (dd, J=11.4, 6.6 Hz, 1H), 2.91 (s, 3H), 2.50 (s, 3H), 2.35 (s, 3H).

EXAMPLE 6(13)

3-(2-chloro-4-((2S)-4-methyl-3,4-dihydro-2H-1,4-benzoxazin-2-ylmethoxy)benzoylamino)-4-methylphenylacetic acid TLC: Rf 0.42 (chloroform:methanol=9:1); NMR (300 MHz, CDCl$_3$): δ 8.02 (s, 2H), 7.90 (d, J=8.7 Hz, 1H), 7.19 (d, J=8.1 Hz, 1H), 7.09-7.00 (m, 2H), 7.00-6.93 (m, 1H), 6.93-6.81 (m, 2H), 6.76-6.66 (m, 2H), 4.70-4.60 (m, 1H), 4.27 (dd, J=9.6, 5.1 Hz, 1H), 4.18 (dd, J=9.6, 6.3 Hz, 1H), 3.68 (s, 2H), 3.39 (dd, J=11.7, 2.7 Hz, 1H), 3.25 (dd, J=11.7, 6.3 Hz, 1H), 2.91 (s, 3H), 2.32 (s, 3H).

EXAMPLE 6(14)

3-(2-chloro-4-((2S)-4-methyl-3,4-dihydro-2H-1,4-benzoxazin-2-ylmethoxy)benzoylamino)-5-methylphenylacetic acid TLC: Rf 0.39 (chloroform:methanol=9:1); NMR (300 MHz, CDCl$_3$): δ 8.00 (s, 1H), 7.81 (d, J=8.7 Hz, 1H), 7.41 (s, 2H), 7.01 (d, J=2.4 Hz, 1H), 6.98-6.81 (m, 4H), 6.75-6.67 (m, 2H), 4.70-4.60 (m, 1H), 4.26 (dd, J=9.9, 5.1 Hz, 1H), 4.17 (dd, J=9.9, 6.3 Hz, 1H), 3.64 (s, 2H), 3.38 (dd, J=11.4, 2.7 Hz, 1H), 3.25 (dd, J=11.4, 6.3 Hz, 1H), 2.91 (s, 3H), 2.36 (s, 3H).

REFERENCE EXAMPLE 11

2-methoxy-5-nitrophenylacetonitrile

To a solution of 2-methoxy-5-nitrobenzyl bromide (984 mg) in dimethylsulfoxide (5 mL) was added sodium cyanide (216 mg) and the mixture was stirred at 80 degrees for 10 minutes. To the reaction mixture was added water and the mixture was extracted with ethyl acetate. The organic layer was washed with water and a saturated aqueous solution of sodium chloride, successively, dried over anhydrous sodium sulfate, and concentrated to give the title compound having the following physical data. The obtained title compound was used to next reaction without further purification.

TLC: Rf 0.30 (ethyl acetate:hexane=3:7).

REFERENCE EXAMPLE 12

2-methoxy-5-nitrophenylacetic acid ethyl ester

To the compound prepared in Reference Example 11 were added conc. sulfuric acid (10 mL), water (10 mL), ethanol (10 mL) and dimethoxyethane (10 mL), and the mixture was refluxed overnight. The reaction mixture was diluted with water and ethyl acetate, and then extracted with ethyl acetate. The organic layer was washed with 1N aqueous solution of sodium hydroxide, water, a saturated aqueous sodium chloride, successively, dried over anhydrous sodium sulfate, and concentrated to give the title compound (500 mg) having the following physical data.

TLC: Rf 0.44 (ethyl acetate:hexane=3:7); NMR (CDCl$_3$): δ 8.21 (dd, J=9.0, 2.7 Hz, 1H), 8.12 (d, J=2.7 Hz, 1H), 6.93 (d, J=9.0 Hz, 1H), 4.18 (q, J=7.2 Hz, 2H), 3.93 (s, 3H), 3.67 (s, 2H), 1.26 (t, J=7.2 Hz, 3H).

REFERENCE EXAMPLE 13

2-methoxy-5-aminophenylacetic acid ethyl ester

The compound prepared in Reference Example 12 (250 mg) was dissolved in a mixed solvent of ethyl acetate (3 mL), methanol (3 mL) and THF (3 mL) under an atmosphere of argon. To the mixture was added 10% palladium carbon (65 mg) and the mixture was stirred at room temperature for 1 hour under an atmosphere of hydrogen. The reaction mixture was filtered through Celite (trade mark). The filtrate was concentrated and the obtained residue was purified by column chromatography on silica gel (hexane:ethyl acetate=7:3) to give the title compound (90 mg) having the following physical data.

TLC: Rf 0.55 (ethyl acetate:hexane=1:1).

REFERENCE EXAMPLE 14

2-hydroxy-5-nitrophenylacetic acid ethyl ester

To a solution of the compound prepared in Reference Example 12 (250 mg) in methylene chloride (4 mL) was added boron tribromide (1M methylene chloride solution; 3.1 mL) at −15 degrees and the mixture was stirred at room temperature overnight. To the reaction mixture was added crash ice. The mixture was extracted with ethyl acetate. The organic layer was washed with water and a saturated aqueous solution of sodium chloride, successively, dried over anhydrous sodium sulfate, and concentrated. The residue was purified by column chromatography on silica gel (hexane:ethyl acetate=7:3) to give the title compound (100 mg) having the following physical data.

TLC: Rf 0.49 (ethyl acetate:hexane=1:1); NMR (CDCl$_3$): δ 8.88 (s, 1H), 8.12 (dd, J=8.7, 2.7 Hz, 1H), 8.06 (d, J=2.7 Hz, 1H), 7.02 (d, J=8.7 Hz, 1H), 4.25 (q, J=7.2 Hz, 2H), 3.76 (s, 2H), 1.33 (t, J=7.2 Hz, 3H).

REFERENCE EXAMPLE 15

2-hydroxy-5-aminophenylacetic acid ethyl ester

The title compound having the following physical data was obtained in the same manner as in Reference Example 13 using the compound prepared in Reference Example 14 instead of the compound prepared in Reference Example 12.

TLC: Rf 0.29 (ethyl acetate:hexane=1:1); NMR (CDCl$_3$): δ 6.79 (d, J=8.4 Hz, 1H), 6.56 (dd, J=8.4, 3.0 Hz, 1H), 6.48 (d, J=3.0 Hz, 1H), 4.19 (q, J=7.2 Hz, 2H), 3.58 (s, 2H), 1.29 (t, J=7.2 Hz, 3H).

EXAMPLE 7

5-(4-((2S)-4-methyl-3,4-dihydro-2H-1,4-benzoxazin-2-ylmethoxy)benzoylamino)-2-methoxyphenylacetic acid ethyl ester The title compound having the following physical data was obtained in the same manner as in Example 1 using the compound prepared in Reference Example 13 instead of the compound prepared in Reference Example 9.

TLC: Rf 0.51 (ethyl acetate:hexane=1:1); NMR (CDCl$_3$): δ 7.82 (d, J=8.7 Hz, 2H), 7.63 (s, 1H), 7.30-7.24 (m, 1H), 7.08-6.80 (m, 5H), 6.75-6.65 (m, 2H), 4.70-4.60 (m, 1H), 4.36-4.05 (m, 4H), 3.83 (s, 3H), 3.69 (s, 2H), 3.40 (dd, J=11.7, 2.7 Hz, 1H), 3.27 (dd, J=11.7, 6.9 Hz, 1H), 2.91 (s, 3H), 1.30 (t, J=7.2 Hz, 3H).

EXAMPLE 7(1)

5-(4-((2S)-4-methyl-3,4-dihydro-2H-1,4-benzoxazin-2-ylmethoxy)benzoylamino)-2-hydroxyphenylacetic acid ethyl ester The title compound having the following physical data was obtained in the same manner as in Example 1 using the compound prepared in Reference Example 15 instead of the compound prepared in Reference Example 9.

TLC: Rf 0.68 (ethyl acetate:hexane=1:1).

EXAMPLE 8

5-(4-((2S)-4-methyl-3,4-dihydro-2H-1,4-benzoxazin-2-ylmethoxy)benzoylamino)-2-methoxyphenylacetic acid The title compound having the following physical data was obtained in the same manner as in Example 2 using the compound prepared in Example 7 instead of the compound prepared in Example 1.

TLC: Rf 0.38 (chloroform:methanol=9:1); NMR (CDCl$_3$): δ 7.82 (d, J=8.7 Hz, 2H), 7.71 (s, 1H), 7.55 (dd, J=8.7, 2.7 Hz, 1H), 7.44 (d, J=2.7 Hz, 1H), 6.99 (d, J=8.7 Hz, 2H), 6.94-6.80 (m, 3H), 6.75-6.66 (m, 2H), 4.72-4.62 (m, 1H), 4.28 (dd, J=9.9, 5.1 Hz, 1H), 4.17 (dd, J=9.9, 6.3 Hz, 1H), 3.83 (s, 3H), 3.67 (s, 2H), 3.39 (dd, J=11.4, 2.7 Hz, 1H), 3.26 (dd, J=11.4, 6.6 Hz, 1H), 2.91 (s, 3H).

EXAMPLE 8(1)

5-(4-((2S)-4-methyl-3,4-dihydro-2H-1,4-benzoxazin-2-ylmethoxy)benzoylamino)-2-hydroxyphenylacetic acid The title compound having the following physical data was obtained in the same manner as in Example 2 using the compound prepared in Example 7(1) instead of the compound prepared in Example 1.

TLC: Rf 0.29 (chloroform:methanol=5:1); NMR (CDCl$_3$): δ 7.86-7.72 (m, 3H), 7.43-7.35 (m, 1H), 7.24-7.16 (m, 1H), 7.04-6.92 (m, 2H), 6.92-6.78 (m, 3H), 6.74-6.64 (m, 2H), 4.70-4.56 (m, 1H), 4.30-4.20 (m, 1H), 4.20-4.10 (m, 1H), 3.63 (s, 2H), 3.42-3.32 (m, 1H), 3.30-3.20 (m, 1H), 2.89 (s, 3H).

REFERENCE EXAMPLE 16

2-methyl-5-nitrophenylacetic acid benzyl ester

To a solution of 2-methyl-5-nitrobenzoic acid (2.45 g) in toluene (10 mL) was added oxalyl chloride (1.88 mL) under an atmosphere of argon and the mixture was stirred at room temperature for 5 hours. After the mixture was concentrated, the residue was dissolved in mixed solvent of THF (25 mL) and acetnitrile (25 mL). To the mixture was added trimethylsilyldiazomethane (2M hexane solution; 12.5 mL) under ice cooling and the mixture was stirred at 0 degrees for 1 hour. After removed the solvent, to the obtained residue were added benzyl alcohol (15 mL) and collidine (15 mL) and the mixture was stirred at 180 degrees for 2 hours. The reaction mixture was cooled to room temperature. To the mixture was added 1N hydrochloric acid. The mixture was extracted with ethyl acetate. The organic layer was washed with water and a saturated aqueous solution of sodium chloride, successively, dried over anhydrous magnesium sulfate, and concentrated. The residue was purified by column chromatography on silica gel (hexane:ethyl acetate=9:1) to give the title compound (1.4 g) having the following physical data.

TLC: Rf 0.60 (ethyl acetate:hexane=3:7).

REFERENCE EXAMPLE 17

2-methyl-5-aminophenylacetic acid benzyl ester

The compound prepared in Reference Example 16 (1.4 g) was dissolved in mixed solvent of acetic acid (100 mL) and water (10 mL). To the solution was added iron powder (3.77 g) and the mixture was stirred at 60 degrees for 1 hour. The reaction mixture was diluted with ethyl acetate and filtered through Celite (trade mark). The filtrate was concentrated. The obtained residue was diluted with ethyl acetate, washed with a saturated aqueous solution of sodium bicarbonate, water, and a saturated aqueous solution of sodium chloride, successively, dried over anhydrous sodium sulfate and concentrated. The residue was purified by column chromatography on silica gel (hexane:ethyl acetate=9:1) to give the title compound (1.1 g) having the following physical data.

TLC: Rf 0.31 (ethyl acetate:hexane=3:7); NMR (CDCl$_3$): δ 7.40-7.24 (m, 5H), 6.95 (d, J=7.8 Hz, 1H), 6.60-6.50 (m, 2H), 5.13 (s, 2H), 4.00-3.60 (br, 2H), 3.58 (s, 2H), 2.17 (s, 3H).

EXAMPLE 9

5-(4-((2S)-4-methyl-3,4-dihydro-2H-1,4-benzoxazin-2-ylmethoxy)benzoylamino)-2-methylphenylacetic acid benzyl ester The title compound having the following physical data was obtained in the same manner as in Example 1 using the compound prepared in Reference Example 17 instead of the compound prepared in Reference Example 9.

TLC: Rf 0.19 (ethyl acetate:hexane=3:7); NMR (CDCl$_3$): δ 7.82 (d, J=9.0 Hz, 2H), 7.66 (s, 1H), 7.52 (d, J=8.1, 2.4 Hz, 1H), 7.41 (d, J=2.1 Hz, 1H), 7.40-7.24 (m, 5H), 7.17 (d, J=8.1 Hz, 1H), 7.01 (d, J=9.0 Hz, 2H), 6.92-6.81 (m, 2H), 6.74-6.66 (m, 2H), 5.15 (s, 2H), 4.72-4.62 (m, 1H), 4.29 (dd, J=9.6, 5.1 Hz, 1H), 4.18 (dd, J=9.6, 6.6 Hz, 1H), 3.68 (s, 2H), 3.40 (dd, J=11.7, 2.7 Hz, 1H), 3.27 (dd, J=11.7, 6.3 Hz, 1H), 2.91 (s, 3H), 2.26 (s, 3H).

EXAMPLE 9(1)~9(5)

The following compounds were obtained in the same manner as in Example 9 using corresponding compounds.

EXAMPLE 9(1)

3-(4-((2S)-4-methyl-3,4-dihydro-2H-1,4-benzoxazin-2-ylmethoxy)benzoylamino)-4-fluorophenylacetic acid benzyl ester TLC: Rf 0.28 (ethyl acetate:hexane=3:7); NMR (CDCl$_3$): δ 8.43 (dd, J=7.2, 2.1 Hz, 1H), 8.00-7.94 (m, 1H), 7.85 (d, J=9.0 Hz, 2H), 7.50-7.20 (m, 5H), 7.14-6.92 (m, 4H), 6.92-6.80 (m, 2H), 6.76-6.64 (m, 2H), 5.15 (s, 2H), 4.72-4.62 (m, 1H), 4.30 (dd, J=9.6, 4.8 Hz, 1H), 4.19 (dd, J=9.6, 6.6 Hz, 1H), 3.69 (s, 2H), 3.40 (dd, J=12.0, 3.3 Hz, 1H), 3.27 (dd, J=12.0, 6.6 Hz, 1H), 2.91 (s, 3H).

EXAMPLE 9(2)

5-(2-methyl-4-((2S)-4-methyl-3,4-dihydro-2H-1,4-benzoxazin-2-ylmethoxy)benzoylamino)-2-methylphenylacetic acid benzyl ester TLC: Rf 0.63 (ethyl acetate:hexane=1:1); NMR (CDCl$_3$): δ 7.50-7.24 (m, 9H), 7.16 (d, J=8.4 Hz, 1H), 6.92-6.76 (m, 4H), 6.75-6.66 (m, 2H), 5.15 (s, 2H), 4.70-4.60 (m, 1H), 4.26 (dd, J=9.9, 5.1 Hz, 1H), 4.15 (dd, J=9.9, 6.6 Hz, 1H), 3.68 (s, 2H), 3.39 (dd, J=11.4, 2.7 Hz, 1H), 3.26 (dd, J=11.4, 6.3 Hz, 1H), 2.91 (s, 3H), 2.50 (s, 3H), 2.26 (s, 3H).

EXAMPLE 9(3)

3-(2-methyl-4-((2S)-4-methyl-3,4-dihydro-2H-1,4-benzoxazin-2-ylmethoxy)benzoylamino)-4-fluorophenylacetic acid benzyl ester TLC: Rf 0.66 (hexane:ethyl acetate=1:1); NMR (300 MHz, CDCl$_3$): δ 7.68-7.60 (m, 1H), 7.50 (d, J=8.4 Hz, 1H), 7.40-7.28 (m, 6H), 7.10-6.76 (m, 6H), 6.76-6.64 (m, 2H), 5.15 (s, 2H), 4.70-4.60 (m, 1H), 4.26 (dd, J=9.9, 5.1 Hz, 1H), 4.15 (dd, J=9.9, 6.6 Hz, 1H), 3.70 (s, 2H), 3.39 (dd, J=11.1, 2.4 Hz, 1H), 3.26 (dd, J=11.1, 6.6 Hz, 1H), 2.91 (s, 3H), 2.53 (s, 3H).

EXAMPLE 9(4)

3-(2-chloro-4-((2S)-4-methyl-3,4-dihydro-2H-1,4-benzoxazin-2-ylmethoxy)benzoylamino)-4-fluorophenylacetic acid benzyl ester TLC: Rf 0.61 (hexane:ethyl acetate=1:1); NMR (300 MHz, CDCl$_3$): δ 8.50-8.40 (m, 1H), 7.87 (d, J=8.7 Hz, 1H), 7.44-7.24 (m, 6H), 7.13-6.80 (m, 6H), 6.76-6.66 (m, 2H), 5.15 (s, 2H), 4.70-4.60 (m, 1H), 4.27 (dd, J=9.6, 5.4 Hz, 1H), 4.19 (dd, J=9.6, 6.0 Hz, 1H), 3.69 (s, 2H), 3.38 (dd, J=12.0, 2.7 Hz, 1H), 3.25 (dd, J=12.0, 6.6 Hz, 1H), 2.91 (s, 3H).

EXAMPLE 9(5)

5-(2-chloro-4-((2S)-4-methyl-3,4-dihydro-2H-1,4-benzoxazin-2-ylmethoxy)benzoylamino)-2-methylphenylacetic acid benzyl ester TLC: Rf 0.58 (hexane:ethyl acetate=1:1); NMR (300 MHz, CDCl$_3$): δ 7.94 (s, 1H), 7.81 (d, J=8.7 Hz, 1H), 7.54-7.47 (m, 1H), 7.46-7.42 (m, 1H), 7.40-7.28 (m, 5H), 7.17 (d, J=8.7 Hz, 1H), 7.02 (d, J=2.1 Hz, 1H), 6.98-6.80 (m, 3H), 6.75-6.67 (m, 2H), 5.15 (s, 2H), 4.71-4.61 (m, 1H), 4.26 (dd, J=9.9, 5.1 Hz, 1H), 4.17 (dd, J=9.9, 6.3 Hz, 1H), 3.69 (s, 2H), 3.38 (dd, J=11.4, 2.7 Hz, 1H), 3.25 (dd, J=11.4, 6.3 Hz, 1H), 2.91 (s, 3H), 2.26 (s, 3H).

EXAMPLE 10

5-(4-((2S)-4-methyl-3,4-dihydro-2H-1,4-benzoxazin-2-ylmethoxy)benzoylamino)-2-methylphenylacetic acid The title compound having the following physical data was obtained in the same manner as in Example 2 using the compound prepared in Example 9 instead of the compound prepared in Example 1.

TLC: Rf 0.37 (chloroform:methanol=9:1); NMR (CDCl$_3$): δ 7.81 (d, J=8.7 Hz, 2H), 7.78 (s, 1H), 7.52-7.41 (m, 2H), 7.15 (d, J=8.4 Hz, 1H), 6.98 (d, J=8.7 Hz, 2H), 6.92-6.81 (m, 2H), 6.75-6.66 (m, 2H), 4.70-4.60 (m, 1H), 4.27 (dd, J=9.6, 4.8 Hz, 1H), 4.16 (dd, J=9.6, 6.3 Hz, 1H), 3.65 (s, 2H), 3.39 (dd, J=12.0, 3.0 Hz, 1H), 3.26 (dd, J=12.0, 6.3 Hz, 1H), 2.91 (s, 3H), 2.28 (s, 3H).

EXAMPLE 10(1)~10(5)

The following compounds were obtained in the same manner as in Example 10 using corresponding derivatives instead of the compounds prepared in Example 9(1)~9(5).

EXAMPLE 10(1)

3-(4-((2S)-4-methyl-3,4-dihydro-2H-1,4-benzoxazin-2-ylmethoxy)benzoylamino)-4-fluorophenylacetic acid TLC: Rf 0.29 (chloroform:methanol=9:1); NMR (CDCl$_3$): δ 8.45 (dd, J=7.5, 2.1 Hz, 1H), 7.98 (d, J=2.1 Hz, 1H), 7.85 (d, J=9.0 Hz, 2H), 7.16-6.93 (m, 4H), 6.93-6.80 (m, 2H), 6.76-6.66 (m, 2H), 4.72-4.62 (m, 1H), 4.30 (dd, J=9.6, 4.8 Hz, 1H), 4.19 (dd, J=9.6, 6.6 Hz, 1H), 3.69 (s, 2H), 3.40 (dd, J=12.0, 3.3 Hz, 1H), 3.27 (dd, J=12.0, 6.6 Hz, 1H), 2.91 (s, 3H).

EXAMPLE 10(2)

5-(2-methyl-4-((2S)-4-methyl-3,4-dihydro-2H-1,4-benzoxazin-2-ylmethoxy)benzoylamino)-2-methylphenylacetic acid TLC: Rf 0.32 (chloroform:methanol=9:1); NMR (CDCl$_3$): δ 7.56-7.34 (m, 4H), 7.18 (d, J=8.4 Hz, 1H), 6.92-6.76 (m, 4H), 6.75-6.66 (m, 2H), 4.70-4.60 (m, 1H), 4.26 (dd, J=9.6, 4.5 Hz, 1H), 4.14 (dd, J=9.6, 6.3 Hz, 1H), 3.69 (s, 2H), 3.39 (dd, J=11.4, 2.1 Hz, 1H), 3.25 (dd, J=11.4, 6.6 Hz, 1H), 2.91 (s, 3H), 2.50 (s, 3H), 2.30 (s, 3H).

EXAMPLE 10(3)

3-(2-methyl-4-((2S)-4-methyl-3,4-dihydro-2H-1,4-benzoxazin-2-ylmethoxy)benzoylamino)-4-fluorophenylacetic acid TLC: Rf 0.31 (chloroform:methanol=9:1); NMR (300 MHz, CDCl$_3$): δ 7.67 (d, J=2.7 Hz, 1H), 7.50 (d, J=8.4 Hz, 1H), 7.37 (s, 1H), 7.14-6.76 (m, 6H), 6.76-6.68 (m, 2H), 4.70-4.60 (m, 1H), 4.27 (dd, J=9.3, 5.1 Hz, 1H), 4.15 (dd, J=9.3, 6.6 Hz, 1H), 3.69 (s, 2H), 3.40 (dd, J=11.7, 2.7 Hz, 1H), 3.26 (dd, J=11.7, 6.9 Hz, 1H), 2.92 (s, 3H), 2.53 (s, 3H).

EXAMPLE 10(4)

3-(2-chloro-4-((2S)-4-methyl-3,4-dihydro-2H-1,4-benzoxazin-2-ylmethoxy)benzoylamino)-4-fluorophenylacetic acid TLC: Rf 0.43 (chloroform:methanol=9:1); NMR (300 MHz, CDCl$_3$): δ 8.51-8.42 (m, 1H), 7.88 (d, J=9.6 Hz, 1H), 7.15-6.80 (m, 7H), 6.76-6.66 (m, 2H), 4.71-4.61 (m, 1H), 4.26 (dd, J=9.6, 5.4 Hz, 1H), 4.18 (dd, J=9.6, 6.3 Hz, 1H), 3.70 (s, 2H), 3.40 (dd, J=12.0, 3.3 Hz, 1H), 3.25 (dd, J=12.0, 6.6 Hz, 1H), 2.91 (s, 3H).

EXAMPLE 10(5)

5-(2-chloro-4-((2S)-4-methyl-3,4-dihydro-2H-1,4-benzoxazin-2-ylmethoxy)benzoylamino)-2-methylphenylacetic acid TLC: Rf 0.47 (chloroform:methanol=9:1); NMR (300 MHz, CDCl$_3$): δ 8.00 (s, 1H), 7.81 (d, J=9.0 Hz, 1H), 7.57-7.52 (m, 1H), 7.49-7.42 (m, 1H), 7.19 (d, J=8.4 Hz, 1H), 7.01 (d, J=2.4 Hz, 1H), 6.98-6.81 (m, 3H), 6.76-6.66 (m, 2H), 4.70-4.60 (m, 1H), 4.26 (dd, J=9.9, 5.1 Hz, 1H), 4.17 (dd, J=9.9, 6.3 Hz, 1H), 3.69 (s, 2H), 3.38 (dd, J=11.4, 2.7 Hz, 1H), 3.25 (dd, J=11.4, 6.6 Hz, 1H), 2.91 (s, 3H), 2.31 (s, 3H).

REFERENCE EXAMPLE 18

4-(acetyloxy)benzenesulfonic acid pyridine salt

A solution of 4-(hydroxy)benzenesulfonic acid (3 g) in pyridine (10 mL) and acetic anhydride (10 mL) was stirred at room temperature for 3 hours. The obtained crystal was collected by filtration and washed with hexane to give the title compound (4 g) having the following physical data.

NMR (300 MHz, CDCl$_3$): δ 8.95 (d, J=6.0 Hz, 2H), 8.42 (t J=7.5 Hz, 1H), 8.02-7.89 (m, 4H), 7.12 (d, J=8.7 Hz, 2H).

REFERENCE EXAMPLE 19

4-(chlorosulfonyl)phenyl acetate

To a solution of the compound prepared in Reference Example 18 (4 g) in dimethoxyethane (20 mL) was added thionyl chloride (2.5 mL) under an atmosphere of argon. The mixture was stirred at 0 degrees for 1 hour. To the reaction mixture was poured water and the mixture was extracted with ethyl acetate. The organic layer was washed with water and a saturated aqueous solution of sodium chloride, dried over anhydrous magnesium sulfate, and concentrated. The residue was purified by column chromatography on silica gel to give the title compound (2.76 g) having the following physical data.

TLC: Rf 0.50 (hexane:ethyl acetate=7:3).

REFERENCE EXAMPLE 20

3-(((((4-acetyloxy)phenyl)sulfonyl)amino)phenylacetic acid methyl ester

The title compound having the following physical data was obtained in the same manner as in Example 1 using the compound prepared in Reference Example 9 (300 mg) and the compound prepared in Reference Example 19 (426 mg).

TLC: Rf 0.11 (hexane:ethyl acetate=7:3).

REFERENCE EXAMPLE 21

3-(((((4-hydroxy)phenyl)sulfonyl)amino)phenylacetic acid methyl ester

To a solution of the compound prepared in Reference Example 20 in methanol (10 mL) and dimethoxyethane (5 mL) was added potassium carbonate (354 mg) at room temperature, and the mixture was stirred for 30 minutes. The reaction mixture was filtered through Celite (trade mark) and the filtrate was concentrated. The residue was purified by column chromatography on silica gel to give the title compound (370 mg) having the following physical data.

TLC: Rf 0.22 (hexane:ethyl acetate=1:1).

EXAMPLE 11

3-(((4-((2S)-4-methyl-3,4-dihydro-2H-1,4-benzoxazin-2-ylmethoxy)phenyl)sulfonyl)amino)phenylacetic acid methyl ester To a solution of the compound prepared in Reference Example 21 (370 mg) in DMF (15 mL) was added (2S)-2-tosyloxymethyl-4-methyl-3,4-dihydro-2H-1,4-benzoxazine (384 mg), which is prepared in the same manner as in Reference Example 1→Reference Example 2→Reference Example 3→Reference Example 4→Reference Example 5 using a corresponding compound, in the presence of cesium carbonate (750 mg) at room temperature. The mixture was stirred at 60 degrees for 2 hours. To the reaction mixture was added water, and the mixture was extracted with ethyl acetate. The organic layer was washed with water and a saturated aqueous solution of sodium chloride, dried over anhydrous sodium sulfate, and concentrated. The residue was purified by column chromatography on silica gel to give the title compound (282 mg) having the following physical data.

TLC: Rf 0.46 (hexane:ethyl acetate=1:1); NMR (300 MHz, CDCl$_3$): δ 7.74-7.66 (m, 2H), 7.19 (t, J=8.1 Hz, 1H), 7.06-6.78 (m, 7H), 6.75-6.65 (m, 2H), 6.41 (s, 1H), 4.68-4.58 (m, 1H), 4.23 (dd, J=9.6, 4.8 Hz, 1H), 4.13 (dd, J=9.6, 6.0 Hz, 1H), 3.67 (s, 3H), 3.55 (s, 2H), 3.36 (dd, J=11.7, 2.7 Hz, 1H), 3.23 (dd, J=11.7, 6.6 Hz, 1H), 2.89 (s, 3H).

EXAMPLE 12

3-(((4-((2S)-4-methyl-3,4-dihydro-2H-1,4-benzoxazin-2-ylmethoxy)phenyl)sulfonyl)amino)phenylacetic acid The title compound (90 mg) having the following physical data was obtained in the same manner as in Example 2 using the compound prepared in Reference Example 11 (111 mg).

TLC: Rf 0.33 (chloroform:methanol=9:1); NMR (300 MHz, CDCl$_3$): δ 7.63 (d, J=9.3 Hz, 2H), 7.24-7.17 (m, 1H), 7.13-7.06 (m, 1H), 7.04-6.97 (m, 1H), 6.94-6.70 (m, 8H), 4.67-4.57 (m, 1H), 4.27 (dd, J=10.2, 5.1 Hz, 1H), 4.14 (dd, J=10.2, 5.7 Hz, 1H), 3.53 (s, 2H), 3.37 (dd, J=11.4, 2.4 Hz, 1H), 3.17 (dd, J=11.4, 7.2 Hz, 1H), 2.88 (s, 3H).

EXAMPLE 12(1)~12(6)

The following compounds were obtained in the same manner as in Reference Example 18→Reference Example 19→Reference Example 20→Reference Example 21→Example 11→Example 12 using corresponding compounds.

EXAMPLE 12(1)

3-(N-((4-((2S)-4-methyl-3,4-dihydro-2H-1,4-benzoxazin-2-ylmethoxy)phenyl)sulfonyl)-N-methylamino)phenylacetic acid TLC: Rf 0.47 (chloroform:methanol=9:1); NMR (300 MHz, CDCl$_3$): δ 7.46-7.39 (m, 2H), 7.28 (t, J=7.5 Hz, 1H), 7.21-7.12 (m, 2H), 6.96-6.72 (m, 7H), 4.72-4.62 (m, 1H), 4.31 (dd, J=10.5, 5.4 Hz, 1H), 4.20 (dd, J=10.5, 6.0 Hz, 1H), 3.54 (s, 2H), 3.41 (dd, J=11.7, 2.4 Hz, 1H), 3.19 (dd, J=11.7, 7.2 Hz, 1H), 3.15 (s, 3H), 2.90 (s, 3H).

EXAMPLE 12(2)

3-(N-((4-((2S)-4-methyl-3,4-dihydro-2H-1,4-benzoxazin-2-ylmethoxy)phenyl)sulfonyl)-N-ethylamino)phenylacetic acid TLC: Rf 0.56 (chloroform:methanol=9:1); NMR (300 MHz, CDCl$_3$): δ 7.52-7.44 (m, 2H), 7.30 (t, J=7.8 Hz, 1H), 7.21-7.10 (m, 2H), 6.96-6.80 (m, 4H), 6.80-6.71 (m, 3H), 4.74-4.64 (m, 1H), 4.32 (dd, J=10.8, 5.4 Hz, 1H), 4.20 (dd, J=10.8, 6.0 Hz, 1H), 3.70-3.50 (m, 4H), 3.41 (dd, J=11.7, 2.4 Hz, 1H), 3.20 (dd, J=11.7, 7.2 Hz, 1H), 2.90 (s, 3H), 1.07 (t, J=7.2 Hz, 3H).

EXAMPLE 12(3)

3-(N-((4-((2S)-4-methyl-3,4-dihydro-2H-1,4-benzoxazin-2-ylmethoxy)phenyl)sulfonyl)-N-propylamino)phenylacetic acid TLC: Rf 0.56 (chloroform:methanol=9:1); NMR (300 MHz, CDCl$_3$): δ 7.47 (d, J=8.7 Hz, 2H), 7.32-7.26 (m, 1H), 7.20-7.09 (m, 2H), 6.97-6.71 (m, 7H), 4.73-4.63 (m, 1H), 4.31 (dd, J=10.5, 5.7 Hz, 1H), 4.20 (dd, J=10.5, 6.0 Hz, 1H), 3.55 (s, 2H), 3.54-3.44 (m, 2H), 3.41 (dd, J=11.7, 2.7 Hz, 1H), 3.20 (dd, J=11.7, 6.9 Hz, 1H), 2.90 (s, 3H), 1.50-1.36 (m, 2H), 0.89 (t. J=7.5 Hz, 3H).

EXAMPLE 12(4)

3-(N-((4-((2S)-4-methyl-3,4-dihydro-2H-1,4-benzoxazin-2-ylmethoxy)phenyl)sulfonyl)-N-butylamino)phenylacetic acid TLC: Rf 0.56 (chloroform:methanol=9:1); NMR (300 MHz, CDCl$_3$): δ 7.47 (d, J=9.0 Hz, 2H), 7.34-7.27 (m, 1H), 7.22-7.09 (m, 2H), 7.00-6.70 (m, 7H), 4.73-4.60 (m, 1H), 4.32 (dd, J=10.2, 5.1 Hz, 1H), 4.20 (dd, J=10.2, 6.3 Hz, 1H), 3.60-3.45 (m, 4H), 3.42 (dd, J=11.4, 2.4 Hz, 1H), 3.20 (dd, J=11.4, 7.5 Hz, 1H), 2.90 (s, 3H), 1.45-1.20 (m, 4H), 0.85 (t. J=6.9 Hz, 3H).

EXAMPLE 12(5)

3-(N-((4-((2S)-4-methyl-3,4-dihydro-2H-1,4-benzoxazin-2-ylmethoxy)phenyl)sulfonyl)-N-isopropylamino)phenylacetic acid TLC: Rf 0.50 (chloroform:methanol=9:1); NMR (300 MHz, CDCl$_3$): δ 7.63 (d, J=9.0 Hz, 2H), 7.35-7.22 (m, 2H), 7.11-7.05 (m, 1H), 7.00-6.81 (m, 5H), 6.79-6.69 (m, 2H), 4.72-4.52 (m, 2H), 4.31 (dd, J=10.2, 5.4 Hz, 1H), 4.18 (dd, J=10.2, 6.3 Hz, 1H), 3.57 (s, 2H), 3.41 (dd, J=11.4, 2.4 Hz, 1H), 3.23 (dd, J=11.4, 6.9 Hz, 1H), 2.90 (s, 3H), 1.05 (d, J=6.9 Hz, 6H).

EXAMPLE 12(6)

3-(N-((4-((2S)-4-methyl-3,4-dihydro-2H-1,4-benzoxazin-2-ylmethoxy)phenyl)sulfonyl)-N-isobutylamino)phenylacetic acid TLC: Rf 0.51 (chloroform:methanol=9:1); NMR (300 MHz, CDCl$_3$): δ 7.45 (d, J=9.0 Hz, 2H), 7.29 (t, J=7.2 Hz, 1H), 7.20-7.11 (m, 2H), 6.96-6.80 (m, 4H), 6.80-6.71 (m, 3H), 4.73-4.63 (m, 1H), 4.32 (dd, J=10.8, 5.4 Hz, 1H), 4.20 (dd, J=10.8, 6.0 Hz, 1H), 3.54 (s, 2H), 3.42 (dd, J=12.0, 2.4 Hz, 1H), 3.38-3.24 (m, 2H), 3.19 (dd, J=12.0, 7.5 Hz, 1H), 2.90 (s, 3H), 1.63-1.50 (m, 1H), 0.90 (d, J=6.6 Hz, 3H), 0.89 (d, J=6.6 Hz, 3H).

REFERENCE EXAMPLE 22

4-((2S)-4-methyl-3,4-dihydro-2H-1,4-benzoxazin-2-ylmethoxy)benzaldehyde

The title compound (270 mg) having the following physical data was obtained in the same manner as in Example 11 using 4-hydroxybenzaldehyde (150 mg).

TLC: Rf 0.43 (hexane:ethyl acetate=7:3).

EXAMPLE 13

3-((4-((2S)-4-methyl-3,4-dihydro-2H-1,4-benzoxazin-2-ylmethoxy)benzyl)amino)phenylacetic acid methyl ester To a solution of the compound prepared in Reference Example 22 (270 mg) and the compound prepared in Reference Example 9 (180 mg) in dichloroethane (5 mL) was added acetic acid (0.097 mL) and sodium triacetoxyborohydride (462 mg) at room temperature and the mixture was stirred for 1 hour. To the reaction mixture was added water and then the mixture was extracted with ethyl acetate. The organic layer was washed with water and a saturated aqueous solution of sodium chloride, dried over anhydrous sodium sulfate, and concentrated to give the title compound (330 mg) having the following physical data.

TLC: Rf 0.46 (toluene:ethyl acetate=1:9); NMR (300 MHz, CDCl$_3$): δ 7.32-7.24 (m, 2H), 7.12 (t, J=7.8 Hz, 1H), 6.91 (d, J=9.0 Hz, 2H), 6.88-6.80 (m, 2H), 6.72-6.60 (m, 3H), 6.58-6.50 (m, 2H), 4.68-4.58 (m, 1H), 4.25 (s, 2H), 4.26-4.17 (m, 1H), 4.15-4.05 (m, 1H), 4.00-3.92 (m, 1H), 3.67 (s, 3H), 3.53 (s, 2H), 3.39 (dd, J=11.7, 2.7 Hz, 1H), 3.25 (dd, J=11.7, 6.6 Hz, 1H), 2.90 (s, 3H).

EXAMPLE 14

3-((4-((2S)-4-methyl-3,4-dihydro-2H-1,4-benzoxazin-2-ylmethoxy)benzyl)amino)phenylacetic acid The title compound (48 mg) having the following physical data was obtained in the same manner as in Example 2 using the compound prepared in Example 13 (110 mg).

TLC: Rf 0.47 (chloroform:methanol=9:1); NMR (300 MHz, CDCl$_3$): δ 7.32-7.24 (m, 2H), 7.12 (t, J=7.8 Hz, 1H), 6.94-6.80 (m, 4H), 6.70 (d, J=7.8 Hz, 2H), 6.64 (t, J=7.2 Hz, 1H), 6.57-6.51 (m, 2H), 4.67-4.57 (m, 1H), 4.30-4.19 (m, 3H), 4.17-4.05 (m, 1H), 3.55 (s, 2H), 3.38 (dd, J=11.4, 2.7 Hz, 1H), 3.23 (dd, J=11.4, 6.9 Hz, 1H), 2.89 (s, 3H).

EXAMPLE 14(1)~14(2)

The following compounds were obtained in the same manner as in Reference Example 22→Example 13→Example 14 using corresponding compounds.

EXAMPLE 14(1)

3-(N-(4-((2S)-4-methyl-3,4-dihydro-2H-1,4-benzoxazin-2-ylmethoxy)benzyl)-N-methylamino)phenylacetic acid TLC: Rf 0.50 (chloroform:methanol=9:1); NMR (300 MHz, CDCl$_3$): δ 7.22-7.10 (m, 3H), 6.94-6.79 (m, 4H), 6.75-6.60 (m, 5H), 4.66-4.56 (m, 1H), 4.46 (s, 2H), 4.22 (dd, J=9.6, 5.1 Hz, 1H), 4.08 (dd, J=9.6, 6.6 Hz, 1H), 3.57 (s, 2H), 3.38 (dd, J=11.4, 2.4 Hz, 1H), 3.22 (dd, J=11.4, 6.9 Hz, 1H), 2.98 (s, 3H), 2.89 (s, 3H).

EXAMPLE 14(2)

3-(N-(4-((2S)-4-methyl-3,4-dihydro-2H-1,4-benzoxazin-2-ylmethoxy)benzyl)-N-ethylamino)phenylacetic acid TLC: Rf 0.49 (chloroform:methanol=9:1); NMR (300 MHz, CDCl$_3$): δ 7.19-7.09 (m, 3H), 6.92-6.79 (m, 4H), 6.74-6.64 (m, 2H), 6.64-6.55 (m, 3H), 4.65-4.55 (m, 1H), 4.44 (s, 2H), 4.22 (dd, J=9.6, 4.8 Hz, 1H), 4.08 (dd, J=9.6, 6.6 Hz, 1H), 3.54 (s, 2H), 3.44 (q, J=7.2 Hz, 2H), 3.38 (dd, J=11.7, 2.7 Hz, 1H), 3.21 (dd, J=11.7, 6.9 Hz, 1H), 2.88 (s, 3H), 1.18 (t, J=7.2 Hz, 3H).

FORMULATION EXAMPLE 1

The following components were admixed in a conventional method and punched out to obtain 100 tablets each containing 50 mg of the active ingredient.

| | |
|---|---|
| 3-(4-((2S)-4-methyl-3, 4-dihydro-2H-1, 4-benzoxazin-2-ylmethoxy)benzoylamino)phenylacetic acid | 5.0 g |
| Carboxymethyl cellulose calcium (disintegrating agent) | 0.2 g |
| Magnesium stearate (lubricant) | 0.1 g |
| Microcrystalline cellulose | 4.7 g |

FORMULATION EXAMPLE 2

The following components were admixed in a conventional method, and the solution was sterilized in a conventional method, placed at 5 ml into ampoules and freeze-dried in a conventional method to thereby obtain 100 ampoules each containing 20 mg of the active ingredient.

| | |
|---|---|
| 3-(4-((2S)-4-methyl-3, 4-dihydro-2H-1,4-benzoxazin-2-ylmethoxy)benzoylamino)phenylacetic acid | 2.0 g |
| Mannitol | 20 g |
| Distilled water | 1000 ml |

The invention claimed is:
1. A carboxylic acid compound represented by formula (I):

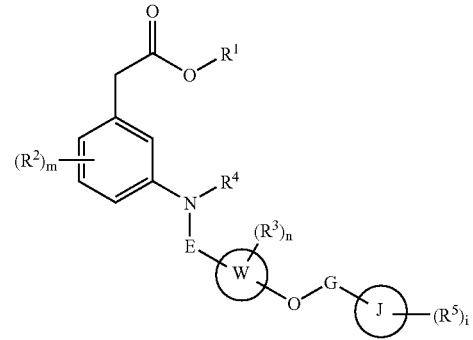

wherein $R^1$ represents (1) a hydrogen atom, (2) $C_{1-4}$ alkyl, (3) $C_{2-4}$ alkenyl or (4) benzyl;

E represents —C(=O)—, —SO$_2$— or —CH$_2$—;

$R^2$ represents (1) a halogen atom, (2) $C_{1-6}$ alkyl, (3) $C_{1-6}$ alkoxy, (4) hydroxyl, (5) trihalomethyl, (6) cyano, (7) phenyl, (8) pyridyl, (9) nitro, (10) —NR$^6$R$^7$ or (11) $C_{1-4}$ alkyl substituted with —OR$^8$;

$R^3$ represents (1) a halogen atom, (2) $C_{1-6}$ alky, (3) $C_{1-6}$ alkoxy, (4) hydroxyl, (5) trihalomethyl, (6) cyano, (7) phenyl, (8) pyridyl, (9) nitro, (10) —NR$^6$R$^7$ or (11) $C_{1-4}$ alkyl substituted with —OR$^8$;

$R^6$ and $R^7$ each independently represents a hydrogen atom or $C_{1-4}$ alkyl;

$R^8$ represents $C_{1-4}$ alkyl, phenyl or pyridyl;

$R^4$ represents (1) a hydrogen atom, (2) $C_{1-6}$ alkyl or (3) benzyl;

$R^5$ represents (1) $C_{1-6}$ alkyl, (2) $C_{1-10}$ alkoxy, (3) $C_{1-6}$ alkyl substituted with $C_{1-6}$ alkoxy, (4) a halogen atom, (5) hydroxyl, (6) trihalomethyl, (7) nitro, (8) —$NR^9R^{10}$, (9) phenyl, (10) phenoxy, (11) oxo, (12) $C_{2-6}$ acyl, (13) cyano or (14) —$SO_2R^{11}$;

$R^9$ and $R^{10}$ each independently represents a hydrogen atom or $C_{1-4}$ alkyl;

$R^{11}$ represents $C_{1-6}$ alkyl;

Ⓦ represents a $C_{5-12}$ monocyclic or bicyclic carbon ring or a 5- to 12-membered monocyclic or bicyclic hetero ring aryl having hetero atom(s) selected from one to four nitrogen atom(s), one to two oxygen atom(s) and/or one to two sulfur atom(s) and such hetero ring is saturated either partially or wholly;

G represents (1) $C_{1-6}$ alkylene having 0 to 2 hetero atom(s) selected from an nitrogen atom, an oxygen atom and a sulfur atom, (2) $C_{2-6}$ alkenylene having 0 to 2 hetero atom(s) selected from an nitrogen atom, an oxygen atom and a sulfur atom or (3) $C_{2-6}$ alkynylene having 0 to 2 a hetero atom(s) selected from an nitrogen atom, an oxygen atom and a sulfur atom;

Ⓙ represents a dihydrobenzoxazine ring;

m represents 0 or an integer of 1 to 4;

n represents 0 or an integer of 1 to 4; and i represents 0 or an integer of 1 to 11;

wherein when m is 2 or more, $R^2$ are the same or different; when n is 2 or more, $R^3$ are the same or different; and i is 2 or more, $R^5$ are the same or different)

or a pharmaceutically acceptable salt thereof.

2. The compound according to claim 1, wherein

Ⓦ is a $C_{5-6}$ monocyclic carbon ring.

3. The compound according to claim 2, wherein the $C_{5-6}$ monocyclic carbon ring is a benzene ring.

4. A pharmaceutical composition, comprising the compound according to claim 1, or a pharmaceutically acceptable salt thereof, and a pharmaceutically acceptable carrier.

5. A method for treating allergic rhinitis, allergic conjunctivitis, atopic dermatitis, bronchial asthma or food allergy, which comprises administering an effective amount of the compound according to claim 1 to a mammal.

* * * * *